US012187762B2

(12) United States Patent
Oscarson et al.

(10) Patent No.: US 12,187,762 B2
(45) Date of Patent: Jan. 7, 2025

(54) DITHIOLSACCHARIDE MUCOLYTIC AGENTS AND USES THEREOF

(71) Applicants:The Regents of the University of California, Oakland, CA (US); University College Dublin, Dublin (IE)

(72) Inventors: Stefan Oscarson, Dublin (IE); John Vincent Fahy, San Francisco, CA (US); Irina Gitlin, San Francisco, CA (US); Wilfred Raymond, San Francisco, CA (US)

(73) Assignees: The Regents of the University of California, Oakland, CA (US); University College Dublin, Dublin (IE)

( * ) Notice: Subject to any disclaimer, the term of this patent is extended or adjusted under 35 U.S.C. 154(b) by 824 days.

(21) Appl. No.: 17/270,805

(22) PCT Filed: Sep. 10, 2019

(86) PCT No.: PCT/US2019/050475
§ 371 (c)(1),
(2) Date: Feb. 23, 2021

(87) PCT Pub. No.: WO2020/055916
PCT Pub. Date: Mar. 19, 2020

(65) Prior Publication Data
US 2021/0230202 A1    Jul. 29, 2021

Related U.S. Application Data

(60) Provisional application No. 62/755,073, filed on Nov. 2, 2018, provisional application No. 62/729,327, filed on Sep. 10, 2018.

(51) Int. Cl.
| C07H 5/10 | (2006.01) |
| A61K 9/00 | (2006.01) |
| A61K 47/26 | (2006.01) |
| A61P 11/12 | (2006.01) |

(52) U.S. Cl.
CPC ............. *C07H 5/10* (2013.01); *A61K 9/0075* (2013.01); *A61K 9/0078* (2013.01); *A61K 9/008* (2013.01); *A61K 47/26* (2013.01); *A61P 11/12* (2018.01)

(58) Field of Classification Search
CPC .......... C07H 5/10; C07H 13/04; C07H 15/04; C07H 15/12; A61P 11/12; A61K 9/0075; A61K 9/0078; A61K 9/008; A61K 47/26
See application file for complete search history.

(56) References Cited

U.S. PATENT DOCUMENTS

| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 6,624,190 B2 | 9/2003 | Khoury et al. |
| 9,346,753 B2 | 5/2016 | Johnson et al. |
| 9,856,283 B2 | 1/2018 | Oscarson et al. |
| 10,106,551 B2 | 10/2018 | Johnson et al. |
| 10,526,283 B2 | 1/2020 | Johnson et al. |
| 10,526,359 B2 | 1/2020 | Oscarson et al. |
| 11,021,506 B2 | 6/2021 | Oscarson et al. |
| 2004/0037780 A1 | 2/2004 | Parsons et al. |
| 2005/0130240 A1 | 6/2005 | Lin et al. |
| 2007/0232836 A1 | 10/2007 | Steenkamp |
| 2008/0269163 A1 | 10/2008 | Sostaric et al. |
| 2010/0172845 A1 | 7/2010 | Stoops et al. |
| 2012/0171291 A1 | 7/2012 | Rademacher et al. |
| 2015/0056305 A1 | 2/2015 | Johnson et al. |
| 2015/0307530 A1 | 10/2015 | Johnson et al. |
| 2016/0060284 A1 | 3/2016 | Oscarson et al. |
| 2016/0222023 A1 | 8/2016 | Johnson et al. |
| 2018/0111955 A1 | 4/2018 | Oscarson et al. |

FOREIGN PATENT DOCUMENTS

| EP | 0 552 551 A1 | 7/1993 |
| JP | 2001-231593 A | 8/2001 |
| WO | WO-96/05309 A2 | 2/1996 |
| WO | WO-96/05309 A3 | 2/1996 |
| WO | WO-00/64485 A2 | 11/2000 |
| WO | WO-2007/091040 A2 | 8/2007 |
| WO | WO-2007/091040 A3 | 8/2007 |
| WO | WO-2010/075514 A1 | 7/2010 |
| WO | WO-2014/153009 A2 | 9/2014 |
| WO | WO-2014/153009 A3 | 9/2014 |
| WO | WO-2014/160377 A1 | 10/2014 |
| WO | WO-2017/114867 A1 | 7/2017 |

OTHER PUBLICATIONS

Ge et al., J. Org. Chem., 2017, 82, p. 7008-7014. (Year: 2017).*
Ajayi, K. et al. (Jun. 4, 2010). "Intramolecular alpha-glucosaminidation: synthesis of mycothiol," *Org Lett* 12(11):2630-2633.
Akagi, M. et al. (Jul. 1962). "Biochemical studies on Thiosugars. III. Synthesis of 6-Deoxy-6-mercapto-D-glucose," *Chem Pharm Bull* 10:562-566.
Ali, M.A. et al. (Sep. 2, 1991). "Thio and epidithio derivatives of methyl beta-lactoside," *Carbohydrate Research* 216:271-287.
Al-Muhammed, J. et al. (May-Jun. 1996). "In-vivo studies on dexamethasone sodium phosphate liposomes," *J Microencapsul* 13(3):293-306.
Berge, S.M. et al. (Jan. 1977). "Pharmaceutical salts," *J Pharm Sci* 66(1):1-19.
Bock, K. et al. (Feb. 3, 1994). "Conformational equilibria of 4-thiomaltose and nitrogen analogues of maltose in aqueous solutions," *Carbohydr Res* 253:51-67.

(Continued)

*Primary Examiner* — Jonathan S Lau
(74) *Attorney, Agent, or Firm* — Mintz, Levin, Cohn, Ferris, Glovsky and Popeo, P.C.

(57) ABSTRACT

There are provided, inter alia, methods for decreasing mucus elasticity or decreasing mucus viscosity in a subject in need thereof, the methods including administering to the subject an effective amount of a dithiolsaccharide mucolytic agent, and compounds and pharmaceutical compositions useful for the methods.

27 Claims, 10 Drawing Sheets

(56) References Cited

OTHER PUBLICATIONS

Boigegrain, R-A et al. (May 1975). "Synthèse du methyl-3,4,6-tridésoxy-3,4-épithio-2-O-méthylsulfonyl-α-D-allopyranoside et des 1,2,3-Tri-O-acetyl-4-S-acétyl-6-désoxy-4-thio-α- etβ-D-gulopyranoses," *Carbohydr Res* 41(1):135-142.
Brady, B. et al. (Jul. 3, 1998). Bisthiocyclomalto-oligosaccharides with trehalosyl and octyl links: their synthesis for dual-cavity inclusion, *Carbohydrate Research* 309(3):237-241.
CAS Registry No. 10593-29-0, 1-thio-β-D-Glucose (sodium salt), 1 page, accessed May 12, 2017.
CAS Registry No. 853782-73-7, STN Entry Date Jul. 5, 2005, 1 page.
CAS Registry No. 869880-85-3, STN Entry Date Dec. 14, 2005, 1 page.
CAS Registry No. 869880-86-4, STN Entry Date Dec. 14, 2005, 1 page.
CAS Registry No. 40652-97-9, STN Entry Date Nov. 16, 1984, 1 page.
CAS Registry No. 10489-79-9, STN Entry Date Nov. 16, 1984, 1 page.
CAS Registry No. 908023-45-0, STN Entry Date Sep. 20, 2006, 1 page.
CAS Registry No. 304439-16-5, STN Entry Date Nov. 27, 2000, 1 page.
CAS Registry No. 482593-16-8, STN Entry Date Jan. 29, 2003, 1 page.
CAS Registry No. 482593-15-7, STN Entry Date Jan. 29, 2003, 1 page.
CAS Registry No. 114329-71-4, STN Entry Date May 7, 1988, 1 page.
Castro, B. et al. (1972). *Tetrahedron Letters* 49:5001-5004. (English translation not available).
Chen, L. et al. (May 1, 2016). "Amorphous powders for inhalation drug delivery," *Advanced Drug Delivery Reviews* 100:102-115.
Chonn, A. et al. (Dec. 1995). "Recent advances in liposomal drug-delivery systems," *Curr Opin Biotechnol* 6(6):698-708.
Cicero, D. et al. (1990). Synthesis of furanoid and pyranoid derivatives of 6-deoxy-4-thio-D-galactose, *Tetrahedron* 46(4):1131-1144.
Du, J. et al. (Sep. 1, 2011, e-published May 19, 2011). "Deciphering glycan linkages involved in Jurkat cell interactions with gold-coated nanofibers via sugar-displayed thiols," *Bioorg Med Chem Lett* 21(17):4980-4984.
Dunican, E.M. et al. (Mar. 1, 2018). "Mucus plugs in patients with asthma linked to eosinophilia and airflow obstruction," *J Clin Invest* 128(3):997-1009.
Eyles, J.E. et al. (Jul. 1997). "Oral delivery and fate of poly(lactic acid) microsphere-encapsulated interferon in rats," *J Pharm Pharmacol* 49(7):669-674.
Fadlan, A. et al. (May 1, 2018). "Synthesis, photophysical properties, and photodynamic activity of positional isomers of TFPP-glucose conjugates," *Bioorg Med Chem* 26(8):1848-1858.
Gao, Z.H. et al. (Jun. 1995). "Controlled release of a contraceptive steroid from biodegradable and injectable gel formulations: in vitro evaluation," *Pharm Res* 12(6):857-863.
Hardegger, E. et al. (1970). "Synthese der 2-Thio-D-glucose and einiger 3-Thio-D-altrose-Derivate," *Helvetica Chimica Acta* 53(5):951-959.
Hinou, H. et al. (2002). "Bisubstrate-type inhibitor of sialyltransferases," *Tetrahedron Letters* 43:9147-9150.
Houseman, B.T. et al. (2003). "Maleimide-Functionalized Self-Assembled Monolayers for the Preparation of Peptide and Carbohydrate Biochips," *Langmuir* 19(5):1522-1531.
International Search Report mailed on Sep. 26, 2014, for PCT Application No. PCT/US2014/028656, filed Mar. 14, 2014, 5 pages.
International Search Report mailed on Jan. 21, 2020, for PCT Application No. PCT/US2019/050475, filed Sep. 10, 2019, 5 pages.

Kajihara, Y. et al. (1998). "Novel features of acceptor recognition by β-(1-4)-galactosyltransferase," *Carbohydr Res* 306:361-378.
Konstantinovic, S. et al. (2005). "$SnCl_4$ Induced Formation of $C_3$-$C_{11}$ Alkenyl Galactopyranosides as Precursors for Unsaturated Neutral Bolaforms," *J. Serbian Chem. Soc.* 70(7):925-929.
Lachowicz-Scroggins, M.E. et al. (Feb. 2018). "Cadherin-26 (CDH26) regulates airway epithelial cell cytoskeletal structure and polarity," *Cell Discov*, 4:7.
Leitner, V.M. et al. (Sep. 2003). "Thiolated polymers: evidence for the formation of disulphide bonds with mucus glycoproteins," *Eur J Pharm Biopharm* 56(2):207-214.
Machell, G. et al. (1961). "Methyl Glucosides as Transfer Agents in Polymerisation of Acrylonitrile and Styrene," *Journal of the Chemical Society* 3308-3312.
Maradufu, A. et al. (Jan. 1974). "A non-hydrogen-bonding role for the 4-hydroxyl group of D-Galactose in its reaction with D-Galactose oxidase," *Carbohydr Res* 32(1):93-99.
Ostro, M.J. et al. (Aug. 1989). "Use of liposomes as injectable-drug delivery systems," *Am J Hosp Pharm* 46(8):1576-1587.
Otterson, G.A. et al. (Feb. 15, 2007). "Phase I study of inhaled Doxorubicin for patients with metastatic tumors to the lungs," *Clin Cancer Res* 13(4):1246-1252.
Pei, Z. et al. (Jun. 2, 2005). "Redox-responsive and calcium-dependent switching of glycosyldisulfide interactions with Concanavalin A," *Bioorg Med Chem Lett* 15(11):2707-2710.
Pei, Z. et al. (2007). "Synthesis of Positional Thiol Analogs of β-D-Galactopyranose," *Eur J Org Chem* 4927-4934.
Priebe, W. et al. (1991). "A Facile Method for Preparation of 3-Thio-Sugars and 3-Thio-Glycals. Synthesis of 3'-Mercapto-3'-Deamino-Doxorubicin," *Tetrahedron Letters* 32(28):3313-3316.
PubChem-CID-101783535, Create Date: Dec. 18, 2015, 7 pages.
PubChem-CID-102012810, Create Date: Dec. 24, 2015, 7 pages.
PubChem-CID-118724522, Create Date: Mar. 8, 2016, 7 pages.
PubChem-CID-134459995, Create Date: Jun. 23, 2018, 9 pages.
Rao, K.P. et al. (1995). "Recent developments of collagen-based materials for medical applications and drug delivery systems," *J Biomater Sci Polym Ed* 7(7):623-645.
RN 92379-73-2, Registry, *STN Columbus*, Dec. 17, 1984, 2 pages.
RN 1422971-07-0, Registry, *STN Columbus*, Mar. 11, 2013, 2 pages.
Shu, P. et al. (Feb. 16, 2015). "Selective S-deacetylation inspired by native chemical ligation: practical syntheses of glycosyl thiols and drug mercaplo-analogues," *Green Chem*,17:2545-2551.
Stewart, M.J.G. (2007). "Mycothiol disulfide reductase: solid phase synthesis and evaluation of alternative substrate analogues," *Organic & Biomolecular Chemistry* 6:385-390.
STN Accession No. 1966:104576, Entered STN Apr. 22, 2001, 2 pages.
Widdicombe, J.H. et al. (Aug. 2005). "Expansion of cultures of human tracheal epithelium with maintenance of differentiated structure and function," *Biotechniques* 39(2):249-255.
Wirz, P. et al. (Nov. 1, 1971). "Synthese von 2-Thioaldosen über α,β-ungesättigte Nitrokörper," *Helvetica Chimica Acta* 54(7):2017-2025.
Written Opinion mailed on Sep. 26, 2014, for PCT Application No. PCT/US2014/028656, filed Mar. 14, 2014, 7 pages.
Written Opinion mailed on Jan. 21, 2020, for PCT Application No. PCT/US2019/050475, filed Sep. 10, 2019, 5 pages.
Yuan, S. et al. (Feb. 25, 2015). "Oxidation increases mucin polymer cross-links to stiffen airway mucus gels," *Sci Transl Med* 7(276):276ra27.
Lees, W. J. et al. (1993) "Interpretation of the Reduction Potential of 6,6'-Dithiosucrose Cyclic Disulfide by Comparison of the Conformations of 6,6'-Dithiosucrose Cyclic Disulfide, 6,6'-Dithiosucrose, and Sucrose in Aqueous Solution," Journal of the American Chemical Society 115:1860-1869.
Partial Supplementary European Search Report mailed on Apr. 12, 2022, for EP Application No. 19861202.0, 14 pages.
Ma, M. et al. (Mar. 14, 2011). "Stabilization of vesicular and supported membranes by glycolipid oxime polymers," *Chem Commun (Camb)* 47(10):2853-2855.

\* cited by examiner

DITHIOLSACCHARIDE MUCOLYTIC AGENTS AND USES THEREOF

CROSS-REFERENCES TO RELATED APPLICATIONS

This application is the national stage filing under 35 U.S.C. § 371 of International Application No. PCT/US2019/050475, which claims the benefit of U.S. Provisional Application No. 62/729,327, filed Sep. 10, 2018, and U.S. Provisional Application No. 62/755,073, filed Nov. 2, 2018, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. P01 HL128191 and R01 HL080414, awarded by the National Institutes of Health. The government has certain rights in the invention.

BACKGROUND

Increased mucus elasticity is a major cause of morbidity in patients with lower and upper airway diseases such as asthma, cystic fibrosis (CF), acute and chronic bronchitis, and acute and chronic sinusitis, and it also causes clinical problems such as pneumonia and respiratory failure in patients on mechanical ventilators. There is a need for novel mucolytic therapies for a wide range of acute and chronic airway diseases. Disclosed herein, inter alia, are solutions to these and other problems in the art.

BRIEF SUMMARY OF THE INVENTION

Provided herein, inter alia, methods for decreasing mucus elasticity or decreasing mucus viscosity in a subject in need thereof, the methods including administering to the subject an effective amount of a dithiolsaccharide mucolytic agent, and compounds and pharmaceutical compositions useful for the methods.

In an aspect is provided a compound having the formula:

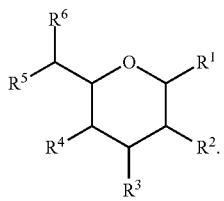

(I)

$R^1$ is $—SR^{1A}$, $—OR^{1A}$, $—NR^{1B}R^{1C}$, $—NR^{1B}C(O)R^{1C}$, $—NR^{1B}C(O)OR^{1C}$, substituted or unsubstituted $C_1$-$C_{10}$ alkyl, or substituted or unsubstituted 2 to 10 membered heteroalkyl. $R^2$ is $—SR^{2A}$, $—OR^{2A}$, $—NR^{2B}R^{2C}$, $—NR^{2B}C(O)R^{2C}$, $—NR^{2B}C(O)OR^{2C}$, substituted or unsubstituted $C_1$-$C_{10}$ alkyl, or substituted or unsubstituted 2 to 10 membered heteroalkyl. $R^3$ is $—SR^{3A}$, $—OR^{3A}$, $—NR^{3B}R^{3C}$, $—NR^{3B}C(O)R^{3C}$, $—NR^{3B}C(O)OR^{3C}$, substituted or unsubstituted $C_1$-$C_{10}$ alkyl, or substituted or unsubstituted 2 to 10 membered heteroalkyl. $R^4$ is $—SR^{4A}$, $—SC(O)R^{4A}$, $—OR^{4A}$, $—NR^{4B}R^{4C}$, $—NR^{4B}C(O)R^{4C}$, $—NR^{4B}C(O)OR^{4C}$, substituted or unsubstituted $C_1$-$C_{10}$ alkyl, or substituted or unsubstituted 2 to 10 membered heteroalkyl. $R^5$ is hydrogen, $—SR^{5A}$, $—OR^{5A}$, $—NR^{5B}R^{5C}$, $—NR^{5B}C(O)R^{5C}$, $—NR^{5B}C(O)OR^{5C}$, or substituted or unsubstituted $C_1$-$C_{10}$ alkyl, substituted or unsubstituted 2 to 10 membered heteroalkyl. $R^6$ is $—SR^{6A}$, $—OR^{6A}$, $—NR^{6B}R^{6C}$, $—NR^{6B}C(O)R^{6C}$, $—NR^{6B}C(O)OR^{6C}$, or substituted or unsubstituted $C_1$-$C_{10}$ alkyl, substituted or unsubstituted 2 to 10 membered heteroalkyl. $R^{1A}$, $R^{2A}$, $R^{3A}$, $R^{4A}$, $R^{5A}$, $R^{6A}$, $R^{1B}$, $R^{2B}$, $R^{3B}$, $R^{4B}$, $R^{5B}$, $R^{6B}$, $R^{1C}$, $R^{2C}$, $R^{3C}$, $R^{4C}$, $R^{5C}$, and $R^{6C}$ are each independently hydrogen, substituted or unsubstituted $C_1$-$C_{10}$ alkyl, substituted or unsubstituted 2 to 10 membered heteroalkyl, wherein the compound comprises at least two thiol moieties, or a pharmaceutically acceptable salt thereof.

In an aspect is provided a compound having the formula:

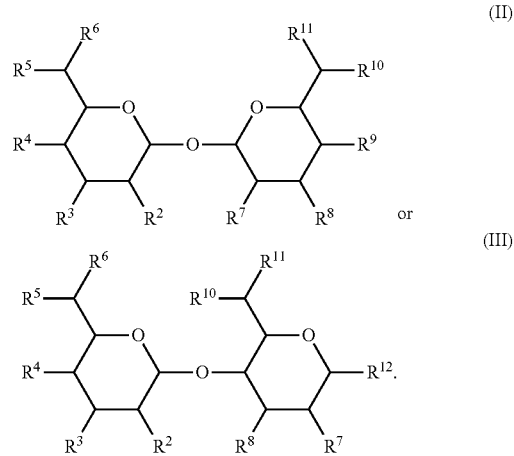

$R^2$ is $—SR^{2A}$, $—OR^{2A}$, $—NR^{2B}R^{2C}$, $—NR^{2B}C(O)R^{2C}$, $—NR^{2B}C(O)OR^{2C}$, substituted or unsubstituted $C_1$-$C_{10}$ alkyl, or substituted or unsubstituted 2 to 10 membered heteroalkyl. $R^3$ is $—SR^{3A}$, $—OR^{3A}$, $—NR^{3B}R^{3C}$, $—NR^{3B}C(O)R^{3C}$, $—NR^{3B}C(O)OR^{3C}$, substituted or unsubstituted $C_1$-$C_{10}$ alkyl, or substituted or unsubstituted 2 to 10 membered heteroalkyl. $R^4$ is $—SR^{4A}$, $—SC(O)R^{4A}$, $—OR^{4A}$, $—NR^{4B}R^{4C}$, $—NR^{4B}C(O)R^{4C}$, $—NR^{4B}C(O)OR^{4C}$, substituted or unsubstituted $C_1$-$C_{10}$ alkyl, or substituted or unsubstituted 2 to 10 membered heteroalkyl. $R^5$ is hydrogen, $—SR^{5A}$, $—OR^{5A}$, $—NR^{5B}R^{5C}$, $—NR^{5B}C(O)R^{5C}$, $—NR^{5B}C(O)OR^{5C}$, or substituted or unsubstituted $C_1$-$C_{10}$ alkyl, substituted or unsubstituted 2 to 10 membered heteroalkyl. $R^6$ is $—SR^{6A}$, $—OR^{6A}$, $—NR^{6B}R^{6C}$, $—NR^{6B}C(O)R^{6C}$, $—NR^{6B}C(O)OR^{6C}$, or substituted or unsubstituted $C_1$-$C_{10}$ alkyl, substituted or unsubstituted 2 to 10 membered heteroalkyl. $R^7$ is $—SR^{7A}$, $—OR^{7A}$, $—NR^{7B}R^{7C}$, $—NR^{7B}C(O)R^{7C}$, $—NR^{7B}C(O)OR^{7C}$, substituted or unsubstituted $C_1$-$C_{10}$ alkyl, or substituted or unsubstituted 2 to 10 membered heteroalkyl. $R^8$ is $—SR^{8A}$, $—OR^{8A}$, $—NR^{8B}R^{8C}$, $—NR^{8B}C(O)R^{8C}$, $—NR^{8B}C(O)OR^{8C}$, substituted $C_1$-$C_{10}$ alkyl, or substituted or unsubstituted 2 to 10 membered heteroalkyl. $R^9$ is $—SR^{9A}$, $—SC(O)R^{9A}$, $—OR^{9A}$, $—NR^{9B}R^{9C}$, $—NR^{9B}C(O)R^{9C}$, $—NR^{9B}C(O)OR^{9C}$, substituted or unsubstituted $C_1$-$C_{10}$ alkyl, or substituted or unsubstituted 2 to 10 membered heteroalkyl. $R^{10}$ is hydrogen, $—SR^{10A}$, $—OR^{10A}$, $—NR^{10B}R^{10C}$, $—NR^{10B}C(O)R^{10C}$, $—NR^{10B}C(O)OR^{10C}$, or substituted or unsubstituted $C_1$-$C_{10}$ alkyl, substituted or unsubstituted 2 to 10 membered heteroalkyl. $R^{11}$ is $—SR^{11A}$, $—OR^{11A}$, $—NR^{11B}R^{11C}$, $—NR^{10B}C(O)R^{11C}$, $—NR^{10B}C(O)OR^{11C}$, or substituted or unsubstituted $C_1$-$C_{10}$ alkyl, substituted or unsubstituted 2 to 10 membered heteroalkyl. $R^{12}$ is —$SR^{12A}$, —$OR^{12A}$, —$NR^{12B}R^{12C}$, —$NR^{12B}C(O)R^{12C}$, —$NR^{12B}C(O)OR^{12C}$, substituted or unsubstituted $C_1$-$C_{10}$ alkyl, or substituted or unsubstituted 2 to 10 membered heteroalkyl. $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ are each independently hydrogen, substituted or unsubstituted $C_1$-$C_{10}$ alkyl, substituted or unsubstituted 2 to 10 membered heteroalkyl, wherein the compound comprises at least two thiol moieties, or a pharmaceutically acceptable salt thereof.

In an aspect is provided a compound having the formula:

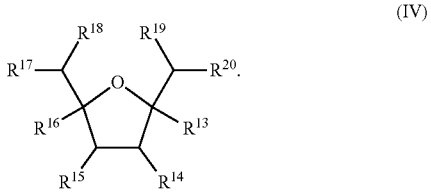

(IV)

$R^{13}$ is hydrogen, —$SR^{13A}$, —$OR^{13A}$, —$NR^{13B}R^{13C}$, —$NR^{13B}C(O)R^{13C}$, —$NR^{13B}C(O)OR^{13C}$, substituted or unsubstituted $C_1$-$C_{10}$ alkyl, or substituted or unsubstituted 2 to 10 membered heteroalkyl. $R^{14}$ is —$SR^{14A}$, —$OR^{14A}$, —$NR^{14B}R^{14C}$, —$NR^{14B}C(O)R^{14C}$, —$NR^{14B}C(O)OR^{14C}$, substituted or unsubstituted $C_1$-$C_{10}$ alkyl, or substituted or unsubstituted 2 to 10 membered heteroalkyl. $R^{15}$ is —$SR^{15A}$, —$OR^{15A}$, —$NR^{15B}R^{15C}$, —$NR^{15B}C(O)R^{15C}$, —$NR^{15B}C(O)OR^{15C}$, substituted or unsubstituted $C_1$-$C_{10}$ alkyl, or substituted or unsubstituted 2 to 10 membered heteroalkyl. $R^{16}$ is hydrogen, —$SR^{16A}$, —$OR^{16A}$, —$NR^{16B}R^{16C}$, —$NR^{16B}C(O)R^{16C}$, —$NR^{16B}C(O)OR^{16C}$, substituted or unsubstituted $C_1$-$C_{10}$ alkyl, or substituted or unsubstituted 2 to 10 membered heteroalkyl. $R^{17}$ is hydrogen, —$SR^{17A}$, —$OR^{17A}$, —$NR^{17B}R^{17C}$, —$NR^{17B}C(O)R^{17C}$, —$NR^{17B}C(O)OR^{17C}$, or substituted or unsubstituted $C_1$-$C_{10}$ alkyl, or substituted or unsubstituted 2 to 10 membered heteroalkyl. $R^{18}$ is —$SR^{18A}$, —$OR^{18A}$, —$NR^{18B}R^{18C}$, —$NR^{18B}C(O)R^{18C}$, —$NR^{18B}C(O)OR^{18C}$, or substituted or unsubstituted $C_1$-$C_{10}$ alkyl, substituted or unsubstituted 2 to 10 membered heteroalkyl. $R^{19}$ is hydrogen, —$SR^{19A}$, —$OR^{19A}$, —$NR^{19B}R^{19C}$, —$NR^{19B}C(O)R^{19C}$, —$NR^{19B}C(O)OR^{19C}$, or substituted or unsubstituted $C_1$-$C_{10}$ alkyl, or substituted or unsubstituted 2 to 10 membered heteroalkyl. $R^{20}$ is —$SR^{20A}$, —$OR^{20A}$, —$NR^{20B}R^{20C}$, —$NR^{20B}C(O)R^{20C}$, —$NR^{20B}C(O)OR^{20C}$, or substituted or unsubstituted $C_1$-$C_{10}$ alkyl, substituted or unsubstituted 2 to 10 membered heteroalkyl. $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{16B}$, $R^{17B}$, $R^{18B}$, $R^{19B}$, $R^{20B}$, $R^{13C}$, $R^{14C}$, $R^{15C}$, $R^{16C}$, $R^{17C}$, $R^{18C}$, $R^{19C}$, and $R^{20C}$ are each independently hydrogen, substituted or unsubstituted $C_1$-$C_{10}$ alkyl, substituted or unsubstituted 2 to 10 membered heteroalkyl; and provided the compound comprises at least two thiol moieties, or a pharmaceutically acceptable salt thereof.

In an aspect is provided a compound having the formula:

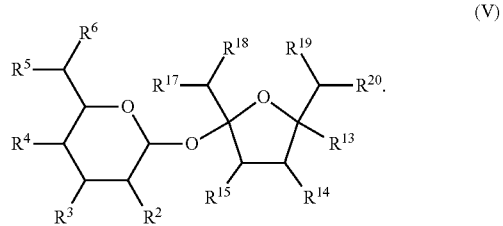

(V)

$R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted $C_1$-$C_{10}$ alkyl, or substituted or unsubstituted 2 to 10 membered heteroalkyl. $R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted $C_1$-$C_{10}$ alkyl, or substituted or unsubstituted 2 to 10 membered heteroalkyl. $R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted $C_1$-$C_{10}$ alkyl, or substituted or unsubstituted 2 to 10 membered heteroalkyl. $R^5$ is hydrogen, —$SR^{5A}$, —$OR^{5A}$, —$NR^{5B}R^{5C}$, —$NR^{5B}C(O)R^{5C}$, —$NR^{5B}C(O)OR^{5C}$, or substituted or unsubstituted $C_1$-$C_{10}$ alkyl, substituted or unsubstituted 2 to 10 membered heteroalkyl. $R^6$ is —$SR^{6A}$, —$OR^{6A}$, —$NR^{6B}R^{6C}$, —$NR^{6B}C(O)R^{6C}$, —$NR^{6B}C(O)OR^{6C}$, or substituted or unsubstituted $C_1$-$C_{10}$ alkyl, substituted or unsubstituted 2 to 10 membered heteroalkyl. $R^{13}$ is hydrogen, —$SR^{13A}$, —$OR^{13A}$, —$NR^{13B}R^{13C}$, —$NR^{13B}C(O)R^{13C}$, —$NR^{13B}C(O)OR^{13C}$, substituted or unsubstituted $C_1$-$C_{10}$ alkyl, or substituted or unsubstituted 2 to 10 membered heteroalkyl. $R^{14}$ is —$SR^{14A}$, —$OR^{14A}$, —$NR^{14B}R^{14C}$, —$NR^{14B}C(O)R^{14C}$, —$NR^{14B}C(O)OR^{14C}$, substituted or unsubstituted $C_1$-$C_{10}$ alkyl, or substituted or unsubstituted 2 to 10 membered heteroalkyl. $R^{15}$ is —$SR^{15A}$, —$OR^{15A}$, —$NR^{15B}R^{15C}$, —$NR^{15B}C(O)R^{15C}$, —$NR^{15B}C(O)OR^{15C}$, substituted or unsubstituted $C_1$-$C_{10}$ alkyl, or substituted or unsubstituted 2 to 10 membered heteroalkyl. $R^{17}$ is hydrogen, —$SR^{17A}$, —$OR^{17A}$, —$NR^{17B}R^{17C}$, —$NR^{17B}C(O)R^{17C}$, —$NR^{17B}C(O)OR^{17C}$, or substituted or unsubstituted $C_1$-$C_{10}$, alkyl, substituted or unsubstituted 2 to 10 membered heteroalkyl. $R^{18}$ is —$SR^{18A}$, —$OR^{18A}$, —$NR^{18B}R^{18C}$, —$NR^{18B}C(O)R^{18C}$, —$NR^{18B}C(O)OR^{18C}$, or substituted or unsubstituted $C_1$-$C_{10}$, alkyl, substituted or unsubstituted 2 to 10 membered heteroalkyl. $R^{19}$ is hydrogen, —$SR^{19A}$, —$OR^{19A}$, —$NR^{19B}R^{19C}$, —$NR^{19B}C(O)R^{19C}$, —$NR^{19B}C(O)OR^{19C}$, or substituted or unsubstituted $C_1$-$C_{10}$, alkyl, substituted or unsubstituted 2 to 10 membered heteroalkyl. $R^{20}$ is —$SR^{20A}$, —$OR^{20A}$, —$NR^{20B}R^{20C}$, —$NR^{20B}C(O)R^{20C}$, —$NR^{20B}C(O)OR^{20C}$, or substituted or unsubstituted $C_1$-$C_{10}$, alkyl, substituted or unsubstituted 2 to 10 membered heteroalkyl; and $R^{2A}$, $R^{3A}$, $R^{4A}$, $R^{5A}$, $R^{6A}$, $R^{2B}$, $R^{3B}$, $R^{4B}$, $R^{5B}$, $R^{6B}$, $R^{2C}$, $R^{3C}$, $R^{4C}$, $R^{5C}$, $R^{6C}$, $R^{13A}$, $R^{14A}$, $R^{15A}$, $R^{17A}$, $R^{18A}$, $R^{19A}$, $R^{20A}$, $R^{13B}$, $R^{14B}$, $R^{15B}$, $R^{17B}$, $R^{18B}$, $R^{19B}$, $R^{20B}$, $R^{13C}$, $R^{14C}$, $R^{15C}$, $R^{17C}$, $R^{18C}$, $R^{19C}$, and $R^{20C}$ are each independently hydrogen, substituted or unsubstituted $C_1$-$C_{10}$ alkyl, substituted or unsubstituted 2 to 10 membered heteroalkyl; and provided the compound comprises at least two thiol moieties, or a pharmaceutically acceptable salt thereof.

In an aspect, there is provided a pulmonary pharmaceutical composition including a pulmonary pharmaceutical carrier and a dithiolsaccharide mucolytic agent (e.g., a compound as described herein).

In an aspect, there is provided a pharmaceutical composition including a pharmaceutically acceptable excipient and a compound, or pharmaceutically acceptable salt thereof, as described herein, or embodiments thereof.

In one aspect, there is provided a method of decreasing mucus elasticity or decreasing mucus viscosity in a subject in need thereof.

In an aspect, there is provided a method for treatment in a subject in need thereof. The method includes administering an effective amount of a compound disclosed herein in combination with another therapeutic agent, wherein the therapeutic action of the therapeutic agent is enhanced by decreasing mucus elasticity or decreasing mucus viscosity. In embodiments, administration of a compound disclosed herein in combination with another therapeutic agent provides additive or synergistic treatment for the subject. In embodiments, the other therapeutic agent is a mucoactive drug (e.g., recombinant human DNAse, or hypertonic saline) or a steroid (e.g., fluticasone, budesonide, beclomethasone, mometasone) or an antibiotic. In embodiments, as a result of the decrease in mucus elasticity or decrease in mucus viscosity in a subject in need thereof upon administration of a compound disclosed herein, the dosage requirements for the other therapeutic agent are reduced, or the efficacy of the other therapeutic agent is improved.

In an aspect, there is provided a method for treatment in a subject in need thereof, the method including administering an effective amount of a compound disclosed herein in combination with another therapeutic agent. In embodiments, the "another therapeutic agent" is a beta agonist, an anticholinergic, a corticosteroid, an antibiotic, recombinant human DNAse (rhDNAse), or a treatment designed to modulate the genome of airway or alveolar epithelial cells using RNA interference with siRNA, cDNA overexpression, zinc finger nucleases, transcription activator-like effector nucleases, or the clustered regularly interspaced short palindromic repeats (CRISPR)-associated protein 9 (Cas9)-mediated system.

DETAILED DESCRIPTION

Figure 1A:
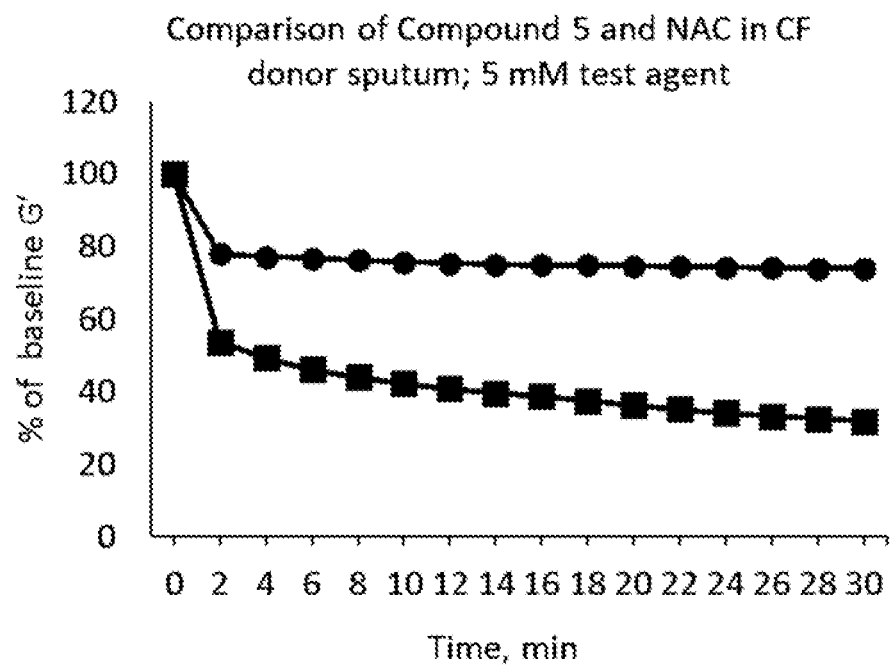
FIG. 1A. is a graph showing the effect of 6,6'-dithio-6,6'dideoxy-α,α-trehalose (Compound 5, square) vs N-acetylcysteine (NAC, circle) on the elastic modulus (G') of spontaneously expectorated sputum collected from a patient with cystic fibrosis (CF). The G' of the sputum is measured using a cone and plate rheometer. The Y-axis is the % of baseline G' of the sputum sample as a function of time, after addition of Compound 5 or NAC to a final concentration of 5 mM in the sputum.

Provided herein is, inter alia, a set of compounds—saccharide scaffolds modified with two thiol groups—that liquefy elastic mucus gels and have potential utility as mucolytic drugs for the treatment of patients with mucus-associated diseases of the lower airways (e.g., asthma, cystic fibrosis, chronic bronchitis, and others), upper airways (e.g., chronic sinusitis and others), and eye. In embodiments, these compounds markedly decrease mucus elasticity and mucus viscosity when applied ex vivo to sputum from patients with cystic fibrosis, and they have similar biophysical effects in a synthetic thiolated hydrogel model of pathologic airway mucus. In embodiments, the compounds are safe when administered in vitro to airway epithelial cells in air liquid interface culture and in vivo to the airways of mice. In embodiments, the compounds are amenable to being formulated in solution for inhaled delivery by a nebulizer. In embodiments, a compound provided herein is formulated in a dry powder composition. Dithiolsaccharide mucolytic agents included herein provide for safe and effective therapies for patients with diseases associated with highly elastic occlusive mucus, e.g., in their lungs, sinuses, or eyes.

I. Definitions

The abbreviations used herein have their conventional meaning within the chemical and biological arts. The chemical structures and formulae set forth herein are constructed according to the standard rules of chemical valency known in the chemical arts.

As used herein, the term "about" in the context of a numerical value or range means±10% of the numerical value or range recited or claimed, unless the context requires a more limited range.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

As used in the description herein and throughout the claims that follow, the meaning of "a," "an," and "the" includes plural reference unless the context clearly dictates otherwise.

The transitional term "comprising," which is synonymous with "including," "containing," or "characterized by," is inclusive or open-ended and does not exclude additional, unrecited elements, method steps, or ingredients (depending on context). By contrast, the transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. Where methods and compositions are disclosed using the transitional term "comprising" it will be understood that corresponding methods and compositions with the transitional term "consisting of" and "consisting essentially of" are also disclosed.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R'', —OR', —SR', and/or —SO$_2$R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The symbol "⌇" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In embodiments, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers, and individual isomers are encompassed within the scope of the present invention. The compounds of the present invention do not include those that are known in the art to be too unstable to synthesize and/or isolate.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things. In embodiments, treatment includes prophylactic treatment. Treatment methods include administering to a subject a therapeutically effective amount of an active agent. In embodiments, the administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

An "effective amount" is an amount sufficient to accomplish a stated purpose (e.g., achieve the effect for which it is administered, treat a disease, reduce mucus at a target organ, reduce one or more symptoms of a disease or condition, and the like). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of a compound disclosed herein required to decrease mucus elasticity or decrease mucus viscosity in a subject in need thereof. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Subject," "patient," "subject in need thereof" refers to a living member of the animal kingdom suffering from or that may suffer from the indicated disease or disorder. In embodiments, the subject is a member of a species that includes individuals who naturally suffer from the disease or disorder. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human. In embodiments, the subject is a non-mammalian animal such as a turkey, a duck, or a chicken. In embodiments, a subject is a living organism suffering from or prone to a disease or condition that can be treated by administration of a composition or pharmaceutical composition as provided herein. The terms "subject," "patient," "individual," etc. are not intended to be limiting and can be generally interchanged. In embodiments, an individual described as a "patient" does not necessarily have a given disease, but may, e.g., be merely seeking medical advice.

In embodiments, a disease or disorder is, or includes, an abnormal (e.g., increased) amount of mucus (e.g. in a mucus membrane, eye, or airway) or mucus with abnormal (e.g., increased) viscosity or elasticity compared to the mucus of a typical healthy subject. In embodiments, an abnormal increase is an increase of at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, or 1000%. In embodiments, an abnormal increase is an increase of from 5%, 10%, 15%, 20%, 25%, 30%, 35%, 40%, 45%, or 50% to about 60%, 65%, 70%, 75%, 80%, 85%, 90%, 95%, 100%, 200%, 300%, 400%, 500%, 600%, 700%, 800%, 900%, or 1000%.

As used herein, a "symptom" of a disease includes any clinical or laboratory manifestation associated with the disease, and is not limited to what a subject can feel or observe.

"Pharmaceutically acceptable excipient" and "pharmaceutically acceptable carrier" refer to a substance that aids the administration of an active agent to a subject, or aids absorption by a subject, or improves stability or other properties of the active agent, and can be included in the compositions of the present invention without causing a significant adverse toxicological effect on the patient. Unless indicated to the contrary, the terms "active agent," "active ingredient," "therapeutically active agent," "therapeutic agent" and like are used synonymously. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, polyethylene glycol, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As used herein, the term "administering" means oral administration, administration as an inhaled aerosol or as an inhaled dry powder, suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example bronchodilators (beta agonists, anticholinergics), corticosteroids, antibiotics, cancer therapies such as chemotherapy, hormonal therapy, radiotherapy, or immunotherapy. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g., to reduce metabolic degradation, or to promote the penetration of tissues, mucus, or pathologic biofilms by the active substance). The preparations may also be combined with other mucolytic drug classes (e.g., rhDNase, as known in the art) or with inhaled bronchodilators (short or long acting beta agonists, short or long acting anticholinergics), inhaled corticosteroids, or inhaled antibiotics to improve the efficacy of these drugs by providing additive or synergistic effects. The compositions of the present invention can be delivered transdermally, by a topical route, formulated as applicator sticks, solutions, suspensions, emulsions, gels, creams, ointments, nanoparticles, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Pharmaceutical compositions provided by the present invention include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Additionally, where multiple substituents are present on a moiety, each substituent may be optionally differently.

The term "thiol" is used in accordance with its ordinary meaning in the art and refers to the moiety.

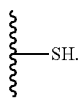

The terms "dithiolsaccharide mucolytic agent" and "mucolytic dithiolsaccharide agent" refer to a compound comprising at least one saccharide moiety covalently attached to at least two thiol moieties.

I. Compounds

In an aspect is provided a compound having the formula:

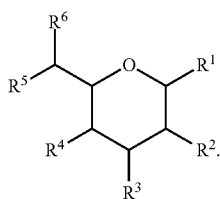

(I)

$R^1$ is —$SR^{1A}$, —$OR^{1A}$, —$NR^{1B}R^{1C}$, —$NR^{1B}C(O)R^{1C}$, —$NR^{1B}C(O)OR^{1C}$, substituted or unsubstituted $C_1$-$C_{10}$ alkyl, or substituted or unsubstituted 2 to 10 membered heteroalkyl. $R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted $C_1$-$C_{10}$ alkyl, or substituted or unsubstituted 2 to 10 membered heteroalkyl. $R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted $C_1$-$C_{10}$, alkyl, or substituted or unsubstituted 2 to 10 membered heteroalkyl. $R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted $C_1$-$C_{10}$ alkyl, or substituted or unsubstituted 2 to 10 membered heteroalkyl. $R^5$ is hydrogen, —$SR^{5A}$, —$OR^{5A}$, —$NR^{5B}R^{5C}$, —$NR^{5B}C(O)R^{5C}$, —$NR^{5B}C(O)OR^{5C}$, or substituted or unsubstituted $C_1$-$C_{10}$ alkyl, substituted or unsubstituted 2 to 10 membered heteroalkyl. $R^6$ is —$SR^{6A}$, —$OR^{6A}$, —$NR^{6B}R^{6C}$, —$NR^{6B}C(O)R^{6C}$, —$NR^{6B}C(O)OR^{6C}$, or substituted or unsubstituted $C_1$-$C_{10}$ alkyl, substituted or unsubstituted 2 to 10 membered heteroalkyl. $R^{1A}$, $R^{2A}$, $R^{3A}$, $R^{4A}$, $R^{5A}$, $R^{6A}$, $R^{1B}$, $R^{2B}$, $R^{3B}$, $R^{4B}$, $R^{5B}$, $R^{6B}$, $R^{1C}$, $R^{2C}$, $R^{3C}$, $R^{4C}$, $R^{5C}$, and $R^{6C}$ are each independently hydrogen, substituted or unsubstituted $C_1$-$C_{10}$ alkyl, substituted or unsubstituted 2 to 10 membered heteroalkyl, or a pharmaceutically acceptable salt thereof.

In embodiments, the compound comprises at least two thiol moieties. In embodiments, the compound is not

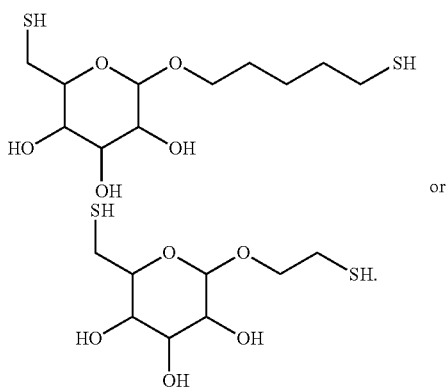

In embodiments, the compound includes at a maximum two thiol moieties

In an aspect is provided a compound having the formula:

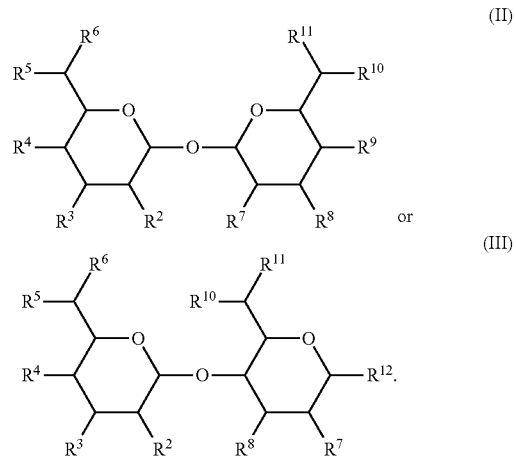

$R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted $C_1$-$C_{10}$, alkyl, or substituted or unsubstituted 2 to 10 membered heteroalkyl. $R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted $C_1$-$C_{10}$ alkyl, or substituted or unsubstituted 2 to 10 membered heteroalkyl. $R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted $C_1$-$C_{10}$ alkyl, or substituted or unsubstituted 2 to 10 membered heteroalkyl. $R^5$ is hydrogen, —$SR^{5A}$, —$OR^{5A}$, —$NR^{5B}R^{5C}$, —$NR^{5B}C(O)R^{5C}$, —$NR^{5B}C(O)OR^{5C}$, or substituted or unsubstituted $C_1$-$C_{10}$ alkyl, substituted or unsubstituted 2 to 10 membered heteroalkyl. $R^6$ is —$SR^{6A}$, —$OR^{6A}$, —$NR^{6B}R^{6C}$, —$NR^{6B}C(O)R^{6C}$, —$NR^{6B}C(O)OR^{6C}$, or substituted or unsubstituted $C_1$-$C_{10}$ alkyl, substituted or unsubstituted 2 to 10 membered heteroalkyl. $R^7$ is —$SR^{7A}$, —$OR^{7A}$, —$NR^{7B}R^{7C}$, —$NR^{7B}C(O)R^{7C}$, —$NR^{7B}C(O)OR^{7C}$, substituted or unsubstituted $C_1$-$C_{10}$ alkyl, or substituted or unsubstituted 2 to 10 membered heteroalkyl. $R^8$ is —$SR^{8A}$, —$OR^{8A}$, —$NR^{8B}R^{8C}$, —$NR^{8B}C(O)R^{8C}$, —$NR^{8B}C(O)OR^{8C}$, substituted or unsubstituted $C_1$-$C_{10}$ alkyl, or substituted or unsubstituted 2 to 10 membered heteroalkyl. $R^9$ is —$SR^{9A}$, —$SC(O)R^{9A}$, —$OR^{9A}$, —$NR^{9B}R^{9C}$, —$NR^{9B}C(O)R^{9C}$, —$NR^{9B}C(O)OR^{9C}$, substituted or unsubstituted $C_1$-$C_{10}$ alkyl, or substituted or unsubstituted 2 to 10 membered heteroalkyl. $R^{10}$ is hydrogen, —$SR^{10A}$, —$OR^{10A}$, —$NR^{10B}R^{10C}$, —$NR^{10B}C(O)R^{10C}$, —$NR^{10B}C(O)OR^{10C}$, or substituted or unsubstituted $C_1$-$C_{10}$, alkyl, or substituted or unsubstituted 2 to 10 membered heteroalkyl. $R^{11}$ is —$SR^{11A}$, —$OR^{11A}$, —$NR^{11B}R^{11C}$, —$NR^{11B}C(O)R^{11C}$, —$NR^{11B}C(O)OR^{11C}$, or substituted or unsubstituted $C_1$-$C_{10}$ alkyl, substituted or unsubstituted 2 to 10 membered heteroalkyl. $R^{12}$ is —$SR^{12A}$, —$OR^{12A}$, —$NR^{12B}R^{12C}$, —$NR^{12B}C(O)R^{12C}$, —$NR^{12B}C(O)OR^{12C}$, substituted or unsubstituted $C_1$-$C_{10}$ alkyl, or substituted or unsubstituted 2 to 10 membered heteroalkyl. $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ are each independently hydrogen, substituted or unsubstituted $C_1$-$C_{10}$ alkyl, substituted or unsubstituted 2 to 10 membered heteroalkyl, or a pharmaceutically acceptable salt thereof.

In embodiments, the compound comprises at least two thiol moieties. In embodiments, the compound is not:

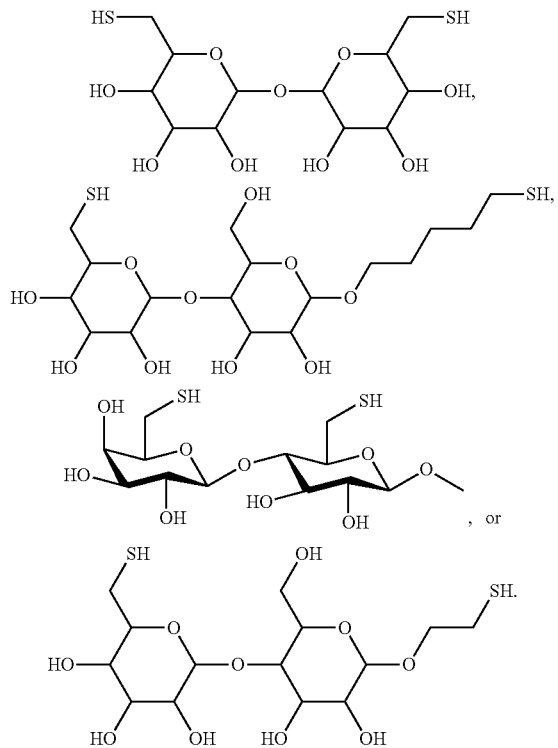

, or

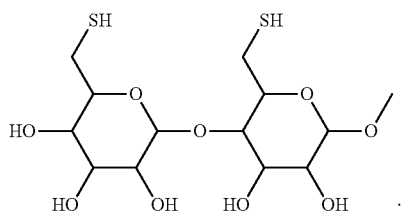 [SMILES: COC1OC(CS)C(OC2OC(CS)C(O)C(O)C2O)C(O)C1O]

In embodiments, the compound is not 6,6'-dithiol-6,6'-dideoxy-α,α-trehalose. In embodiments, the compound is not methyl-6,6'-dithio-6,6'-dideoxy-β-lactoside. In embodiments, the compound is not:

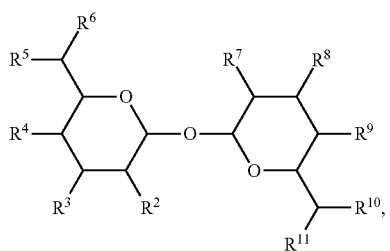

In embodiments, the compound has the formula:

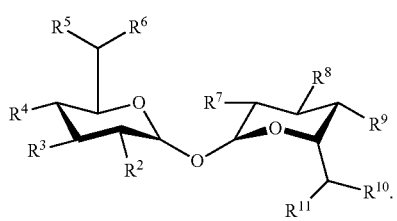

wherein $R^2$, $R^3$, $R^4$, $R^5$, $R^6$, $R^7$, R, $R^9$, $R^{10}$, and $R^{11}$ are as described herein.

In embodiments, the compound has the formula:

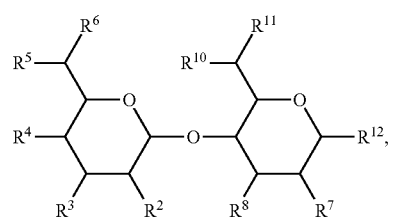

wherein $R^2$, $R^3$, $R^4$, $R^5$, $R^6$, $R^7$, $R^8$, $R^{10}$, $R^{11}$, and $R^{12}$ areas described herein.

In embodiments, the compound has the formula:

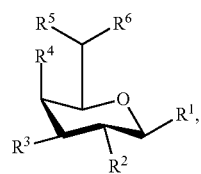

(Ia)

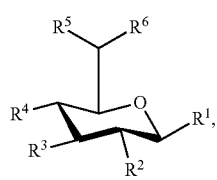

(Ib)

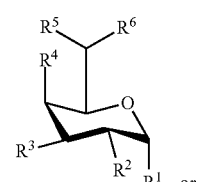

(Ic)

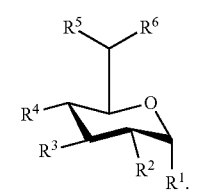

(Id)

In embodiments, the compound has the formula:

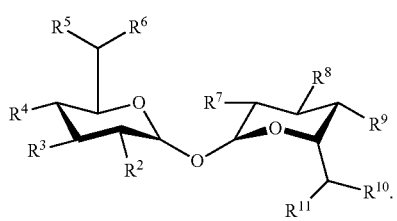

(IIa)

In embodiments, the compound has the formula:

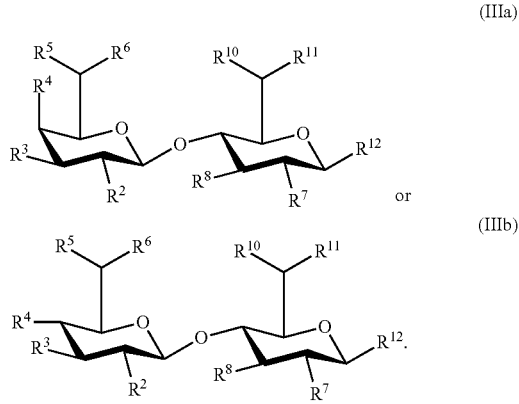

(IIIa)

or (IIIb)

In embodiments, $R^1$ is —$SR^{1A}$, —$OR^{1A}$, substituted or unsubstituted $C_1$-$C_{10}$ alkyl, or substituted or unsubstituted 2 to 10 membered heteroalkyl. In embodiments, $R^1$ is —$SR^{1A}$, —$OR^{1A}$, thiol-substituted or unsubstituted $C_1$-$C_{10}$ alkyl, or thiol-substituted or unsubstituted 2 to 10 membered heteroalkyl. In embodiments, $R^1$ is —$SR^{1A}$ or —$OR^{1A}$. In embodiments, $R^1$ is —$SR^{1A}$. In embodiments, $R^1$ is —$OR^{1A}$. In embodiments, $R^1$ is —SH. In embodiments, $R^1$ is —OH.

In embodiments, $R^1$ is —SH, —OH, —$OCH_3$, —$NH_2$, —NHC(O)H, —NHC(O)OH, substituted or unsubstituted $C_1$-$C_{10}$ alkyl, or substituted or unsubstituted 2 to 10 membered heteroalkyl. In embodiments, $R^1$ is —$OCH_3$.

In embodiments, $R^1$ is substituted or unsubstituted methyl. In embodiments, $R^1$ is substituted or unsubstituted $C_2$ alkyl. In embodiments, $R^1$ is substituted or unsubstituted $C_3$ alkyl. In embodiments, $R^1$ is substituted or unsubstituted $C_4$ alkyl. In embodiments, $R^1$ is substituted or unsubstituted $C_5$ alkyl. In embodiments, $R^1$ is substituted or unsubstituted $C_6$ alkyl. In embodiments, $R^1$ is substituted or unsubstituted $C_7$ alkyl. In embodiments, $R^1$ is substituted or unsubstituted $C_8$ alkyl. In embodiments, $R^1$ is substituted methyl. In embodiments, $R^1$ is substituted $C_2$ alkyl. In embodiments, $R^1$ is substituted $C_3$ alkyl. In embodiments, $R^1$ is substituted $C_4$ alkyl. In embodiments, $R^1$ is substituted $C_5$ alkyl. In embodiments, $R^1$ is substituted $C_6$ alkyl. In embodiments, $R^1$ is substituted $C_7$ alkyl. In embodiments, $R^1$ is substituted $C_8$ alkyl. In embodiments, $R^1$ is an unsubstituted methyl. In embodiments, $R^1$ is an unsubstituted $C_2$ alkyl. In embodiments, $R^1$ is an unsubstituted $C_3$ alkyl. In embodiments, $R^1$ is an unsubstituted $C_4$ alkyl. In embodiments, $R^1$ is an unsubstituted $C_5$ alkyl. In embodiments, $R^1$ is an unsubstituted $C_6$ alkyl. In embodiments, $R^1$ is an unsubstituted $C_7$ alkyl. In embodiments, $R^1$ is an unsubstituted $C_8$ alkyl.

In embodiments, $R^1$ is substituted or unsubstituted 2 to 10 membered heteroalkyl. In embodiments, $R^1$ is substituted 2 to 10 membered heteroalkyl. In embodiments, $R^1$ is an unsubstituted 2 to 10 membered heteroalkyl. In embodiments, $R^1$ is substituted or unsubstituted 2 to 6 membered heteroalkyl. In embodiments, $R^1$ is substituted 2 to 6 membered heteroalkyl. In embodiments, $R^1$ is an unsubstituted 2 to 6 membered heteroalkyl. In embodiments, $R^1$ is substituted or unsubstituted 2 membered heteroalkyl. In embodiments, $R^1$ is substituted 2 membered heteroalkyl. In embodiments, $R^1$ is an unsubstituted 2 membered heteroalkyl. In embodiments, $R^1$ is substituted or unsubstituted 3 membered heteroalkyl. In embodiments, $R^1$ is substituted 3 membered heteroalkyl. In embodiments, $R^1$ is an unsubstituted 3 membered heteroalkyl. In embodiments, $R^1$ is substituted or unsubstituted 4 membered heteroalkyl. In embodiments, $R^1$ is substituted 4 membered heteroalkyl. In embodiments, $R^1$ is an unsubstituted 4 membered heteroalkyl. In embodiments, $R^1$ is substituted or unsubstituted 5 membered heteroalkyl. In embodiments, $R^1$ is substituted 5 membered heteroalkyl. In embodiments, $R^1$ is an unsubstituted 5 membered heteroalkyl. In embodiments, $R^1$ is substituted or unsubstituted 6 membered heteroalkyl. In embodiments, $R^1$ is substituted 6 membered heteroalkyl. In embodiments, $R^1$ is an unsubstituted 6 membered heteroalkyl.

In embodiments, $R^1$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^1$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^1$ is unsubstituted alkyl or unsubstituted heteroalkyl.

In embodiments, a substituted $R^1$ (e.g., substituted alkyl and/or substituted heteroalkyl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, $R^2$ is —$SR^{2A}$, —$OR^{2A}$, substituted or unsubstituted $C_1$-$C_{10}$ alkyl, or substituted or unsubstituted 2 to 10 membered heteroalkyl. In embodiments, $R^2$ is —$SR^{2A}$, —$OR^{2A}$, thiol-substituted or unsubstituted $C_1$-$C_{10}$ alkyl, or thiol-substituted or unsubstituted 2 to 10 membered heteroalkyl. In embodiments, $R^2$ is —$SR^{2A}$ or —$OR^{2A}$. In embodiments, $R^2$ is —$SR^{2A}$ or —$OR^{2A}$. In embodiments, $R^2$ is —$SR^{2A}$. In embodiments, $R^2$ is —$OR^{2A}$. In embodiments, $R^2$ is —SH. In embodiments, $R^2$ is —OH.

In embodiments, $R^2$ is —SH, —OH, —$OCH_3$, —$NH_2$, —NHC(O)H, —NHC(O)OH, substituted or unsubstituted $C_1$-$C_{10}$ alkyl, or substituted or unsubstituted 2 to 10 membered heteroalkyl. In embodiments, $R^2$ is —$OCH_3$.

In embodiments, $R^2$ is substituted or unsubstituted methyl. In embodiments, $R^2$ is substituted or unsubstituted $C_2$ alkyl. In embodiments, $R^2$ is substituted or unsubstituted $C_3$ alkyl. In embodiments, $R^2$ is substituted or unsubstituted $C_4$ alkyl. In embodiments, $R^2$ is substituted or unsubstituted $C_5$ alkyl. In embodiments, $R^2$ is substituted or unsubstituted $C_6$ alkyl. In embodiments, $R^2$ is substituted or unsubstituted $C_7$ alkyl. In embodiments, $R^2$ is substituted or unsubstituted $C_8$ alkyl. In embodiments, $R^2$ is substituted methyl. In embodiments, $R^2$ is substituted $C_2$ alkyl. In embodiments, $R^2$ is substituted $C_3$ alkyl. In embodiments, $R^2$ is substituted $C_4$ alkyl. In embodiments, $R^2$ is substituted $C_5$ alkyl. In embodiments, $R^2$ is substituted $C_6$ alkyl. In embodiments, $R^2$ is substituted $C_7$ alkyl. In embodiments, $R^2$ is substituted $C_8$ alkyl. In embodiments, $R^2$ is an unsubstituted methyl. In embodiments, $R^2$ is an unsubstituted $C_2$ alkyl. In embodiments, $R^2$ is an unsubstituted $C_3$ alkyl. In embodiments, $R^2$ is an unsubstituted $C_4$ alkyl. In embodiments, $R^2$ is an unsubstituted $C_5$ alkyl. In embodiments, $R^2$ is an unsubstituted $C_6$ alkyl. In embodiments, $R^2$ is an unsubstituted $C_7$ alkyl. In embodiments, $R^2$ is an unsubstituted $C_8$ alkyl.

In embodiments, $R^2$ is substituted or unsubstituted 2 to 10 membered heteroalkyl. In embodiments, $R^2$ is substituted 2 to 10 membered heteroalkyl. In embodiments, $R^2$ is an unsubstituted 2 to 10 membered heteroalkyl. In embodiments, $R^2$ is substituted or unsubstituted 2 to 6 membered heteroalkyl. In embodiments, $R^2$ is substituted 2 to 6 membered heteroalkyl. In embodiments, $R^2$ is an unsubstituted 2 to 6 membered heteroalkyl. In embodiments, $R^2$ is substituted or unsubstituted 2 membered heteroalkyl. In embodiments, $R^2$ is substituted 2 membered heteroalkyl. In embodiments, $R^2$ is an unsubstituted 2 membered heteroalkyl. In embodiments, $R^2$ is substituted or unsubstituted 3 membered heteroalkyl. In embodiments, $R^2$ is substituted 3 membered heteroalkyl. In embodiments, $R^2$ is an unsubstituted 3 membered heteroalkyl. In embodiments, $R^2$ is substituted or unsubstituted 4 membered heteroalkyl. In embodiments, $R^2$ is substituted 4 membered heteroalkyl. In embodiments, $R^2$ is an unsubstituted 4 membered heteroalkyl. In embodiments, $R^2$ is substituted or unsubstituted 5 membered heteroalkyl. In embodiments, $R^2$ is substituted 5 membered heteroalkyl. In embodiments, $R^2$ is an unsubstituted 5 membered heteroalkyl. In embodiments, $R^2$ is substituted or unsubstituted 6 membered heteroalkyl. In embodiments, $R^2$ is substituted 6 membered heteroalkyl. In embodiments, $R^2$ is an unsubstituted 6 membered heteroalkyl.

In embodiments, $R^2$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^2$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^2$ is unsubstituted alkyl or unsubstituted heteroalkyl.

In embodiments, a substituted $R^2$ (e.g., substituted alkyl and/or substituted heteroalkyl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^3$ is —$SR^{3A}$, —$OR^{3A}$, substituted or unsubstituted $C_1$-$C_{10}$ alkyl, or substituted or unsubstituted 2 to 10 membered heteroalkyl. In embodiments, $R^3$ is —$SR^{3A}$—$OR^{3A}$, thiol-substituted or unsubstituted $C_1$-$C_{10}$ alkyl, or thiol-substituted or unsubstituted 2 to 10 membered heteroalkyl. In embodiments, $R^3$ is —$SR^{3A}$ or —$OR^{3A}$. In embodiments, $R^3$ is —$SR^{3A}$ or —$OR^{3A}$. In embodiments, $R^3$ is —$SR^{3A}$. In embodiments, $R^3$ is —$OR^{3A}$. In embodiments, $R^3$ is —SH. In embodiments, $R^3$ is —OH.

In embodiments, $R^3$ is —SH, —OH, —$OCH_3$, —$NH_2$, —NHC(O)H, —NHC(O)OH, substituted or unsubstituted $C_1$-$C_{10}$ alkyl, or substituted or unsubstituted 2 to 10 membered heteroalkyl. In embodiments, $R^3$ is —$OCH_3$.

In embodiments, $R^3$ is substituted or unsubstituted methyl. In embodiments, $R^3$ is substituted or unsubstituted $C_2$ alkyl. In embodiments, $R^3$ is substituted or unsubstituted $C_3$ alkyl. In embodiments, $R^3$ is substituted or unsubstituted $C_4$ alkyl. In embodiments, $R^3$ is substituted or unsubstituted $C_5$ alkyl. In embodiments, $R^3$ is substituted or unsubstituted $C_6$ alkyl. In embodiments, $R^3$ is substituted or unsubstituted $C_7$ alkyl. In embodiments, $R^3$ is substituted or unsubstituted $C_8$ alkyl. In embodiments, $R^3$ is substituted methyl. In embodiments, $R^3$ is substituted $C_2$ alkyl. In embodiments, $R^3$ is substituted $C_3$ alkyl. In embodiments, $R^3$ is substituted $C_4$ alkyl. In embodiments, $R^3$ is substituted $C_5$ alkyl. In embodiments, $R^3$ is substituted $C_6$ alkyl. In embodiments, $R^3$ is substituted $C_7$ alkyl. In embodiments, $R^3$ is substituted $C_8$ alkyl. In embodiments, $R^3$ is an unsubstituted methyl. In embodiments, $R^3$ is an unsubstituted $C_2$ alkyl. In embodiments, $R^3$ is an unsubstituted $C_3$ alkyl. In embodiments, $R^3$ is an unsubstituted $C_4$ alkyl. In embodiments, $R^3$ is an unsubstituted $C_5$ alkyl. In embodiments, $R^3$ is an unsubstituted $C_6$ alkyl. In embodiments, $R^3$ is an unsubstituted $C_7$ alkyl. In embodiments, $R^3$ is an unsubstituted $C_8$ alkyl.

In embodiments, $R^3$ is substituted or unsubstituted 2 to 10 membered heteroalkyl. In embodiments, $R^3$ is substituted 2 to 10 membered heteroalkyl. In embodiments, $R^3$ is an unsubstituted 2 to 10 membered heteroalkyl. In embodiments, $R^3$ is substituted or unsubstituted 2 to 6 membered heteroalkyl. In embodiments, $R^3$ is substituted 2 to 6 membered heteroalkyl. In embodiments, $R^3$ is an unsubstituted 2 to 6 membered heteroalkyl. In embodiments, $R^3$ is substituted or unsubstituted 2 membered heteroalkyl. In embodiments, $R^3$ is substituted 2 membered heteroalkyl. In embodiments, $R^3$ is an unsubstituted 2 membered heteroalkyl. In embodiments, $R^3$ is substituted or unsubstituted 3 membered heteroalkyl. In embodiments, $R^3$ is substituted 3 membered heteroalkyl. In embodiments, $R^3$ is an unsubstituted 3 membered heteroalkyl. In embodiments, $R^3$ is substituted or unsubstituted 4 membered heteroalkyl. In embodiments, $R^3$ is substituted 4 membered heteroalkyl. In embodiments, $R^3$ is an unsubstituted 4 membered heteroalkyl. In embodiments, $R^3$ is substituted or unsubstituted 5 membered heteroalkyl. In embodiments, $R^3$ is substituted 5 membered heteroalkyl. In embodiments, $R^3$ is an unsubstituted 5 membered heteroalkyl. In embodiments, $R^3$ is substituted or unsubstituted 6 membered heteroalkyl. In embodiments, $R^3$ is substituted 6 membered heteroalkyl. In embodiments, $R^3$ is an unsubstituted 6 membered heteroalkyl.

In embodiments, $R^3$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^3$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^3$ is unsubstituted alkyl or unsubstituted heteroalkyl.

In embodiments, a substituted $R^3$ (e.g., substituted alkyl and/or substituted heteroalkyl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, $R^4$ is $—SR^{4A}$, $—OR^{4A}$, substituted or unsubstituted $C_1$-$C_{10}$ alkyl, or substituted or unsubstituted 2 to 10 membered heteroalkyl. In embodiments, $R^4$ is $—SR^{4A}$, $—OR^{4A}$, thiol-substituted or unsubstituted $C_1$-$C_{10}$ alkyl, or thiol-substituted or unsubstituted 2 to 10 membered heteroalkyl. In embodiments, $R^4$ is $—SR^{4A}$ or $—OR^{4A}$. In embodiments, $R^4$ is $—SR^{4A}$ or $—OR^{4A}$. In embodiments, $R^4$ is $—SR^{4A}$. In embodiments, $R^4$ is $—OR^{4A}$. In embodiments, $R^4$ is $—SH$. In embodiments, $R^4$ is $—OH$.

In embodiments, $R^4$ is $—SH$, $—OH$, $—OCH_3$, $—NH_2$, $—NHC(O)H$, $—NHC(O)OH$, substituted or unsubstituted $C_1$-$C_{10}$ alkyl, or substituted or unsubstituted 2 to 10 membered heteroalkyl. In embodiments, $R^4$ is $—OCH_3$.

In embodiments, $R^4$ is substituted or unsubstituted methyl. In embodiments, $R^4$ is substituted or unsubstituted $C_2$ alkyl. In embodiments, $R^4$ is substituted or unsubstituted $C_3$ alkyl. In embodiments, $R^4$ is substituted or unsubstituted $C_4$ alkyl. In embodiments, $R^4$ is substituted or unsubstituted $C_5$ alkyl. In embodiments, $R^4$ is substituted or unsubstituted $C_6$ alkyl. In embodiments, $R^4$ is substituted or unsubstituted $C_7$ alkyl. In embodiments, $R^4$ is substituted or unsubstituted $C_8$ alkyl. In embodiments, $R^4$ is substituted methyl. In embodiments, $R^4$ is substituted $C_2$ alkyl. In embodiments, $R^4$ is substituted $C_3$ alkyl. In embodiments, $R^4$ is substituted $C_4$ alkyl. In embodiments, $R^4$ is substituted $C_5$ alkyl. In embodiments, $R^4$ is substituted $C_6$ alkyl. In embodiments, $R^4$ is substituted $C_7$ alkyl. In embodiments, $R^4$ is substituted $C_8$ alkyl. In embodiments, $R^4$ is an unsubstituted methyl. In embodiments, $R^4$ is an unsubstituted $C_2$ alkyl. In embodiments, $R^4$ is an unsubstituted $C_3$ alkyl. In embodiments, $R^4$ is an unsubstituted $C_4$ alkyl. In embodiments, $R^4$ is an unsubstituted $C_5$ alkyl. In embodiments, $R^4$ is an unsubstituted $C_6$ alkyl. In embodiments, $R^4$ is an unsubstituted $C_7$ alkyl. In embodiments, $R^4$ is an unsubstituted $C_8$ alkyl.

In embodiments, $R^4$ is substituted or unsubstituted 2 to 10 membered heteroalkyl. In embodiments, $R^4$ is substituted 2 to 10 membered heteroalkyl. In embodiments, $R^4$ is an unsubstituted 2 to 10 membered heteroalkyl. In embodiments, $R^4$ is substituted or unsubstituted 2 to 6 membered heteroalkyl. In embodiments, $R^4$ is substituted 2 to 6 membered heteroalkyl. In embodiments, $R^4$ is an unsubstituted 2 to 6 membered heteroalkyl. In embodiments, $R^4$ is substituted or unsubstituted 2 membered heteroalkyl. In embodiments, $R^4$ is substituted 2 membered heteroalkyl. In embodiments, $R^4$ is an unsubstituted 2 membered heteroalkyl. In embodiments, $R^4$ is substituted or unsubstituted 3 membered heteroalkyl. In embodiments, $R^4$ is substituted 3 membered heteroalkyl. In embodiments, $R^4$ is an unsubstituted 3 membered heteroalkyl. In embodiments, $R^4$ is substituted or unsubstituted 4 membered heteroalkyl. In embodiments, $R^4$ is substituted 4 membered heteroalkyl. In embodiments, $R^4$ is an unsubstituted 4 membered heteroalkyl. In embodiments, $R^4$ is substituted or unsubstituted 5 membered heteroalkyl. In embodiments, $R^4$ is substituted 5 membered heteroalkyl. In embodiments, $R^4$ is an unsubstituted 5 membered heteroalkyl. In embodiments, $R^4$ is substituted or unsubstituted 6 membered heteroalkyl. In embodiments, $R^4$ is substituted 6 membered heteroalkyl. In embodiments, $R^4$ is an unsubstituted 6 membered heteroalkyl.

In embodiments, $R^4$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^4$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^4$ is unsubstituted alkyl or unsubstituted heteroalkyl.

In embodiments, a substituted $R^4$ (e.g., substituted alkyl and/or substituted heteroalkyl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^5$ is hydrogen, $—SR^{5A}$, $—OR^{5A}$ or substituted or unsubstituted $C_1$-$C_{10}$ alkyl, substituted or unsubstituted 2 to 10 membered heteroalkyl. In embodiments, $R^5$ is hydrogen, $—SR^{5A}$, $—OR^{5A}$, or thiol-substituted or unsubstituted $C_1$-$C_{10}$ alkyl, thiol-substituted or unsubstituted 2 to 10 membered heteroalkyl. In embodiments, $R^5$ is $—SR^{5A}$ or $—OR^{5A}$. In embodiments, $R^5$ is $—SR^{5A}$. In embodiments, $R^5$ is $—OR^{5A}$. In embodiments, $R^5$ is $—SH$. In embodiments, $R^5$ is $—OH$. In embodiments, $R^5$ is hydrogen.

In embodiments, $R^5$ is $—SH$, $—OH$, $—OCH_3$, $—NH_2$, $—NHC(O)H$, $—NHC(O)OH$, substituted or unsubstituted $C_1$-$C_{10}$ alkyl, or substituted or unsubstituted 2 to 10 membered heteroalkyl. In embodiments, $R^5$ is $—OCH_3$.

In embodiments, $R^5$ is substituted or unsubstituted methyl. In embodiments, $R^5$ is substituted or unsubstituted $C_2$ alkyl. In embodiments, $R^5$ is substituted or unsubstituted $C_3$ alkyl. In embodiments, $R^5$ is substituted or unsubstituted $C_4$ alkyl. In embodiments, $R^5$ is substituted or unsubstituted $C_5$ alkyl. In embodiments, $R^5$ is substituted or unsubstituted $C_6$ alkyl. In embodiments, $R^5$ is substituted or unsubstituted $C_7$ alkyl. In embodiments, $R^5$ is substituted or unsubstituted $C_8$ alkyl. In embodiments, $R^5$ is substituted methyl. In embodiments, $R^5$ is substituted $C_2$ alkyl. In embodiments, $R^5$ is substituted $C_3$ alkyl. In embodiments, $R^5$ is substituted $C_4$ alkyl. In embodiments, $R^5$ is substituted $C_5$ alkyl. In embodiments, $R^5$ is substituted $C_6$ alkyl. In embodiments, $R^5$ is substituted $C_7$ alkyl. In embodiments, $R^5$ is substituted $C_8$ alkyl. In embodiments, $R^5$ is an unsubstituted methyl. In embodiments, $R^5$ is an unsubstituted $C_2$ alkyl. In embodiments, $R^5$ is an unsubstituted $C_3$ alkyl. In embodiments, $R^5$ is an unsubstituted $C_4$ alkyl. In embodiments, $R^5$ is an unsubstituted $C_5$ alkyl. In embodiments, $R^5$ is an unsubstituted $C_6$ alkyl. In embodiments, $R^5$ is an unsubstituted $C_7$ alkyl. In embodiments, $R^5$ is an unsubstituted $C_8$ alkyl.

In embodiments, $R^5$ is substituted or unsubstituted 2 to 10 membered heteroalkyl. In embodiments, $R^5$ is substituted 2 to 10 membered heteroalkyl. In embodiments, $R^5$ is an unsubstituted 2 to 10 membered heteroalkyl. In embodiments, $R^5$ is substituted or unsubstituted 2 to 6 membered heteroalkyl. In embodiments, $R^5$ is substituted 2 to 6 membered heteroalkyl. In embodiments, $R^5$ is an unsubstituted 2 to 6 membered heteroalkyl. In embodiments, $R^5$ is substituted or unsubstituted 2 membered heteroalkyl. In embodiments, $R^5$ is substituted 2 membered heteroalkyl. In embodiments, $R^5$ is an unsubstituted 2 membered heteroalkyl. In embodiments, $R^5$ is substituted or unsubstituted 3 membered heteroalkyl. In embodiments, $R^5$ is substituted 3 membered heteroalkyl. In embodiments, $R^5$ is an unsubstituted 3 membered heteroalkyl. In embodiments, $R^5$ is substituted or unsubstituted 4 membered heteroalkyl. In embodiments, $R^5$ is substituted 4 membered heteroalkyl. In embodiments, $R^5$ is an unsubstituted 4 membered heteroalkyl. In embodiments, $R^5$ is substituted or unsubstituted 5 membered heteroalkyl. In embodiments, $R^5$ is substituted 5 membered heteroalkyl. In embodiments, $R^5$ is an unsubstituted 5 membered heteroalkyl. In embodiments, $R^5$ is substituted or unsubstituted 6 membered heteroalkyl. In embodiments, $R^5$ is substituted 6 membered heteroalkyl. In embodiments, $R^5$ is an unsubstituted 6 membered heteroalkyl.

In embodiments, $R^5$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^5$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^5$ is unsubstituted alkyl or unsubstituted heteroalkyl.

In embodiments, a substituted $R^5$ (e.g., substituted alkyl and/or substituted heteroalkyl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, $R^6$ is —$SR^{6A}$, —$OR^{6A}$, or substituted or unsubstituted $C_1$-$C_{10}$ alkyl, substituted or unsubstituted 2 to 10 membered heteroalkyl. In embodiments, $R^6$ is —$SR^{6A}$, —$OR^{6A}$, or thiol-substituted or unsubstituted $C_1$-$C_{10}$ alkyl, thiol-substituted or unsubstituted 2 to 10 membered heteroalkyl. In embodiments, $R^6$ is —$SR^{6A}$, or —$OR^{6A}$. In embodiments, $R^6$ is —$SR^{6A}$ or —$OR^{6A}$. In embodiments, $R^6$ is —$SR^{6A}$. In embodiments, $R^6$ is —$OR^{6A}$. In embodiments, $R^6$ is —SH. In embodiments, $R^6$ is —OH.

In embodiments, $R^6$ is —SH, —OH, —$OCH_3$, —$NH_2$, —NHC(O)H, —NHC(O)OH, substituted or unsubstituted $C_1$-$C_{10}$ alkyl, or substituted or unsubstituted 2 to 10 membered heteroalkyl. In embodiments, $R^6$ is —$OCH_3$.

In embodiments, $R^6$ is substituted or unsubstituted methyl. In embodiments, $R^6$ is substituted or unsubstituted $C_2$ alkyl. In embodiments, $R^6$ is substituted or unsubstituted $C_3$ alkyl. In embodiments, $R^6$ is substituted or unsubstituted $C_4$ alkyl. In embodiments, $R^6$ is substituted or unsubstituted $C_5$ alkyl. In embodiments, $R^6$ is substituted or unsubstituted $C_6$ alkyl. In embodiments, $R^6$ is substituted or unsubstituted $C_7$ alkyl. In embodiments, $R^6$ is substituted or unsubstituted $C_8$ alkyl. In embodiments, $R^6$ is substituted methyl. In embodiments, $R^6$ is substituted $C_2$ alkyl. In embodiments, $R^6$ is substituted $C_3$ alkyl. In embodiments, $R^6$ is substituted $C_4$ alkyl. In embodiments, $R^6$ is substituted $C_8$ alkyl. In embodiments, $R^6$ is substituted $C_6$ alkyl. In embodiments, $R^6$ is substituted $C_7$ alkyl. In embodiments, $R^6$ is substituted $C_8$ alkyl. In embodiments, $R^6$ is an unsubstituted methyl. In embodiments, $R^6$ is an unsubstituted $C_2$ alkyl. In embodiments, $R^6$ is an unsubstituted $C_3$ alkyl. In embodiments, $R^6$ is an unsubstituted $C_4$ alkyl. In embodiments, $R^6$ is an unsubstituted $C_8$ alkyl. In embodiments, $R^6$ is an unsubstituted $C_6$ alkyl. In embodiments, $R^6$ is an unsubstituted $C_7$ alkyl. In embodiments, $R^6$ is an unsubstituted $C_8$ alkyl.

In embodiments, $R^6$ is substituted or unsubstituted 2 to 10 membered heteroalkyl. In embodiments, $R^6$ is substituted 2 to 10 membered heteroalkyl. In embodiments, $R^6$ is an unsubstituted 2 to 10 membered heteroalkyl. In embodiments, $R^6$ is substituted or unsubstituted 2 to 6 membered heteroalkyl. In embodiments, $R^6$ is substituted 2 to 6 membered heteroalkyl. In embodiments, $R^6$ is an unsubstituted 2 to 6 membered heteroalkyl. In embodiments, $R^6$ is substituted or unsubstituted 2 membered heteroalkyl. In embodiments, $R^6$ is substituted 2 membered heteroalkyl. In embodiments, $R^6$ is an unsubstituted 2 membered heteroalkyl. In embodiments, $R^6$ is substituted or unsubstituted 3 membered heteroalkyl. In embodiments, $R^6$ is substituted 3 membered heteroalkyl. In embodiments, $R^6$ is an unsubstituted 3 membered heteroalkyl. In embodiments, $R^6$ is substituted or unsubstituted 4 membered heteroalkyl. In embodiments, $R^6$ is substituted 4 membered heteroalkyl. In embodiments, $R^6$ is an unsubstituted 4 membered heteroalkyl. In embodiments, $R^6$ is substituted or unsubstituted 5 membered heteroalkyl. In embodiments, $R^6$ is substituted 5 membered heteroalkyl. In embodiments, $R^6$ is an unsubstituted 5 membered heteroalkyl. In embodiments, $R^6$ is substituted or unsubstituted 6 membered heteroalkyl. In embodiments, $R^6$ is substituted 6 membered heteroalkyl. In embodiments, $R^6$ is an unsubstituted 6 membered heteroalkyl.

In embodiments, $R^6$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^6$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^6$ is unsubstituted alkyl or unsubstituted heteroalkyl.

In embodiments, a substituted $R^6$ (e.g., substituted alkyl and/or substituted heteroalkyl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, $R^7$ is —$SR^{7A}$, —$OR^{7A}$ or substituted or unsubstituted $C_1$-$C_{10}$ alkyl, substituted or unsubstituted 2 to 10 membered heteroalkyl. In embodiments, $R^7$ is —$SR^{7A}$, —$OR^{7A}$, or thiol-substituted or unsubstituted $C_1$-$C_{10}$ alkyl, thiol-substituted or unsubstituted 2 to 10 membered heteroalkyl. In embodiments, $R^7$ is —$SR^{7A}$, or —$OR^{7A}$. In embodiments, $R^7$ is —$SR^{7A}$ or —$OR^{7A}$. In embodiments, $R^7$ is —$SR^{7A}$. In embodiments, $R^7$ is —$OR^{7A}$. In embodiments, $R^7$ is —SH. In embodiments, $R^7$ is —OH.

In embodiments, $R^7$ is —SH, —OH, —$OCH_3$, —$NH_2$, —NHC(O)H, —NHC(O)OH, substituted or unsubstituted $C_1$-$C_{10}$ alkyl, or substituted or unsubstituted 2 to 10 membered heteroalkyl. In embodiments, $R^7$ is —$OCH_3$.

In embodiments, $R^7$ is substituted or unsubstituted methyl. In embodiments, $R^7$ is substituted or unsubstituted $C_2$ alkyl. In embodiments, $R^7$ is substituted or unsubstituted $C_3$ alkyl. In embodiments, $R^7$ is substituted or unsubstituted $C_4$ alkyl. In embodiments, $R^7$ is substituted or unsubstituted $C_5$ alkyl. In embodiments, $R^7$ is substituted or unsubstituted $C_6$ alkyl. In embodiments, $R^7$ is substituted or unsubstituted $C_7$ alkyl. In embodiments, $R^7$ is substituted or unsubstituted $C_8$ alkyl. In embodiments, $R^7$ is substituted methyl. In embodiments, $R^7$ is substituted $C_2$ alkyl. In embodiments, $R^7$ is substituted $C_3$ alkyl. In embodiments, $R^7$ is substituted $C_4$ alkyl. In embodiments, $R^7$ is substituted $C_5$ alkyl. In embodiments, $R^7$ is substituted $C_6$ alkyl. In embodiments, $R^7$ is substituted $C_7$ alkyl. In embodiments, $R^7$ is substituted $C_8$ alkyl. In embodiments, $R^7$ is an unsubstituted methyl. In embodiments, $R^7$ is an unsubstituted $C_2$ alkyl. In embodiments, $R^7$ is an unsubstituted $C_3$ alkyl. In embodiments, $R^7$ is an unsubstituted $C_4$ alkyl. In embodiments, $R^7$ is an unsubstituted $C_5$ alkyl. In embodiments, $R^7$ is an unsubstituted $C_6$ alkyl. In embodiments, $R^7$ is an unsubstituted $C_7$ alkyl. In embodiments, $R^7$ is an unsubstituted $C_8$ alkyl.

In embodiments, $R^7$ is substituted or unsubstituted 2 to 10 membered heteroalkyl. In embodiments, $R^7$ is substituted 2 to 10 membered heteroalkyl. In embodiments, $R^7$ is an unsubstituted 2 to 10 membered heteroalkyl. In embodiments, $R^7$ is substituted or unsubstituted 2 to 6 membered heteroalkyl. In embodiments, $R^7$ is substituted 2 to 6 membered heteroalkyl. In embodiments, $R^7$ is an unsubstituted 2 to 6 membered heteroalkyl. In embodiments, $R^7$ is substituted or unsubstituted 2 membered heteroalkyl. In embodiments, $R^7$ is substituted 2 membered heteroalkyl. In embodiments, $R^7$ is an unsubstituted 2 membered heteroalkyl. In embodiments, $R^7$ is substituted or unsubstituted 3 membered heteroalkyl. In embodiments, $R^7$ is substituted 3 membered heteroalkyl. In embodiments, $R^7$ is an unsubstituted 3 membered heteroalkyl. In embodiments, $R^7$ is substituted or unsubstituted 4 membered heteroalkyl. In embodiments, $R^7$ is substituted 4 membered heteroalkyl. In embodiments, $R^7$ is an unsubstituted 4 membered heteroalkyl. In embodiments, $R^7$ is substituted or unsubstituted 5 membered heteroalkyl. In embodiments, $R^7$ is substituted 5 membered heteroalkyl. In embodiments, $R^7$ is an unsubstituted 5 membered heteroalkyl. In embodiments, $R^7$ is substituted or unsubstituted 6 membered heteroalkyl. In embodiments, $R^7$ is substituted 6 membered heteroalkyl. In embodiments, $R^7$ is an unsubstituted 6 membered heteroalkyl.

In embodiments, $R^7$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^7$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^7$ is unsubstituted alkyl or unsubstituted heteroalkyl.

In embodiments, a substituted $R^7$ (e.g., substituted alkyl and/or substituted heteroalkyl) is substituted with at least one substituent group, size-limited substituent group, or lower substituent group; wherein if the substituted $R^7$ is substituted with a plurality of groups selected from substituent groups, size-limited substituent groups, and lower substituent groups; each substituent group, size-limited substituent group, and/or lower substituent group may optionally be different. In embodiments, when $R^7$ is substituted, it is substituted with at least one substituent group. In embodiments, when $R^7$ is substituted, it is substituted with at least one size-limited substituent group. In embodiments, when $R^7$ is substituted, it is substituted with at least one lower substituent group.

In embodiments, $R^8$ is —$SR^{8A}$, —$OR^{8A}$, or substituted or unsubstituted $C_1$-$C_{10}$ alkyl, substituted or unsubstituted 2 to 10 membered heteroalkyl. In embodiments, $R^8$ is —$SR^{8A}$, —$OR^{8A}$, or thiol-substituted or unsubstituted $C_1$-$C_{10}$ alkyl, thiol-substituted or unsubstituted 2 to 10 membered heteroalkyl. In embodiments, $R^8$ is —$SR^{8A}$, or —$OR^{8A}$. In embodiments, $R^8$ is —$SR^{8A}$ or —$OR^{8A}$. In embodiments, $R^8$ is —$SR^{8A}$. In embodiments, $R^8$ is —$OR^{8A}$. In embodiments, $R^8$ is —SH. In embodiments, $R^8$ is —OH.

In embodiments, $R^8$ is —SH, —OH, —$OCH_3$, —$NH_2$, —NHC(O)H, —NHC(O)OH, substituted or unsubstituted $C_1$-$C_{10}$ alkyl, or substituted or unsubstituted 2 to 10 membered heteroalkyl. In embodiments, $R^8$ is —$OCH_3$.

In embodiments, $R^8$ is substituted or unsubstituted methyl. In embodiments, $R^8$ is substituted or unsubstituted $C_2$ alkyl. In embodiments, $R^8$ is substituted or unsubstituted $C_3$ alkyl. In embodiments, $R^8$ is substituted or unsubstituted $C_4$ alkyl. In embodiments, $R^8$ is substituted or unsubstituted $C_5$ alkyl. In embodiments, $R^8$ is substituted or unsubstituted $C_6$ alkyl. In embodiments, $R^8$ is substituted or unsubstituted $C_7$ alkyl. In embodiments, $R^8$ is substituted or unsubstituted $C_8$ alkyl. In embodiments, $R^8$ is substituted methyl. In embodiments, $R^8$ is substituted $C_2$ alkyl. In embodiments, $R^8$ is substituted $C_3$ alkyl. In embodiments, $R^8$ is substituted $C_4$ alkyl. In embodiments, $R^8$ is substituted $C_5$ alkyl. In embodiments, $R^8$ is substituted $C_6$ alkyl. In embodiments, $R^8$ is substituted $C_7$ alkyl. In embodiments, $R^8$ is substituted $C_8$ alkyl. In embodiments, $R^8$ is an unsubstituted methyl. In embodiments, $R^8$ is an unsubstituted $C_2$ alkyl. In embodiments, $R^8$ is an unsubstituted $C_3$ alkyl. In embodiments, $R^8$ is an unsubstituted $C_4$ alkyl. In embodiments, $R^8$ is an unsubstituted $C_5$ alkyl. In embodiments, $R^8$ is an unsubstituted $C_6$ alkyl. In embodiments, $R^8$ is an unsubstituted $C_7$ alkyl. In embodiments, $R^8$ is an unsubstituted $C_8$ alkyl.

In embodiments, $R^8$ is substituted or unsubstituted 2 to 10 membered heteroalkyl. In embodiments, $R^8$ is substituted 2 to 10 membered heteroalkyl. In embodiments, $R^8$ is an unsubstituted 2 to 10 membered heteroalkyl. In embodiments, $R^8$ is substituted or unsubstituted 2 to 6 membered heteroalkyl. In embodiments, $R^8$ is substituted 2 to 6 membered heteroalkyl. In embodiments, $R^8$ is an unsubstituted 2 to 6 membered heteroalkyl. In embodiments, $R^8$ is substituted or unsubstituted 2 membered heteroalkyl. In embodiments, $R^8$ is substituted 2 membered heteroalkyl. In embodiments, $R^8$ is an unsubstituted 2 membered heteroalkyl. In embodiments, $R^8$ is substituted or unsubstituted 3 membered heteroalkyl. In embodiments, $R^8$ is substituted 3 membered heteroalkyl. In embodiments, $R^8$ is an unsubstituted 3 membered heteroalkyl. In embodiments, $R^8$ is substituted or unsubstituted 4 membered heteroalkyl. In embodiments, $R^8$ is substituted 4 membered heteroalkyl. In embodiments, $R^8$ is an unsubstituted 4 membered heteroalkyl. In embodiments, $R^8$ is substituted or unsubstituted 5 membered heteroalkyl. In embodiments, $R^8$ is substituted 5 membered heteroalkyl. In embodiments, $R^8$ is an unsubstituted 5 membered heteroalkyl. In embodiments, $R^8$ is substituted or unsubstituted 6 membered heteroalkyl. In embodiments, $R^8$ is substituted 6 membered heteroalkyl. In embodiments, $R^8$ is an unsubstituted 6 membered heteroalkyl.

In embodiments, $R^8$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^8$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^8$ is unsubstituted alkyl or unsubstituted heteroalkyl.

In embodiments, a substituted $R^8$ (e.g., substituted alkyl and/or substituted heteroalkyl) is substituted with at least one substituent group, size-limited substituent group, or lower substituent group; wherein if the substituted $R^8$ is substituted with a plurality of groups selected from substituent groups, size-limited substituent groups, and lower substituent groups; each substituent group, size-limited substituent group, and/or lower substituent group may optionally be different. In embodiments, when $R^8$ is substituted, it is substituted with at least one substituent group. In embodiments, when $R^8$ is substituted, it is substituted with at least one size-limited substituent group. In embodiments, when $R^8$ is substituted, it is substituted with at least one lower substituent group.

In embodiments, $R^9$ is —$SR^{9A}$, —$OR^{9A}$, or substituted or unsubstituted $C_1$-$C_{10}$ alkyl, substituted or unsubstituted 2 to 10 membered heteroalkyl. In embodiments, $R^9$ is —$SR^{9A}$, —$OR^{9A}$, or thiol-substituted or unsubstituted $C_1$-$C_{10}$ alkyl, thiol-substituted or unsubstituted 2 to 10 membered heteroalkyl. In embodiments, $R^9$ is —$SR^{9A}$, or —$OR^{9A}$. In embodiments, $R^9$ is —$SR^{9A}$ or —$OR^{9A}$. In embodiments, $R^9$ is —$SR^{9A}$. In embodiments, $R^9$ is —$OR^{9A}$. In embodiments, $R^9$ is —SH. In embodiments, $R^9$ is —OH.

In embodiments, $R^9$ is —SH, —OH, —$OCH_3$, —$NH_2$, —NHC(O)H, —NHC(O)OH, substituted or unsubstituted $C_1$-$C_{10}$ alkyl, or substituted or unsubstituted 2 to 10 membered heteroalkyl. In embodiments, $R^9$ is —$OCH_3$.

In embodiments, $R^9$ is substituted or unsubstituted methyl. In embodiments, $R^9$ is substituted or unsubstituted $C_2$ alkyl. In embodiments, $R^9$ is substituted or unsubstituted $C_3$ alkyl. In embodiments, $R^9$ is substituted or unsubstituted $C_4$ alkyl. In embodiments, $R^9$ is substituted or unsubstituted $C_5$ alkyl. In embodiments, $R^9$ is substituted or unsubstituted $C_6$ alkyl. In embodiments, $R^9$ is substituted or unsubstituted $C_7$ alkyl. In embodiments, $R^9$ is substituted or unsubstituted $C_8$ alkyl. In embodiments, $R^9$ is substituted methyl. In embodiments, $R^9$ is substituted $C_2$ alkyl. In embodiments, $R^9$ is substituted $C_3$ alkyl. In embodiments, $R^9$ is substituted $C_4$ alkyl. In embodiments, $R^9$ is substituted $C_5$ alkyl. In embodiments, $R^9$ is substituted $C_6$ alkyl. In embodiments, $R^9$ is substituted $C_7$ alkyl. In embodiments, $R^9$ is substituted $C_8$ alkyl. In embodiments, $R^9$ is an unsubstituted methyl. In embodiments, $R^9$ is an unsubstituted $C_2$ alkyl. In embodiments, $R^9$ is an unsubstituted $C_3$ alkyl. In embodiments, $R^9$ is an unsubstituted $C_4$ alkyl. In embodiments, $R^9$ is an unsubstituted $C_5$ alkyl. In embodiments, $R^9$ is an unsubstituted $C_6$ alkyl. In embodiments, $R^9$ is an unsubstituted $C_7$ alkyl. In embodiments, $R^9$ is an unsubstituted $C_8$ alkyl.

In embodiments, $R^9$ is substituted or unsubstituted 2 to 10 membered heteroalkyl. In embodiments, $R^9$ is substituted 2 to 10 membered heteroalkyl. In embodiments, $R^9$ is an unsubstituted 2 to 10 membered heteroalkyl. In embodiments, $R^9$ is substituted or unsubstituted 2 to 6 membered heteroalkyl. In embodiments, $R^9$ is substituted 2 to 6 membered heteroalkyl. In embodiments, $R^9$ is an unsubstituted 2 to 6 membered heteroalkyl. In embodiments, $R^9$ is substituted or unsubstituted 2 membered heteroalkyl. In embodiments, $R^9$ is substituted 2 membered heteroalkyl. In embodiments, $R^9$ is an unsubstituted 2 membered heteroalkyl. In embodiments, $R^9$ is substituted or unsubstituted 3 membered heteroalkyl. In embodiments, $R^9$ is substituted 3 membered heteroalkyl. In embodiments, $R^9$ is an unsubstituted 3 membered heteroalkyl. In embodiments, $R^9$ is substituted or unsubstituted 4 membered heteroalkyl. In embodiments, $R^9$ is substituted 4 membered heteroalkyl. In embodiments, $R^9$ is an unsubstituted 4 membered heteroalkyl. In embodiments, $R^9$ is substituted or unsubstituted 5 membered heteroalkyl. In embodiments, $R^9$ is substituted 5 membered heteroalkyl. In embodiments, $R^9$ is an unsubstituted 5 membered heteroalkyl. In embodiments, $R^9$ is substituted or unsubstituted 6 membered heteroalkyl. In embodiments, $R^9$ is substituted 6 membered heteroalkyl. In embodiments, $R^9$ is an unsubstituted 6 membered heteroalkyl.

In embodiments, $R^9$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^9$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^9$ is unsubstituted alkyl or unsubstituted heteroalkyl.

In embodiments, a substituted $R^9$ (e.g., substituted alkyl and/or substituted heteroalkyl) is substituted with at least one substituent group, size-limited substituent group, or lower substituent group; wherein if the substituted $R^9$ is substituted with a plurality of groups selected from substituent groups, size-limited substituent groups, and lower substituent groups; each substituent group, size-limited substituent group, and/or lower substituent group may optionally be different. In embodiments, when $R^9$ is substituted, it is substituted with at least one substituent group. In embodiments, when $R^9$ is substituted, it is substituted with at least one size-limited substituent group. In embodiments, when $R^9$ is substituted, it is substituted with at least one lower substituent group.

In embodiments, $R^{10}$ is hydrogen, —$SR^{10A}$, —$OR^{10A}$, or substituted or unsubstituted $C_1$-$C_{10}$ alkyl, substituted or unsubstituted 2 to 10 membered heteroalkyl. In embodiments, $R^{10}$ is hydrogen, —$SR^{10A}$, —$OR^{10A}$, or thiol-substituted or unsubstituted $C_1$-$C_{10}$ alkyl, thiol-substituted or unsubstituted 2 to 10 membered heteroalkyl. In embodiments, $R^{10}$ is —$SR^{10A}$ or —$OR^{10A}$. In embodiments, $R^{10}$ is —$SR^{10A}$. In embodiments, $R^{10}$ is —$OR^{10A}$. In embodiments, $R^{10}$ is —SH. In embodiments, $R^{10}$ is —OH. In embodiments, $R^{10}$ is hydrogen.

In embodiments, $R^{10}$ is —SH, —OH, —$OCH_3$, —$NH_2$, —NHC(O)H, —NHC(O)OH, substituted or unsubstituted $C_1$-$C_{10}$ alkyl, or substituted or unsubstituted 2 to 10 membered heteroalkyl. In embodiments, $R^{10}$ is —$OCH_3$.

In embodiments, $R^{10}$ is substituted or unsubstituted methyl. In embodiments, $R^{10}$ is substituted or unsubstituted $C_2$ alkyl. In embodiments, $R^{10}$ is substituted or unsubstituted $C_3$ alkyl. In embodiments, $R^{10}$ is substituted or unsubstituted $C_4$ alkyl. In embodiments, $R^{10}$ is substituted or unsubstituted $C_5$ alkyl. In embodiments, $R^{10}$ is substituted or unsubstituted $C_6$ alkyl. In embodiments, $R^{10}$ is substituted or unsubstituted $C_7$ alkyl. In embodiments, $R^{10}$ is substituted or unsubstituted $C_8$ alkyl. In embodiments, $R^{10}$ is substituted methyl. In embodiments, $R^{10}$ is substituted $C_2$ alkyl. In embodiments, $R^{10}$ is substituted $C_3$ alkyl. In embodiments, $R^{10}$ is substituted $C_4$ alkyl. In embodiments, $R^{10}$ is substituted $C_5$ alkyl. In embodiments, $R^{10}$ is substituted $C_6$ alkyl. In embodiments, $R^{10}$ is substituted $C_7$ alkyl. In embodiments, $R^{10}$ is substituted $C_8$ alkyl. In embodiments, $R^{10}$ is an unsubstituted methyl. In embodiments, $R^{10}$ is an unsubstituted $C_2$ alkyl. In embodiments, $R^{10}$ is an unsubstituted $C_3$ alkyl. In embodiments, $R^{10}$ is an unsubstituted $C_4$ alkyl. In embodiments, $R^{10}$ is an unsubstituted $C_5$ alkyl. In embodiments, $R^{10}$ is an unsubstituted $C_6$ alkyl. In embodiments, $R^{10}$ is an unsubstituted $C_7$ alkyl. In embodiments, $R^{10}$ is an unsubstituted $C_8$ alkyl.

In embodiments, $R^{10}$ is substituted or unsubstituted 2 to 10 membered heteroalkyl. In embodiments, $R^{10}$ is substituted 2 to 10 membered heteroalkyl. In embodiments, $R^{10}$ is an unsubstituted 2 to 10 membered heteroalkyl. In embodiments, $R^{10}$ is substituted or unsubstituted 2 to 6 membered heteroalkyl. In embodiments, $R^{10}$ is substituted 2 to 6 membered heteroalkyl. In embodiments, $R^{10}$ is an unsubstituted 2 to 6 membered heteroalkyl. In embodiments, $R^{10}$ is substituted or unsubstituted 2 membered heteroalkyl. In embodiments, $R^{10}$ is substituted 2 membered heteroalkyl. In embodiments, $R^{10}$ is an unsubstituted 2 membered heteroalkyl. In embodiments, $R^{10}$ is substituted or unsubstituted 3 membered heteroalkyl. In embodiments, $R^{10}$ is substituted 3 membered heteroalkyl. In embodiments, $R^{10}$ is an unsubstituted 3 membered heteroalkyl. In embodiments, $R^{10}$ is substituted or unsubstituted 4 membered heteroalkyl. In embodiments, $R^{10}$ is substituted 4 membered heteroalkyl. In embodiments, $R^{10}$ is an unsubstituted 4 membered heteroalkyl. In embodiments, $R^{10}$ is substituted or unsubstituted 5 membered heteroalkyl. In embodiments, $R^{10}$ is substituted 5 membered heteroalkyl. In embodiments, $R^{10}$ is an unsubstituted 5 membered heteroalkyl. In embodiments, $R^{10}$ is substituted or unsubstituted 6 membered heteroalkyl. In embodiments, $R^{10}$ is substituted 6 membered heteroalkyl. In embodiments, $R^{10}$ is an unsubstituted 6 membered heteroalkyl.

In embodiments, $R^{10}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{10}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{10}$ is unsubstituted alkyl or unsubstituted heteroalkyl.

In embodiments, a substituted $R^{10}$ (e.g., substituted alkyl and/or substituted heteroalkyl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group.

In embodiments, $R^{11}$ is —$SR^{11A}$, —$OR^{11A}$, or substituted or unsubstituted $C_1$-$C_{10}$ alkyl, substituted or unsubstituted 2 to 10 membered heteroalkyl. In embodiments, $R^{11}$ is —$SR^{11A}$, —$OR^{11A}$, or thiol-substituted or unsubstituted $C_1$-$C_{10}$ alkyl, thiol-substituted or unsubstituted 2 to 10 membered heteroalkyl. In embodiments, $R^{11}$ is —$SR^{11A}$, or —$OR^{11A}$. In embodiments, $R^{11}$ is —$SR^{11A}$ or —$OR^{11A}$. In embodiments, $R^{11}$ is —$SR^{11A}$. In embodiments, $R^{11}$ is —$OR^{11A}$. In embodiments, $R^{11}$ is —SH. In embodiments, $R^{11}$ is —OH.

In embodiments, $R^{11}$ is —SH, —OH, —$OCH_3$, —$NH_2$, —NHC(O)H, —NHC(O)OH, substituted or unsubstituted $C_1$-$C_{10}$ alkyl, or substituted or unsubstituted 2 to 10 membered heteroalkyl. In embodiments, $R^{11}$ is —$OCH_3$.

In embodiments, $R^{11}$ is substituted or unsubstituted methyl. In embodiments, $R^{11}$ is substituted or unsubstituted $C_2$ alkyl. In embodiments, $R^{11}$ is substituted or unsubstituted $C_3$ alkyl. In embodiments, $R^{11}$ is substituted or unsubstituted $C_4$ alkyl. In embodiments, $R^{11}$ is substituted or unsubstituted $C_5$ alkyl. In embodiments, $R^{11}$ is substituted or unsubstituted $C_6$ alkyl. In embodiments, $R^{11}$ is substituted or unsubstituted $C_7$ alkyl. In embodiments, $R^{11}$ is substituted or unsubstituted $C_8$ alkyl. In embodiments, $R^{11}$ is substituted methyl. In embodiments, $R^{11}$ is substituted $C_2$ alkyl. In embodiments, $R^{11}$ is substituted $C_3$ alkyl. In embodiments, $R^{11}$ is substituted $C_4$ alkyl. In embodiments, $R^{11}$ is substituted $C_5$ alkyl. In embodiments, $R^{11}$ is substituted $C_6$ alkyl. In embodiments, $R^{11}$ is substituted $C_7$ alkyl. In embodiments, $R^{11}$ is substituted $C_4$ alkyl. In embodiments, $R^{11}$ is an unsubstituted methyl. In embodiments, $R^{11}$ is an unsubstituted $C_2$ alkyl. In embodiments, $R^{11}$ is an unsubstituted $C_3$ alkyl. In embodiments, $R^{11}$ is an unsubstituted $C_4$ alkyl. In embodiments, $R^{11}$ is an unsubstituted $C_5$ alkyl. In embodiments, $R^{11}$ is an unsubstituted $C_6$ alkyl. In embodiments, $R^{11}$ is an unsubstituted $C_7$ alkyl. In embodiments, $R^{11}$ is an unsubstituted $C_8$ alkyl.

In embodiments, $R^{11}$ is substituted or unsubstituted 2 to 10 membered heteroalkyl. In embodiments, $R^{11}$ is substituted 2 to 10 membered heteroalkyl. In embodiments, $R^{11}$ is an unsubstituted 2 to 10 membered heteroalkyl. In embodiments, $R^{11}$ is substituted or unsubstituted 2 to 6 membered heteroalkyl. In embodiments, $R^{11}$ is substituted 2 to 6 membered heteroalkyl. In embodiments, $R^{11}$ is an unsubstituted 2 to 6 membered heteroalkyl. In embodiments, $R^{11}$ is substituted or unsubstituted 2 membered heteroalkyl. In embodiments, $R^{11}$ is substituted 2 membered heteroalkyl. In embodiments, $R^{11}$ is an unsubstituted 2 membered heteroalkyl. In embodiments, $R^{11}$ is substituted or unsubstituted 3 membered heteroalkyl. In embodiments, $R^{11}$ is substituted 3 membered heteroalkyl. In embodiments, $R^{11}$ is an unsubstituted 3 membered heteroalkyl. In embodiments, $R^{11}$ is substituted or unsubstituted 4 membered heteroalkyl. In embodiments, $R^{11}$ is substituted 4 membered heteroalkyl. In embodiments, $R^{11}$ is an unsubstituted 4 membered heteroalkyl. In embodiments, $R^{11}$ is substituted or unsubstituted 5 membered heteroalkyl. In embodiments, $R^{11}$ is substituted 5 membered heteroalkyl. In embodiments, $R^{11}$ is an unsubstituted 5 membered heteroalkyl. In embodiments, $R^{11}$ is substituted or unsubstituted 6 membered heteroalkyl. In embodiments, $R^{11}$ is substituted 6 membered heteroalkyl. In embodiments, $R^{11}$ is an unsubstituted 6 membered heteroalkyl.

In embodiments, $R^{11}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{11}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{11}$ is unsubstituted alkyl or unsubstituted heteroalkyl.

In embodiments, a substituted $R^{11}$ (e.g., substituted alkyl and/or substituted heteroalkyl) is substituted with at least one substituent group, size-limited substituent group, or lower substituent group; wherein if the substituted $R^{11}$ is substituted with a plurality of groups selected from substituent groups, size-limited substituent groups, and lower substituent groups; each substituent group, size-limited substituent group, and/or lower substituent group may optionally be different. In embodiments, when $R^{11}$ is substituted, it is substituted with at least one substituent group. In embodiments, when $R^{11}$ is substituted, it is substituted with at least one size-limited substituent group. In embodiments, when $R^{11}$ is substituted, it is substituted with at least one lower substituent group.

In embodiments, $R^{12}$ is $-SR^{12A}$, $-OR^{12A}$, or substituted or unsubstituted $C_1$-$C_{10}$ alkyl, substituted or unsubstituted 2 to 10 membered heteroalkyl. In embodiments, $R^{12}$ is $-SR^{12A}$, $-OR^{12A}$, or thiol-substituted or unsubstituted $C_1$-$C_{10}$ alkyl, thiol-substituted or unsubstituted 2 to 10 membered heteroalkyl. In embodiments, $R^{12}$ is $-SR^{12A}$, or $-OR^{12A}$. In embodiments, $R^{12}$ is $-SR^{12A}$ or $-OR^{12A}$. In embodiments, $R^{12}$ is $-SR^{12A}$. In embodiments, $R^{12}$ is $-OR^{12A}$. In embodiments, $R^{12}$ is $-SH$. In embodiments, $R^{12}$ is $-OH$.

In embodiments, $R^{12}$ is $-SH$, $-OH$, $-OCH_3$, $-NH_2$, $-NHC(O)H$, $-NHC(O)OH$, substituted or unsubstituted $C_1$-$C_{10}$ alkyl, or substituted or unsubstituted 2 to 10 membered heteroalkyl. In embodiments, $R^{12}$ is $-OCH_3$. In embodiments, $R^{12}$ is not $-OCH_3$.

In embodiments, $R^{12}$ is substituted or unsubstituted methyl. In embodiments, $R^{12}$ is substituted or unsubstituted $C_2$ alkyl. In embodiments, $R^{12}$ is substituted or unsubstituted $C_3$ alkyl. In embodiments, $R^{12}$ is substituted or unsubstituted $C_4$ alkyl. In embodiments, $R^{12}$ is substituted or unsubstituted $C_5$ alkyl. In embodiments, $R^{12}$ is substituted or unsubstituted $C_6$ alkyl. In embodiments, $R^{12}$ is substituted or unsubstituted $C_7$ alkyl. In embodiments, $R^{12}$ is substituted or unsubstituted $C_8$ alkyl. In embodiments, $R^{12}$ is substituted methyl. In embodiments, $R^{12}$ is substituted $C_2$ alkyl. In embodiments, $R^{12}$ is substituted $C_3$ alkyl. In embodiments, $R^{12}$ is substituted $C_4$ alkyl. In embodiments, $R^{12}$ is substituted $C_5$ alkyl. In embodiments, $R^{12}$ is substituted $C_6$ alkyl. In embodiments, $R^{12}$ is substituted $C_7$ alkyl. In embodiments, $R^{12}$ is substituted $C_8$ alkyl. In embodiments, $R^{12}$ is an unsubstituted methyl. In embodiments, $R^{12}$ is an unsubstituted $C_2$ alkyl. In embodiments, $R^{12}$ is an unsubstituted $C_3$ alkyl. In embodiments, $R^{12}$ is an unsubstituted $C_4$ alkyl. In embodiments, $R^{12}$ is an unsubstituted $C_5$ alkyl. In embodiments, $R^{12}$ is an unsubstituted $C_6$ alkyl. In embodiments, $R^{12}$ is an unsubstituted $C_7$ alkyl. In embodiments, $R^{12}$ is an unsubstituted $C_8$ alkyl.

In embodiments, $R^{12}$ is substituted or unsubstituted 2 to 10 membered heteroalkyl. In embodiments, $R^{12}$ is substituted 2 to 10 membered heteroalkyl. In embodiments, $R^{12}$ is an unsubstituted 2 to 10 membered heteroalkyl. In embodiments, $R^{12}$ is substituted or unsubstituted 2 to 6 membered heteroalkyl. In embodiments, $R^{12}$ is substituted 2 to 6 membered heteroalkyl. In embodiments, $R^{12}$ is an unsubstituted 2 to 6 membered heteroalkyl. In embodiments, $R^{12}$ is substituted or unsubstituted 2 membered heteroalkyl. In embodiments, $R^{12}$ is substituted 2 membered heteroalkyl. In embodiments, $R^{12}$ is an unsubstituted 2 membered heteroalkyl. In embodiments, $R^{12}$ is substituted or unsubstituted 3 membered heteroalkyl. In embodiments, $R^{12}$ is substituted 3 membered heteroalkyl. In embodiments, $R^{12}$ is an unsubstituted 3 membered heteroalkyl. In embodiments, $R^{12}$ is substituted or unsubstituted 4 membered heteroalkyl. In embodiments, $R^{12}$ is substituted 4 membered heteroalkyl. In embodiments, $R^{12}$ is an unsubstituted 4 membered heteroalkyl. In embodiments, $R^{12}$ is substituted or unsubstituted 5 membered heteroalkyl. In embodiments, $R^{12}$ is substituted 5 membered heteroalkyl. In embodiments, $R^{12}$ is an unsubstituted 5 membered heteroalkyl. In embodiments, $R^{12}$ is substituted or unsubstituted 6 membered heteroalkyl. In embodiments, $R^{12}$ is substituted 6 membered heteroalkyl. In embodiments, $R^{12}$ is an unsubstituted 6 membered heteroalkyl.

In embodiments, $R^{12}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{12}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{12}$ is unsubstituted alkyl or unsubstituted heteroalkyl.

In embodiments, a substituted $R^{12}$ (e.g., substituted alkyl and/or substituted heteroalkyl) is substituted with at least one substituent group, size-limited substituent group, or lower substituent group; wherein if the substituted $R^{12}$ is substituted with a plurality of groups selected from substituent groups, size-limited substituent groups, and lower substituent groups; each substituent group, size-limited substituent group, and/or lower substituent group may optionally be different. In embodiments, when $R^{12}$ is substituted, it is substituted with at least one substituent group. In embodiments, when $R^{12}$ is substituted, it is substituted with at least one size-limited substituent group. In embodiments, when $R^{12}$ is substituted, it is substituted with at least one lower substituent group.

In embodiments, $R^{1A}$ is hydrogen. In embodiments, $R^{2A}$ is hydrogen. In embodiments, $R^{3A}$ is hydrogen. In embodiments, $R^{4A}$ is hydrogen. In embodiments, $R^{5A}$ is hydrogen. In embodiments, $R^{6A}$ is hydrogen. In embodiments, $R^{1B}$ is hydrogen. In embodiments, $R^{2B}$ is hydrogen. In embodiments, $R^{3B}$ is hydrogen. In embodiments, $R^{4B}$ is hydrogen. In embodiments, $R^{5B}$ is hydrogen. In embodiments, $R^{6B}$ is hydrogen. In embodiments, $R^{1C}$ is hydrogen. In embodiments, $R^{2C}$ is hydrogen. In embodiments, $R^{3C}$ is hydrogen. In embodiments, $R^{4C}$ is hydrogen. In embodiments, $R^{5C}$ is hydrogen. In embodiments, $R^{6C}$ is hydrogen.

In embodiments, $R^{7A}$ is hydrogen. In embodiments, $R^{8A}$ is hydrogen. In embodiments, $R^{9A}$ is hydrogen. In embodiments, $R^{10A}$ is hydrogen. In embodiments, $R^{11A}$ is hydrogen. In embodiments, $R^{12A}$ is hydrogen. In embodiments, $R^{7B}$ is hydrogen. In embodiments, $R^{8B}$ is hydrogen. In embodiments, $R^{9B}$ is hydrogen. In embodiments, $R^{10B}$ is hydrogen. In embodiments, $R^{11B}$ is hydrogen. In embodiments, $R^{12B}$ is hydrogen. In embodiments, $R^{7C}$ is hydrogen. In embodiments, $R^{8C}$ is hydrogen. In embodiments, $R^{9C}$ is hydrogen. In embodiments, $R^{10C}$ is hydrogen. In embodiments, $R^{11C}$ is hydrogen. In embodiments, $R^{12C}$ is hydrogen.

In embodiments, $R^{1A}$ is substituted or unsubstituted $C_1$-$C_{10}$ alkyl. In embodiments, $R^{2A}$ is substituted or unsubstituted $C_1$-$C_{10}$ alkyl. In embodiments, $R^{3A}$ is substituted or unsubstituted $C_1$-$C_{10}$ alkyl. In embodiments, $R^{4A}$ is substituted or unsubstituted $C_1$-$C_{10}$ alkyl. In embodiments, $R^{5A}$ is substituted or unsubstituted $C_1$-$C_{10}$ alkyl. In embodiments, $R^{6A}$ is substituted or unsubstituted $C_1$-$C_{10}$ alkyl. In embodiments, $R^{1B}$ is substituted or unsubstituted $C_1$-$C_{10}$ alkyl. In embodiments, $R^{2B}$ is substituted or unsubstituted $C_1$-$C_{10}$ alkyl. In embodiments, $R^{3B}$ is substituted or unsubstituted $C_1$-$C_{10}$ alkyl. In embodiments, $R^{4B}$ is substituted or unsubstituted $C_1$-$C_{10}$ alkyl. In embodiments, $R^{5B}$ is substituted or unsubstituted $C_1$-$C_{10}$ alkyl. In embodiments, $R^{6B}$ is substituted or unsubstituted $C_1$-$C_{10}$ alkyl. In embodiments, $R^{1C}$ is substituted or unsubstituted $C_1$-$C_{10}$ alkyl. In embodiments, $R^{2C}$ is substituted or unsubstituted $C_1$-$C_{10}$ alkyl. In embodiments, $R^{3C}$ is substituted or unsubstituted $C_1$-$C_{10}$ alkyl. In embodiments, $R^{4C}$ is substituted or unsubstituted $C_1$-$C_{10}$ alkyl. In embodiments, $R^{5C}$ is substituted or unsubstituted $C_1$-$C_{10}$ alkyl. In embodiments, $R^{6C}$ is substituted or unsubstituted $C_1$-$C_{10}$ alkyl. In embodiments, $R^{1A}$ is substituted $C_1$-$C_{10}$ alkyl. In embodiments, $R^{2A}$ is substituted $C_1$-$C_{10}$ alkyl. In embodiments, $R^{3A}$ is substituted $C_1$-$C_{10}$ alkyl. In embodiments, $R^{4A}$ is substituted $C_1$-$C_{10}$ alkyl. In embodiments, $R^{5A}$ is substituted $C_1$-$C_{10}$ alkyl. In embodiments, $R^{6A}$ is substituted $C_1$-$C_{10}$ alkyl. In embodiments, $R^{1B}$ is substituted $C_1$-$C_{10}$ alkyl. In embodiments, $R^{2B}$ is substituted $C_1$-$C_{10}$ alkyl. In embodiments, $R^{3B}$ is substituted $C_1$-$C_{10}$ alkyl. In embodiments, $R^{4B}$ is substituted $C_1$-$C_{10}$ alkyl. In embodiments, $R^{5B}$ is substituted $C_1$-$C_{10}$ alkyl. In embodiments, $R^{6B}$ is substituted $C_1$-$C_{10}$ alkyl. In embodiments, $R^{1C}$ is substituted $C_1$-$C_{10}$ alkyl. In embodiments, $R^{2C}$ is substituted $C_1$-$C_{10}$ alkyl. In embodiments, $R^{3C}$ is substituted $C_1$-$C_{10}$ alkyl. In embodiments, $R^{4C}$ is substituted $C_1$-$C_{10}$ alkyl. In embodiments, $R^{5C}$ is substituted $C_1$-$C_{10}$ alkyl. In embodiments, $R^{6C}$ is substituted $C_1$-$C_{10}$ alkyl. In embodiments, $R^{1A}$ is unsubstituted $C_1$-$C_{10}$ alkyl. In embodiments, $R^{2A}$ is unsubstituted $C_1$-$C_{10}$ alkyl. In embodiments, $R^{3A}$ is unsubstituted $C_1$-$C_{10}$ alkyl. In embodiments, $R^{4A}$ is unsubstituted $C_1$-$C_{10}$ alkyl. In embodiments, $R^{5A}$ is unsubstituted $C_1$-$C_{10}$ alkyl. In embodiments, $R^{6A}$ is unsubstituted $C_1$-$C_{10}$ alkyl. In embodiments, $R^{1B}$ is unsubstituted $C_1$-$C_{10}$ alkyl. In embodiments, $R^{2B}$ is unsubstituted $C_1$-$C_{10}$ alkyl. In embodiments, $R^{3B}$ is unsubstituted $C_1$-$C_{10}$ alkyl. In embodiments, $R^{4B}$ is unsubstituted $C_1$-$C_{10}$ alkyl. In embodiments, $R^{5B}$ is unsubstituted $C_1$-$C_{10}$ alkyl. In embodiments, $R^{6B}$ is unsubstituted $C_1$-$C_{10}$ alkyl. In embodiments, $R^{1C}$ is unsubstituted $C_1$-$C_{10}$ alkyl. In embodiments, $R^{2C}$ is unsubstituted $C_1$-$C_{10}$ alkyl. In embodiments, $R^{3C}$ is unsubstituted $C_1$-$C_{10}$ alkyl. In embodiments, $R^{4C}$ is unsubstituted $C_1$-$C_{10}$ alkyl. In embodiments, $R^{5C}$ is unsubstituted $C_1$-$C_{10}$ alkyl. In embodiments, $R^{6C}$ is unsubstituted $C_1$-$C_{10}$ alkyl.

In embodiments, $R^{1A}$ is substituted or unsubstituted 2 to 10 membered heteroalkyl. In embodiments, $R^{2A}$ is substituted or unsubstituted 2 to 10 membered heteroalkyl. In embodiments, $R^{3A}$ is substituted or unsubstituted 2 to 10 membered heteroalkyl. In embodiments, $R^{4A}$ is substituted or unsubstituted 2 to 10 membered heteroalkyl. In embodiments, $R^{5A}$ is substituted or unsubstituted 2 to 10 membered heteroalkyl. In embodiments, $R^{6A}$ is substituted or unsubstituted 2 to 10 membered heteroalkyl. In embodiments, $R^{1B}$ is substituted or unsubstituted 2 to 10 membered heteroalkyl. In embodiments, $R^{2B}$ is substituted or unsubstituted 2 to 10 membered heteroalkyl. In embodiments, $R^{3B}$ is substituted or unsubstituted 2 to 10 membered heteroalkyl. In embodiments, $R^{4B}$ is substituted or unsubstituted 2 to 10 membered heteroalkyl. In embodiments, $R^{5B}$ is substituted or unsubstituted 2 to 10 membered heteroalkyl. In embodiments, $R^{6B}$ is substituted or unsubstituted 2 to 10 membered heteroalkyl. In embodiments, $R^{1C}$ is substituted or unsubstituted 2 to 10 membered heteroalkyl. In embodiments, $R^{2C}$ is substituted or unsubstituted 2 to 10 membered heteroalkyl. In embodiments, $R^{3C}$ is substituted or unsubstituted 2 to 10 membered heteroalkyl. In embodiments, $R^{4C}$ is substituted or unsubstituted 2 to 10 membered heteroalkyl. In embodiments, $R^{5C}$ is substituted or unsubstituted 2 to 10 membered heteroalkyl. In embodiments, $R^{6C}$ is substituted or unsubstituted 2 to 10 membered heteroalkyl. In embodiments, $R^{1A}$ is substituted 2 to 10 membered heteroalkyl. In embodiments, $R^{2A}$ is substituted 2 to 10 membered heteroalkyl. In embodiments, $R^{3A}$ is substituted 2 to 10 membered heteroalkyl. In embodiments, $R^{4A}$ is substituted 2 to 10 membered heteroalkyl. In embodiments, $R^{5A}$ is substituted 2 to 10 membered heteroalkyl. In embodiments, $R^{6A}$ is substituted 2 to 10 membered heteroalkyl. In embodiments, $R^{1B}$ is substituted 2 to 10 membered heteroalkyl. In embodiments, $R^{2B}$ is substituted 2 to 10 membered heteroalkyl. In embodiments, $R^{3B}$ is substituted 2 to 10 membered heteroalkyl. In embodiments, $R^{4B}$ is substituted 2 to 10 membered heteroalkyl. In embodiments, $R^{5B}$ is substituted 2 to 10 membered heteroalkyl. In embodiments, $R^{6B}$ is substituted 2 to 10 membered heteroalkyl. In embodiments, $R^{1C}$ is substituted 2 to 10 membered heteroalkyl. In embodiments, $R^{2C}$ is substituted 2 to 10 membered heteroalkyl. In embodiments, $R^{3C}$ is substituted 2 to 10 membered heteroalkyl. In embodiments, $R^{4C}$ is substituted 2 to 10 membered heteroalkyl. In embodiments, $R^{5C}$ is substituted 2 to 10 membered heteroalkyl. In embodiments, $R^{6C}$ is substituted 2 to 10 membered heteroalkyl. In embodiments, $R^{1A}$ is unsubstituted 2 to 10 membered heteroalkyl. In embodiments, $R^{2A}$ is unsubstituted 2 to 10 membered heteroalkyl. In embodiments, $R^{3A}$ is unsubstituted 2 to 10 membered heteroalkyl. In embodiments, $R^{4A}$ is unsubstituted 2 to 10 membered heteroalkyl. In embodiments, $R^{5A}$ is unsubstituted 2 to 10 membered heteroalkyl. In embodiments, $R^{6A}$ is unsubstituted 2 to 10 membered heteroalkyl. In embodiments, $R^{1B}$ is unsubstituted 2 to 10 membered heteroalkyl. In embodiments, $R^{2B}$ is unsubstituted 2 to 10 membered heteroalkyl. In embodiments, $R^{3B}$ is unsubstituted 2 to 10 membered heteroalkyl. In embodiments, $R^{4B}$ is unsubstituted 2 to 10 membered heteroalkyl. In embodiments, $R^{5B}$ is unsubstituted 2 to 10 membered heteroalkyl. In embodiments, $R^{6B}$ is unsubstituted 2 to 10 membered heteroalkyl. In embodiments, $R^{1C}$ is unsubstituted 2 to 10 membered heteroalkyl. In embodiments, $R^{2C}$ is unsubstituted 2 to 10 membered heteroalkyl. In embodiments, $R^{3C}$ is unsubstituted 2 to 10 membered heteroalkyl. In embodiments, $R^{4C}$ is unsubstituted 2 to 10 membered heteroalkyl. In embodiments, $R^{5C}$ is unsubstituted 2 to 10 membered heteroalkyl. In embodiments, $R^{6C}$ is unsubstituted 2 to 10 membered heteroalkyl.

In embodiments, $R^{1A}$ is substituted or unsubstituted 2 to 6 membered heteroalkyl. In embodiments, $R^{2A}$ is substituted or unsubstituted 2 to 6 membered heteroalkyl. In embodiments, $R^{3A}$ is substituted or unsubstituted 2 to 6 membered heteroalkyl. In embodiments, $R^{4A}$ is substituted or unsubstituted 2 to 6 membered heteroalkyl. In embodiments, $R^{5A}$ is substituted or unsubstituted 2 to 6 membered heteroalkyl. In embodiments, $R^{6A}$ is substituted or unsubstituted 2 to 6 membered heteroalkyl. In embodiments, $R^{1B}$ is substituted or unsubstituted 2 to 6 membered heteroalkyl. In embodiments, $R^{2B}$ is substituted or unsubstituted 2 to 6 membered heteroalkyl. In embodiments, $R^{3B}$ is substituted or unsubstituted 2 to 6 membered heteroalkyl. In embodiments, $R^{4B}$ is substituted or unsubstituted 2 to 6 membered heteroalkyl. In embodiments, $R^{5B}$ is substituted or unsubstituted 2 to 6 membered heteroalkyl. In embodiments, $R^{6B}$ is substituted or unsubstituted 2 to 6 membered heteroalkyl. In embodiments, $R^{1C}$ is substituted or unsubstituted 2 to 6 membered heteroalkyl. In embodiments, $R^{2C}$ is substituted or unsubstituted 2 to 6 membered heteroalkyl. In embodiments, $R^{3C}$ is substituted or unsubstituted 2 to 6 membered heteroalkyl. In embodiments, $R^{4C}$ is substituted or unsubstituted 2 to 6 membered heteroalkyl. In embodiments, $R^{5C}$ is substituted or unsubstituted 2 to 6 membered heteroalkyl. In embodiments, $R^{6C}$ is substituted or unsubstituted 2 to 6 membered heteroalkyl. In embodiments, $R^{1A}$ is substituted 2 to 6 membered heteroalkyl. In embodiments, $R^{2A}$ is substituted 2 to 6 membered heteroalkyl. In embodiments, $R^{3A}$ is substituted 2 to 6 membered heteroalkyl. In embodiments, $R^{4A}$ is substituted 2 to 6 membered heteroalkyl. In embodiments, $R^{5A}$ is substituted 2 to 6 membered heteroalkyl. In embodiments, $R^{6A}$ is substituted 2 to 6 membered heteroalkyl. In embodiments, $R^{1B}$ is substituted 2 to 6 membered heteroalkyl. In embodiments, $R^{2B}$ is substituted 2 to 6 membered heteroalkyl. In embodiments, $R^{3B}$ is substituted 2 to 6 membered heteroalkyl. In embodiments, $R^{4B}$ is substituted 2 to 6 membered heteroalkyl. In embodiments, $R^{5B}$ is substituted 2 to 6 membered heteroalkyl. In embodiments, $R^{6B}$ is substituted 2 to 6 membered heteroalkyl. In embodiments, $R^{1C}$ is substituted 2 to 6 membered heteroalkyl. In embodiments, $R^{2C}$ is substituted 2 to 6 membered heteroalkyl. In embodiments, $R^{3C}$ is substituted 2 to 6 membered heteroalkyl. In embodiments, $R^{4C}$ is substituted 2 to 6 membered heteroalkyl. In embodiments, $R^{5C}$ is substituted 2 to 6 membered heteroalkyl. In embodiments, $R^{6C}$ is substituted 2 to 6 membered heteroalkyl. In embodiments, $R^{1A}$ is unsubstituted 2 to 6 membered heteroalkyl. In embodiments, $R^{2A}$ is unsubstituted 2 to 6 membered heteroalkyl. In embodiments, $R^{3A}$ is unsubstituted 2 to 6 membered heteroalkyl. In embodiments, $R^{4A}$ is unsubstituted 2 to 6 membered heteroalkyl. In embodiments, $R^{5A}$ is unsubstituted 2 to 6 membered heteroalkyl. In embodiments, $R^{6A}$ is unsubstituted 2 to 6 membered heteroalkyl. In embodiments, $R^{1B}$ is unsubstituted 2 to 6 membered heteroalkyl. In embodiments, $R^{2B}$ is unsubstituted 2 to 6 membered heteroalkyl. In embodiments, $R^{3B}$ is unsubstituted 2 to 6 membered heteroalkyl. In embodiments, $R^{4B}$ is unsubstituted 2 to 6 membered heteroalkyl. In embodiments, $R^{5B}$ is unsubstituted 2 to 6 membered heteroalkyl. In embodiments, $R^{6B}$ is unsubstituted 2 to 6 membered heteroalkyl. In embodiments, $R^{1C}$ is unsubstituted 2 to 6 membered heteroalkyl. In embodiments, $R^{2C}$ is unsubstituted 2 to 6 membered heteroalkyl. In embodiments, $R^{3C}$ is unsubstituted 2 to 6 membered heteroalkyl. In embodiments, $R^{4C}$ is unsubstituted 2 to 6 membered heteroalkyl. In embodiments, $R^{5C}$ is unsubstituted 2 to 6 membered heteroalkyl. In embodiments, $R^{6C}$ is unsubstituted 2 to 6 membered heteroalkyl.

In embodiments, $R^{1A}$ is substituted or unsubstituted 2 membered heteroalkyl. In embodiments, $R^{2A}$ is substituted or unsubstituted 2 membered heteroalkyl. In embodiments, $R^{3A}$ is substituted or unsubstituted 2 membered heteroalkyl. In embodiments, $R^{4A}$ is substituted or unsubstituted 2 membered heteroalkyl. In embodiments, $R^{5A}$ is substituted or unsubstituted 2 membered heteroalkyl. In embodiments, $R^{6A}$ is substituted or unsubstituted 2 membered heteroalkyl. In embodiments, $R^{1B}$ is substituted or unsubstituted 2 membered heteroalkyl. In embodiments, $R^{2B}$ is substituted or unsubstituted 2 membered heteroalkyl. In embodiments, $R^{3B}$ is substituted or unsubstituted 2 membered heteroalkyl. In embodiments, $R^{4B}$ is substituted or unsubstituted 2 membered heteroalkyl. In embodiments, $R^{5B}$ is substituted or unsubstituted 2 membered heteroalkyl. In embodiments, $R^{6B}$ is substituted or unsubstituted 2 membered heteroalkyl. In embodiments, $R^{1C}$ is substituted or unsubstituted 2 membered heteroalkyl. In embodiments, $R^{2C}$ is substituted or unsubstituted 2 membered heteroalkyl. In embodiments, $R^{3C}$ is substituted or unsubstituted 2 membered heteroalkyl. In embodiments, $R^{4C}$ is substituted or unsubstituted 2 membered heteroalkyl. In embodiments, $R^{5C}$ is substituted or unsubstituted 2 membered heteroalkyl. In embodiments, $R^{6C}$ is substituted or unsubstituted 2 membered heteroalkyl.

In embodiments, $R^{1A}$ is substituted 2 membered heteroalkyl. In embodiments, $R^{2A}$ is substituted 2 membered heteroalkyl. In embodiments, $R^{3A}$ is substituted 2 membered heteroalkyl. In embodiments, $R^{4A}$ is substituted 2 membered heteroalkyl. In embodiments, $R^{5A}$ is substituted 2 membered heteroalkyl. In embodiments, $R^{6A}$ is substituted 2 membered heteroalkyl. In embodiments, $R^{1B}$ is substituted 2 membered heteroalkyl. In embodiments, $R^{2B}$ is substituted 2 membered heteroalkyl. In embodiments, $R^{3B}$ is substituted 2 membered heteroalkyl. In embodiments, $R^{4B}$ is substituted 2 membered heteroalkyl. In embodiments, $R^{5B}$ is substituted 2 membered heteroalkyl. In embodiments, $R^{6B}$ is substituted 2 membered heteroalkyl. In embodiments, $R^{1C}$ is substituted 2 membered heteroalkyl. In embodiments, $R^{2C}$ is substituted 2 membered heteroalkyl. In embodiments, $R^{3C}$ is substituted 2 membered heteroalkyl. In embodiments, $R^{4C}$ is substituted 2 membered heteroalkyl. In embodiments, $R^{5C}$ is substituted 2 membered heteroalkyl. In embodiments, $R^{6C}$ is substituted 2 membered heteroalkyl. In embodiments, $R^{1A}$ is unsubstituted 2 membered heteroalkyl. In embodiments, $R^{2A}$ is unsubstituted 2 membered heteroalkyl. In embodiments, $R^{3A}$ is unsubstituted 2 membered heteroalkyl. In embodiments, $R^{4A}$ is unsubstituted 2 membered heteroalkyl. In embodiments, $R^{5A}$ is unsubstituted 2 membered heteroalkyl. In embodiments, $R^{6A}$ is unsubstituted 2 membered heteroalkyl. In embodiments, $R^{1B}$ is unsubstituted 2 membered heteroalkyl. In embodiments, $R^{2B}$ is unsubstituted 2 membered heteroalkyl. In embodiments, $R^{3B}$ is unsubstituted 2 membered heteroalkyl. In embodiments, $R^{4B}$ is unsubstituted 2 membered heteroalkyl. In embodiments, $R^{5B}$ is unsubstituted 2 membered heteroalkyl. In embodiments, $R^{6B}$ is unsubstituted 2 membered heteroalkyl. In embodiments, $R^{1C}$ is unsubstituted 2 membered heteroalkyl. In embodiments, $R^{2C}$ is unsubstituted 2 membered heteroalkyl. In embodiments, $R^{3C}$ is unsubstituted 2 membered heteroalkyl. In embodiments, $R^{4C}$ is unsubstituted 2 membered heteroalkyl. In embodiments, $R^{5C}$ is unsubstituted 2 membered heteroalkyl. In embodiments, $R^{6C}$ is unsubstituted 2 membered heteroalkyl.

In embodiments, $R^{1A}$ is substituted or unsubstituted 3 membered heteroalkyl. In embodiments, $R^{2A}$ is substituted or unsubstituted 3 membered heteroalkyl. In embodiments, $R^{3A}$ is substituted or unsubstituted 3 membered heteroalkyl. In embodiments, $R^{4A}$ is substituted or unsubstituted 3 membered heteroalkyl. In embodiments, $R^{5A}$ is substituted or unsubstituted 3 membered heteroalkyl. In embodiments, $R^{6A}$ is substituted or unsubstituted 3 membered heteroalkyl. In embodiments, $R^{1B}$ is substituted or unsubstituted 3 membered heteroalkyl. In embodiments, $R^{2B}$ is substituted or unsubstituted 3 membered heteroalkyl. In embodiments, $R^{3B}$ is substituted or unsubstituted 3 membered heteroalkyl. In embodiments, $R^{4B}$ is substituted or unsubstituted 3 membered heteroalkyl. In embodiments, $R^{5B}$ is substituted or unsubstituted 3 membered heteroalkyl. In embodiments, $R^{6B}$ is substituted or unsubstituted 3 membered heteroalkyl. In embodiments, $R^{1C}$ is substituted or unsubstituted 3 membered heteroalkyl. In embodiments, $R^{2C}$ is substituted or unsubstituted 3 membered heteroalkyl. In embodiments, $R^{3C}$ is substituted or unsubstituted 3 membered heteroalkyl. In embodiments, $R^{4C}$ is substituted or unsubstituted 3 membered heteroalkyl. In embodiments, $R^{5C}$ is substituted or unsubstituted 3 membered heteroalkyl. In embodiments, $R^{6C}$ is substituted or unsubstituted 3 membered heteroalkyl. In embodiments, $R^{1A}$ is substituted 3 membered heteroalkyl. In embodiments, $R^{2A}$ is substituted 3 membered heteroalkyl. In embodiments, $R^{3A}$ is substituted 3 membered heteroalkyl. In embodiments, $R^{4A}$ is substituted 3 membered heteroalkyl. In embodiments, $R^{5A}$ is substituted 3 membered heteroalkyl.

In embodiments, $R^{6A}$ is substituted 3 membered heteroalkyl. In embodiments, $R^{1B}$ is substituted 3 membered heteroalkyl. In embodiments, $R^{2B}$ is substituted 3 membered heteroalkyl. In embodiments, $R^{3B}$ is substituted 3 membered heteroalkyl. In embodiments, $R^{4B}$ is substituted 3 membered heteroalkyl. In embodiments, $R^{5B}$ is substituted 3 membered heteroalkyl. In embodiments, $R^{6B}$ is substituted 3 membered heteroalkyl. In embodiments, $R^{1C}$ is substituted 3 membered heteroalkyl. In embodiments, $R^{2C}$ is substituted 3 membered heteroalkyl. In embodiments, $R^{3C}$ is substituted 3 membered heteroalkyl. In embodiments, $R^{4C}$ is substituted 3 membered heteroalkyl. In embodiments, $R^{5C}$ is substituted 3 membered heteroalkyl. In embodiments, $R^{6C}$ is substituted 3 membered heteroalkyl. In embodiments, $R^{1A}$ is unsubstituted 3 membered heteroalkyl. In embodiments, $R^{2A}$ is unsubstituted 3 membered heteroalkyl. In embodiments, $R^{3A}$ is unsubstituted 3 membered heteroalkyl. In embodiments, $R^{4A}$ is unsubstituted 3 membered heteroalkyl. In embodiments, $R^{5A}$ is unsubstituted 3 membered heteroalkyl. In embodiments, $R^{6A}$ is unsubstituted 3 membered heteroalkyl. In embodiments, $R^{1B}$ is unsubstituted 3 membered heteroalkyl. In embodiments, $R^{2B}$ is unsubstituted 3 membered heteroalkyl. In embodiments, $R^{3B}$ is unsubstituted 3 membered heteroalkyl. In embodiments, $R^{4B}$ is unsubstituted 3 membered heteroalkyl. In embodiments, $R^{5B}$ is unsubstituted 3 membered heteroalkyl. In embodiments, $R^{6B}$ is unsubstituted 3 membered heteroalkyl. In embodiments, $R^{1C}$ is unsubstituted 3 membered heteroalkyl. In embodiments, $R^{2C}$ is unsubstituted 3 membered heteroalkyl. In embodiments, $R^{3C}$ is unsubstituted 3 membered heteroalkyl. In embodiments, $R^{4C}$ is unsubstituted 3 membered heteroalkyl. In embodiments, $R^{5C}$ is unsubstituted 3 membered heteroalkyl. In embodiments, $R^{6C}$ is unsubstituted 3 membered heteroalkyl.

In embodiments, $R^{1A}$ is substituted or unsubstituted 4 membered heteroalkyl. In embodiments, $R^{2A}$ is substituted or unsubstituted 4 membered heteroalkyl. In embodiments, $R^{3A}$ is substituted or unsubstituted 4 membered heteroalkyl. In embodiments, $R^{4A}$ is substituted or unsubstituted 4 membered heteroalkyl. In embodiments, $R^{5A}$ is substituted or unsubstituted 4 membered heteroalkyl. In embodiments, $R^{6A}$ is substituted or unsubstituted 4 membered heteroalkyl. In embodiments, $R^{1B}$ is substituted or unsubstituted 4 membered heteroalkyl. In embodiments, $R^{2B}$ is substituted or unsubstituted 4 membered heteroalkyl. In embodiments, $R^{3B}$ is substituted or unsubstituted 4 membered heteroalkyl. In embodiments, $R^{4B}$ is substituted or unsubstituted 4 membered heteroalkyl. In embodiments, $R^{5B}$ is substituted or unsubstituted 4 membered heteroalkyl. In embodiments, $R^{6B}$ is substituted or unsubstituted 4 membered heteroalkyl. In embodiments, $R^{1C}$ is substituted or unsubstituted 4 membered heteroalkyl. In embodiments, $R^{2C}$ is substituted or unsubstituted 4 membered heteroalkyl. In embodiments, $R^{3C}$ is substituted or unsubstituted 4 membered heteroalkyl. In embodiments, $R^{4C}$ is substituted or unsubstituted 4 membered heteroalkyl. In embodiments, $R^{5C}$ is substituted or unsubstituted 4 membered heteroalkyl. In embodiments, $R^{6C}$ is substituted or unsubstituted 4 membered heteroalkyl. In embodiments, $R^{1A}$ is substituted 4 membered heteroalkyl. In embodiments, $R^{2A}$ is substituted 4 membered heteroalkyl. In embodiments, $R^{3A}$ is substituted 4 membered heteroalkyl. In embodiments, $R^{4A}$ is substituted 4 membered heteroalkyl. In embodiments, $R^{5A}$ is substituted 4 membered heteroalkyl. In embodiments, $R^{6A}$ is substituted 4 membered heteroalkyl. In embodiments, $R^{1B}$ is substituted 4 membered heteroalkyl. In embodiments, $R^{2B}$ is substituted 4 membered heteroalkyl. In embodiments, $R^{3B}$ is substituted 4 membered heteroalkyl. In embodiments, $R^{4B}$ is substituted 4 membered heteroalkyl. In embodiments, $R^{5B}$ is substituted 4 membered heteroalkyl. In embodiments, $R^{6B}$ is substituted 4 membered heteroalkyl. In embodiments, $R^{1C}$ is substituted 4 membered heteroalkyl. In embodiments, $R^{2C}$ is substituted 4 membered heteroalkyl. In embodiments, $R^{3C}$ is substituted 4 membered heteroalkyl. In embodiments, $R^{4C}$ is substituted 4 membered heteroalkyl. In embodiments, $R^{5C}$ is substituted 4 membered heteroalkyl. In embodiments, $R^{6C}$ is substituted 4 membered heteroalkyl. In embodiments, $R^{1A}$ is unsubstituted 4 membered heteroalkyl. In embodiments, $R^{2A}$ is unsubstituted 4 membered heteroalkyl. In embodiments, $R^{3A}$ is unsubstituted 4 membered heteroalkyl. In embodiments, $R^{4A}$ is unsubstituted 4 membered heteroalkyl. In embodiments, $R^{5A}$ is unsubstituted 4 membered heteroalkyl. In embodiments, $R^{6A}$ is unsubstituted 4 membered heteroalkyl. In embodiments, $R^{1B}$ is unsubstituted 4 membered heteroalkyl. In embodiments, $R^{2B}$ is unsubstituted 4 membered heteroalkyl. In embodiments, $R^{3B}$ is unsubstituted 4 membered heteroalkyl. In embodiments, $R^{4B}$ is unsubstituted 4 membered heteroalkyl. In embodiments, $R^{5B}$ is unsubstituted 4 membered heteroalkyl. In embodiments, $R^{6B}$ is unsubstituted 4 membered heteroalkyl. In embodiments, $R^{1C}$ is unsubstituted 4 membered heteroalkyl. In embodiments, $R^{2C}$ is unsubstituted 4 membered heteroalkyl. In embodiments, $R^{3C}$ is unsubstituted 4 membered heteroalkyl. In embodiments, $R^{4C}$ is unsubstituted 4 membered heteroalkyl. In embodiments, $R^{5C}$ is unsubstituted 4 membered heteroalkyl. In embodiments, $R^{6C}$ is unsubstituted 4 membered heteroalkyl.

In embodiments, $R^{1A}$ is substituted or unsubstituted 5 membered heteroalkyl. In embodiments, $R^{2A}$ is substituted or unsubstituted 5 membered heteroalkyl. In embodiments, $R^{3A}$ is substituted or unsubstituted 5 membered heteroalkyl. In embodiments, $R^{4A}$ is substituted or unsubstituted 5 membered heteroalkyl. In embodiments, $R^{5A}$ is substituted or unsubstituted 5 membered heteroalkyl. In embodiments, $R^{6A}$ is substituted or unsubstituted 5 membered heteroalkyl. In embodiments, $R^{1B}$ is substituted or unsubstituted 5 membered heteroalkyl. In embodiments, $R^{2B}$ is substituted or unsubstituted 5 membered heteroalkyl. In embodiments, $R^{3B}$ is substituted or unsubstituted 5 membered heteroalkyl. In embodiments, $R^{4B}$ is substituted or unsubstituted 5 membered heteroalkyl. In embodiments, $R^{5B}$ is substituted or unsubstituted 5 membered heteroalkyl. In embodiments, $R^{6B}$ is substituted or unsubstituted 5 membered heteroalkyl. In embodiments, $R^{1C}$ is substituted or unsubstituted 5 membered heteroalkyl. In embodiments, $R^{2C}$ is substituted or unsubstituted 5 membered heteroalkyl. In embodiments, $R^{3C}$ is substituted or unsubstituted 5 membered heteroalkyl. In embodiments, $R^{4C}$ is substituted or unsubstituted 5 membered heteroalkyl. In embodiments, $R^{5C}$ is substituted or unsubstituted 5 membered heteroalkyl. In embodiments, $R^{6C}$ is substituted or unsubstituted 5 membered heteroalkyl. In embodiments, $R^{1A}$ is substituted 5 membered heteroalkyl. In embodiments, $R^{2A}$ is substituted 5 membered heteroalkyl. In embodiments, $R^{3A}$ is substituted 5 membered heteroalkyl. In embodiments, $R^{4A}$ is substituted 5 membered heteroalkyl. In embodiments, $R^{5A}$ is substituted 5 membered heteroalkyl. In embodiments, $R^{6A}$ is substituted 5 membered heteroalkyl. In embodiments, $R^{1B}$ is substituted 5 membered heteroalkyl. In embodiments, $R^{2B}$ is substituted 5 membered heteroalkyl. In embodiments, $R^{3B}$ is substituted 5 membered heteroalkyl. In embodiments, $R^{4B}$ is substituted 5 membered heteroalkyl. In embodiments, $R^{5B}$ is substituted 5 membered heteroalkyl. In embodiments, $R^{6B}$ is substituted 5 membered heteroalkyl. In embodiments, $R^{1C}$ is substituted 5 membered heteroalkyl. In embodiments, $R^{2C}$ is substituted 5 membered heteroalkyl. In embodiments, $R^{3C}$ is substituted 5 membered heteroalkyl.

In embodiments, $R^{4C}$ is substituted 5 membered heteroalkyl. In embodiments, $R^{5C}$ is substituted 5 membered heteroalkyl. In embodiments, $R^{6C}$ is substituted 5 membered heteroalkyl. In embodiments, $R^{1A}$ is unsubstituted 5 membered heteroalkyl. In embodiments, $R^{2A}$ is unsubstituted 5 membered heteroalkyl. In embodiments, $R^{3A}$ is unsubstituted 5 membered heteroalkyl. In embodiments, $R^{4A}$ is unsubstituted 5 membered heteroalkyl. In embodiments, $R^{5A}$ is unsubstituted 5 membered heteroalkyl. In embodiments, $R^{6A}$ is unsubstituted 5 membered heteroalkyl. In embodiments, $R^{1B}$ is unsubstituted 5 membered heteroalkyl. In embodiments, $R^{2B}$ is unsubstituted 5 membered heteroalkyl. In embodiments, $R^{3B}$ is unsubstituted 5 membered heteroalkyl. In embodiments, $R^{4B}$ is unsubstituted 5 membered heteroalkyl. In embodiments, $R^{5B}$ is unsubstituted 5 membered heteroalkyl. In embodiments, $R^{6B}$ is unsubstituted 5 membered heteroalkyl. In embodiments, $R^{1C}$ is unsubstituted 5 membered heteroalkyl. In embodiments, $R^{2C}$ is unsubstituted 5 membered heteroalkyl. In embodiments, $R^{3C}$ is unsubstituted 5 membered heteroalkyl. In embodiments, $R^{4C}$ is unsubstituted 5 membered heteroalkyl. In embodiments, $R^{5C}$ is unsubstituted 5 membered heteroalkyl. In embodiments, $R^{6C}$ is unsubstituted 5 membered heteroalkyl.

In embodiments, $R^{1A}$ is substituted or unsubstituted 6 membered heteroalkyl. In embodiments, $R^{2A}$ is substituted or unsubstituted 6 membered heteroalkyl. In embodiments, $R^{3A}$ is substituted or unsubstituted 6 membered heteroalkyl. In embodiments, $R^{4A}$ is substituted or unsubstituted 6 membered heteroalkyl. In embodiments, $R^{5A}$ is substituted or unsubstituted 6 membered heteroalkyl. In embodiments, $R^{6A}$ is substituted or unsubstituted 6 membered heteroalkyl. In embodiments, $R^{1B}$ is substituted or unsubstituted 6 membered heteroalkyl. In embodiments, $R^{2B}$ is substituted or unsubstituted 6 membered heteroalkyl. In embodiments, $R^{3B}$ is substituted or unsubstituted 6 membered heteroalkyl. In embodiments, $R^{4B}$ is substituted or unsubstituted 6 membered heteroalkyl. In embodiments, $R^{5B}$ is substituted or unsubstituted 6 membered heteroalkyl. In embodiments, $R^{6B}$ is substituted or unsubstituted 6 membered heteroalkyl. In embodiments, $R^{1C}$ is substituted or unsubstituted 6 membered heteroalkyl. In embodiments, $R^{2C}$ is substituted or unsubstituted 6 membered heteroalkyl. In embodiments, $R^{3C}$ is substituted or unsubstituted 6 membered heteroalkyl. In embodiments, $R^{4C}$ is substituted or unsubstituted 6 membered heteroalkyl. In embodiments, $R^{5C}$ is substituted or unsubstituted 6 membered heteroalkyl. In embodiments, $R^{6C}$ is substituted or unsubstituted 6 membered heteroalkyl. In embodiments, $R^{1A}$ is substituted 6 membered heteroalkyl. In embodiments, $R^{2A}$ is substituted 6 membered heteroalkyl. In embodiments, $R^{3A}$ is substituted 6 membered heteroalkyl. In embodiments, $R^{4A}$ is substituted 6 membered heteroalkyl. In embodiments, $R^{5A}$ is substituted 6 membered heteroalkyl. In embodiments, $R^{6A}$ is substituted 6 membered heteroalkyl. In embodiments, $R^{1B}$ is substituted 6 membered heteroalkyl. In embodiments, $R^{2B}$ is substituted 6 membered heteroalkyl. In embodiments, $R^{3B}$ is substituted 6 membered heteroalkyl. In embodiments, $R^{4B}$ is substituted 6 membered heteroalkyl. In embodiments, $R^{5B}$ is substituted 6 membered heteroalkyl. In embodiments, $R^{6B}$ is substituted 6 membered heteroalkyl. In embodiments, $R^{1C}$ is substituted 6 membered heteroalkyl. In embodiments, $R^{2C}$ is substituted 6 membered heteroalkyl. In embodiments, $R^{3C}$ is substituted 6 membered heteroalkyl. In embodiments, $R^{4C}$ is substituted 6 membered heteroalkyl. In embodiments, $R^{5C}$ is substituted 6 membered heteroalkyl. In embodiments, $R^{6C}$ is substituted 6 membered heteroalkyl. In embodiments, $R^{1A}$ is unsubstituted 6 membered heteroalkyl. In embodiments, $R^{2A}$ is unsubstituted 6 membered heteroalkyl. In embodiments, $R^{3A}$ is unsubstituted 6 membered heteroalkyl. In embodiments, $R^{4A}$ is unsubstituted 6 membered heteroalkyl. In embodiments, $R^{5A}$ is unsubstituted 6 membered heteroalkyl. In embodiments, $R^{6A}$ is unsubstituted 6 membered heteroalkyl. In embodiments, $R^{1B}$ is unsubstituted 6 membered heteroalkyl. In embodiments, $R^{2B}$ is unsubstituted 6 membered heteroalkyl. In embodiments, $R^{3B}$ is unsubstituted 6 membered heteroalkyl. In embodiments, $R^{4B}$ is unsubstituted 6 membered heteroalkyl. In embodiments, $R^{5B}$ is unsubstituted 6 membered heteroalkyl. In embodiments, $R^{6B}$ is unsubstituted 6 membered heteroalkyl. In embodiments, $R^{1C}$ is unsubstituted 6 membered heteroalkyl. In embodiments, $R^{2C}$ is unsubstituted 6 membered heteroalkyl. In embodiments, $R^{3C}$ is unsubstituted 6 membered heteroalkyl. In embodiments, $R^{4C}$ is unsubstituted 6 membered heteroalkyl. In embodiments, $R^{5C}$ is unsubstituted 6 membered heteroalkyl. In embodiments, $R^{6C}$ is unsubstituted 6 membered heteroalkyl.

In embodiments, $R^{1A}$ is

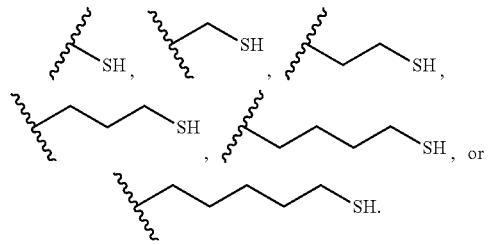

In embodiments, $R^{2A}$ is

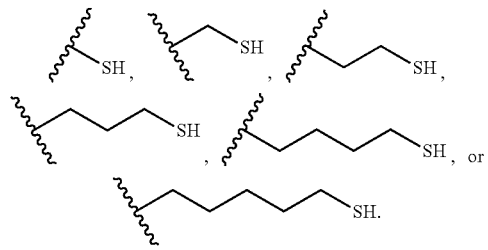

In embodiments, $R^{3A}$ is

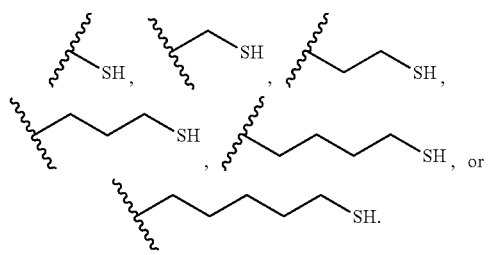

In embodiments, $R^{4A}$ is

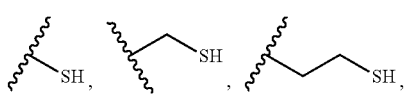

-continued

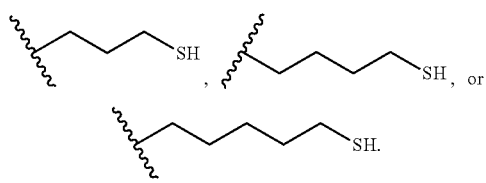

In embodiments, $R^{5A}$ is

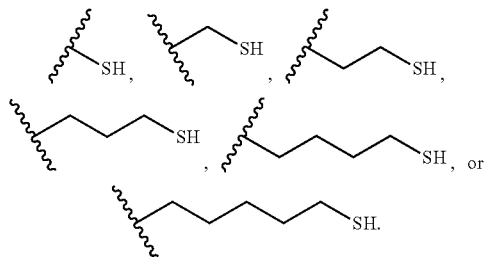

In embodiments, $R^{6A}$ is

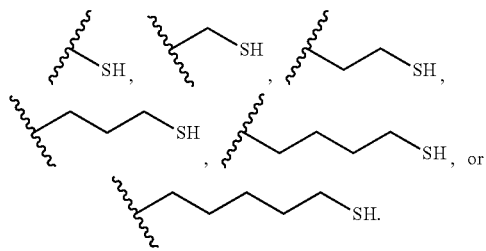

In embodiments, $R^{1A}$ is

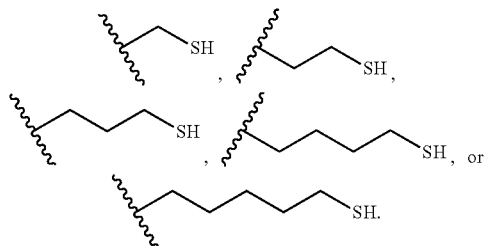

In embodiments, $R^{2A}$ is

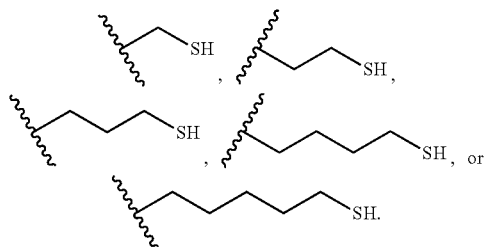

In embodiments, $R^{3A}$ is

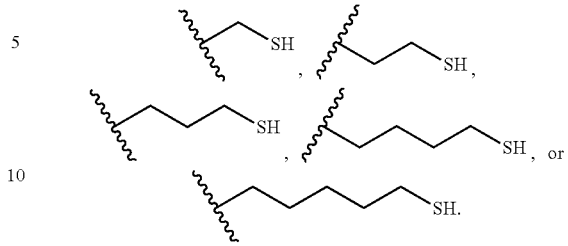

In embodiments, $R^{4A}$ is

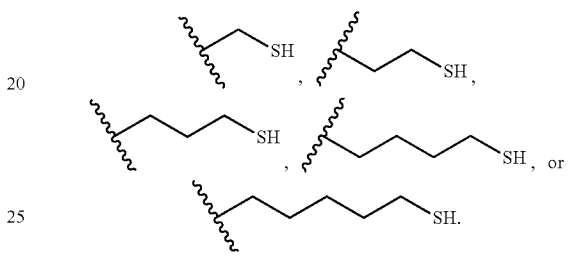

In embodiments, $R^{5A}$ is

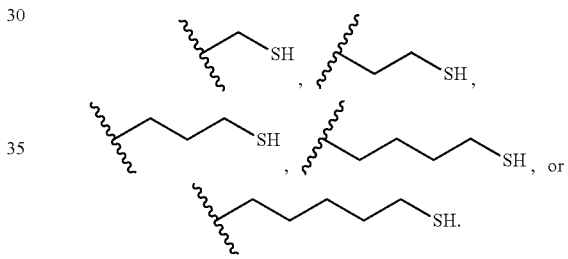

In embodiments, $R^{6A}$ is

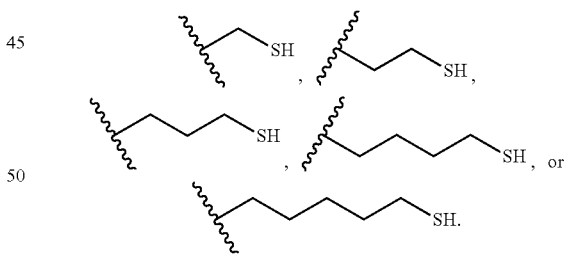

In embodiments, $R^{1A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{1A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{1A}$ is unsubstituted alkyl or unsubstituted heteroalkyl.

In embodiments, a substituted $R^{1A}$ (e.g., substituted alkyl and/or substituted heteroalkyl) is substituted with at least one substituent group, size-limited substituent group, or lower substituent group; wherein if the substituted $R^{1A}$ is substituted with a plurality of groups selected from substituent groups, size-limited substituent groups, and lower substituent groups; each substituent group, size-limited substituent group, and/or lower substituent group may optionally be different. In embodiments, when $R^{1A}$ is substituted, it is substituted with at least one substituent group. In embodiments, when $R^{1A}$ is substituted, it is substituted with at least one size-limited substituent group. In embodiments, when $R^{1A}$ is substituted, it is substituted with at least one lower substituent group.

In embodiments, $R^{1B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{1B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{1B}$ is unsubstituted alkyl or unsubstituted heteroalkyl.

In embodiments, a substituted $R^{1B}$ (e.g., substituted alkyl and/or substituted heteroalkyl) is substituted with at least one substituent group, size-limited substituent group, or lower substituent group; wherein if the substituted $R^{1B}$ is substituted with a plurality of groups selected from substituent groups, size-limited substituent groups, and lower substituent groups; each substituent group, size-limited substituent group, and/or lower substituent group may optionally be different. In embodiments, when $R^{1B}$ is substituted, it is substituted with at least one substituent group. In embodiments, when $R^{1B}$ is substituted, it is substituted with at least one size-limited substituent group. In embodiments, when $R^{1B}$ is substituted, it is substituted with at least one lower substituent group.

In embodiments, $R^{1C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{1C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{1C}$ is unsubstituted alkyl or unsubstituted heteroalkyl.

In embodiments, a substituted $R^{1C}$ (e.g., substituted alkyl and/or substituted heteroalkyl) is substituted with at least one substituent group, size-limited substituent group, or lower substituent group; wherein if the substituted $R^{1C}$ is substituted with a plurality of groups selected from substituent groups, size-limited substituent groups, and lower substituent groups; each substituent group, size-limited substituent group, and/or lower substituent group may optionally be different. In embodiments, when $R^{1C}$ is substituted, it is substituted with at least one substituent group. In embodiments, when $R^{1C}$ is substituted, it is substituted with at least one size-limited substituent group. In embodiments, when $R^{1C}$ is substituted, it is substituted with at least one lower substituent group.

In embodiments, $R^{2A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{2A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{2A}$ is unsubstituted alkyl or unsubstituted heteroalkyl.

In embodiments, a substituted $R^{2A}$ (e.g., substituted alkyl and/or substituted heteroalkyl) is substituted with at least one substituent group, size-limited substituent group, or lower substituent group; wherein if the substituted $R^{2A}$ is substituted with a plurality of groups selected from substituent groups, size-limited substituent groups, and lower substituent groups; each substituent group, size-limited substituent group, and/or lower substituent group may optionally be different. In embodiments, when $R^{2A}$ is substituted, it is substituted with at least one substituent group. In embodiments, when $R^{2A}$ is substituted, it is substituted with at least one size-limited substituent group. In embodiments, when $R^{2A}$ is substituted, it is substituted with at least one lower substituent group.

In embodiments, $R^{2B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{2B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{2B}$ is unsubstituted alkyl or unsubstituted heteroalkyl.

In embodiments, a substituted $R^{2B}$ (e.g., substituted alkyl and/or substituted heteroalkyl) is substituted with at least one substituent group, size-limited substituent group, or lower substituent group; wherein if the substituted $R^{2B}$ is substituted with a plurality of groups selected from substituent groups, size-limited substituent groups, and lower substituent groups; each substituent group, size-limited substituent group, and/or lower substituent group may optionally be different. In embodiments, when $R^{2B}$ is substituted, it is substituted with at least one substituent group. In embodiments, when $R^{2B}$ is substituted, it is substituted with at least one size-limited substituent group. In embodiments, when $R^{2B}$ is substituted, it is substituted with at least one lower substituent group.

In embodiments, $R^{2C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{2C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{2C}$ is unsubstituted alkyl or unsubstituted heteroalkyl.

In embodiments, a substituted $R^{2C}$ (e.g., substituted alkyl and/or substituted heteroalkyl) is substituted with at least one substituent group, size-limited substituent group, or lower substituent group; wherein if the substituted $R^{2C}$ is substituted with a plurality of groups selected from substituent groups, size-limited substituent groups, and lower substituent groups; each substituent group, size-limited substituent group, and/or lower substituent group may optionally be different. In embodiments, when $R^{2C}$ is substituted, it is substituted with at least one substituent group. In embodiments, when $R^{2C}$ is substituted, it is substituted with at least one size-limited substituent group. In embodiments, when $R^{2C}$ is substituted, it is substituted with at least one lower substituent group.

In embodiments, $R^{3A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{3A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{3A}$ is unsubstituted alkyl or unsubstituted heteroalkyl.

In embodiments, a substituted $R^{3A}$ (e.g., substituted alkyl and/or substituted heteroalkyl) is substituted with at least one substituent group, size-limited substituent group, or lower substituent group; wherein if the substituted $R^{3A}$ is substituted with a plurality of groups selected from substituent groups, size-limited substituent groups, and lower substituent groups; each substituent group, size-limited substituent group, and/or lower substituent group may optionally be different. In embodiments, when $R^{3A}$ is substituted, it is substituted with at least one substituent group. In embodiments, when $R^{3A}$ is substituted, it is substituted with at least one size-limited substituent group. In embodiments, when $R^{3A}$ is substituted, it is substituted with at least one lower substituent group.

In embodiments, $R^{3B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{3B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{3B}$ is unsubstituted alkyl or unsubstituted heteroalkyl.

In embodiments, a substituted $R^{3B}$ (e.g., substituted alkyl and/or substituted heteroalkyl) is substituted with at least one substituent group, size-limited substituent group, or lower substituent group; wherein if the substituted $R^{3B}$ is substituted with a plurality of groups selected from substituent groups, size-limited substituent groups, and lower substituent groups; each substituent group, size-limited substituent group, and/or lower substituent group may optionally be different. In embodiments, when $R^{3B}$ is substituted, it is substituted with at least one substituent group. In embodiments, when $R^{3B}$ is substituted, it is substituted with at least one size-limited substituent group. In embodiments, when $R^{3B}$ is substituted, it is substituted with at least one lower substituent group.

In embodiments, $R^{3C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{3C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{3C}$ is unsubstituted alkyl or unsubstituted heteroalkyl.

In embodiments, a substituted $R^{3C}$ (e.g., substituted alkyl and/or substituted heteroalkyl) is substituted with at least one substituent group, size-limited substituent group, or lower substituent group; wherein if the substituted $R^{3C}$ is substituted with a plurality of groups selected from substituent groups, size-limited substituent groups, and lower substituent groups; each substituent group, size-limited substituent group, and/or lower substituent group may optionally be different. In embodiments, when $R^{3C}$ is substituted, it is substituted with at least one substituent group. In embodiments, when $R^{3C}$ is substituted, it is substituted with at least one size-limited substituent group. In embodiments, when $R^{3C}$ is substituted, it is substituted with at least one lower substituent group.

In embodiments, $R^{4A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{4A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{4A}$ is unsubstituted alkyl or unsubstituted heteroalkyl.

In embodiments, a substituted $R^{4A}$ (e.g., substituted alkyl and/or substituted heteroalkyl) is substituted with at least one substituent group, size-limited substituent group, or lower substituent group; wherein if the substituted $R^{4A}$ is substituted with a plurality of groups selected from substituent groups, size-limited substituent groups, and lower substituent groups; each substituent group, size-limited substituent group, and/or lower substituent group may optionally be different. In embodiments, when $R^{4A}$ is substituted, it is substituted with at least one substituent group. In embodiments, when $R^{4A}$ is substituted, it is substituted with at least one size-limited substituent group. In embodiments, when $R^{4A}$ is substituted, it is substituted with at least one lower substituent group.

In embodiments, $R^{4B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{4B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{4B}$ is unsubstituted alkyl or unsubstituted heteroalkyl.

In embodiments, a substituted $R^{4B}$ (e.g., substituted alkyl and/or substituted heteroalkyl) is substituted with at least one substituent group, size-limited substituent group, or lower substituent group; wherein if the substituted $R^{4B}$ is substituted with a plurality of groups selected from substituent groups, size-limited substituent groups, and lower substituent groups; each substituent group, size-limited substituent group, and/or lower substituent group may optionally be different. In embodiments, when $R^{4B}$ is substituted, it is substituted with at least one substituent group. In embodiments, when $R^{4B}$ is substituted, it is substituted with at least one size-limited substituent group. In embodiments, when $R^{4B}$ is substituted, it is substituted with at least one lower substituent group.

In embodiments, $R^{4C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{4C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{4C}$ is unsubstituted alkyl or unsubstituted heteroalkyl.

In embodiments, a substituted $R^{4C}$ (e.g., substituted alkyl and/or substituted heteroalkyl) is substituted with at least one substituent group, size-limited substituent group, or lower substituent group; wherein if the substituted $R^{4C}$ is substituted with a plurality of groups selected from substituent groups, size-limited substituent groups, and lower substituent groups; each substituent group, size-limited substituent group, and/or lower substituent group may optionally be different. In embodiments, when $R^{4C}$ is substituted, it is substituted with at least one substituent group. In embodiments, when $R^{4C}$ is substituted, it is substituted with at least one size-limited substituent group. In embodiments, when $R^{4C}$ is substituted, it is substituted with at least one lower substituent group.

In embodiments, $R^{5A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{5A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{5A}$ is unsubstituted alkyl or unsubstituted heteroalkyl.

In embodiments, a substituted $R^{5A}$ (e.g., substituted alkyl and/or substituted heteroalkyl) is substituted with at least one substituent group, size-limited substituent group, or lower substituent group; wherein if the substituted $R^{5A}$ is substituted with a plurality of groups selected from substituent groups, size-limited substituent groups, and lower substituent groups; each substituent group, size-limited substituent group, and/or lower substituent group may optionally be different. In embodiments, when $R^{5A}$ is substituted, it is substituted with at least one substituent group. In embodiments, when $R^{5A}$ is substituted, it is substituted with at least one size-limited substituent group. In embodiments, when $R^{5A}$ is substituted, it is substituted with at least one lower substituent group.

In embodiments, $R^{5B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{5B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{5B}$ is unsubstituted alkyl or unsubstituted heteroalkyl.

In embodiments, a substituted $R^{5B}$ (e.g., substituted alkyl and/or substituted heteroalkyl) is substituted with at least one substituent group, size-limited substituent group, or lower substituent group; wherein if the substituted $R^{5B}$ is substituted with a plurality of groups selected from substituent groups, size-limited substituent groups, and lower substituent groups; each substituent group, size-limited substituent group, and/or lower substituent group may optionally be different. In embodiments, when $R^{5B}$ is substituted, it is substituted with at least one substituent group. In embodiments, when $R^{5B}$ is substituted, it is substituted with at least one size-limited substituent group. In embodiments, when $R^{5B}$ is substituted, it is substituted with at least one lower substituent group.

In embodiments, $R^{5C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{5C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{5C}$ is unsubstituted alkyl or unsubstituted heteroalkyl.

In embodiments, a substituted $R^{5C}$ (e.g., substituted alkyl and/or substituted heteroalkyl) is substituted with at least one substituent group, size-limited substituent group, or lower substituent group; wherein if the substituted $R^{5C}$ is substituted with a plurality of groups selected from substituent groups, size-limited substituent groups, and lower substituent groups; each substituent group, size-limited substituent group, and/or lower substituent group may optionally be different. In embodiments, when $R^{5C}$ is substituted, it is substituted with at least one substituent group. In embodiments, when $R^{5C}$ is substituted, it is substituted with at least one size-limited substituent group. In embodiments, when $R^{5C}$ is substituted, it is substituted with at least one lower substituent group.

In embodiments, $R^{6A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{6A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{6A}$ is unsubstituted alkyl or unsubstituted heteroalkyl.

In embodiments, a substituted $R^{6A}$ (e.g., substituted alkyl and/or substituted heteroalkyl) is substituted with at least one substituent group, size-limited substituent group, or lower substituent group; wherein if the substituted $R^{6A}$ is substituted with a plurality of groups selected from substituent groups, size-limited substituent groups, and lower substituent groups; each substituent group, size-limited substituent group, and/or lower substituent group may optionally be different. In embodiments, when $R^{6A}$ is substituted, it is substituted with at least one substituent group. In embodiments, when $R^{6A}$ is substituted, it is substituted with at least one size-limited substituent group. In embodiments, when $R^{6A}$ is substituted, it is substituted with at least one lower substituent group.

In embodiments, $R^{6B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{6B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{6B}$ is unsubstituted alkyl or unsubstituted heteroalkyl.

In embodiments, a substituted $R^{6B}$ (e.g., substituted alkyl and/or substituted heteroalkyl) is substituted with at least one substituent group, size-limited substituent group, or lower substituent group; wherein if the substituted $R^{6B}$ is substituted with a plurality of groups selected from substituent groups, size-limited substituent groups, and lower substituent groups; each substituent group, size-limited substituent group, and/or lower substituent group may optionally be different. In embodiments, when $R^{6B}$ is substituted, it is substituted with at least one substituent group. In embodiments, when $R^{6B}$ is substituted, it is substituted with at least one size-limited substituent group. In embodiments, when $R^{6B}$ is substituted, it is substituted with at least one lower substituent group.

In embodiments, $R^{6C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{6C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{6C}$ is unsubstituted alkyl or unsubstituted heteroalkyl.

In embodiments, a substituted $R^{6C}$ (e.g., substituted alkyl and/or substituted heteroalkyl) is substituted with at least one substituent group, size-limited substituent group, or lower substituent group; wherein if the substituted $R^{6C}$ is substituted with a plurality of groups selected from substituent groups, size-limited substituent groups, and lower substituent groups; each substituent group, size-limited substituent group, and/or lower substituent group may optionally be different. In embodiments, when $R^{6C}$ is substituted, it is substituted with at least one substituent group. In embodiments, when $R^{6C}$ is substituted, it is substituted with at least one size-limited substituent group. In embodiments, when $R^{6C}$ is substituted, it is substituted with at least one lower substituent group.

In embodiments, $R^{7A}$ is substituted or unsubstituted $C_1$-$C_{10}$ alkyl. In embodiments, $R^{8A}$ is substituted or unsubstituted $C_1$-$C_{10}$ alkyl. In embodiments, $R^{9A}$ is substituted or unsubstituted $C_1$-$C_{10}$ alkyl. In embodiments, $R^{10A}$ is substituted or unsubstituted $C_1$-$C_{10}$ alkyl. In embodiments, $R^{11A}$ is substituted or unsubstituted $C_1$-$C_{10}$ alkyl. In embodiments, $R^{12A}$ is substituted or unsubstituted $C_1$-$C_{10}$ alkyl. In embodiments, $R^{7B}$ is substituted or unsubstituted $C_1$-$C_{10}$ alkyl. In embodiments, $R^{8B}$ is substituted or unsubstituted $C_1$-$C_{10}$ alkyl. In embodiments, $R^{9B}$ is substituted or unsubstituted $C_1$-$C_{10}$ alkyl. In embodiments, $R^{10B}$ is substituted or unsubstituted $C_1$-$C_{10}$ alkyl. In embodiments, $R^{7B}$ is substituted or unsubstituted $C_1$-$C_{10}$ alkyl. In embodiments, $R^{8B}$ is substituted or unsubstituted $C_1$-$C_{10}$ alkyl. In embodiments, $R^{7C}$ is substituted or unsubstituted $C_1$-$C_{10}$ alkyl. In embodiments, $R^{8C}$ is substituted or unsubstituted $C_1$-$C_{10}$ alkyl. In embodiments, $R^{9C}$ is substituted or unsubstituted $C_1$-$C_{10}$ alkyl. In embodiments, $R^{10C}$ is substituted or unsubstituted $C_1$-$C_{10}$ alkyl. In embodiments, $R^{11C}$ is substituted or unsubstituted $C_1$-$C_{10}$ alkyl. In embodiments, $R^{12C}$ is substituted or unsubstituted $C_1$-$C_{10}$ alkyl. In embodiments, $R^{7A}$ is substituted $C_1$-$C_{10}$ alkyl. In embodiments, $R^{8A}$ is substituted $C_1$-$C_{10}$ alkyl. In embodiments, $R^{9A}$ is substituted $C_1$-$C_{10}$ alkyl. In embodiments, $R^{10A}$ is substituted $C_1$-$C_{10}$ alkyl. In embodiments, $R^{11A}$ is substituted $C_1$-$C_{10}$ alkyl. In embodiments, $R^{12A}$ is substituted $C_1$-$C_{10}$ alkyl. In embodiments, $R^{7B}$ is substituted $C_1$-$C_{10}$ alkyl. In embodiments, $R^{8B}$ is substituted $C_1$-$C_{10}$ alkyl. In embodiments, $R^{9B}$ is substituted $C_1$-$C_{10}$ alkyl. In embodiments, $R^{10B}$ is substituted $C_1$-$C_{10}$ alkyl. In embodiments, $R^{7B}$ is substituted $C_1$-$C_{10}$ alkyl. In embodiments, $R^{8B}$ is substituted $C_1$-$C_{10}$ alkyl. In embodiments, $R^{7C}$ is substituted $C_1$-$C_{10}$ alkyl. In embodiments, $R^{8C}$ is substituted $C_1$-$C_{10}$ alkyl. In embodiments, $R^{9C}$ is substituted $C_1$-$C_{10}$ alkyl. In embodiments, $R^{10C}$ is substituted $C_1$-$C_{10}$ alkyl. In embodiments, $R^{11C}$ is substituted $C_1$-$C_{10}$ alkyl. In embodiments, $R^{12C}$ is substituted $C_1$-$C_{10}$ alkyl. In embodiments, $R^{7A}$ is unsubstituted $C_1$-$C_{10}$ alkyl. In embodiments, $R^{8A}$ is unsubstituted $C_1$-$C_{10}$ alkyl. In embodiments, $R^{9A}$ is unsubstituted $C_1$-$C_{10}$ alkyl. In embodiments, $R^{10A}$ is unsubstituted $C_1$-$C_{10}$ alkyl. In embodiments, $R^{11A}$ is unsubstituted $C_1$-$C_{10}$ alkyl. In embodiments, $R^{12A}$ is unsubstituted $C_1$-$C_{10}$ alkyl. In embodiments, $R^{7B}$ is unsubstituted $C_1$-$C_{10}$ alkyl. In embodiments, $R^{8B}$ is unsubstituted $C_1$-$C_{10}$ alkyl. In embodiments, $R^{9B}$ is unsubstituted $C_1$-$C_{10}$ alkyl. In embodiments, $R^{10B}$ is unsubstituted $C_1$-$C_{10}$ alkyl. In embodiments, $R^{7B}$ is unsubstituted $C_1$-$C_{10}$ alkyl. In embodiments, $R^{8B}$ is unsubstituted $C_1$-$C_{10}$ alkyl. In embodiments, $R^{7C}$ is unsubstituted $C_1$-$C_{10}$ alkyl. In embodiments, $R^{8C}$ is unsubstituted $C_1$-$C_{10}$ alkyl. In embodiments, $R^{9C}$ is unsubstituted $C_1$-$C_{10}$ alkyl. In embodiments, $R^{10C}$ is unsubstituted $C_1$-$C_{10}$ alkyl. In embodiments, $R^{11C}$ is unsubstituted $C_1$-$C_{10}$ alkyl. In embodiments, $R^{12C}$ is unsubstituted $C_1$-$C_{10}$ alkyl.

In embodiments, $R^{7A}$ is substituted or unsubstituted 2 to 10 membered heteroalkyl. In embodiments, $R^{8A}$ is substituted or unsubstituted 2 to 10 membered heteroalkyl. In embodiments, $R^{9A}$ is substituted or unsubstituted 2 to 10 membered heteroalkyl. In embodiments, $R^{10A}$ is substituted or unsubstituted 2 to 10 membered heteroalkyl. In embodiments, $R^{11A}$ is substituted or unsubstituted 2 to 10 membered heteroalkyl. In embodiments, $R^{12A}$ is substituted or unsubstituted 2 to 10 membered heteroalkyl. In embodiments, $R^{7B}$ is substituted or unsubstituted 2 to 10 membered heteroalkyl. In embodiments, $R^{8B}$ is substituted or unsubstituted 2 to 10 membered heteroalkyl. In embodiments, $R^{9B}$ is substituted or unsubstituted 2 to 10 membered heteroalkyl. In embodiments, $R^{10B}$ is substituted or unsubstituted 2 to 10 membered heteroalkyl. In embodiments, $R^{7B}$ is substituted or unsubstituted 2 to 10 membered heteroalkyl. In embodiments, $R^{8B}$ is substituted or unsubstituted 2 to 10 membered heteroalkyl. In embodiments, $R^{7C}$ is substituted or unsubstituted 2 to 10 membered heteroalkyl. In embodiments, $R^{8C}$ is substituted or unsubstituted 2 to 10 membered heteroalkyl. In embodiments, $R^{9C}$ is substituted or unsubstituted 2 to 10 membered heteroalkyl. In embodiments, $R^{10C}$ is substituted or unsubstituted 2 to 10 membered heteroalkyl. In embodiments, $R^{11C}$ is substituted or unsubstituted 2 to 10 membered heteroalkyl. In embodiments, $R^{12C}$ is substituted or unsubstituted 2 to 10 membered heteroalkyl. In embodiments, $R^{7A}$ is substituted 2 to 10 membered heteroalkyl. In embodiments, $R^{8A}$ is substituted 2 to 10 membered heteroalkyl. In embodiments, $R^{9A}$ is substituted 2 to 10 membered heteroalkyl. In embodiments, $R^{10A}$ is substituted 2 to 10 membered heteroalkyl. In embodiments, $R^{11A}$ is substituted 2 to 10 membered heteroalkyl. In embodiments, $R^{12A}$ is substituted 2 to 10 membered heteroalkyl. In embodiments, $R^{7B}$ is substituted 2 to 10 membered heteroalkyl. In embodiments, $R^{8B}$ is substituted 2 to 10 membered heteroalkyl. In embodiments, $R^{9B}$ is substituted 2 to 10 membered heteroalkyl. In embodiments, $R^{10B}$ is substituted 2 to 10 membered heteroalkyl. In embodiments, $R^{7B}$ is substituted 2 to 10 membered heteroalkyl. In embodiments, $R^{8B}$ is substituted 2 to 10 membered heteroalkyl. In embodiments, $R^{7C}$ is substituted 2 to 10 membered heteroalkyl. In embodiments, $R^{8C}$ is substituted 2 to 10 membered heteroalkyl. In embodiments, $R^{9C}$ is substituted 2 to 10 membered heteroalkyl. In embodiments, $R^{10C}$ is substituted 2 to 10 membered heteroalkyl. In embodiments, $R^{11C}$ is substituted 2 to 10 membered heteroalkyl. In embodiments, $R^{12C}$ is substituted 2 to 10 membered heteroalkyl. In embodiments, $R^{7A}$ is unsubstituted 2 to 10 membered heteroalkyl. In embodiments, $R^{8A}$ is unsubstituted 2 to 10 membered heteroalkyl. In embodiments, $R^{9A}$ is unsubstituted 2 to 10 membered heteroalkyl. In embodiments, $R^{10A}$ is unsubstituted 2 to 10 membered heteroalkyl. In embodiments, $R^{11A}$ is unsubstituted 2 to 10 membered heteroalkyl. In embodiments, $R^{12A}$ is unsubstituted 2 to 10 membered heteroalkyl. In embodiments, $R^{7B}$ is unsubstituted 2 to 10 membered heteroalkyl. In embodiments, $R^{8B}$ is unsubstituted 2 to 10 membered heteroalkyl. In embodiments, $R^{9B}$ is unsubstituted 2 to 10 membered heteroalkyl. In embodiments, $R^{10B}$ is unsubstituted 2 to 10 membered heteroalkyl. In embodiments, $R^{7B}$ is unsubstituted 2 to 10 membered heteroalkyl. In embodiments, $R^{8B}$ is unsubstituted 2 to 10 membered heteroalkyl. In embodiments, $R^{7C}$ is unsubstituted 2 to 10 membered heteroalkyl. In embodiments, $R^{8C}$ is unsubstituted 2 to 10 membered heteroalkyl. In embodiments, $R^{9C}$ is unsubstituted 2 to 10 membered heteroalkyl. In embodiments, $R^{10C}$ is unsubstituted 2 to 10 membered heteroalkyl. In embodiments, $R^{11C}$ is unsubstituted 2 to 10 membered heteroalkyl. In embodiments, $R^{12C}$ is unsubstituted 2 to 10 membered heteroalkyl.

In embodiments, $R^{7A}$ is substituted or unsubstituted 2 to 6 membered heteroalkyl. In embodiments, $R^{8A}$ is substituted or unsubstituted 2 to 6 membered heteroalkyl. In embodiments, $R^{9A}$ is substituted or unsubstituted 2 to 6 membered heteroalkyl. In embodiments, $R^{10A}$ is substituted or unsubstituted 2 to 6 membered heteroalkyl. In embodiments, $R^{11A}$ is substituted or unsubstituted 2 to 6 membered heteroalkyl. In embodiments, $R^{12A}$ is substituted or unsubstituted 2 to 6 membered heteroalkyl. In embodiments, $R^{7B}$ is substituted or unsubstituted 2 to 6 membered heteroalkyl. In embodiments, $R^{8B}$ is substituted or unsubstituted 2 to 6 membered heteroalkyl. In embodiments, $R^{9B}$ is substituted or unsubstituted 2 to 6 membered heteroalkyl. In embodiments, $R^{10B}$ is substituted or unsubstituted 2 to 6 membered heteroalkyl. In embodiments, $R^{7B}$ is substituted or unsubstituted 2 to 6 membered heteroalkyl. In embodiments, $R^{8B}$ is substituted or unsubstituted 2 to 6 membered heteroalkyl. In embodiments, $R^{7C}$ is substituted or unsubstituted 2 to 6 membered heteroalkyl. In embodiments, $R^{8C}$ is substituted or unsubstituted 2 to 6 membered heteroalkyl. In embodiments, $R^{9C}$ is substituted or unsubstituted 2 to 6 membered heteroalkyl. In embodiments, $R^{10C}$ is substituted or unsubstituted 2 to 6 membered heteroalkyl. In embodiments, $R^{11C}$ is substituted or unsubstituted 2 to 6 membered heteroalkyl. In embodiments, $R^{12C}$ is substituted or unsubstituted 2 to 6 membered heteroalkyl. In embodiments, $R^{7A}$ is substituted 2 to 6 membered heteroalkyl. In embodiments, $R^{8A}$ is substituted 2 to 6 membered heteroalkyl. In embodiments, $R^{9A}$ is substituted 2 to 6 membered heteroalkyl. In embodiments, $R^{10A}$ is substituted 2 to 6 membered heteroalkyl. In embodiments, $R^{11A}$ is substituted 2 to 6 membered heteroalkyl. In embodiments, $R^{12A}$ is substituted 2 to 6 membered heteroalkyl. In embodiments, $R^{7B}$ is substituted 2 to 6 membered heteroalkyl. In embodiments, $R^{8B}$ is substituted 2 to 6 membered heteroalkyl. In embodiments, $R^{9B}$ is substituted 2 to 6 membered heteroalkyl. In embodiments, $R^{10B}$ is substituted 2 to 6 membered heteroalkyl. In embodiments, $R^{7B}$ is substituted 2 to 6 membered heteroalkyl. In embodiments, $R^{8B}$ is substituted 2 to 6 membered heteroalkyl. In embodiments, $R^{7C}$ is substituted 2 to 6 membered heteroalkyl. In embodiments, $R^{8C}$ is substituted 2 to 6 membered heteroalkyl. In embodiments, $R^{9C}$ is substituted 2 to 6 membered heteroalkyl. In embodiments, $R^{10C}$ is substituted 2 to 6 membered heteroalkyl. In embodiments, $R^{11C}$ is substituted 2 to 6 membered heteroalkyl. In embodiments, $R^{12C}$ is substituted 2 to 6 membered heteroalkyl. In embodiments, $R^{7A}$ is unsubstituted 2 to 6 membered heteroalkyl. In embodiments, $R^{8A}$ is unsubstituted 2 to 6 membered heteroalkyl. In embodiments, $R^{9A}$ is unsubstituted 2 to 6 membered heteroalkyl. In embodiments, $R^{10A}$ is unsubstituted 2 to 6 membered heteroalkyl. In embodiments, $R^{11A}$ is unsubstituted 2 to 6 membered heteroalkyl. In embodiments, $R^{12A}$ is unsubstituted 2 to 6 membered heteroalkyl. In embodiments, $R^{7B}$ is unsubstituted 2 to 6 membered heteroalkyl. In embodiments, $R^{8B}$ is unsubstituted 2 to 6 membered heteroalkyl. In embodiments, $R^{9B}$ is unsubstituted 2 to 6 membered heteroalkyl. In embodiments, $R^{10B}$ is unsubstituted 2 to 6 membered heteroalkyl. In embodiments, $R^{7B}$ is unsubstituted 2 to 6 membered heteroalkyl. In embodiments, $R^{8B}$ is unsubstituted 2 to 6 membered heteroalkyl. In embodiments, $R^{7C}$ is unsubstituted 2 to 6 membered heteroalkyl. In embodiments, $R^{8C}$ is unsubstituted 2 to 6 membered heteroalkyl. In embodiments, $R^{9C}$ is unsubstituted 2 to 6 membered heteroalkyl. In embodiments, $R^{10C}$ is unsubstituted 2 to 6 membered heteroalkyl. In embodiments, $R^{11C}$ is unsubstituted 2 to 6 membered heteroalkyl. In embodiments, $R^{12C}$ is unsubstituted 2 to 6 membered heteroalkyl.

In embodiments, $R^{7A}$ is substituted or unsubstituted 2 membered heteroalkyl. In embodiments, $R^{8A}$ is substituted or unsubstituted 2 membered heteroalkyl. In embodiments, $R^{9A}$ is substituted or unsubstituted 2 membered heteroalkyl. In embodiments, $R^{10A}$ is substituted or unsubstituted 2 membered heteroalkyl. In embodiments, $R^{11A}$ is substituted or unsubstituted 2 membered heteroalkyl. In embodiments, $R^{12A}$ is substituted or unsubstituted 2 membered heteroalkyl. In embodiments, $R^{7B}$ is substituted or unsubstituted 2 membered heteroalkyl. In embodiments, $R^{8B}$ is substituted or unsubstituted 2 membered heteroalkyl. In embodiments, $R^{9B}$ is substituted or unsubstituted 2 membered heteroalkyl. In embodiments, $R^{10B}$ is substituted or unsubstituted 2 membered heteroalkyl. In embodiments, $R^{7B}$ is substituted or unsubstituted 2 membered heteroalkyl. In embodiments, $R^{8B}$ is substituted or unsubstituted 2 membered heteroalkyl. In embodiments, $R^{7C}$ is substituted or unsubstituted 2 membered heteroalkyl. In embodiments, $R^{8C}$ is substituted or unsubstituted 2 membered heteroalkyl. In embodiments, $R^{9C}$ is substituted or unsubstituted 2 membered heteroalkyl. In embodiments, $R^{10C}$ is substituted or unsubstituted 2 membered heteroalkyl. In embodiments, $R^{11C}$ is substituted or unsubstituted 2 membered heteroalkyl. In embodiments, $R^{12C}$ is substituted or unsubstituted 2 membered heteroalkyl. In embodiments, $R^{7A}$ is substituted 2 membered heteroalkyl. In embodiments, $R^{8A}$ is substituted 2 membered heteroalkyl. In embodiments, $R^{9A}$ is substituted 2 membered heteroalkyl. In embodiments, $R^{10A}$ is substituted 2 membered heteroalkyl. In embodiments, $R^{11A}$ is substituted 2 membered heteroalkyl. In embodiments, $R^{12A}$ is substituted 2 membered heteroalkyl. In embodiments, $R^{7B}$ is substituted 2 membered heteroalkyl. In embodiments, $R^{8B}$ is substituted 2 membered heteroalkyl. In embodiments, $R^{9B}$ is substituted 2 membered heteroalkyl. In embodiments, $R^{10B}$ is substituted 2 membered heteroalkyl. In embodiments, $R^{7B}$ is substituted 2 membered heteroalkyl. In embodiments, $R^{8B}$ is substituted 2 membered heteroalkyl. In embodiments, $R^{7C}$ is substituted 2 membered heteroalkyl. In embodiments, $R^{8C}$ is substituted 2 membered heteroalkyl. In embodiments, $R^{9C}$ is substituted 2 membered heteroalkyl. In embodiments, $R^{10C}$ is substituted 2 membered heteroalkyl. In embodiments, $R^{11C}$ is substituted 2 membered heteroalkyl. In embodiments, $R^{12C}$ is substituted 2 membered heteroalkyl. In embodiments, $R^{7A}$ is unsubstituted 2 membered heteroalkyl. In embodiments, $R^{8A}$ is unsubstituted 2 membered heteroalkyl. In embodiments, $R^{9A}$ is unsubstituted 2 membered heteroalkyl. In embodiments, $R^{10A}$ is unsubstituted 2 membered heteroalkyl. In embodiments, $R^{11A}$ is unsubstituted 2 membered heteroalkyl. In embodiments, $R^{12A}$ is unsubstituted 2 membered heteroalkyl. In embodiments, $R^{7B}$ is unsubstituted 2 membered heteroalkyl. In embodiments, $R^{8B}$ is unsubstituted 2 membered heteroalkyl. In embodiments, $R^{9B}$ is unsubstituted 2 membered heteroalkyl. In embodiments, $R^{10B}$ is unsubstituted 2 membered heteroalkyl. In embodiments, $R^{7B}$ is unsubstituted 2 membered heteroalkyl. In embodiments, $R^{8B}$ is unsubstituted 2 membered heteroalkyl. In embodiments, $R^{7C}$ is unsubstituted 2 membered heteroalkyl. In embodiments, $R^{8C}$ is unsubstituted 2 membered heteroalkyl. In embodiments, $R^{9C}$ is unsubstituted 2 membered heteroalkyl. In embodiments, $R^{10C}$ is unsubstituted 2 membered heteroalkyl. In embodiments, $R^{11C}$ is unsubstituted 2 membered heteroalkyl. In embodiments, $R^{12C}$ is unsubstituted 2 membered heteroalkyl.

In embodiments, $R^{7A}$ is substituted or unsubstituted 3 membered heteroalkyl. In embodiments, $R^{8A}$ is substituted or unsubstituted 3 membered heteroalkyl. In embodiments, $R^{9A}$ is substituted or unsubstituted 3 membered heteroalkyl. In embodiments, $R^{10A}$ is substituted or unsubstituted 3 membered heteroalkyl. In embodiments, $R^{11A}$ is substituted or unsubstituted 3 membered heteroalkyl. In embodiments, $R^{12A}$ is substituted or unsubstituted 3 membered heteroalkyl. In embodiments, $R^{7B}$ is substituted or unsubstituted 3 membered heteroalkyl. In embodiments, $R^{8B}$ is substituted or unsubstituted 3 membered heteroalkyl. In embodiments, $R^{9B}$ is substituted or unsubstituted 3 membered heteroalkyl. In embodiments, $R^{10B}$ is substituted or unsubstituted 3 membered heteroalkyl. In embodiments, $R^{7B}$ is substituted or unsubstituted 3 membered heteroalkyl. In embodiments, $R^{8B}$ is substituted or unsubstituted 3 membered heteroalkyl. In embodiments, $R^{7C}$ is substituted or unsubstituted 3 membered heteroalkyl. In embodiments, $R^{8C}$ is substituted or unsubstituted 3 membered heteroalkyl. In embodiments, $R^{9C}$ is substituted or unsubstituted 3 membered heteroalkyl. In embodiments, $R^{10C}$ is substituted or unsubstituted 3 membered heteroalkyl. In embodiments, $R^{11C}$ is substituted or unsubstituted 3 membered heteroalkyl. In embodiments, $R^{12C}$ is substituted or unsubstituted 3 membered heteroalkyl. In embodiments, $R^{7A}$ is substituted 3 membered heteroalkyl. In embodiments, $R^{8A}$ is substituted 3 membered heteroalkyl. In embodiments, $R^{9A}$ is substituted 3 membered heteroalkyl. In embodiments, $R^{10A}$ is substituted 3 membered heteroalkyl. In embodiments, $R^{11A}$ is substituted 3 membered heteroalkyl. In embodiments, $R^{12A}$ is substituted 3 membered heteroalkyl. In embodiments, $R^{7B}$ is substituted 3 membered heteroalkyl. In embodiments, $R^{8B}$ is substituted 3 membered heteroalkyl. In embodiments, $R^{9B}$ is substituted 3 membered heteroalkyl. In embodiments, $R^{10B}$ is substituted 3 membered heteroalkyl. In embodiments, $R^{7B}$ is substituted 3 membered heteroalkyl. In embodiments, $R^{8B}$ is substituted 3 membered heteroalkyl. In embodiments, $R^{7C}$ is substituted 3 membered heteroalkyl. In embodiments, $R^{8C}$ is substituted 3 membered heteroalkyl. In embodiments, $R^{9C}$ is substituted 3 membered heteroalkyl. In embodiments, $R^{10C}$ is substituted 3 membered heteroalkyl. In embodiments, $R^{11C}$ is substituted 3 membered heteroalkyl. In embodiments, $R^{12C}$ is substituted 3 membered heteroalkyl. In embodiments, $R^{7A}$ is unsubstituted 3 membered heteroalkyl. In embodiments, $R^{8A}$ is unsubstituted 3 membered heteroalkyl. In embodiments, $R^{9A}$ is unsubstituted 3 membered heteroalkyl. In embodiments, $R^{10A}$ is unsubstituted 3 membered heteroalkyl. In embodiments, $R^{11A}$ is unsubstituted 3 membered heteroalkyl. In embodiments, $R^{12A}$ is unsubstituted 3 membered heteroalkyl. In embodiments, $R^{7B}$ is unsubstituted 3 membered heteroalkyl. In embodiments, $R^{8B}$ is unsubstituted 3 membered heteroalkyl. In embodiments, $R^{9B}$ is unsubstituted 3 membered heteroalkyl. In embodiments, $R^{10B}$ is unsubstituted 3 membered heteroalkyl. In embodiments, $R^{7B}$ is unsubstituted 3 membered heteroalkyl. In embodiments, $R^{8B}$ is unsubstituted 3 membered heteroalkyl. In embodiments, $R^{7C}$ is unsubstituted 3 membered heteroalkyl. In embodiments, $R^{8C}$ is unsubstituted 3 membered heteroalkyl. In embodiments, $R^{9C}$ is unsubstituted 3 membered heteroalkyl. In embodiments, $R^{10C}$ is unsubstituted 3 membered heteroalkyl. In embodiments, $R^{11C}$ is unsubstituted 3 membered heteroalkyl. In embodiments, $R^{12C}$ is unsubstituted 3 membered heteroalkyl.

In embodiments, $R^{7A}$ is substituted or unsubstituted 4 membered heteroalkyl. In embodiments, $R^{8A}$ is substituted or unsubstituted 4 membered heteroalkyl. In embodiments, $R^{9A}$ is substituted or unsubstituted 4 membered heteroalkyl. In embodiments, $R^{10A}$ is substituted or unsubstituted 4 membered heteroalkyl. In embodiments, $R^{11A}$ is substituted or unsubstituted 4 membered heteroalkyl. In embodiments, $R^{12A}$ is substituted or unsubstituted 4 membered heteroalkyl. In embodiments, $R^{7B}$ is substituted or unsubstituted 4 membered heteroalkyl. In embodiments, $R^{8B}$ is substituted or unsubstituted 4 membered heteroalkyl. In embodiments, $R^{9B}$ is substituted or unsubstituted 4 membered heteroalkyl. In embodiments, $R^{10B}$ is substituted or unsubstituted 4 membered heteroalkyl. In embodiments, $R^{7B}$ is substituted or unsubstituted 4 membered heteroalkyl. In embodiments, $R^{8B}$ is substituted or unsubstituted 4 membered heteroalkyl. In embodiments, $R^{7C}$ is substituted or unsubstituted 4 membered heteroalkyl. In embodiments, $R^{8C}$ is substituted or unsubstituted 4 membered heteroalkyl. In embodiments, $R^{9C}$ is substituted or unsubstituted 4 membered heteroalkyl. In embodiments, $R^{10C}$ is substituted or unsubstituted 4 membered heteroalkyl. In embodiments, $R^{11C}$ is substituted or unsubstituted 4 membered heteroalkyl. In embodiments, $R^{12C}$ is substituted or unsubstituted 4 membered heteroalkyl. In embodiments, $R^{7A}$ is substituted 4 membered heteroalkyl. In embodiments, $R^{8A}$ is substituted 4 membered heteroalkyl. In embodiments, $R^{9A}$ is substituted 4 membered heteroalkyl. In embodiments, $R^{10A}$ is substituted 4 membered heteroalkyl. In embodiments, $R^{11A}$ is substituted 4 membered heteroalkyl. In embodiments, $R^{12A}$ is substituted 4 membered heteroalkyl. In embodiments, $R^{7B}$ is substituted 4 membered heteroalkyl. In embodiments, $R^{8B}$ is substituted 4 membered heteroalkyl. In embodiments, $R^{9B}$ is substituted 4 membered heteroalkyl. In embodiments, $R^{10B}$ is substituted 4 membered heteroalkyl. In embodiments, $R^{7B}$ is substituted 4 membered heteroalkyl. In embodiments, $R^{8B}$ is substituted 4 membered heteroalkyl. In embodiments, $R^{7C}$ is substituted 4 membered heteroalkyl. In embodiments, $R^{8C}$ is substituted 4 membered heteroalkyl. In embodiments, $R^{9C}$ is substituted 4 membered heteroalkyl. In embodiments, $R^{10C}$ is substituted 4 membered heteroalkyl. In embodiments, $R^{11C}$ is substituted 4 membered heteroalkyl. In embodiments, $R^{12C}$ is substituted 4 membered heteroalkyl. In embodiments, $R^{7A}$ is unsubstituted 4 membered heteroalkyl. In embodiments, $R^{8A}$ is unsubstituted 4 membered heteroalkyl. In embodiments, $R^{9A}$ is unsubstituted 4 membered heteroalkyl. In embodiments, $R^{10A}$ is unsubstituted 4 membered heteroalkyl. In embodiments, $R^{11A}$ is unsubstituted 4 membered heteroalkyl. In embodiments, $R^{12A}$ is unsubstituted 4 membered heteroalkyl. In embodiments, $R^{7B}$ is unsubstituted 4 membered heteroalkyl. In embodiments, $R^{8B}$ is unsubstituted 4 membered heteroalkyl. In embodiments, $R^{9B}$ is unsubstituted 4 membered heteroalkyl. In embodiments, $R^{10B}$ is unsubstituted 4 membered heteroalkyl. In embodiments, $R^{7B}$ is unsubstituted 4 membered heteroalkyl. In embodiments, $R^{8B}$ is unsubstituted 4 membered heteroalkyl. In embodiments, $R^{7C}$ is unsubstituted 4 membered heteroalkyl. In embodiments, $R^{8C}$ is unsubstituted 4 membered heteroalkyl. In embodiments, $R^{9C}$ is unsubstituted 4 membered heteroalkyl. In embodiments, $R^{10C}$ is unsubstituted 4 membered heteroalkyl. In embodiments, $R^{11C}$ is unsubstituted 4 membered heteroalkyl. In embodiments, $R^{12C}$ is unsubstituted 4 membered heteroalkyl.

In embodiments, $R^{7A}$ is substituted or unsubstituted 5 membered heteroalkyl. In embodiments, $R^{8A}$ is substituted or unsubstituted 5 membered heteroalkyl. In embodiments, $R^{9A}$ is substituted or unsubstituted 5 membered heteroalkyl. In embodiments, $R^{10A}$ is substituted or unsubstituted 5 membered heteroalkyl. In embodiments, $R^{11A}$ is substituted or unsubstituted 5 membered heteroalkyl. In embodiments, $R^{12A}$ is substituted or unsubstituted 5 membered heteroalkyl. In embodiments, $R^{7B}$ is substituted or unsubstituted 5 membered heteroalkyl. In embodiments, $R^{8B}$ is substituted or unsubstituted 5 membered heteroalkyl. In embodiments, $R^{9B}$ is substituted or unsubstituted 5 membered heteroalkyl. In embodiments, $R^{10B}$ is substituted or unsubstituted 5 membered heteroalkyl. In embodiments, $R^{7B}$ is substituted or unsubstituted 5 membered heteroalkyl. In embodiments, $R^{8B}$ is substituted or unsubstituted 5 membered heteroalkyl. In embodiments, $R^{7C}$ is substituted or unsubstituted 5 membered heteroalkyl. In embodiments, $R^{8C}$ is substituted or unsubstituted 5 membered heteroalkyl. In embodiments, $R^{9C}$ is substituted or unsubstituted 5 membered heteroalkyl. In embodiments, $R^{10C}$ is substituted or unsubstituted 5 membered heteroalkyl. In embodiments, $R^{11C}$ is substituted or unsubstituted 5 membered heteroalkyl. In embodiments, $R^{12C}$ is substituted or unsubstituted 5 membered heteroalkyl. In embodiments, $R^{7A}$ is substituted 5 membered heteroalkyl. In embodiments, $R^{8A}$ is substituted 5 membered heteroalkyl. In embodiments, $R^{9A}$ is substituted 5 membered heteroalkyl. In embodiments, $R^{10A}$ is substituted 5 membered heteroalkyl. In embodiments, $R^{11A}$ is substituted 5 membered heteroalkyl. In embodiments, $R^{12A}$ is substituted 5 membered heteroalkyl. In embodiments, $R^{7B}$ is substituted 5 membered heteroalkyl. In embodiments, $R^{8B}$ is substituted 5 membered heteroalkyl. In embodiments, $R^{9B}$ is substituted 5 membered heteroalkyl. In embodiments, $R^{10B}$ is substituted 5 membered heteroalkyl. In embodiments, $R^{7B}$ is substituted 5 membered heteroalkyl. In embodiments, $R^{8B}$ is substituted 5 membered heteroalkyl. In embodiments, $R^{7C}$ is substituted 5 membered heteroalkyl. In embodiments, $R^{8C}$ is substituted 5 membered heteroalkyl. In embodiments, $R^{9C}$ is substituted 5 membered heteroalkyl. In embodiments, $R^{10C}$ is substituted 5 membered heteroalkyl. In embodiments, $R^{11C}$ is substituted 5 membered heteroalkyl. In embodiments, $R^{12C}$ is substituted 5 membered heteroalkyl. In embodiments, $R^{7A}$ is unsubstituted 5 membered heteroalkyl. In embodiments, $R^{8A}$ is unsubstituted 5 membered heteroalkyl. In embodiments, $R^{9A}$ is unsubstituted 5 membered heteroalkyl. In embodiments, $R^{10A}$ is unsubstituted 5 membered heteroalkyl. In embodiments, $R^{11A}$ is unsubstituted 5 membered heteroalkyl. In embodiments, $R^{12A}$ is unsubstituted 5 membered heteroalkyl. In embodiments, $R^{7B}$ is unsubstituted 5 membered heteroalkyl. In embodiments, $R^{8B}$ is unsubstituted 5 membered heteroalkyl. In embodiments, $R^{9B}$ is unsubstituted 5 membered heteroalkyl. In embodiments, $R^{10B}$ is unsubstituted 5 membered heteroalkyl. In embodiments, $R^{7B}$ is unsubstituted 5 membered heteroalkyl. In embodiments, $R^{8B}$ is unsubstituted 5 membered heteroalkyl. In embodiments, $R^{7C}$ is unsubstituted 5 membered heteroalkyl. In embodiments, $R^{8C}$ is unsubstituted 5 membered heteroalkyl. In embodiments, $R^{9C}$ is unsubstituted 5 membered heteroalkyl. In embodiments, $R^{10C}$ is unsubstituted 5 membered heteroalkyl. In embodiments, $R^{11C}$ is unsubstituted 5 membered heteroalkyl. In embodiments, $R^{12C}$ is unsubstituted 5 membered heteroalkyl.

In embodiments, $R^{7A}$ is substituted or unsubstituted 6 membered heteroalkyl. In embodiments, $R^{8A}$ is substituted or unsubstituted 6 membered heteroalkyl. In embodiments, $R^{9A}$ is substituted or unsubstituted 6 membered heteroalkyl. In embodiments, $R^{10A}$ is substituted or unsubstituted 6 membered heteroalkyl. In embodiments, $R^{11A}$ is substituted or unsubstituted 6 membered heteroalkyl. In embodiments, $R^{12A}$ is substituted or unsubstituted 6 membered heteroalkyl. In embodiments, $R^{7B}$ is substituted or unsubstituted 6 membered heteroalkyl. In embodiments, $R^{8B}$ is substituted or unsubstituted 6 membered heteroalkyl. In embodiments, $R^{9B}$ is substituted or unsubstituted 6 membered heteroalkyl. In embodiments, $R^{10B}$ is substituted or unsubstituted 6 membered heteroalkyl. In embodiments, $R^{7B}$ is substituted or unsubstituted 6 membered heteroalkyl. In embodiments, $R^{8B}$ is substituted or unsubstituted 6 membered heteroalkyl. In embodiments, $R^{7C}$ is substituted or unsubstituted 6 membered heteroalkyl. In embodiments, $R^{8C}$ is substituted or unsubstituted 6 membered heteroalkyl. In embodiments, $R^{9C}$ is substituted or unsubstituted 6 membered heteroalkyl. In embodiments, $R^{10C}$ is substituted or unsubstituted 6 membered heteroalkyl. In embodiments, $R^{11C}$ is substituted or unsubstituted 6 membered heteroalkyl. In embodiments, $R^{12C}$ is substituted or unsubstituted 6 membered heteroalkyl. In embodiments, $R^{7A}$ is substituted 6 membered heteroalkyl. In embodiments, $R^{8A}$ is substituted 6 membered heteroalkyl. In embodiments, $R^{9A}$ is substituted 6 membered heteroalkyl. In embodiments, $R^{10A}$ is substituted 6 membered heteroalkyl. In embodiments, $R^{11A}$ is substituted 6 membered heteroalkyl. In embodiments, $R^{12A}$ is substituted 6 membered heteroalkyl. In embodiments, $R^{7B}$ is substituted 6 membered heteroalkyl. In embodiments, $R^{8B}$ is substituted 6 membered heteroalkyl. In embodiments, $R^{9B}$ is substituted 6 membered heteroalkyl. In embodiments, $R^{10B}$ is substituted 6 membered heteroalkyl. In embodiments, $R^{7B}$ is substituted 6 membered heteroalkyl. In embodiments, $R^{8B}$ is substituted 6 membered heteroalkyl. In embodiments, $R^{7C}$ is substituted 6 membered heteroalkyl. In embodiments, $R^{8C}$ is substituted 6 membered heteroalkyl. In embodiments, $R^{9C}$ is substituted 6 membered heteroalkyl. In embodiments, $R^{10C}$ is substituted 6 membered heteroalkyl. In embodiments, $R^{11C}$ is substituted 6 membered heteroalkyl. In embodiments, $R^{12C}$ is substituted 6 membered heteroalkyl. In embodiments, $R^{7A}$ is unsubstituted 6 membered heteroalkyl. In embodiments, $R^{8A}$ is unsubstituted 6 membered heteroalkyl. In embodiments, $R^{9A}$ is unsubstituted 6 membered heteroalkyl. In embodiments, $R^{10A}$ is unsubstituted 6 membered heteroalkyl. In embodiments, $R^{11A}$ is unsubstituted 6 membered heteroalkyl. In embodiments, $R^{12A}$ is unsubstituted 6 membered heteroalkyl. In embodiments, $R^{7B}$ is unsubstituted 6 membered heteroalkyl. In embodiments, $R^{8B}$ is unsubstituted 6 membered heteroalkyl. In embodiments, $R^{9B}$ is unsubstituted 6 membered heteroalkyl. In embodiments, $R^{10B}$ is unsubstituted 6 membered heteroalkyl. In embodiments, $R^{7B}$ is unsubstituted 6 membered heteroalkyl. In embodiments, $R^{8B}$ is unsubstituted 6 membered heteroalkyl. In embodiments, $R^{7C}$ is unsubstituted 6 membered heteroalkyl. In embodiments, $R^{8C}$ is unsubstituted 6 membered heteroalkyl. In embodiments, $R^{9C}$ is unsubstituted 6 membered heteroalkyl. In embodiments, $R^{10C}$ is unsubstituted 6 membered heteroalkyl. In embodiments, $R^{11C}$ is unsubstituted 6 membered heteroalkyl. In embodiments, $R^{12C}$ is unsubstituted 6 membered heteroalkyl.

In embodiments, $R^{7A}$ is

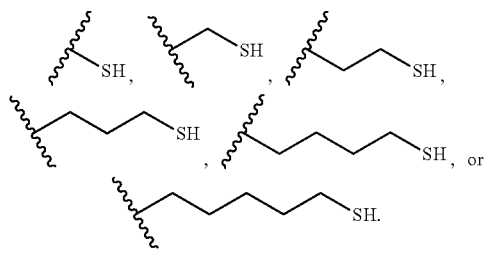

In embodiments, $R^{8A}$ is

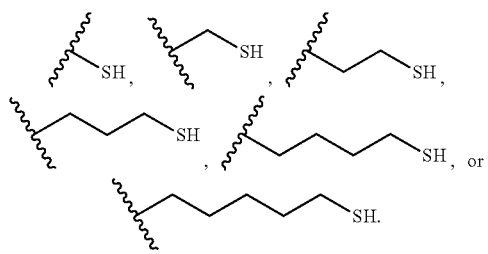

In embodiments, $R^{9A}$ is

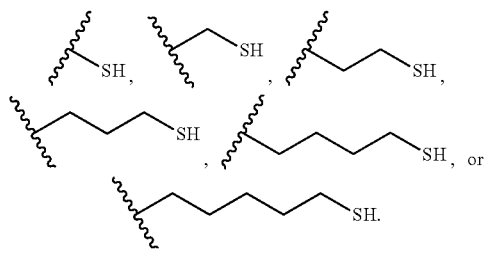

In embodiments, $R^{10A}$ is

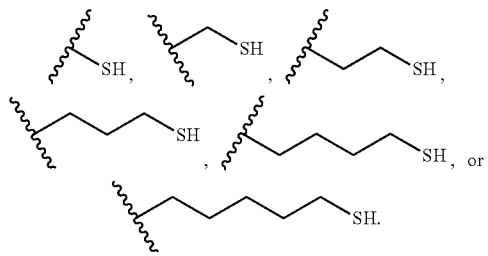

In embodiments, $R^{11A}$ is

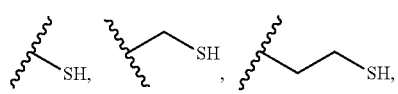

-continued

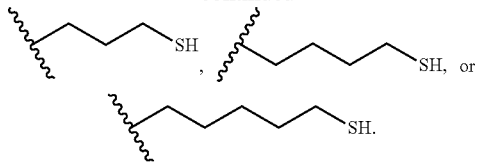

In embodiments, $R^{12A}$ is

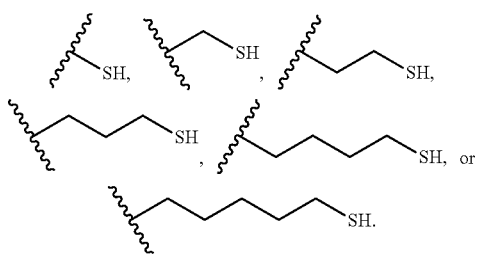

In embodiments, $R^{7A}$ is

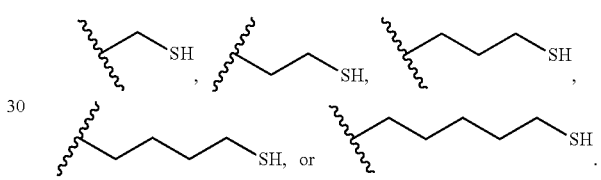

In embodiments, $R^{8A}$ is

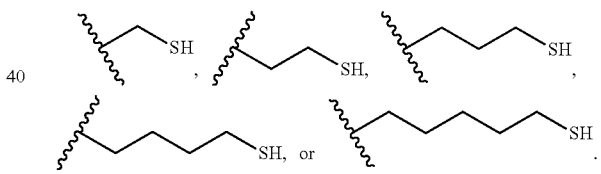

In embodiments, $R^{9A}$ is

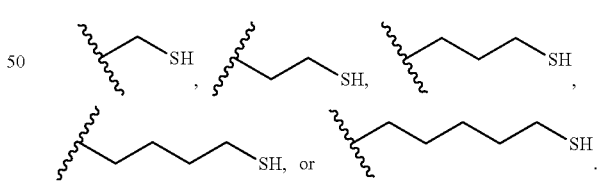

In embodiments, $R^{10A}$ is

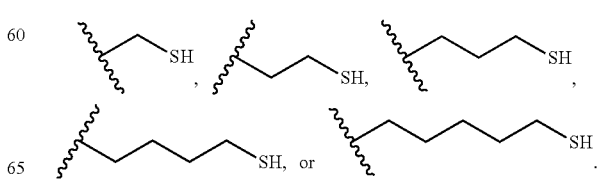

In embodiments, $R^{11A}$ is

[chemical structures showing thiol-containing alkyl chains of varying lengths ending in SH]

In embodiments $R^{12A}$ is

[chemical structures showing thiol-containing alkyl chains of varying lengths ending in SH]

In embodiments, $R^{7A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{7A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{7A}$ is unsubstituted alkyl or unsubstituted heteroalkyl.

In embodiments, a substituted $R^{7A}$ (e.g., substituted alkyl and/or substituted heteroalkyl) is substituted with at least one substituent group, size-limited substituent group, or lower substituent group; wherein if the substituted $R^{7A}$ is substituted with a plurality of groups selected from substituent groups, size-limited substituent groups, and lower substituent groups; each substituent group, size-limited substituent group, and/or lower substituent group may optionally be different. In embodiments, when $R^{7A}$ is substituted, it is substituted with at least one substituent group. In embodiments, when $R^{7A}$ is substituted, it is substituted with at least one size-limited substituent group. In embodiments, when $R^{7A}$ is substituted, it is substituted with at least one lower substituent group.

In embodiments, $R^{7B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{7B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{7B}$ is unsubstituted alkyl or unsubstituted heteroalkyl.

In embodiments, a substituted $R^{7B}$ (e.g., substituted alkyl and/or substituted heteroalkyl) is substituted with at least one substituent group, size-limited substituent group, or lower substituent group; wherein if the substituted $R^{7B}$ is substituted with a plurality of groups selected from substituent groups, size-limited substituent groups, and lower substituent groups; each substituent group, size-limited substituent group, and/or lower substituent group may optionally be different. In embodiments, when $R^{7B}$ is substituted, it is substituted with at least one substituent group. In embodiments, when $R^{7B}$ is substituted, it is substituted with at least one size-limited substituent group. In embodiments, when $R^{7B}$ is substituted, it is substituted with at least one lower substituent group.

In embodiments, $R^{7C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{7C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{7C}$ is unsubstituted alkyl or unsubstituted heteroalkyl.

In embodiments, a substituted $R^{7C}$ (e.g., substituted alkyl and/or substituted heteroalkyl) is substituted with at least one substituent group, size-limited substituent group, or lower substituent group; wherein if the substituted $R^{7C}$ is substituted with a plurality of groups selected from substituent groups, size-limited substituent groups, and lower substituent groups; each substituent group, size-limited substituent group, and/or lower substituent group may optionally be different. In embodiments, when $R^{7C}$ is substituted, it is substituted with at least one substituent group. In embodiments, when $R^{7C}$ is substituted, it is substituted with at least one size-limited substituent group. In embodiments, when $R^{7C}$ is substituted, it is substituted with at least one lower substituent group.

In embodiments, $R^{8A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{8A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{8A}$ is unsubstituted alkyl or unsubstituted heteroalkyl.

In embodiments, a substituted $R^{8A}$ (e.g., substituted alkyl and/or substituted heteroalkyl) is substituted with at least one substituent group, size-limited substituent group, or lower substituent group; wherein if the substituted $R^{8A}$ is substituted with a plurality of groups selected from substituent groups, size-limited substituent groups, and lower substituent groups; each substituent group, size-limited substituent group, and/or lower substituent group may optionally be different. In embodiments, when $R^{8A}$ is substituted, it is substituted with at least one substituent group. In embodiments, when $R^{8A}$ is substituted, it is substituted with at least one size-limited substituent group. In embodiments, when $R^{8A}$ is substituted, it is substituted with at least one lower substituent group.

In embodiments, $R^{8B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{8B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{8B}$ is unsubstituted alkyl or unsubstituted heteroalkyl.

In embodiments, a substituted $R^{8B}$ (e.g., substituted alkyl and/or substituted heteroalkyl) is substituted with at least one substituent group, size-limited substituent group, or lower substituent group; wherein if the substituted $R^{8B}$ is substituted with a plurality of groups selected from substituent groups, size-limited substituent groups, and lower substituent groups; each substituent group, size-limited substituent group, and/or lower substituent group may optionally be different. In embodiments, when $R^{8B}$ is substituted, it is substituted with at least one substituent group. In embodiments, when $R^{8B}$ is substituted, it is substituted with at least one size-limited substituent group. In embodiments, when $R^{8B}$ is substituted, it is substituted with at least one lower substituent group.

In embodiments, $R^{8C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{8C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{8C}$ is unsubstituted alkyl or unsubstituted heteroalkyl.

In embodiments, a substituted $R^{8C}$ (e.g., substituted alkyl and/or substituted heteroalkyl) is substituted with at least one substituent group, size-limited substituent group, or lower substituent group; wherein if the substituted $R^{8C}$ is substituted with a plurality of groups selected from substituent groups, size-limited substituent groups, and lower substituent groups; each substituent group, size-limited substituent group, and/or lower substituent group may optionally be different. In embodiments, when $R^{8C}$ is substituted, it is substituted with at least one substituent group. In embodiments, when $R^{8C}$ is substituted, it is substituted with at least one size-limited substituent group. In embodiments, when $R^{8C}$ is substituted, it is substituted with at least one lower substituent group.

In embodiments, $R^{9A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{9A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{9A}$ is unsubstituted alkyl or unsubstituted heteroalkyl.

In embodiments, a substituted $R^{9A}$ (e.g., substituted alkyl and/or substituted heteroalkyl) is substituted with at least one substituent group, size-limited substituent group, or lower substituent group; wherein if the substituted $R^{9A}$ is substituted with a plurality of groups selected from substituent groups, size-limited substituent groups, and lower substituent groups; each substituent group, size-limited substituent group, and/or lower substituent group may optionally be different. In embodiments, when $R^{9A}$ is substituted, it is substituted with at least one substituent group. In embodiments, when $R^{9A}$ is substituted, it is substituted with at least one size-limited substituent group. In embodiments, when $R^{9A}$ is substituted, it is substituted with at least one lower substituent group.

In embodiments, $R^{9B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{9B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{9B}$ is unsubstituted alkyl or unsubstituted heteroalkyl.

In embodiments, a substituted $R^{9B}$ (e.g., substituted alkyl and/or substituted heteroalkyl) is substituted with at least one substituent group, size-limited substituent group, or lower substituent group; wherein if the substituted $R^{9B}$ is substituted with a plurality of groups selected from substituent groups, size-limited substituent groups, and lower substituent groups; each substituent group, size-limited substituent group, and/or lower substituent group may optionally be different. In embodiments, when $R^{9B}$ is substituted, it is substituted with at least one substituent group. In embodiments, when $R^{9B}$ is substituted, it is substituted with at least one size-limited substituent group. In embodiments, when $R^{9B}$ is substituted, it is substituted with at least one lower substituent group.

In embodiments, $R^{9C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{9C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{9C}$ is unsubstituted alkyl or unsubstituted heteroalkyl.

In embodiments, a substituted $R^{9C}$ (e.g., substituted alkyl and/or substituted heteroalkyl) is substituted with at least one substituent group, size-limited substituent group, or lower substituent group; wherein if the substituted $R^{9C}$ is substituted with a plurality of groups selected from substituent groups, size-limited substituent groups, and lower substituent groups; each substituent group, size-limited substituent group, and/or lower substituent group may optionally be different. In embodiments, when $R^{9C}$ is substituted, it is substituted with at least one substituent group. In embodiments, when $R^{9C}$ is substituted, it is substituted with at least one size-limited substituent group. In embodiments, when $R^{9C}$ is substituted, it is substituted with at least one lower substituent group.

In embodiments, $R^{10A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{10A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{10A}$ is unsubstituted alkyl or unsubstituted heteroalkyl.

In embodiments, a substituted $R^{10A}$ (e.g., substituted alkyl and/or substituted heteroalkyl) is substituted with at least one substituent group, size-limited substituent group, or lower substituent group; wherein if the substituted $R^{10A}$ is substituted with a plurality of groups selected from substituent groups, size-limited substituent groups, and lower substituent groups; each substituent group, size-limited substituent group, and/or lower substituent group may optionally be different. In embodiments, when $R^{10A}$ is substituted, it is substituted with at least one substituent group. In embodiments, when $R^{10A}$ is substituted, it is substituted with at least one size-limited substituent group. In embodiments, when $R^{10A}$ is substituted, it is substituted with at least one lower substituent group.

In embodiments, $R^{10B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{10B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{10B}$ is unsubstituted alkyl or unsubstituted heteroalkyl.

In embodiments, a substituted $R^{10B}$ (e.g., substituted alkyl and/or substituted heteroalkyl) is substituted with at least one substituent group, size-limited substituent group, or lower substituent group; wherein if the substituted $R^{10B}$ is substituted with a plurality of groups selected from substituent groups, size-limited substituent groups, and lower substituent groups; each substituent group, size-limited substituent group, and/or lower substituent group may optionally be different. In embodiments, when $R^{10B}$ is substituted, it is substituted with at least one substituent group. In embodiments, when $R^{10B}$ is substituted, it is substituted with at least one size-limited substituent group. In embodiments, when $R^{10B}$ is substituted, it is substituted with at least one lower substituent group.

In embodiments, $R^{10C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{10C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{10C}$ is unsubstituted alkyl or unsubstituted heteroalkyl.

In embodiments, a substituted $R^{10C}$ (e.g., substituted alkyl and/or substituted heteroalkyl) is substituted with at least one substituent group, size-limited substituent group, or lower substituent group; wherein if the substituted $R^{10C}$ is substituted with a plurality of groups selected from substituent groups, size-limited substituent groups, and lower substituent groups; each substituent group, size-limited substituent group, and/or lower substituent group may optionally be different. In embodiments, when $R^{10C}$ is substituted, it is substituted with at least one substituent group. In embodiments, when $R^{10C}$ is substituted, it is substituted with at least one size-limited substituent group. In embodiments, when $R^{10C}$ is substituted, it is substituted with at least one lower substituent group.

In embodiments, $R^{11A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{11A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{11A}$ is unsubstituted alkyl or unsubstituted heteroalkyl.

In embodiments, a substituted $R^{11A}$ (e.g., substituted alkyl and/or substituted heteroalkyl) is substituted with at least one substituent group, size-limited substituent group, or lower substituent group; wherein if the substituted $R^{11A}$ is substituted with a plurality of groups selected from substituent groups, size-limited substituent groups, and lower substituent groups; each substituent group, size-limited substituent group, and/or lower substituent group may optionally be different. In embodiments, when $R^{11A}$ is substituted, it is substituted with at least one substituent group. In embodiments, when $R^{11A}$ is substituted, it is substituted with at least one size-limited substituent group. In embodiments, when $R^{11A}$ is substituted, it is substituted with at least one lower substituent group.

In embodiments, $R^{11B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{11B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{11B}$ is unsubstituted alkyl or unsubstituted heteroalkyl.

In embodiments, a substituted $R^{11B}$ (e.g., substituted alkyl and/or substituted heteroalkyl) is substituted with at least one substituent group, size-limited substituent group, or lower substituent group; wherein if the substituted $R^{11B}$ is substituted with a plurality of groups selected from substituent groups, size-limited substituent groups, and lower substituent groups; each substituent group, size-limited substituent group, and/or lower substituent group may optionally be different. In embodiments, when $R^{11B}$ is substituted, it is substituted with at least one substituent group. In embodiments, when $R^{11B}$ is substituted, it is substituted with at least one size-limited substituent group. In embodiments, when $R^{11B}$ is substituted, it is substituted with at least one lower substituent group.

In embodiments, $R^{11C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{11C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{11C}$ is unsubstituted alkyl or unsubstituted heteroalkyl.

In embodiments, a substituted $R^{11C}$ (e.g., substituted alkyl and/or substituted heteroalkyl) is substituted with at least one substituent group, size-limited substituent group, or lower substituent group; wherein if the substituted $R^{11C}$ is substituted with a plurality of groups selected from substituent groups, size-limited substituent groups, and lower substituent groups; each substituent group, size-limited substituent group, and/or lower substituent group may optionally be different. In embodiments, when $R^{11C}$ is substituted, it is substituted with at least one substituent group. In embodiments, when $R^{11C}$ is substituted, it is substituted with at least one size-limited substituent group. In embodiments, when $R^{11C}$ is substituted, it is substituted with at least one lower substituent group.

In embodiments, $R^{12A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{12A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{12A}$ is unsubstituted alkyl or unsubstituted heteroalkyl.

In embodiments, a substituted $R^{12A}$ (e.g., substituted alkyl and/or substituted heteroalkyl) is substituted with at least one substituent group, size-limited substituent group, or lower substituent group; wherein if the substituted $R^{12A}$ is substituted with a plurality of groups selected from substituent groups, size-limited substituent groups, and lower substituent groups; each substituent group, size-limited substituent group, and/or lower substituent group may optionally be different. In embodiments, when $R^{12A}$ is substituted, it is substituted with at least one substituent group. In embodiments, when $R^{12A}$ is substituted, it is substituted with at least one size-limited substituent group. In embodiments, when $R^{12A}$ is substituted, it is substituted with at least one lower substituent group.

In embodiments, $R^{12B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{12B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{12B}$ is unsubstituted alkyl or unsubstituted heteroalkyl.

In embodiments, a substituted $R^{12B}$ (e.g., substituted alkyl and/or substituted heteroalkyl) is substituted with at least one substituent group, size-limited substituent group, or lower substituent group; wherein if the substituted $R^{12B}$ is substituted with a plurality of groups selected from substituent groups, size-limited substituent groups, and lower substituent groups; each substituent group, size-limited substituent group, and/or lower substituent group may optionally be different. In embodiments, when $R^{12B}$ is substituted, it is substituted with at least one substituent group. In embodiments, when $R^{12B}$ is substituted, it is substituted with at least one size-limited substituent group. In embodiments, when $R^{12B}$ is substituted, it is substituted with at least one lower substituent group.

In embodiments, $R^{12C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{12C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{12C}$ is unsubstituted alkyl or unsubstituted heteroalkyl.

In embodiments, a substituted $R^{12C}$ (e.g., substituted alkyl and/or substituted heteroalkyl) is substituted with at least one substituent group, size-limited substituent group, or lower substituent group; wherein if the substituted $R^{12C}$ is substituted with a plurality of groups selected from substituent groups, size-limited substituent groups, and lower substituent groups; each substituent group, size-limited substituent group, and/or lower substituent group may optionally be different. In embodiments, when $R^{12C}$ is substituted, it is substituted with at least one substituent group. In embodiments, when $R^{12C}$ is substituted, it is substituted with at least one size-limited substituent group. In embodiments, when $R^{12C}$ is substituted, it is substituted with at least one lower substituent group.

In embodiments, $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ are each independently substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ are each independently substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ are each independently unsubstituted alkyl, or unsubstituted heteroalkyl.

In embodiments, $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ are each independently substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{1C}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ are each independently substituted (e.g., substituted with a substituent group, a size-limited substituent group, or lower substituent group) or unsubstituted alkyl (e.g., $C_1$-$C_8$, $C_1$-$C_6$, $C_1$-$C_4$, or $C_1$-$C_2$), or substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered). In embodiments, $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{1C}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ are each independently unsubstituted alkyl (e.g., $C_1$-$C_8$, $C_1$-$C_6$, $C_1$-$C_4$, or $C_1$-$C_2$), or unsubstituted heteroalkyl (e.g., 2 to 8 membered, 2 to 6 membered, 4 to 6 membered, 2 to 3 membered, or 4 to 5 membered).

In embodiments, a substituted $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{1C}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, or $R^{12C}$ (e.g. substituted alkyl and/or substituted heteroalkyl) is substituted with at least one substituent group, size-limited substituent group, or lower substituent group; wherein if the substituted $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{1C}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ is substituted with a plurality of groups selected from substituent groups, size-limited substituent groups, and lower substituent groups; each substituent group, size-limited substituent group, and/or lower substituent group may optionally be different. In embodiments, when $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{1C}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, or $R^{12C}$ is substituted, it is substituted with at least one substituent group. In embodiments, when $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{1C}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, or $R^{12C}$ is substituted, it is substituted with at least one size-limited substituent group. In embodiments, when $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{1C}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, or $R^{12C}$ is substituted, it is substituted with at least one lower substituent group.

In embodiments, the compound has the formula:

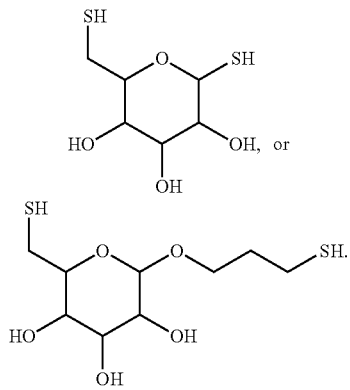

In embodiments, the compound has the formula:

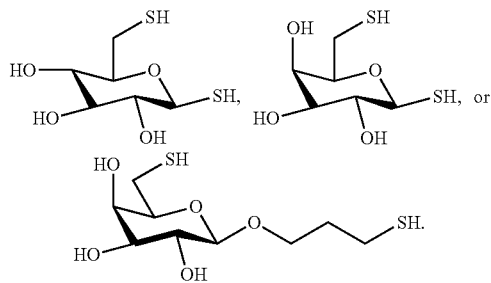

In embodiments, the compound has the formula

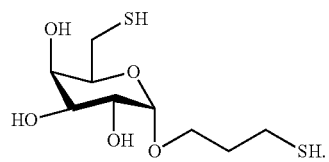

In embodiments, the compound has the formula:

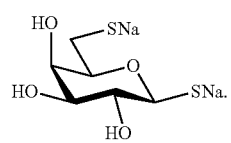

A person having skill in the art will recognize that this salt form is within the scope of formula I and embodiments thereof.

In embodiments, the compound has the formula:

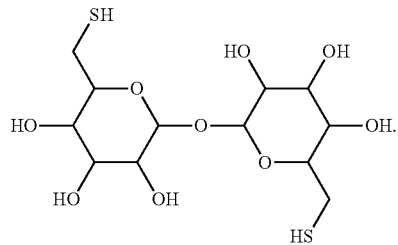 [SMILES: OC1C(CS)OC(OC2OC(CS)C(O)C(O)C2O)C(O)C1O]

In embodiments, the compound has the structure:

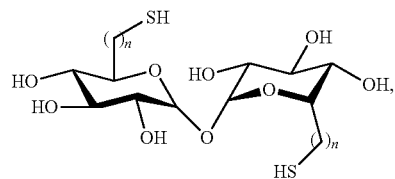

wherein n is 1 to 5. In embodiments, n is 1 to 3. In embodiments, n is 1.

In embodiments, the compound has the formula:

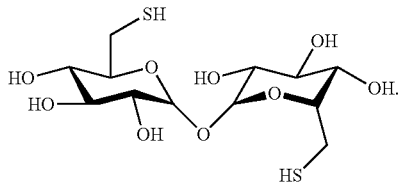

In embodiments, the compound has the formula:

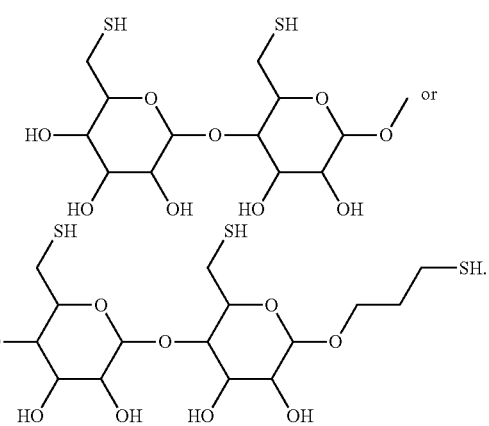

In embodiments, the compound has the structure:

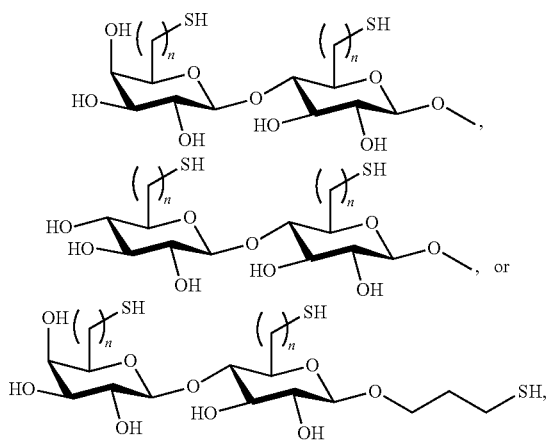

wherein n is 1 to 5. In embodiments, n is 1 to 3. In embodiments, n is 1.

In embodiments, the compound has the formula:

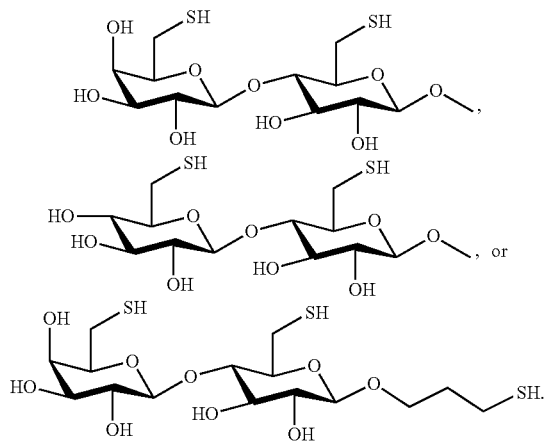

In an aspect is provided a compound having the formula:

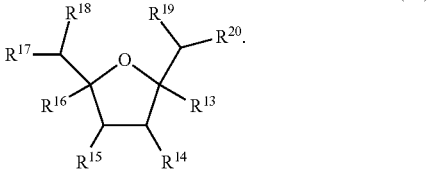

(IV)

$R^{13}$ is hydrogen, —$SR^{13A}$, —$OR^{13A}$, —$NR^{13B}R^{13C}$, —$NR^{13B}C(O)R^{13C}$, —$NR^{13B}C(O)OR^{13C}$, substituted or unsubstituted $C_1$-$C_{10}$ alkyl, or substituted or unsubstituted 2 to 10 membered heteroalkyl. $R^{14}$ is —$SR^{14A}$, —$OR^{14A}$, —$NR^{14B}R^{14C}$, —$NR^{14B}C(O)R^{14C}$, —$NR^{14B}C(O)OR^{14C}$, substituted or unsubstituted $C_1$-$C_{10}$ alkyl, or substituted or unsubstituted 2 to 10 membered heteroalkyl. $R^{15}$ is —$SR^{15A}$, —$OR^{15A}$, —$NR^{15B}R^{15C}$, —$NR^{15B}C(O)R^{15C}$, —$NR^{15B}C(O)OR^{15C}$, substituted or unsubstituted $C_1$-$C_{10}$ alkyl, or substituted or unsubstituted 2 to 10 membered heteroalkyl. $R^{16}$ is hydrogen, —$SR^{16A}$, —$OR^{16A}$, —$NR^{16B}R^{16C}$, —$NR^{16B}C(O)R^{16C}$, —$NR^{16B}C(O)OR^{16C}$, substituted or unsubstituted $C_1$-$C_{10}$ alkyl, or substituted or unsubstituted 2 to 10 membered heteroalkyl. $R^{17}$ is hydrogen, —$SR^{17A}$, —$OR^{17A}$, —$NR^{17B}R^{17C}$, —$NR^{17B}C(O)R^{17C}$, —$NR^{17B}C(O)OR^{17C}$, or substituted or unsubstituted $C_1$-$C_{10}$ alkyl, substituted or unsubstituted 2 to 10 membered heteroalkyl. $R^{18}$ is —$SR^{18A}$, —$OR^{18A}$, —$NR^{18B}R^{18C}$, —$NR^{18B}C(O)R^{18C}$, —$NR^{18B}C(O)OR^{18C}$, or substituted or unsubstituted $C_1$-$C_{10}$ alkyl, substituted or unsubstituted 2 to 10 membered heteroalkyl. $R^{19}$ is hydrogen, —$SR^{19A}$, —$OR^{19A}$, —$NR^{19B}R^{19C}$, —$NR^{19B}C(O)R^{19C}$, —$NR^{19B}C(O)OR^{19C}$, or substituted or unsubstituted $C_1$-$C_{10}$ alkyl, substituted or unsubstituted 2 to 10 membered heteroalkyl. $R^{20}$ is —$SR^{20A}$, —$OR^{20A}$, —$NR^{20B}R^{20C}$, —$NR^{20B}C(O)R^{20C}$, —$NR^{20B}C(O)OR^{20C}$, or substituted or unsubstituted $C_1$-$C_{10}$ alkyl, substituted or unsubstituted 2 to 10 membered heteroalkyl. $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{16B}$, $R^{17B}$, $R^{18B}$, $R^{19B}$, $R^{20B}$, $R^{13C}$, $R^{14C}$, $R^{15C}$, $R^{16C}$, $R^{17C}$, $R^{18C}$, $R^{19C}$, and $R^{20C}$ are each independently hydrogen, substituted or unsubstituted $C_1$-$C_{10}$ alkyl, substituted or unsubstituted 2 to 10 membered heteroalkyl; and provided the compound comprises at least two thiol moieties, or a pharmaceutically acceptable salt thereof.

In embodiments, the compound has the formula:

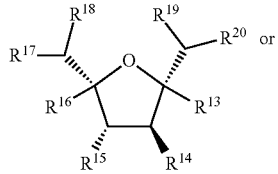

(IVa)

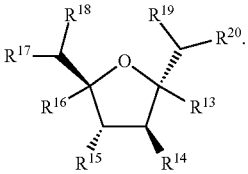

(IVb)

In embodiments, $R^{13}$ is hydrogen, —$SR^{13A}$, —$OR^{13A}$, thiol-substituted or unsubstituted $C_1$-$C_{10}$ alkyl, or thiol-substituted or unsubstituted 2 to 10 membered heteroalkyl. In embodiments, $R^{14}$ is —$SR^{14A}$, —$OR^{14A}$, thiol-substituted or unsubstituted $C_1$-$C_{10}$ alkyl, or thiol-substituted or unsubstituted 2 to 10 membered heteroalkyl. In embodiments, $R^{15}$ is —$SR^{15A}$, —$OR^{15A}$, thiol-substituted or unsubstituted $C_1$-$C_{10}$ alkyl, or thiol-substituted or unsubstituted 2 to 10 membered heteroalkyl. In embodiments, $R^{16}$ is hydrogen, —$SR^{16A}$, —$OR^{16A}$, thiol-substituted or unsubstituted $C_1$-$C_{10}$ alkyl, or thiol-substituted or unsubstituted 2 to 10 membered heteroalkyl. In embodiments, $R^{17}$ is hydrogen, —$SR^{17A}$, —$OR^{17A}$, thiol-substituted or unsubstituted $C_1$-$C_{10}$ alkyl, or thiol-substituted or unsubstituted 2 to 10 membered heteroalkyl. In embodiments, $R^{18}$ is —$SR^{18A}$, —$OR^{18A}$, thiol-substituted or unsubstituted $C_1$-$C_{10}$ alkyl, or thiol-substituted or unsubstituted 2 to 10 membered heteroalkyl. In embodiments, $R^{19}$ is hydrogen, —$SR^{19A}$, —$OR^{19A}$, thiol-substituted or unsubstituted $C_1$-$C_{10}$ alkyl, or thiol-substituted or unsubstituted 2 to 10 membered heteroalkyl. In embodiments, $R^{20}$ is —$SR^{20A}$, —$OR^{20A}$, thiol-substituted or unsubstituted $C_1$-$C_{10}$ alkyl, or thiol-substituted or unsubstituted 2 to 10 membered heteroalkyl.

In embodiments, $R^{13}$ is hydrogen, —$SR^{13A}$, —$OR^{13A}$, thiol-substituted or unsubstituted $C_1$-$C_{10}$ alkyl, or thiol-substituted or unsubstituted 2 to 10 membered heteroalkyl; $R^{14}$ is —$SR^{14A}$, —$OR^{14A}$, thiol-substituted or unsubstituted $C_1$-$C_{10}$ alkyl, or thiol-substituted or unsubstituted 2 to 10 membered heteroalkyl; $R^{15}$ is —$SR^{15A}$, —$OR^{15A}$, thiol-substituted or unsubstituted $C_1$-$C_{10}$ alkyl, or thiol-substituted or unsubstituted 2 to 10 membered heteroalkyl; $R^{16}$ is hydrogen, —$SR^{16A}$, —$OR^{16A}$, thiol-substituted or unsubstituted $C_1$-$C_{10}$ alkyl, or thiol-substituted or unsubstituted 2 to 10 membered heteroalkyl; $R^{17}$ is hydrogen, —$SR^{17A}$, —$OR^{17A}$, thiol-substituted or unsubstituted $C_1$-$C_{10}$ alkyl, or thiol-substituted or unsubstituted 2 to 10 membered heteroalkyl; $R^{18}$ is —$SR^{18A}$, —$OR^{18A}$, thiol-substituted or unsubstituted $C_1$-$C_{10}$ alkyl, or thiol-substituted or unsubstituted 2 to 10 membered heteroalkyl; $R^{19}$ is hydrogen, —$SR^{19A}$, —$OR^{19A}$, thiol-substituted or unsubstituted $C_1$-$C_{10}$ alkyl, or thiol-substituted or unsubstituted 2 to 10 membered heteroalkyl; and $R^{20}$ is —$SR^{20A}$, —$OR^{20A}$, thiol-substituted or unsubstituted $C_1$-$C_{10}$ alkyl, or thiol-substituted or unsubstituted 2 to 10 membered heteroalkyl.

In embodiments, $R^{13}$ is hydrogen, —$SR^{13A}$ or —$OR^{13A}$; $R^{14}$ is —$SR^{14A}$ or —$OR^{14A}$; $R^{15}$ is —$SR^{15A}$ or —$OR^{15A}$; $R^{16}$ is hydrogen, —$SR^{16A}$ or —$OR^{16A}$; $R^{18}$ is —$SR^{18A}$ or —$OR^{18A}$; and $R^{20}$ is —$SR^{20A}$ or —$OR^{20A}$.

In embodiments, the compound has the structure:

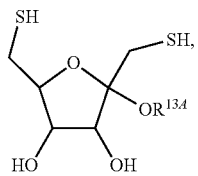

wherein $R^{13A}$ is as described herein.

In embodiments, the compound has the structure:

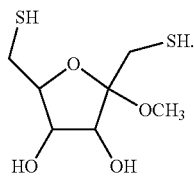

In an aspect is provided a compound having the formula:

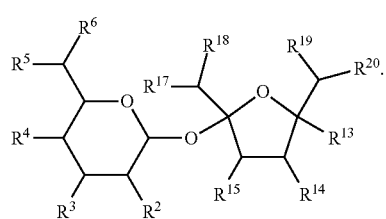

(V)

$R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted $C_1$-$C_{10}$ alkyl, or substituted or unsubstituted 2 to 10 membered heteroalkyl. $R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted $C_1$-$C_{10}$ alkyl, or substituted or unsubstituted 2 to 10 membered heteroalkyl. $R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted $C_1$-$C_{10}$ alkyl, or substituted or unsubstituted 2 to 10 membered heteroalkyl. $R^5$ is hydrogen, —$SR^{5A}$, —$OR^{5A}$, —$NR^{5B}R^{5C}$, —$NR^{5B}C(O)R^{5C}$, —$NR^{5B}C(O)OR^{5C}$, or substituted or unsubstituted $C_1$-$C_{10}$ alkyl, substituted or unsubstituted 2 to 10 membered heteroalkyl. $R^6$ is —$SR^{6A}$, —$OR^{6A}$, —$NR^{6B}R^{6C}$, —$NR^{6B}C(O)R^{6C}$, —$NR^{6B}C(O)OR^{6C}$, or substituted or unsubstituted $C_1$-$C_{10}$ alkyl, substituted or unsubstituted 2 to 10 membered heteroalkyl. $R^{13}$ is hydrogen, —$SR^{13A}$, —$OR^{13A}$, —$NR^{13B}R^{13C}$, —$NR^{13B}C(O)R^{13C}$, —$NR^{13B}C(O)OR^{13C}$, substituted or unsubstituted $C_1$-$C_{10}$ alkyl, or substituted or unsubstituted 2 to 10 membered heteroalkyl. $R^{14}$ is —$SR^{14A}$, —$OR^{14A}$, —$NR^{14B}R^{14C}$, —$NR^{14B}C(O)R^{14C}$, —$NR^{14B}C(O)OR^{14C}$, substituted or unsubstituted $C_1$-$C_{10}$ alkyl, or substituted or unsubstituted 2 to 10 membered heteroalkyl. $R^{15}$ is —$SR^{15A}$, —$OR^{15A}$, —$NR^{15B}R^{15C}$, —$NR^{15B}C(O)R^{15C}$, —$NR^{15B}C(O)OR^{15C}$, substituted or unsubstituted $C_1$-$C_{10}$ alkyl, or substituted or unsubstituted 2 to 10 membered heteroalkyl. $R^{17}$ is hydrogen, —$SR^{17A}$, —$OR^{17A}$, —$NR^{17B}R^{17C}$, —$NR^{17B}C(O)R^{17C}$, —$NR^{17B}C(O)OR^{17C}$, or substituted or unsubstituted $C_1$-$C_{10}$, alkyl, substituted or unsubstituted 2 to 10 membered heteroalkyl. $R^{18}$ is —$SR^{18A}$, —$OR^{18A}$, —$NR^{18B}R^{18C}$, —$NR^{18B}C(O)R^{18C}$, —$NR^{18B}C(O)OR^{18C}$, or substituted or unsubstituted $C_1$-$C_{10}$, alkyl, substituted or unsubstituted 2 to 10 membered heteroalkyl. $R^{19}$ is hydrogen, —$SR^{19A}$, —$OR^{19A}$, —$NR^{19B}R^{19C}$, —$NR^{19B}C(O)R^{19C}$, —$NR^{19B}C(O)OR^{19C}$, or substituted or unsubstituted $C_1$-$C_{10}$, alkyl, substituted or unsubstituted 2 to 10 membered heteroalkyl. $R^{20}$ is —$SR^{20A}$, —$OR^{20A}$, —$NR^{20B}R^{20C}$, —$NR^{20B}C(O)R^{20C}$, —$NR^{20B}C(O)OR^{20C}$, or substituted or unsubstituted $C_1$-$C_{10}$, alkyl, substituted or unsubstituted 2 to 10 membered heteroalkyl; and $R^{2A}$, $R^{3A}$, $R^{4A}$, $R^{5A}$, $R^{6A}$, $R^{2B}$, $R^{3B}$, $R^{4B}$, $R^{5B}$, $R^{6B}$, $R^{2C}$, $R^{3C}$, $R^{4C}$, $R^{5C}$, $R^{6C}$, $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{17B}$, $R^{18B}$, $R^{19B}$, $R^{20B}$, $R^{13C}$, $R^{14C}$, $R^{15C}$, $R^{17C}$, $R^{18C}$, $R^{19C}$, and $R^{20C}$ are each independently hydrogen, substituted or unsubstituted $C_1$-$C_{10}$ alkyl, substituted or unsubstituted 2 to 10 membered heteroalkyl; and provided the compound comprises at least two thiol moieties, or a pharmaceutically acceptable salt thereof. In embodiments, the compound is not

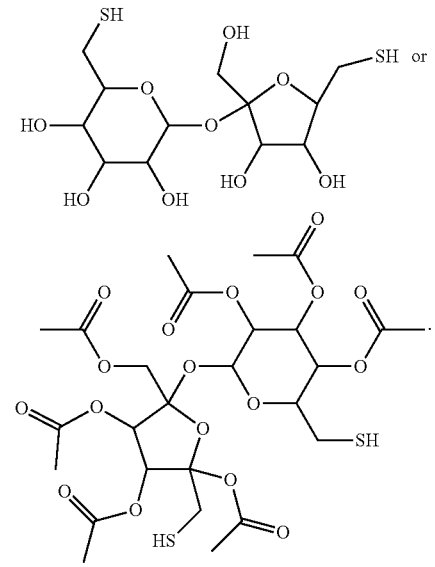

In embodiments, the compound includes at a maximum two thiol moieties.

In embodiments, $R^{13A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{13A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{13A}$ is unsubstituted alkyl or unsubstituted heteroalkyl.

In embodiments, a substituted $R^{13A}$ (e.g., substituted alkyl and/or substituted heteroalkyl) is substituted with at least one substituent group, size-limited substituent group, or lower substituent group; wherein if the substituted $R^{13A}$ is substituted with a plurality of groups selected from substituent groups, size-limited substituent groups, and lower substituent groups; each substituent group, size-limited substituent group, and/or lower substituent group may optionally be different. In embodiments, when $R^{13A}$ is substituted, it is substituted with at least one substituent group. In embodiments, when $R^{13A}$ is substituted, it is substituted with at least one size-limited substituent group. In embodiments, when $R^{13A}$ is substituted, it is substituted with at least one lower substituent group.

In embodiments, $R^{13B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{13B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{13B}$ is unsubstituted alkyl or unsubstituted heteroalkyl.

In embodiments, a substituted $R^{13B}$ (e.g., substituted alkyl and/or substituted heteroalkyl) is substituted with at least one substituent group, size-limited substituent group, or lower substituent group; wherein if the substituted $R^{13B}$ is substituted with a plurality of groups selected from substituent groups, size-limited substituent groups, and lower substituent groups; each substituent group, size-limited substituent group, and/or lower substituent group may optionally be different. In embodiments, when $R^{13B}$ is substituted, it is substituted with at least one substituent group. In embodiments, when $R^{13B}$ is substituted, it is substituted with at least one size-limited substituent group. In embodiments, when $R^{13B}$ is substituted, it is substituted with at least one lower substituent group.

In embodiments, $R^{13C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{13C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{13C}$ is unsubstituted alkyl or unsubstituted heteroalkyl.

In embodiments, a substituted $R^{13C}$ (e.g., substituted alkyl and/or substituted heteroalkyl) is substituted with at least one substituent group, size-limited substituent group, or lower substituent group; wherein if the substituted $R^{13C}$ is substituted with a plurality of groups selected from substituent groups, size-limited substituent groups, and lower substituent groups; each substituent group, size-limited substituent group, and/or lower substituent group may optionally be different. In embodiments, when $R^{13C}$ is substituted, it is substituted with at least one substituent group. In embodiments, when $R^{13C}$ is substituted, it is substituted with at least one size-limited substituent group. In embodiments, when $R^{13C}$ is substituted, it is substituted with at least one lower substituent group.

In embodiments, $R^{14A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{14A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{14A}$ is unsubstituted alkyl or unsubstituted heteroalkyl.

In embodiments, a substituted $R^{14A}$ (e.g., substituted alkyl and/or substituted heteroalkyl) is substituted with at least one substituent group, size-limited substituent group, or lower substituent group; wherein if the substituted $R^{14A}$ is substituted with a plurality of groups selected from substituent groups, size-limited substituent groups, and lower substituent groups; each substituent group, size-limited substituent group, and/or lower substituent group may optionally be different. In embodiments, when $R^{14A}$ is substituted, it is substituted with at least one substituent group. In embodiments, when $R^{14A}$ is substituted, it is substituted with at least one size-limited substituent group. In embodiments, when $R^{14A}$ is substituted, it is substituted with at least one lower substituent group.

In embodiments, $R^{14B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{14B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{14B}$ is unsubstituted alkyl or unsubstituted heteroalkyl.

In embodiments, a substituted $R^{14B}$ (e.g., substituted alkyl and/or substituted heteroalkyl) is substituted with at least one substituent group, size-limited substituent group, or lower substituent group; wherein if the substituted $R^{14B}$ is substituted with a plurality of groups selected from substituent groups, size-limited substituent groups, and lower substituent groups; each substituent group, size-limited substituent group, and/or lower substituent group may optionally be different. In embodiments, when $R^{14B}$ is substituted, it is substituted with at least one substituent group. In embodiments, when $R^{14B}$ is substituted, it is substituted with at least one size-limited substituent group. In embodiments, when $R^{14B}$ is substituted, it is substituted with at least one lower substituent group.

In embodiments, $R^{14C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{14C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{14C}$ is unsubstituted alkyl or unsubstituted heteroalkyl.

In embodiments, a substituted $R^{14C}$ (e.g., substituted alkyl and/or substituted heteroalkyl) is substituted with at least one substituent group, size-limited substituent group, or lower substituent group; wherein if the substituted $R^{14C}$ is substituted with a plurality of groups selected from substituent groups, size-limited substituent groups, and lower substituent groups; each substituent group, size-limited substituent group, and/or lower substituent group may optionally be different. In embodiments, when $R^{14C}$ is substituted, it is substituted with at least one substituent group. In embodiments, when $R^{14C}$ is substituted, it is substituted with at least one size-limited substituent group. In embodiments, when $R^{14C}$ is substituted, it is substituted with at least one lower substituent group.

In embodiments, $R^{15A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{15A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{15A}$ is unsubstituted alkyl or unsubstituted heteroalkyl.

In embodiments, a substituted $R^{15A}$ (e.g., substituted alkyl and/or substituted heteroalkyl) is substituted with at least one substituent group, size-limited substituent group, or lower substituent group; wherein if the substituted $R^{15A}$ is substituted with a plurality of groups selected from substituent groups, size-limited substituent groups, and lower substituent groups; each substituent group, size-limited substituent group, and/or lower substituent group may optionally be different. In embodiments, when $R^{15A}$ is substituted, it is substituted with at least one substituent group. In embodiments, when $R^{15A}$ is substituted, it is substituted with at least one size-limited substituent group. In embodiments, when $R^{15A}$ is substituted, it is substituted with at least one lower substituent group.

In embodiments, $R^{15B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{15B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{15B}$ is unsubstituted alkyl or unsubstituted heteroalkyl.

In embodiments, a substituted $R^{15B}$ (e.g., substituted alkyl and/or substituted heteroalkyl) is substituted with at least one substituent group, size-limited substituent group, or lower substituent group; wherein if the substituted $R^{15B}$ is substituted with a plurality of groups selected from substituent groups, size-limited substituent groups, and lower substituent groups; each substituent group, size-limited substituent group, and/or lower substituent group may optionally be different. In embodiments, when $R^{15B}$ is substituted, it is substituted with at least one substituent group. In embodiments, when $R^{15B}$ is substituted, it is substituted with at least one size-limited substituent group. In embodiments, when $R^{15B}$ is substituted, it is substituted with at least one lower substituent group.

In embodiments, $R^{15C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{15C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{15C}$ is unsubstituted alkyl or unsubstituted heteroalkyl.

In embodiments, a substituted $R^{15C}$ (e.g., substituted alkyl and/or substituted heteroalkyl) is substituted with at least one substituent group, size-limited substituent group, or lower substituent group; wherein if the substituted $R^{15C}$ is substituted with a plurality of groups selected from substituent groups, size-limited substituent groups, and lower substituent groups; each substituent group, size-limited substituent group, and/or lower substituent group may optionally be different. In embodiments, when $R^{15C}$ is substituted, it is substituted with at least one substituent group. In embodiments, when $R^{15C}$ is substituted, it is substituted with at least one size-limited substituent group. In embodiments, when $R^{15C}$ is substituted, it is substituted with at least one lower substituent group.

In embodiments, $R^{16A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{16A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{16A}$ is unsubstituted alkyl or unsubstituted heteroalkyl.

In embodiments, a substituted $R^{16A}$ (e.g., substituted alkyl and/or substituted heteroalkyl) is substituted with at least one substituent group, size-limited substituent group, or lower substituent group; wherein if the substituted $R^{16A}$ is substituted with a plurality of groups selected from substituent groups, size-limited substituent groups, and lower substituent groups; each substituent group, size-limited substituent group, and/or lower substituent group may optionally be different. In embodiments, when $R^{16A}$ is substituted, it is substituted with at least one substituent group. In embodiments, when $R^{16A}$ is substituted, it is substituted with at least one size-limited substituent group. In embodiments, when $R^{16A}$ is substituted, it is substituted with at least one lower substituent group.

In embodiments, $R^{16B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{16B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{16B}$ is unsubstituted alkyl or unsubstituted heteroalkyl.

In embodiments, a substituted $R^{16B}$ (e.g., substituted alkyl and/or substituted heteroalkyl) is substituted with at least one substituent group, size-limited substituent group, or lower substituent group; wherein if the substituted $R^{16B}$ is substituted with a plurality of groups selected from substituent groups, size-limited substituent groups, and lower substituent groups; each substituent group, size-limited substituent group, and/or lower substituent group may optionally be different. In embodiments, when $R^{16B}$ is substituted, it is substituted with at least one substituent group. In embodiments, when $R^{16B}$ is substituted, it is substituted with at least one size-limited substituent group. In embodiments, when $R^{16B}$ is substituted, it is substituted with at least one lower substituent group.

In embodiments, $R^{16C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{16C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{16C}$ is unsubstituted alkyl or unsubstituted heteroalkyl.

In embodiments, a substituted $R^{16C}$ (e.g., substituted alkyl and/or substituted heteroalkyl) is substituted with at least one substituent group, size-limited substituent group, or lower substituent group; wherein if the substituted $R^{16C}$ is substituted with a plurality of groups selected from substituent groups, size-limited substituent groups, and lower substituent groups; each substituent group, size-limited substituent group, and/or lower substituent group may optionally be different. In embodiments, when $R^{16C}$ is substituted, it is substituted with at least one substituent group. In embodiments, when $R^{16C}$ is substituted, it is substituted with at least one size-limited substituent group. In embodiments, when $R^{16C}$ is substituted, it is substituted with at least one lower substituent group.

In embodiments, $R^{17A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{17A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{17A}$ is unsubstituted alkyl or unsubstituted heteroalkyl.

In embodiments, a substituted $R^{17A}$ (e.g., substituted alkyl and/or substituted heteroalkyl) is substituted with at least one substituent group, size-limited substituent group, or lower substituent group; wherein if the substituted $R^{17A}$ is substituted with a plurality of groups selected from substituent groups, size-limited substituent groups, and lower substituent groups; each substituent group, size-limited substituent group, and/or lower substituent group may optionally be different. In embodiments, when $R^{17A}$ is substituted, it is substituted with at least one substituent group. In embodiments, when $R^{17A}$ is substituted, it is substituted with at least one size-limited substituent group. In embodiments, when $R^{17A}$ is substituted, it is substituted with at least one lower substituent group.

In embodiments, $R^{17B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{17B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{17B}$ is unsubstituted alkyl or unsubstituted heteroalkyl.

In embodiments, a substituted $R^{17B}$ (e.g., substituted alkyl and/or substituted heteroalkyl) is substituted with at least one substituent group, size-limited substituent group, or lower substituent group; wherein if the substituted $R^{17B}$ is substituted with a plurality of groups selected from substituent groups, size-limited substituent groups, and lower substituent groups; each substituent group, size-limited substituent group, and/or lower substituent group may optionally be different. In embodiments, when $R^{17B}$ is substituted, it is substituted with at least one substituent group. In embodiments, when $R^{17B}$ is substituted, it is substituted with at least one size-limited substituent group. In embodiments, when $R^{17B}$ is substituted, it is substituted with at least one lower substituent group.

In embodiments, $R^{17C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{17C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{17C}$ is unsubstituted alkyl or unsubstituted heteroalkyl.

In embodiments, a substituted $R^{17C}$ (e.g., substituted alkyl and/or substituted heteroalkyl) is substituted with at least one substituent group, size-limited substituent group, or lower substituent group; wherein if the substituted $R^{17C}$ is substituted with a plurality of groups selected from substituent groups, size-limited substituent groups, and lower substituent groups; each substituent group, size-limited substituent group, and/or lower substituent group may optionally be different. In embodiments, when $R^{17C}$ is substituted, it is substituted with at least one substituent group. In embodiments, when $R^{17C}$ is substituted, it is substituted with at least one size-limited substituent group. In embodiments, when $R^{17C}$ is substituted, it is substituted with at least one lower substituent group.

In embodiments, $R^{18A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{18A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{18A}$ is unsubstituted alkyl or unsubstituted heteroalkyl.

In embodiments, a substituted $R^{18A}$ (e.g., substituted alkyl and/or substituted heteroalkyl) is substituted with at least one substituent group, size-limited substituent group, or lower substituent group; wherein if the substituted $R^{18A}$ is substituted with a plurality of groups selected from substituent groups, size-limited substituent groups, and lower substituent groups; each substituent group, size-limited substituent group, and/or lower substituent group may optionally be different. In embodiments, when $R^{18A}$ is substituted, it is substituted with at least one substituent group. In embodiments, when $R^{18A}$ is substituted, it is substituted with at least one size-limited substituent group. In embodiments, when $R^{18A}$ is substituted, it is substituted with at least one lower substituent group.

In embodiments, $R^{18B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{18B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{18B}$ is unsubstituted alkyl or unsubstituted heteroalkyl.

In embodiments, a substituted $R^{18B}$ (e.g., substituted alkyl and/or substituted heteroalkyl) is substituted with at least one substituent group, size-limited substituent group, or lower substituent group; wherein if the substituted $R^{18B}$ is substituted with a plurality of groups selected from substituent groups, size-limited substituent groups, and lower substituent groups; each substituent group, size-limited substituent group, and/or lower substituent group may optionally be different. In embodiments, when $R^{18B}$ is substituted, it is substituted with at least one substituent group. In embodiments, when $R^{18B}$ is substituted, it is substituted with at least one size-limited substituent group. In embodiments, when $R^{18B}$ is substituted, it is substituted with at least one lower substituent group.

In embodiments, $R^{18C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{18C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{18C}$ is unsubstituted alkyl or unsubstituted heteroalkyl.

In embodiments, a substituted $R^{18C}$ (e.g., substituted alkyl and/or substituted heteroalkyl) is substituted with at least one substituent group, size-limited substituent group, or lower substituent group; wherein if the substituted $R^{18C}$ is substituted with a plurality of groups selected from substituent groups, size-limited substituent groups, and lower substituent groups; each substituent group, size-limited substituent group, and/or lower substituent group may optionally be different. In embodiments, when $R^{18C}$ is substituted, it is substituted with at least one substituent group. In embodiments, when $R^{18C}$ is substituted, it is substituted with at least one size-limited substituent group. In embodiments, when $R^{18C}$ is substituted, it is substituted with at least one lower substituent group.

In embodiments, $R^{19A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{19A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{19A}$ is unsubstituted alkyl or unsubstituted heteroalkyl.

In embodiments, a substituted $R^{19A}$ (e.g., substituted alkyl and/or substituted heteroalkyl) is substituted with at least one substituent group, size-limited substituent group, or lower substituent group; wherein if the substituted $R^{19A}$ is substituted with a plurality of groups selected from substituent groups, size-limited substituent groups, and lower substituent groups; each substituent group, size-limited substituent group, and/or lower substituent group may optionally be different. In embodiments, when $R^{19A}$ is substituted, it is substituted with at least one substituent group. In embodiments, when $R^{19A}$ is substituted, it is substituted with at least one size-limited substituent group. In embodiments, when $R^{19A}$ is substituted, it is substituted with at least one lower substituent group.

In embodiments, $R^{19B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{19B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{19B}$ is unsubstituted alkyl or unsubstituted heteroalkyl.

In embodiments, a substituted $R^{19B}$ (e.g., substituted alkyl and/or substituted heteroalkyl) is substituted with at least one substituent group, size-limited substituent group, or lower substituent group; wherein if the substituted $R^{19B}$ is substituted with a plurality of groups selected from substituent groups, size-limited substituent groups, and lower substituent groups; each substituent group, size-limited substituent group, and/or lower substituent group may optionally be different. In embodiments, when $R^{19B}$ is substituted, it is substituted with at least one substituent group. In embodiments, when $R^{19B}$ is substituted, it is substituted with at least one size-limited substituent group. In embodiments, when $R^{19B}$ is substituted, it is substituted with at least one lower substituent group.

In embodiments, $R^{19C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{19C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{19C}$ is unsubstituted alkyl or unsubstituted heteroalkyl.

In embodiments, a substituted $R^{19C}$ (e.g., substituted alkyl and/or substituted heteroalkyl) is substituted with at least one substituent group, size-limited substituent group, or lower substituent group; wherein if the substituted $R^{19C}$ is substituted with a plurality of groups selected from substituent groups, size-limited substituent groups, and lower substituent groups; each substituent group, size-limited substituent group, and/or lower substituent group may optionally be different. In embodiments, when $R^{19C}$ is substituted, it is substituted with at least one substituent group. In embodiments, when $R^{19C}$ is substituted, it is substituted with at least one size-limited substituent group. In embodiments, when $R^{19C}$ is substituted, it is substituted with at least one lower substituent group.

In embodiments, $R^{20A}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{20A}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{20A}$ is unsubstituted alkyl or unsubstituted heteroalkyl.

In embodiments, a substituted $R^{20A}$ (e.g., substituted alkyl and/or substituted heteroalkyl) is substituted with at least one substituent group, size-limited substituent group, or lower substituent group; wherein if the substituted $R^{20A}$ is substituted with a plurality of groups selected from substituent groups, size-limited substituent groups, and lower substituent groups; each substituent group, size-limited substituent group, and/or lower substituent group may optionally be different. In embodiments, when $R^{20A}$ is substituted, it is substituted with at least one substituent group. In embodiments, when $R^{20A}$ is substituted, it is substituted with at least one size-limited substituent group. In embodiments, when $R^{20A}$ is substituted, it is substituted with at least one lower substituent group.

In embodiments, $R^{20B}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{20B}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{20B}$ is unsubstituted alkyl or unsubstituted heteroalkyl.

In embodiments, a substituted $R^{20B}$ (e.g., substituted alkyl and/or substituted heteroalkyl) is substituted with at least one substituent group, size-limited substituent group, or lower substituent group; wherein if the substituted $R^{20B}$ is substituted with a plurality of groups selected from substituent groups, size-limited substituent groups, and lower substituent groups; each substituent group, size-limited substituent group, and/or lower substituent group may optionally be different. In embodiments, when $R^{20B}$ is substituted, it is substituted with at least one substituent group. In embodiments, when $R^{20B}$ is substituted, it is substituted with at least one size-limited substituent group. In embodiments, when $R^{20B}$ is substituted, it is substituted with at least one lower substituent group.

In embodiments, $R^{20C}$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{20C}$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^{20C}$ is unsubstituted alkyl or unsubstituted heteroalkyl.

In embodiments, a substituted $R^{20C}$ (e.g., substituted alkyl and/or substituted heteroalkyl) is substituted with at least one substituent group, size-limited substituent group, or lower substituent group; wherein if the substituted $R^{20C}$ is substituted with a plurality of groups selected from substituent groups, size-limited substituent groups, and lower substituent groups; each substituent group, size-limited substituent group, and/or lower substituent group may optionally be different. In embodiments, when $R^{20C}$ is substituted, it is substituted with at least one substituent group. In embodiments, when $R^{20C}$ is substituted, it is substituted with at least one size-limited substituent group. In embodiments, when $R^{20C}$ is substituted, it is substituted with at least one lower substituent group.

In embodiments, $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{16B}$, $R^{17B}$, $R^{18B}$, $R^{19B}$, $R^{20B}$, $R^{13C}$, $R^{14C}$, $R^{15C}$, $R^{16C}$, $R^{17C}$, $R^{18C}$, $R^{19C}$, and $R^{20C}$, are each independently substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{17B}$, $R^{18B}$, $R^{19B}$, $R^{20B}$, $R^{13C}$, $R^{14C}$, $R^{15C}$, $R^{17C}$, $R^{18C}$, $R^{19C}$, and $R^{20C}$ are each independently substituted (e.g., substituted with a substituent group, a size-limited substituent group, or lower substituent group) or unsubstituted alkyl (e.g., $C_1$-$C_8$, $C_1$-$C_6$, $C_1$-$C_4$, or $C_1$-$C_2$), or substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered). In embodiments, $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{17B}$, $R^{18B}$, $R^{19B}$, $R^{20B}$, $R^{13C}$, $R^{14C}$, $R^{15C}$, $R^{16C}$, $R^{17C}$, $R^{18C}$, $R^{19C}$, and $R^{20C}$, are each independently unsubstituted alkyl (e.g., $C_1$-$C_8$, $C_1$-$C_6$, $C_1$-$C_4$, or $C_1$-$C_2$), or unsubstituted heteroalkyl (e.g., 2 to 8 membered, 2 to 6 membered, 4 to 6 membered, 2 to 3 membered, or 4 to 5 membered).

In embodiments, a substituted $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{17B}$, $R^{18B}$, $R^{19B}$, $R^{20B}$, $R^{13C}$, $R^{14C}$, $R^{15C}$, $R^{17C}$, $R^{18C}$, $R^{19C}$, and $R^{20C}$ (e.g. substituted alkyl and/or substituted heteroalkyl) is substituted with at least one substituent group, size-limited substituent group, or lower substituent group; wherein if the substituted $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{17B}$, $R^{18B}$, $R^{19B}$, $R^{20B}$, $R^{13C}$, $R^{14C}$, $R^{15C}$, $R^{16C}$, $R^{17C}$, $R^{18C}$, $R^{19C}$, or $R^{20C}$, is substituted with a plurality of groups selected from substituent groups, size-limited substituent groups, and lower substituent groups; each substituent group, size-limited substituent group, and/or lower substituent group may optionally be different. In embodiments, when $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{16B}$, $R^{17B}$, $R^{18B}$, $R^{19B}$, $R^{20B}$, $R^{13C}$, $R^{14C}$, $R^{15C}$, $R^{16C}$, $R^{17C}$, $R^{18C}$, $R^{19C}$, or $R^{20C}$, is substituted, it is substituted with at least one substituent group. In embodiments, when $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{17B}$, $R^{18B}$, $R^{19B}$, $R^{20B}$, $R^{13C}$, $R^{14C}$, $R^{15C}$, $R^{17C}$, $R^{18C}$, $R^{19C}$, or $R^{20C}$, is substituted, it is substituted with at least one size-limited substituent group. In embodiments, when $R^{13A}$, $R^{14A}$, $R^{15A}$, $R^{16A}$, $R^{17A}$, $R^{18A}$, $R^{19A}$, $R^{20A}$, $R^{13B}$, $R^{14B}$, $R^{15B}$, $R^{16B}$, $R^{17B}$, $R^{18B}$, $R^{19B}$, $R^{20B}$, $R^{13C}$, $R^{14C}$, $R^{15C}$, $R^{16C}$, $R^{17C}$, $R^{18C}$, $R^{19C}$, or $R^{20C}$, is substituted, it is substituted with at least one lower substituent group.

II. Pharmaceutical Compositions

In an aspect, there is provided a pulmonary pharmaceutical composition including a pulmonary pharmaceutical carrier and a dithiolsaccharide mucolytic agent, as disclosed herein (e.g. the compounds of formula I, Ia, Ib, Ic, Id, II, IIa, IIIa, IIIb, IVa, IVb, or V, disclosed herein, including embodiments thereof).

In an aspect, there is provided a pharmaceutical composition including a pharmaceutically acceptable excipient and a compound, or pharmaceutically acceptable salt thereof, as described herein, or embodiments thereof.

The terms "pharmaceutical composition" and the like refer, in the usual and customary sense, to a composition which is generally recognized as safe and effective for administration to a subject. The terms "pharmaceutically acceptable excipient," "pharmaceutically acceptable carrier" and the like refer, the usual and customary sense, to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (e.g., Ringer's solution and the like), alcohols, oils, gelatins, and carbohydrates such as lactose, amylose or starch, fatty acid esters, hydroxymethycellulose, polyvinyl pyrrolidine, mannitol, and the parent sugar of a dithiolsaccharide mucolytic agent as disclosed herein, wherein the dithiolsaccharide mucolytic agent lacks a thiol functionality, e.g., D-glucopyranose, D-galactopyranose, D-mannopyranose, D-glucopyranoside, D-galactopyranoside, D-mannopyranoside, sucrose, lactose, lactulose, maltose, trehalose, cellobiose, chitobiose, or maltose. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. The compounds described herein can be administered alone or can be coadministered to a subject. Coadministration is meant to include simultaneous or sequential administration of the compounds individually or in combination (more than one compound). The preparations can also be combined, when desired, with other active substances (e.g., to reduce metabolic degradation).

Formulations

The compounds disclosed herein can be prepared and administered in a wide variety of inhalation, oral, parenteral, and topical dosage forms, preferably inhalation. Thus, the compounds of the present invention can be administered by injection (e.g., intravenously, intramuscularly, intracutaneously, subcutaneously, intraduodenally, or intraperitoneally). Also, the compounds described herein can be administered by inhalation and by the intranasal route. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention. In embodiments, compounds disclosed herein are administered topically to an eye. In embodiments, compounds disclosed herein are administered in an eye drop formulation.

For preparing pharmaceutical compositions from the compounds described herein, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In embodiments, a powder is provided in which the carrier is a finely divided solid in a mixture with the finely divided active component. In embodiments, a tablet is provided in which the active component is mixed with the carrier having the necessary binding properties in suitable proportions and compacted in the shape and size desired.

The powders and tablets preferably contain from 5% to 100% of the active compound. Suitable carriers include, but are not limited to, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in PHARMACEUTICAL SCIENCES (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral or inhaled administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

In an aspect, there is provided a pulmonary pharmaceutical composition comprising a pulmonary pharmaceutical carrier and a dithiolsaccharide mucolytic agent. The terms "pulmonary pharmaceutical composition" and the like refer to pharmaceutical compositions intended for pulmonary administration. The terms "pulmonary administration" and the like refer, in the usual and customary sense, to administration to achieve inhalation therapy. The term "inhalation therapy" and the like refer to direct delivery of medications to the lungs by inhalation. The dithiolsaccharide mucolytic agent disclosed herein are effective as mucolytics when delivered directly to the lung by an inhaled drug delivery system so that the intra-luminal mucus can be directly contacted by the drug to "lyse" or break up the mucus (mucolytic activity). The term "pulmonary pharmaceutical liquid" refers to a pulmonary pharmaceutical composition which is a liquid. The terms "pulmonary pharmaceutical solid," "pulmonary pharmaceutical solid" and the like refer to a pulmonary pharmaceutical composition which is a solid (e.g., a powder).

There are three categories of inhaled drug delivery systems: (i) nebulizers; (ii) pressurized metered-dose inhalers (pMDIs); (iii) dry powder inhalers (DPIs). Nebulizers are distinctly different from both pMDIs and DPIs, in that the active agent is dissolved or suspended in a polar liquid, e.g., water. In contrast, pMDIs and DPIs are bolus drug delivery devices that contain active agent (e.g., solid dithiolsaccharide mucolytic agent), suspended or dissolved in a nonpolar volatile propellant or in a dry powder mix that is fluidized when the patient inhales. pMDIs and DPIs have considerably reduced treatment time compared with nebulizers. The term "pulmonary pharmaceutical delivery device" and the like refer to an inhaled drug delivery system suitable for delivery (e.g., pulmonary delivery) of a pulmonary pharmaceutical composition.

Without wishing to be bound by any theory, it is believed that the lung deposition characteristics and efficacy of an aerosol depend largely on the particle or droplet size. For example, particles of more than 10 µm in diameter are most likely to deposit in the mouth and throat, for those of 5-10 µm diameter a transition from mouth to airway deposition occurs, and particles smaller than 5 µm in diameter deposit more frequently in the lower airways and are appropriate for pharmaceutical aerosols (e.g., pulmonary pharmaceutical compositions). Aerodynamic particle size distribution is measured by methods known in the art, e.g., cascade impaction method. Micronization is a conventional approach for size reduction. Additional drug particle engineering technologies includes spray drying, sonocrystalization, or super critical fluids, and the like as known in the art. In embodiments, the particle is a nanoparticle, as known in the art. In all of these technologies, the particles can be delivered alone or co-formulated with carriers.

In embodiments, ideal inhaled particles are characterized as having uniform particle size with mono-dispersion, uniform density, non-cohesiveness, no agglomeration, no compaction, excellent flowability, and ready dispersal when delivered as an aerosol.

In embodiments, the attributes of an optimized inhaled delivery system include stability (i.e., consistent delivered dose through inhaler life), consistent aerodynamic particle size distribution (i.e., fine particle dose/fraction), and chemical and performance stability, as known in the art.

In embodiments, formulation considerations for the pulmonary pharmaceutical composition disclosed herein include consistent product performance on stability and through the labeled number of doses, uniform formulation upon shaking to ensure metering and delivery of accurate and consistent doses, drug suspension stabilized by forming loose agglomerates and readily re-dispersed upon shaking after storage, no particle growth due to aggregation or crystal growth to ensure aerosolization performance, no drug loss due to deposition on dispenser to ensure consistent doses through inhaler life, and protection from moisture ingression to ensure long term stability.

Regarding nebulizers, as known in the art, nebulizers ("atomizers") may, e.g., employ compressor to force a gas air, or a blended mixture of air and oxygen through a solution) or electrical means (e.g., piezoelectric power to break up pharmaceutical compositions (e.g., solutions and suspensions) into small aerosol droplets that can be directly inhaled from the nebulizer. The term "aerosol" and the like refer, in the usual and customary sense to a mixture of gas and liquid particles. The term "jet nebulizer" and the like refer, in the usual and customary sense, to any of a variety of devices connected by tubing to a compressor that causes compressed air or oxygen to flow at high velocity through a liquid medicine to turn it into an aerosol, which is then inhaled by the patient. Jet nebulizers are commonly used for patients in hospitals who have difficulty using inhalers or who require higher doses of drug than can be delivered with hand held devices such pressurized metered dose inhalers (pMDIs) or dry powder inhalers (DPIs). Jet nebulizers are also common in pediatric practice. The term "vibrating mesh nebulizer" refers to a nebulizer that generates aerosols as liquid passes through a mesh that is oscilated (e.g., by a piezo-element) to generate ultrasonic frequencies, and are becoming preferred devices for home use.

A dry powder inhaler (DPI) is a device that delivers medication to the lungs in the form of a dry powder. When a DPI is actuated, the formulation is fluidized and enters the patient's airways.

In embodiments, a compound disclosed herein is administered in an amorphous powder. Non-limiting descriptions relating to amorphous powders are provided in Chen et al. 2016 Amorphous powders for inhalation drug delivery *Advanced Drug Delivery Reviews* 100:102-115, the entire content of which is incorporated by reference.

In embodiments, a compound disclosed herein is administered as a micronized powder.

In embodiments, a powder composition for use in a DPI is packaged in single dose quantities in blisters or gel capsules containing the powdered medication to be drawn into the lungs by the user's own breath.

In embodiments, a DPI formulation must undergo flow, fluidization, and de-aggregation. In embodiments, an excipient is added to enhance the physical or chemical stability of the active pharmaceutical ingredient mechanical properties, and/or its pharmaceutical properties, such as dissolution and permeation.

In embodiments, a DPI formulation comprises loose agglomerates. In embodiments, these agglomerates can consist of particles of disparate sizes, as is the case when agent is prepared with large carrier particles, or particles of similar sizes prepared by unique methods of formation that result in ease of dispersion.

In embodiments, after the formulation has been produced, it is filled into capsules, multi-dose blisters, or reservoirs for use with the inhaler device.

Regarding pressurized metered-dose inhalers (pMDIs), a formulation can be made up of the agent (e.g., a mucolytic dithiolsaccharide agent), a liquefied gas propellant and, in many cases, stabilizing excipients. The actuator contains the mating discharge nozzle and generally includes a dust cap to prevent contamination. Actuation of the device releases a single metered dose of the formulation which contains the medication either dissolved or suspended in the propellant. Breakup of the volatile propellant into droplets, followed by rapid evaporation of these droplets, results in the generation of an aerosol consisting of micrometer-sized medication particles that are then inhaled. One of the most crucial components of a MDI is its propellant. The propellant provides the force to generate the aerosol cloud and is also the medium in which the active component must be suspended or dissolved. Propellants in MDIs typically make up more than 99% of the delivered dose, so it is the properties of the propellant that dominate more than any other individual factor. Suitable propellants must pass a stringent set of criteria, they must: have a boiling point in the range −100 to +30° C. have a density of approximately 1.2 to 1.5 g cm-3 (approximately that of the drug to be suspended or dissolved) have a vapor pressure of 40 to 80 psig have no toxicity to the patient, be non-flammable and be able to dissolve common additives. Active ingredients can be either fully soluble or fully insoluble. In the early days of MDIs the most commonly used propellants were the chlorofluorocarbons, but hydrofluoroalkane propellants are now preferred because they have fewer environmental toxicities. General considerations for metered dose inhalers include consideration of the following: agent is dissolved in the liquefied propellant, compliance with applicable rules (e.g., formulation agent (e.g., HFA propellant, surfactant, so-solvent and/or excipient)), container closure system (e.g., can, metering valve), actuator, and dose compliance device, as known in the art. Suspension formulation issues can include micronized drug particles suspended in the liquefied propellant (e.g., air, $CO_2$, HFA134a, 227 and the like). The suspension formulation may contain surfactant and co-solvent to aid suspension, particularly with respect irregular particles, polydispersed (e.g., 0.5-10 μm) particles, or amorphous/crystalline particles.

In embodiments of the pulmonary pharmaceutical composition, the pulmonary pharmaceutical carrier is a pulmonary pharmaceutical liquid or pulmonary pharmaceutical powder. In embodiments, the pulmonary pharmaceutical carrier is a pulmonary pharmaceutical liquid. In embodiments, the pulmonary pharmaceutical carrier is a pulmonary pharmaceutical powder.

In embodiments of the pulmonary pharmaceutical composition, the pulmonary pharmaceutical liquid comprises a polar liquid, and the dithiolsaccharide mucolytic agent is dissolved or suspended in the polar liquid. In embodiments, the polar liquid is water.

In embodiments of the pulmonary pharmaceutical composition, the pulmonary pharmaceutical carrier is lactose, mannitol, a phospholipid or cholesterol. In embodiments, the phospholipid is phosphatidyl choline. In embodiments, the pulmonary pharmaceutical carrier is the parent sugar of the dithiolsaccharide mucolytic agent, wherein the parent sugar lacks a thiol moiety, e.g., D-glucopyranose, D-galactopyranose, D-mannopyranose, D-glucopyranoside, D-galactopyranoside, D-mannopyranoside, sucrose, lactose, lactulose, maltose, trehalose, cellobiose, chitobiose, or maltose.

In embodiments of the pulmonary pharmaceutical composition, the pulmonary pharmaceutical composition is within a pulmonary pharmaceutical delivery device. In embodiments, the pulmonary pharmaceutical delivery device is a pulmonary pharmaceutical nebulizer, a pulmonary pharmaceutical dry powder inhaler, or a pulmonary pharmaceutical pressurized metered dose inhaler.

In embodiments of the pulmonary pharmaceutical composition, the pulmonary pharmaceutical composition further includes one or more additional therapeutic agents. In embodiments, the pulmonary pharmaceutical composition further includes one additional therapeutic agent. In embodiments, the pulmonary pharmaceutical composition further includes a plurality of additional therapeutic agents. In embodiments, the pulmonary pharmaceutical composition further includes two additional therapeutic agents. In embodiments, the pulmonary pharmaceutical composition further includes three additional therapeutic agents. In embodiments, the pulmonary pharmaceutical composition further includes four additional therapeutic agents.

In embodiments, the additional therapeutic agent is a beta agonist, as known in the art. In embodiments, the additional therapeutic agent is a short-acting beta agonist, as known in the art. In embodiments, the additional therapeutic agent is a long-acting beta agonist, as known in the art. The term "short-acting" in the context of therapeutic agents refers, in the usual and customary sense, a therapeutic agent that elicits a transient effect, e.g., 1-60 seconds, 1-60 minutes, 1, 2, 3, 4, 5, 6, 7, 8, 9, 10, 11 or even 12 hours, as known in the art. The term "long-acting" in the context of therapeutic agents refers, in the usual and customary sense, a therapeutic agent that elicits a sustained effect, e.g., 1, 2, 3, 4, 5, 6, 7, 8, 9, 10, 11, 12, 13, 14, 15, 16, 17, 18, 19, 20, 21, 22, 23 or even 24 hours, 1, 2, 3, 4, 5, 6, or even 7 days, 1, 2, 3, 4 weeks or longer, as known in the art.

In embodiments, the additional therapeutic agent is a anticholinergic, as known in the art. In embodiments, the additional therapeutic agent is a short-acting anticholinergic, as known in the art. In embodiments, the additional therapeutic agent is a long-acting anticholinergic, as known in the art.

In embodiments, the additional therapeutic agent is a steroid as disclosed herein or as known in the art, e.g., fluticasone, budesonide, beclomethasone, momethasone. In embodiments, the additional therapeutic agent is a corticosteroid as disclosed herein or as known in the art.

In embodiments, the additional therapeutic agent is an antibiotic, as known in the art.

In embodiments, the additional therapeutic agent is rhDNAse, as known in the art.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

Therapeutically effective amounts for use in humans may be determined from animal models. For example, a dose for humans can be formulated to achieve a concentration that has been found to be effective in animals. In embodiments, a dose for humans can be formulated to achieve a concentration that has been found to be effective in liquefying native airway mucus gels (e.g. human sputum) or synthetic thiolated hydrogels.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

III. Methods of Use

In aspect, there is provided a method of decreasing mucus elasticity or decreasing mucus viscosity in a subject in need thereof. For example, the method can be use of a dithiolsaccharide mucolytic agent for decreasing mucus elasticity or decreasing mucus viscosity in a subject in need thereof. The method includes administering to the subject an effective amount of a dithiolsaccharide mucolytic agent. The terms "elastic," "elasticity" and the like refer herein, in the usual and customary sense, to the ability of a material to return to an original shape after experiencing a deformation due to an external force (e.g., solid behavior). Thus, the term "mucus elasticity" refers herein to the ability of mucus to return to an original shape after experiencing a deformation in shape. The terms "viscous," "viscosity" and the like refer herein, in the usual and customary sense, to a measure of the resistance of a material to deformation (e.g., liquid behavior) upon application of a force (e.g., shear stress or tensile stress). Thus, the term "mucus viscosity" refers herein to a measure of the resistance of mucus to deformation upon application of an external force, whereby higher mucus viscosity means that the mucus is less deformable.

Without wishing to be bound by any theory, it is believed that elasticity represents mainly intermolecular cross-links, and viscosity mainly represents molecule/particle sizes. Moreover, in embodiments, the dithiolsaccharide mucolytic agents disclosed herein function by breaking disulfide bond cross-links between mucin polymers in the mucus gel. Accordingly, in embodiments, the reduction of elasticity is a direct effect of breaking disulfide bond crosslinkages between mucin polymers. In considering the mucus network as a whole, by breaking down cross-links the average size of molecule/particles forming the mucus gel may be reduced. In embodiments, the reduction of molecular/particle size and cross linking within mucus gels will increase the mean pore size of the gel. This in turn can increase the penetrability of the gel. Indeed, in embodiments, administration to mucus gel of dithiolsaccharide mucolytic agents disclosed herein will decrease the elastic modulus of the mucus gel. Thus, the dithiolsaccharide mucolytic agents may have the effect of increasing gel pore size. In embodiments, the increase in gel pore size improves the penetration of a variety of additional agents including e.g., natural mucolytics like proteases or co-administered drugs (e.g., aerosol bronchodilators (e.g., beta agonists, anticholinergics, anti-inflammatory drugs (e.g. corticosteroids), aerosolized antibiotics, other classes of mucoactive agents (e.g., rhDNase, hypertonic saline), and therapeutics that aim to modulate the genome of airway epithelial cells or lung alveolar cells. Moreover, in embodiments, the dithiolsaccharide mucolytic agents disclosed herein function by inhibiting reactive oxygen species (e.g. peroxides, superoxides, and hydroxyl radicals) and oxidant acids that have pathophysiologic roles in cross-linking mucin polymers to increase the elasticity of mucus gels. By inhibiting reactive oxygen species and oxidant acids in biological fluids or by preventing cellular damage associated with oxidative stress, dithiolsaccharide agents may act as antioxidants that prevent oxidation and formation of excessive numbers of disulfide bridge cross-links in a mucus gel. Thus, in embodiments, dithiolsaccharide agents facilitate maintaining normal mucus elasticity and viscosity, such as with respect to a reference level for a subject or population.

In embodiments, the method includes decreasing mucus elasticity in the subject. In embodiments, the method includes decreasing mucus viscosity in the subject. In embodiments, the method includes decreasing mucus viscoelasticity in the subject. The term "viscoelasticity" refers herein, in the usual and customary sense, to the property of materials that exhibit both viscous and elastic characteristics in response to a deformation. Thus, the term "mucus viscoelasticity" refers herein to a characteristic of mucus which exhibits both viscous and elastic characteristics when undergoing deformation.

Without wishing to be bound by any theory, it is believed that decreasing mucus elasticity, decreasing mucus viscosity, or decreasing mucus viscoelasticity is useful for a variety of medical, dental and veterinary indications. For example, in embodiments administration of compounds disclosed herein is useful for relief of upper and lower airway congestion by the physiological mechanisms of mucociliary clearance, as known in the art. Specifically, a decrease in mucus elasticity, viscosity or viscoelasticity is known to facilitate mucociliary clearance. In embodiments, increased mucociliary clearance improves airflow and improves measures of lung function such as the forced expired volume in one second (FEV1) or the forced vital capacity (FVC). In embodiments, improved mucociliary clearance decreases mucus plugging (e.g., complete occlusion of an airway lumen) of the airways, which will be reflected in improvements in chest imaging scores that quantify the number of airway mucus plugs. In embodiments, administration of compounds disclosed herein is useful for veterinary (e.g., equine) intervention in strangle or guttural pouch infections (e.g., mycotic or bacterial infections) as a primary treatment for mucus accumulation. In embodiments, administration of compounds disclosed herein is useful to enhance penetration of another therapeutic agent. In embodiments, administration of compounds disclosed herein is useful for veterinary (e.g., equine) intervention in recurrent airway obstruction. In embodiments, the recurrent airway obstruction is caused by fungal allergy, mucus accumulation, or both.

In embodiments, the method is useful for targeted removal of mucus from a mucosal surface. The terms "mucosal surface" and the like refer, in the usual and customary sense, to a layer of cells (e.g., an epithelial layer) having mucus disposed thereon. Exemplary mucosal surfaces include skin, lungs, nostrils, sinuses, gastrointestinal tract, reproductive tract, urinary tract, eye, and the like. In embodiments, the method is useful for targeted removal of mucus from a mucosal surface, wherein the mucus provides a barrier to mucosal or transmucosal drug delivery. In embodiments, the method provides enhanced drug delivery by targeted removal of mucus from a mucosal surface. In embodiments, the mucosal surface includes the gastrointestinal tract, and the drug delivery is oral drug delivery.

In embodiments, the method is useful for removal of accumulated mucus at any mucosal surface. In embodiments, the accumulated mucus contributes directly or indirectly to the existence, symptomatology, or progression of disease.

In embodiments, the method is useful for removal of accumulated mucus at any mucosal surface, wherein the mucus is a component of a microbial biofilm. The terms "microbial biofilm" and the like refer, in the usual and customary sense, to an aggregation of microorganisms in which the component cells adhere to each other on a surface. The aggregation of microorganisms can be embedded within a matrix which can include mucus. Thus, removal of accumulated mucus in a microbial biofilm can facilitate exposure of the microorganisms to antibiotic treatment with an antimicrobial agent. In embodiments, administration of a compound disclosed herein facilitates penetration of an antimicrobial agent into the microbial biofilm. In embodiments, administration of a compound disclosed herein in combination with an antimicrobial agent provides synergistic treatment for the microorganisms within the microbial biofilm. The terms "synergistic" and the like in the context of administration of a compound disclosed herein in combination with another therapeutic agent (e.g., antimicrobial agent) refer, in the usual and customary sense, to a resulting effect (e.g., antibiotic efficacy) for the combination which is greater than the summed effects of the administration of either a compound disclosed herein or an antimicrobial agent alone.

In embodiments, the lung is specifically contemplated as the target organ. In embodiments, the method include administration of the dithiolsaccharide mucolytic agent to the lung of a subject in need thereof. Thus, in embodiments, the subject suffers a condition of the lung including chronic obstructive pulmonary disease (COPD), cystic fibrosis (CF), chronic asthma with symptoms of excessive mucus production, chronic asthma with airway obstruction, chronic asthma in which airway mucus plugging is found on chest imaging studies, acute severe asthma, acute severe asthma in which mucus plugs are life threatening, bronchiectasis, bronchiolitis, allergic bronchopulmonary aspergillosis, pneumonia, and mechanical ventilator-associated lung injury where mucus pathology is prominent. In embodiments, the method is useful to prevent or treat oxidative cross-linking of lung mucins leading to airway mucus problems in subjects undergoing inhaled oxygen therapy or positive pressure mechanical ventilation.

In embodiments, the method is useful for amelioration of recurrent airway obstruction from mucus pathology. In embodiments, the subject is human. In embodiments, the subject is a non-human animal. In embodiments, the subject is a horse. In embodiments, the airway obstruction is a complete obstruction or occlusion of an airway lumen.

In embodiments, the airway is in the upper respiratory tract of the subject. In embodiments, the airway is in a nasal passage, paranasal sinuse, the pharynx, and or larynx of the subject. In embodiments, the airway is in the lower respiratory tract of the subject. In embodiments, the airway is in a trachea, main bronchus, lobar bronchus, segmental bronchus, subsegmental bronchus, conducting bronchiole, terminal bronchiole, respiratory bronchiole, alveolar duct, alveolar sac, or alveolus of the subject. In embodiments, the subject has 1, 2, 3, 4, 5, 6, 7, 8, 9, 10, or more complete mucus airway occlusions of one or more airways within one or two lungs in the subject.

In embodiments, the upper respiratory tract is specifically contemplated as the target organ. In embodiments, the subject suffers chronic rhinitis, acute sinusitis, chronic sinusitis, chronic sinusitis with mucocele, chronic rhinosinusitis with nasal polyps, chronic rhinosinusitis without nasal polyps, and patients who suffer from chronic post-nasal drip from any cause.

In embodiments, the subject in need is in immediate need, presenting symptoms of acute airflow obstruction, acute shortness of breadth, acute asphyxia, acute symptoms of obstructive pulmonary disease (COPD), acute symptoms of cystic fibrosis (CF), acute asthma symptoms with airflow obstruction, acute asthma symptoms in which mucus obstruction is found, acute asthma in which mucus plugs are life threatening, acute symptoms of bronchiectasis, acute symptoms of bronchiolitis, acute symptoms of allergic bronchopulmonary aspergillosis, acute symptoms of pneumonia, or acute symptoms of mechanical ventilator-associated lung injury where mucus pathology is prominent, as known in the art. The term "acute" and the like refer, in the usual and customary sense, to a disease or disorder with rapid onset, often life threatening. Without wishing to be bound by any theory, it is believed that compliance of a subject to a treatment regimen increases with speed of onset of the effects of an administered compound disclosed herein. As discussed herein, compounds disclosed herein provide significantly faster onset of action relative to compounds routinely employed in treatment situations.

In embodiments, the rapid onset of action of compounds disclosed herein provides for less diffusion from the site of action, e.g., the lung. Accordingly, in embodiments, less material and less time is required to achieve a beneficial result, e.g., reduction in acute airflow obstruction, thus implicating smaller dosage requirements and more effective clinical results relative to compounds routinely employed in treatment situations.

In embodiments, the ear is specifically contemplated as the target organ. Thus, in embodiments, the subject suffers from otitis media with mucus accumulation.

In embodiments, the eye is specifically contemplated as the target organ. Thus, in embodiments, the subject suffers from filamentary keratitis, keratitis sicca, dry eye syndrome, blepharitis, conjunctivitis, or any eye disease acute or chronic in which excess mucus forms on the eye.

In an aspect, there is provided a method for treatment in a subject in need thereof. The method includes administering an effective amount of a compound disclosed herein in combination with another therapeutic agent, wherein the therapeutic action of the therapeutic agent is enhanced by decreasing mucus elasticity or decreasing mucus viscosity. In embodiments, penetration of the therapeutic agent is augmented through abnormal mucus by decreasing mucus elasticity or decreasing mucus viscosity of the abnormal mucus. In embodiments, the subject suffers from CF, and penetration of the therapeutic agent into the lung is facilitated by decreasing mucus elasticity or decreasing mucus viscosity of the mucus of the subject suffering from CF. In embodiments, penetration of the therapeutic agent is augmented through normal mucus by decreasing mucus elasticity or decreasing mucus viscosity of the normal mucus. In embodiments, the method is useful for oral drug delivery, nasal drug delivery or inhalation drug delivery. In embodiments, administration of a compound disclosed herein in combination with another therapeutic agent provides synergistic treatment for the subject. In embodiments, the other therapeutic agent is a mucoactive drug (e.g., recombinant human DNAse or hypertonic saline), a steroid (e.g., fluticasone, budesonide, beclomethasone, or mometasone), and inhaled antibiotic, or a therapeutic agent designed to modulate the genome of airway epithelial cells or alveolar epithel cells. In embodiments, as a result of the decrease in mucus elasticity or decrease in mucus viscosity in a subject in need thereof upon administration of a compound disclosed herein, the other therapeutic agent is made clinically effective or its dosage requirement is reduced.

In an aspect, there is provided a method for treatment in a subject in need thereof, the method including administering an effective amount of a compound disclosed herein in combination with another therapeutic agent. In embodiments, the "another therapeutic agent" is a beta agonist, an anticholinergic, a corticosteroid, an antibiotic, another mucoactive drug (recombinant human DNAse, hypertonic saline), a steroid (e.g., fluticasone, budesonide, beclomethasone, mometasone), inhaled antibiotics, or a therapeutic agent designed to modulate the genome of airway epithelial cells or alveolar epithelial cells. In embodiments, administration of a compound disclosed herein in combination with another therapeutic agent provides additive or synergistic treatment for the subject and does so with the ease of use of a combination product containing a dithiolsaccharide and a singularity or plurality (e.g., 1, 2, 3, 4 or even 5) additional active ingredients (i.e., therapeutic agents).

Further to any embodiment disclosed herein, in embodiments, the dithiolsaccharide mucolytic agent is a thiol monosaccharide mucolytic agent, a thiol disaccharide mucolytic agent, or a thiol trisaccharide mucolytic agent. In embodiments, the dithiolsaccharide mucolytic agent is a thiol monosaccharide mucolytic agent. In embodiments, the dithiolsaccharide mucolytic agent is a thiol disaccharide mucolytic agent. In embodiments, the dithiolsaccharide mucolytic agent is a thiol trisaccharide mucolytic agent.

In embodiments, the dithiolsaccharide mucolytic agent includes D-glucopyranose, D-fructofuranose, D-fructopuranose, D-galactopyranose, D-mannopyranose, D-glucopyranoside, D-fructofuranoside, D-fructopuranoside, D-galactopyranoside, or D-mannopyranoside moieties. In embodiments, the dithiolsaccharide mucolytic agent includes D-galactopyranose. In embodiments, the dithiolsaccharide mucolytic agent includes sucrose, lactose, lactulose, maltose, trehalose, cellobiose, chitobiose, or maltose moieties. In embodiments, the specific stereochemical structure of the sugar component of the dithiolsaccharide mucolytic agent can determine the activity in decreasing mucus elasticity or decreasing mucus viscosity in a subject in need thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See e.g., Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used

EXAMPLES

Example 1: Exemplary Chemical Synthesis Schemes 1.1 Synthesis of Compound 1
(1,6-dithio-6-deoxy-β-D-galactopyranose)

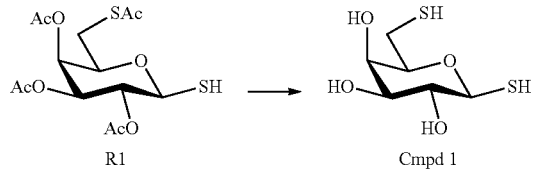

Reagent R1 was prepared by published procedures as in Shu et al, *Selective S-deacetylation inspired by native chemical ligation: practical syntheses of glycosyl thiols and drug mercapto-analogues*, Green Chem, 17 (2015), 2545-2551.

Synthesis of Compound 1: A solution of the thiol R1 (10.8 g, 25.6 mmol) in dichloromethane (30 ml) was nitrogen purged and added to a nitrogen purged solution of methanolic sodium methoxide (~2M, 50 ml) in an ice bath, and the solution was stirred (0° C., 2 h). Dowex (H+ form) resin was added to the solution and the mixture was stirred (5 min). The mixture was filtered and concentrated to give Cmpd 1 (5.4 g, 90%) as a colourless foam. 1H NMR (500 MHz, D2O): δ 4.51 (d, 1H, J=9.38 Hz, H1), 4.12-4.09 (m, 1H, H4), 3.71-3.60 (m, 2H, H5, H3), 3.54-3.46 (m, 1H, H2), 2.78 (dd, 1H, J=13.80, 7.25 Hz, H6), 2.69 (dd, 1H, J=13.80, 6.48 Hz, H6') ppm. 13C NMR (125 MHz, D2O): δ 80.6 (C5), 80.5 (C1), 73.6 (C3), 73.2 (C2), 68.9 (C4), 23.7 (C6) ppm.

1.2 Synthesis of Compound 2
(1,6-dithio-6-deoxy-β-D-glucopyranose)

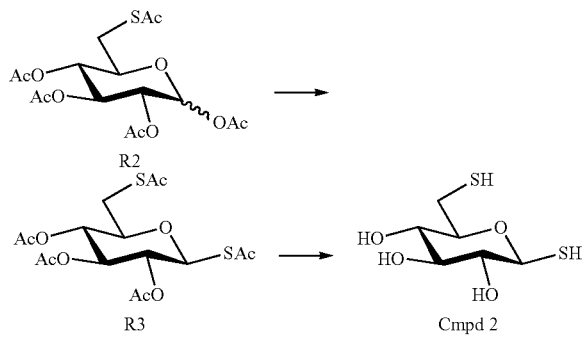

Reagent R2 was prepared by published procedures as in Fadlan et al, *Synthesis, photophysical properties, and photodynamic activity of positional isomers of TFPP-glucose conjugates*, Bioorg. Med. Chem 26 (2018), 1848-1858.

Synthesis of 2,3,4-O-acetyl-1,6-deoxy-1,6-thioacetyl-β-D-glucopyranose (Reagent R3): BF$_3$·OEt$_2$ (0.5 ml) was added to an ice-cooled solution of the peracetate R2 (0.41 g, 1.3 mmol) and thioacetic acid (0.5 ml) in DCM (5 ml), and stood overnight. The solution was then poured into aqueous NaHCO$_3$, extracted with DCM (30 ml), concentrated, and the residue was purified by flash chromatography to give the dithioacetate R4 as a pale yellow oil (0.38 g, 89%). LRMS (M+Na): sought 445.1, found 445.6. $^1$H NMR (300 MHz, CDCl$_3$): 5.26-5.18 (m, 1H), 5.10-5.03 (m, 1H), 5.02-4.94 (m, 1H), 3.84-3.74 (m, 1H), 3.19 (dd, 1H), 3.09 (dd, 1H), 2.37 (s, 3H), 2.31 (s, 3H), 2.06 (s, 3H), 1.99 (s, 3H), 1.97 (s, 3H).

Synthesis of 1,6-dithio-6-deoxy-β-D-glucopyranose (Cmpd 2): The dithioacetate R3 (103 mg, 0.24 mmol) was dissolved in methanol (5 ml), placed in an ice bath, and the solution was purged with nitrogen (15 mins). A methanolic solution of sodium methoxide (~10M, 1 ml) was purged with nitrogen (15 mins), added to the dithioacetate R4 solution, and the resulting solution was kept (1 h, rt). Amberlite IR-120 (H$^+$ form) was added and the mixture was stirred (5 mins). Filtration of the mixture, concentration (<40° C.), and lyophilisation provided Cmpd 2 as a colourless residue (43 mg, 82%). $^1$H NMR (500 MHz, D$_2$O): 4.60 (d, 1H, J=9.51 Hz, H1), 3.53-3.44 (m, 3H, H3, H4, H5), 3.29-3.24 (m, 1H, H2), 3.00 (dd, J=14.5, 2.1 Hz, H6), 2.72 (dd, 1H, J=14.5, 6.3 Hz). $^{13}$C NMR (125 MHz, D$_2$O/CD$_3$OD): 82.54, 82.17, 79.27, 78.57, 73.63, 27.21.

1.3 Synthesis of Compound 3
(3-thiopropyl-6-thio-6-deoxy-O-D galactopyranoside)

Figure 6:
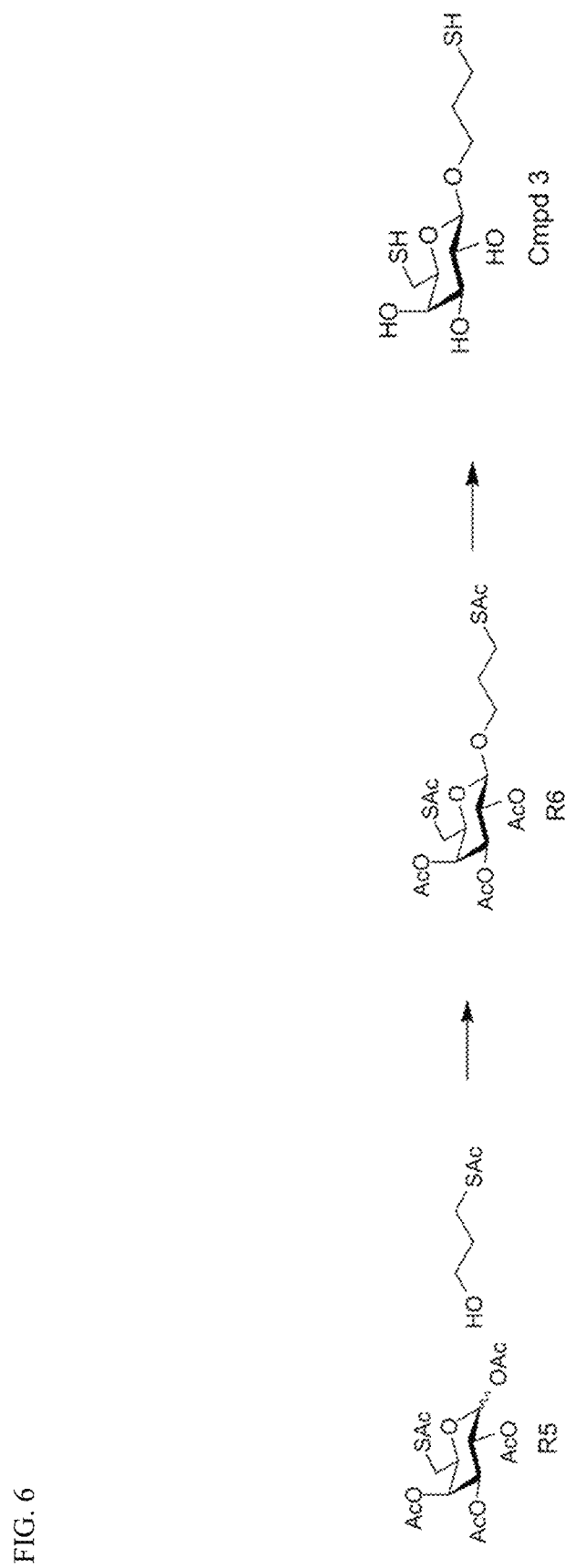
FIG. 6 depicts the synthesis of Compound 3 (3-thiopropyl-6-thio-6-deoxy-β-D galactopyranoside).

FIG. 6 depicts the synthesis of compound 3 (3-thiopropyl-6-thio-6-deoxy-β-D galactopyranoside).

Synthesis of 1,2,3,4-tri-O-acetyl-6-S-acetyl-6-thio-galactopyranose (R5) was performed according to published procedures, e.g. Elhalabi and Rice, *Thiosugar nucleotide analogs: synthesis of 5'-(2, 3,4-tri-O-acetyl-6-S-acetyl-6-thio-alpha-D-galactopyranosyl diphosphate)*, Carbohydrate Research 337 (2002) 1935-1940.

Synthesis of Acetylthiopropyl 2,3,4-O-acetyl-6-deoxy-6-thioacetyl D-galactopyranoside (Reagent R6): BF$_3$·OEt$_2$ (0.5 ml) was added to an ice cooled solution of 3-acetylthio propanol R4 (0.5 g) and the peracetate R5 (0.210 g, 0.52 mmol) in dry dichloromethane (5 ml), and the solution was stirred (rt, 3 h). Upon full consumption of the peracetate R5, trimethylamine (1 ml) butyric anhydride was added (2 ml), and the mixture was stirred (rt, 1 h). The solution was poured into NaHCO$_3$, extracted with dichloromethane, dried, and concentrated. Flash chromatography of the residue (ethyl acetate-cyclohexane) gave the dithioacetate R6 as a colourless oil (0.106 g, 42%). $^1$H NMR (300 MHz, CDCl$_3$): δ 5.43-5.39 (m, 1H), 5.17 (dd, 1H, J=10.4, 7.9 Hz), 4.98 (dd, 1H, J=10.4, 3.4 Hz), 4.42 (d, 1H, J=7.9 Hz), 3.99-3.89 (m, 1H), 3.72-3.63 (m, 1H), 3.60-3.49 (m, 1H), 3.15-3.00 (m, 2H), 2.98-2.87 (m, 2H), 2.34 (s, 3H), 2.33 (s, 3H), 2.16 (s, 3H), 2.06 (s, 3H), 1.98 (s, 3H), 1.94-1.74 (m, 2H). LRMS (M+Na): calcd 503.1, found 502.9.

Synthesis of 3-thiopropyl-6-thio-6-deoxy-β-D-galactopyranoside (Cmpd 3): The dithioacetate R5 (0.1 g, 0.21 mmol) was dissolved in methanol (5 ml), ice-cooled, and the solution was purged with nitrogen (15 mins). A methanolic solution of sodium methoxide (~1M, 1 ml) was purged with nitrogen (15 mins), added to the dithioacetate R5 solution, and the resulting solution was kept (2 h, 0° C.). Amberlite IR-120 (form) was added and the mixture was stirred (5 mins). Filtration of the mixture and concentration (<40° C.) provided Cmpd 3 as a colourless residue (53 mg, 93%). $^1$H NMR (300 MHz, D$_2$O): δ 4.42 (d, 1H, J=7.9 Hz), 4.08-3.98 (m, 2H), 3.87-3.77 (m, 1H), 3.70-3.62 (m, 2H), 3.50 (dd, 1H, J=9.9, 7.9 Hz), 2.86 (dd, J=13.8, 7.9 Hz), 2.76-2.62 (m, 3H), 2.01-1.89 (m, 2H).

1.4 Synthesis of Compound 4
(5-thiopentyl-6-thio-6-deoxy-β-D galactopyranoside)

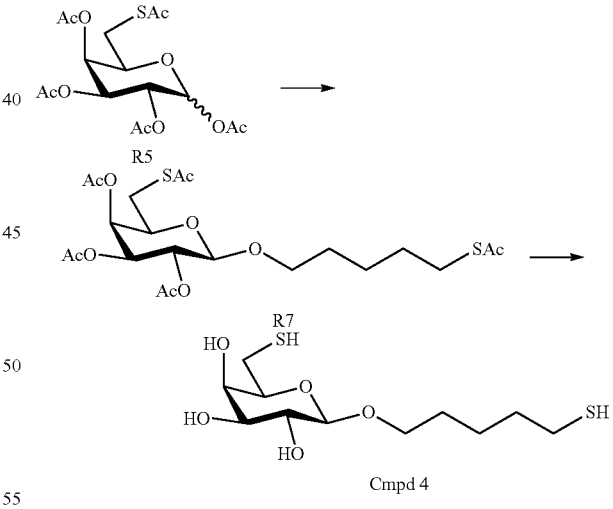

Synthesis of 1,2,3,4-tri-O-acetyl-6-S-acetyl-6-thio-galactopyranose (R5) was performed according to published procedures, e.g. Elhalabi and Rice, *Thiosugar nucleotide analogs: synthesis of 5'-(2, 3,4-tri-O-acetyl-6-S-acetyl-6-thio-alpha-D-galactopyranosyl diphosphate)*, Carbohydrate Research 337 (2002) 1935-1940.

Synthesis of Acetylthiopentyl 2,3,4-O-acetyl-6-deoxy-6-thioacetyl-β-D-galactopyranoside (R7): BF$_3$·OEt$_2$ (0.5 ml) was added to a solution of 4-penten-ol (0.5 ml) and the peracetate R5 (0.495 g, 1.2 mmol) in dry dcm (1 ml) at 0° C., and the solution was stirred while allowing to warm to room temperature. After 2 h stirring full consumption of the peracetate R1 was determined by TLC (Eluent: Acetone-toluene 1:9). Et$_3$N (1 ml) was added, the mixture was diluted with dichloromethane (30 ml), washed with satd aq NaHCO$_3$ (3×20 ml), the organic layer dried over MgSO$_4$, filtered, concentrated, and coevaporated with toluene (3×5 ml). The crude was taken up into dichloromethane (2 ml) along with catechol (230 mg) and thioacetic acid (0.4 ml), and the mixture was stirred. BEt$_3$ (1 M in THF) was added to the mixture portionwise (0.5 ml every 30 min, 2.5 ml) and the mixture was stirred (rt, 2.5 h). The mixture was diluted with dichloromethane (30 ml), washed with satd aq NaHCO$_3$, the organic layer dried over MgSO$_4$, filtered and concentrated. The crude was purified by flash chromatography on silica gel (acetone-toluene) to give the dithioacetate R7 as a colourless oil. (0.268 g, 45%). 1H NMR (300 MHz, CDCl3): δ 5.43-5.37 (m, 1H, H4), 5.21-5.12 (m, 1H, H2), 5.01-4.93 (m, 1H, H3), 4.35 (d, 1H, J=7.9 Hz, H1), 3.85-3.79 (m, 1H), 3.64-3.60 (m, 1H, H5), 3.45-3.38 (m, 1H) 3.07-2.94 (m, 2H, H6, H6'), 2.84-2.79 (m, 2H), 2.34-2.30 (m, 6H), 2.11 (m, 3H), 1.99 (m, 3H), 1.91 (m, 3H), 1.63-1.49 (m, 4H), 1.45-1.30 (m, 2H), 13C NMR (125 MHz, CDCl3): δ 196.1, 195.9, 194.7, 170.3, 170.1, 169.4, 101.1, 72.0, 71.1, 69.8, 68.9, 68.0, 62.3, 32.1, 29.3, 28.9, 24.9, 20.7, 20.67, 20.5. LRMS (M+Na): sought 531.1, found 531.5.

Synthesis of 5-thiopentyl-6-thio-6-deoxy-β-D-galactopyranose (Cmpd 4): the dithioacetate R7 (0.212 g, 0.42 mmol) was dissolved in methanol (5 ml), placed in an ice bath, and the solution was purged with nitrogen (15 mins). A methanolic solution of sodium methoxide (~1M, 2 ml) was purged with nitrogen (15 mins), added to the dithioacetate RX solution, and the resulting solution was kept (3 h, 4° C.) Amberlite IR-120 (H form) was added and the mixture was stirred (5 mins). Filtration of the mixture and concentration (<40° C.) provided Cmpd 4 as a colourless residue (83 mg, 86%). $^1$H NMR (500 MHz, D$_2$O): δ 4.29 (d, 1H, J=8.0 Hz), 3.90-3.87 (m, 1H), 3.83-3.77 (m, 1H), 3.62-3.55 (m, 1H), 3.55-3.50 (m, 2H), 3.36 (dd, 1H, J=9.9, 8.0 Hz), 2.72 (dd, 1H, J=13.7, 8.0 Hz), 2.58 (dd, 1H, J=13.7, 5.9 Hz), 2.47-2.41 (m, 2H), 1.57-1.44 (m, 4H), 1.38-1.29 (m, 2H) ppm. 13C NMR (125 MHz, D$_2$O): δ 103.4, 76.3, 72.8, 70.6, 70.4, 69.0, 48.8, 32.7, 28.2, 23.8, 23.6 ppm.

1.5 Synthesis of Compound 5 (6,6'-dithio-6,6'-dideoxy-α,α-trehalose)

Figure 7:
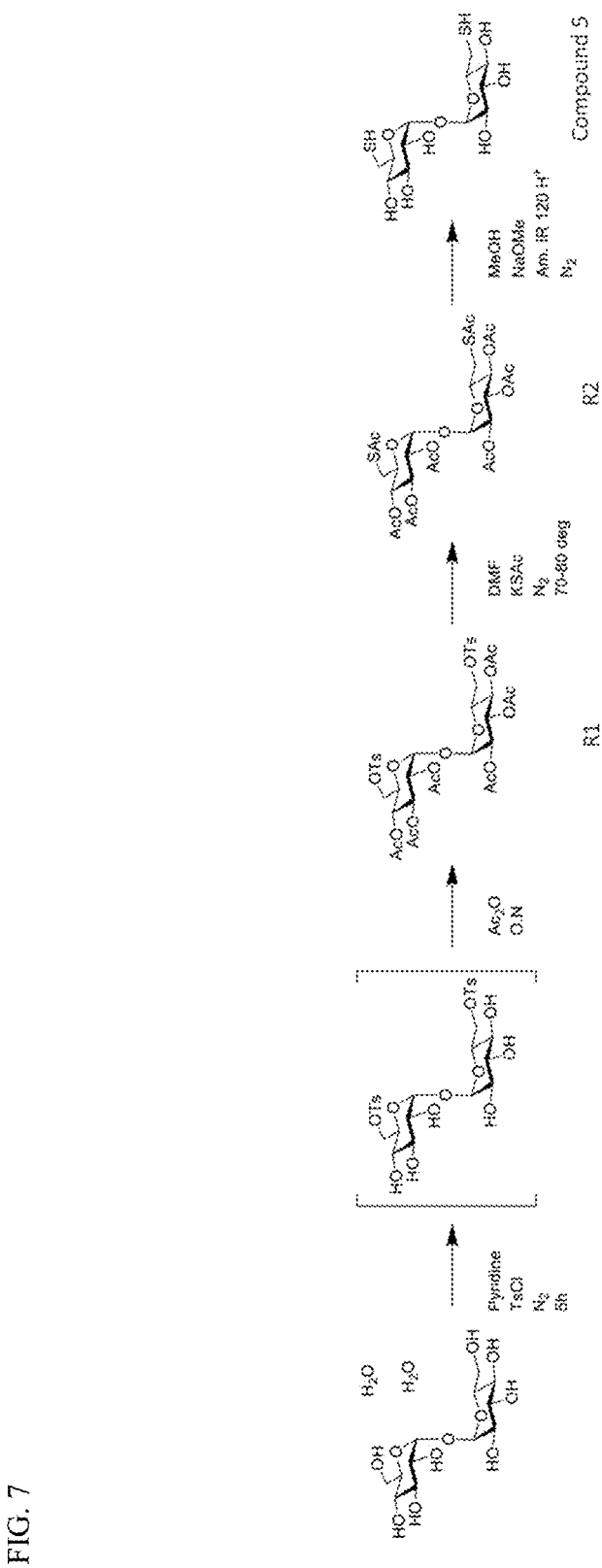
FIG. 7 depicts the synthesis of compound 5 (6,6'-dithio-6,6'-dideoxy-α,α-trehalose).

FIG. 7 depicts the synthesis of compound 5 (6,6'-dithio-6,6'-dideoxy-α,α-trehalose).

Synthesis of Hexa-O-acetyl-6,6'-di-O-toluene-β-sulphonyl-α,α-trehalose (Reagent R1): A solution of p-Toluenesulfonyl Chloride (37.8 g, 0.198 mol) in dry Pyridine (200 mL, 2.49 mol) was added drop-wise over 1 h to an ice-cooled solution of Trehalose Dihydrate (30 g, 79 mmol) in dry Pyridine (200 mL, 2.49 mol) under N$_2$, and the reaction mixture was allowed to warm to room temperature. Further additions of p-Toluenesulfonyl Chloride (7.56 g, 40 mmol) in dry Pyridine (10 mL, 0.125 mol) were made after 3.5 h, 24 h, 29 h, and 47 h. After an additional 3.5 h, the reaction mixture was cooled to 0° C., Acetic anhydride (400 mL, 4.23 mol) was added drop-wise, and allowed to warm to room temperature. After 24 h, the reaction mixture was poured into ice-water (2 L) and stirred overnight. The mixture was filtered, and white solids were collected. Recrystallisation (2×) from MeOH (300 mL+440 mL) gave Reagent R1 (12.3 g, 95% pure, 16%) as white needles: $^1$H NMR (500 MHz, CDCl$_3$) δ 7.74 (d, J=8.3 Hz, 4H, Ar), 7.35 (d, J=8.0 Hz, 4H, Ar), 5.40 (dd, J$_{2,3}$=9.9 Hz, J$_{3,4}$=9.2 Hz, 2H, H-3, H-3'), 4.95 (dd, J$_{2,3}$=9.9 Hz, J$_{1,2}$=3.8 Hz, 2H, H-2, H2'), 4.92 (d, J$_{1,2}$=4.1 Hz, 2H, H-1, H-1'), 4.91 (dd, J$_{4,5}$=10.1 Hz, J$_{3,4}$=9.2 Hz, 2H, H-4, H-4'), 4.10 (ddd, J$_{4,5}$=10.1 Hz, J$_{5,6b}$=5.6 Hz, J$_{5,6a}$=2.8 Hz, 2H, H-5, H-5'), 4.08-4.02 (m, 4H, H-6a, H-6a', H-6b, H6b'), 2.45 (s, 6H, 2×C$_6$H$_4$CH$_3$), 2.08 (s, 6H, 2×OCOCH$_3$), 2.02 (s, 6H, 2×OCOCH$_3$), 2.00 (s, 6H, 2×OCOCH$_3$) ppm. $^{13}$C NMR (126 MHz, CDCl$_3$) δ 170.07 (2C, 2×OCOCH$_3$) 169.71 (2C, 2×OCOCH$_3$), 169.69 (2C, 2×OCOCH$_3$), 145.45 (2C, 2×Ar), 132.56 (2C, 2×Ar), 130.02 (4C, 4×Ar), 128.20 (4C, 4×Ar), 92.95 (2C, C-1, C-1'), 69.95 (2C, C-3, C-3'), 69.36 (2C, C-2, C-2'), 68.73 (2C, C-4, C-4'), 68.32 (2C, C-5, C-5'), 67.70 (2C, C-6, C-6'), 21.82 (2C, 2×C$_6$H$_4$CH$_3$), 20.78 (2C, 2×OCOCH$_3$), 20.73 (2C, 2×OCOCH$_3$), 20.71 (2C, 2×OCOCH$_3$) ppm.

Synthesis of 2,2',3,3',4,4'-Hexa-O-acetyl-6,6'-di-S-acetyl-6,6'-dithio-α,α-trehalose (Reagent R2): Potassium thioacetate (9.3 g, 81 mmol) was added to a solution of Reagent R1 (18.3 g, 20 mmol) in DMF (500 mL) under N$_2$. The solution was heated to 70° C. for 5 days, with Potassium thioacetate (1.2 g, 10 mmol) added after 3 and 4 days. Almost full conversion to Reagent R2 was confirmed by TLC and $^1$H NMR. The reaction mixture was concentrated in vacuo to ~100 mL, diluted with CH$_2$Cl$_2$ (500 mL), washed with H$_2$O (2×500 mL), and a satd. aq. NaHCO$_3$ (300 mL). The organic phase was dried (MgSO$_4$), filtered, and solvents were removed under reduced pressure. Purification by flash chromatography (cyclohexane/EtOAc) gave Reagent R2 (10.2 g, 71%) as an amorphous solid: $^1$H NMR (500 MHz, CDCl$_3$) δ 5.46 (dd, J$_{2,3}$=10.3 Hz, J$_{3,4}$=9.1 Hz, 2H, H-3, H-3'), 5.28 (d, J$_{1,2}$=3.8 Hz, 2H, H-1, H-1'), 5.02 (dd, J$_{2,3}$=10.2 Hz, J$_{1,2}$=3.9 Hz, 2H, H-2, H-2'), 4.95 (dd, J$_{4,5}$=10.0 Hz, J$_{3,4}$=9.2 Hz, 2H, H-4, H-4'), 3.78 (ddd, J$_{4,5}$=10.5 Hz, J$_{5,6b}$=8.3 Hz, J$_{5,6a}$=2.6 Hz, 2H, H-5, H-5'), 3.21 (dd, J$_{6a,6b}$=14.2 Hz, J$_{5,6a}$=2.6 Hz, 2H, H-6a, H-6a'), 2.89 (dd, J$_{6a,6b}$=14.2 Hz, J$_{5,6b}$=8.3 Hz, 2H, H-6b, H-6b'), 2.36 (s, 6H, 2×SCOCH$_3$), 2.11 (s, 6H, 2×OCOCH$_3$), 2.07 (s, 6H, 2×OCOCH$_3$), 2.03 (s, 6H, 2×OCOCH$_3$) ppm. $^{13}$C NMR (126 MHz, CDCl$_3$) δ 194.87 (2C, 2×SCOCH$_3$), 170.06 (2C, 2×OCOCH$_3$), 170.01 (2C, 2×OCOCH$_3$), 169.93 (2C, 2×OCOCH$_3$), 90.66 (2C, C-1, C-1'), 71.27 (2C, C-4, C-4'), 70.10 (2C, C-3, C-3'), 69.90 (2C, C-2, C-2'), 69.60 (2C, C-5, C-5'), 30.56 (2C, 2×SCOCH$_3$), 30.05 (2C, C-6, C-6'), 20.84 (4C, 4×OCOCH$_3$), 20.70 (2C, 2×OCOCH$_3$) ppm.

Synthesis of 6,6'-dithio-6,6'-dideoxy-α,α-trehalose (Cmpd 5): Reagent R2 (1.18 g, 1.7 mmol) was dissolved in NaOMe (degassed, 0.1 M, 66 mL, 6.6 mmol) under N$_2$. After 28 min, the reaction mixture was diluted with MeOH (150 mL), and Amberlite IR 120 H$^+$ resin was added. The mixture was stirred until neutral, filtered, and solvents were removed under reduced pressure. The crude was re-dissolved in water (40 ml, degassed), washed with EtOAc (30 mL), filtered, and freeze-dried to give Cmpd 5 (0.605 g, 98%) as a white amorphous solid. $^1$H NMR (500 MHz, D$_2$O) δ 5.26 (d, J$_{1,2}$=3.8 Hz, 2H, H-1, H-1'), 3.87 (ddd, J$_{4,5}$=9.9 Hz, J$_{5,6b}$=7.3 Hz, J$_{5,6a}$=2.6 Hz, 2H, H-5, H-5'), 3.84 (t, J=9.5, 2H, H-3, H-3'), 3.68 (dd, J=9.9, 3.9 Hz, 2H, H-2, H-2'), 3.45 (t, J=9.4 Hz, 2H, H-4, H-4'), 3.01 (dd, J=14.3, 2.7 Hz, 2H, H-6a, H-6a'), 2.75 (dd, J=14.3, 7.4 Hz, 2H, H-6b, H-6b'). $^{13}$C NMR (126 MHz, D$_2$O) δ 93.08 (2C, C-1, C-1'), 72.32 (2C, C-3, C-3'), 72.19 (2C, C-5, C-5'), 71.88 (2C, C-4, C-4'), 71.04 (2C, C-2, C-2'), 25.05 (2C, C-6, C-6') ppm.

1.6. Synthesis of Compound 6 (Methyl-6,6'-dithio-6,6'-dideoxy-D-lactoside)

Figure 8:
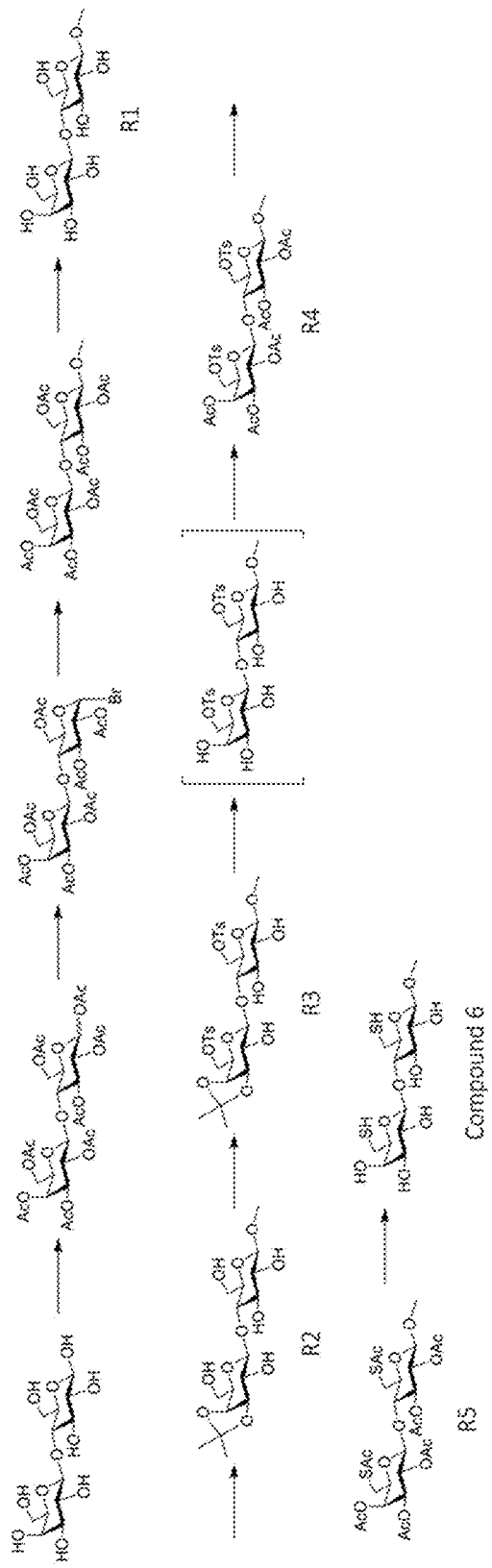
FIG. 8 depicts the synthesis of compound 6 (Methyl-6,6'-dithio-6,6'-dideoxy-β-lactoside).

FIG. 8 depicts the synthesis of compound 6 (Methyl-6,6'-dithio-6,6'-dideoxy-β-lactoside).

Synthesis of Methyl-β-lactoside (Reagent R1)

Acetic anhydride (34.0 mL, 0.36 mol) and 4-Dimethylaminopyridine (0.37 g, 2.92 mmol) were added to a solution of α,β-D-lactose (10.0 g, 29.2 mmol) in pyridine (57.5 mL) and the reaction was stirred at room temperature for 3 h. After 3 h, TLC (EtOAc-cyclohexane 1:1) did not show any starting materials left, and volatile was removed under reduced pressure. Reaction residue was dissolved in $CH_2Cl_2$ (300 mL) and 33% HBr in acetic acid (25.3 ml, 0.146 mol) was added into the reaction slowly in the dark environment. Reaction was stirred at room temperature for 3 h and monitored by TLC (EtOAc-cyclohexane 1:1) to confirm reaction has finished. Reaction was neutralised with a satd. aq. $NaHCO_3$ and dried over $MgSO_4$. The solvent was removed under reduced pressure to afford the crude bromide product. Freshly made solution of NaOMe (50 mM in MeOH) was added to crude lactose bromide in dry MeOH (150 mL) under $N_2$ and the resulting mixture was stirred for 20 h. After completion of the reaction, the mixture was neutralised with Dowex 50 W+ ion exchange resin and the resin filtered off. The filtrate was concentrated and concentrated to dryness in vacuo to obtain Reagent 1 as a colourless solid (8.2 g 79%). $^1$H NMR (500 MHz, $D_2O$) δ 4.46 (d, $J_{1',2'}$=7.8 Hz, 1H, H-1'), 4.42 (d, $J_{1,2}$=8.0 Hz, 1H, H-1), 4.00 (dd, $J_{6a,6b}$=12.3 Hz, $J_{5,6a}$=2.1 Hz, 1H, H-6a), 3.94 (dd, J=3.4, 0.9 Hz, 1H, H-4'), 3.82 (dd, $J_{6a,6b}$=12.3 Hz, $J_{5,6b}$=5.1 Hz), 3.83-3.74 (m, 2H, 2×H-6'), 3.74 (td, $J_{5,6}$=4.2 Hz, $J_{4',5'}$=1.0 Hz, 1H, H-5'), 3.70-3.64 (m, 3H, H-3', H-3, H-4), 3.61 (ddd, $J_{4,5}$=7.5 Hz, $J_{5,6b}$=5.0 Hz, $J_{5,6a}$=2.5 Hz, 1H, H-5), 3.59 (s, 3H, $C^1OCH_3$), 3.56 (dd, $J_{2',3'}$=10.0 Hz, $J_{1',2'}$=7.8 Hz, 1H, H-2'), 3.32 (ddd, J=8.0, 6.7, 2.5 Hz, 1H, H-2) ppm. $^{13}$C NMR (126 MHz, $D_2O$) δ 103.01 (1C, C-1), 102.87 (1C, C-1'), 78.32 (1C), 75.30 (1C, C-5'), 74.71 (1C, C-5), 74.34 (1C), 72.73 (1C, C-2), 72.46 (1C, C-3'), 70.89 (1C, C-2'), 68.49 (1C, C-4'), 60.96 (1C, C-6'), 60.01 (1C, C-6), 57.16 (1C, $C^1OCH_3$) ppm.

Synthesis of Methyl-3',4'-O-isopropylidene-β-lactoside (Reagent R2)

2,2-Dimethoxypropane (12.8 ml, 0.12 mol), and p-TsOH monohydrate (0.84 g, 4.5 mmol) were added to a solution of Reagent 1 (8.0 g, 22.4 mmol) in DMF (50 ml) under $N_2$. The mixture was heated to 85° C. After 22 h, TLC (EtOAc-MeOH 4:1) indicated full consumption of the Reagent 1, and the mixture was left to cool to room temperature, while TEA (3.8 ml) was added to give pH=7-7.5. Solvents were removed under reduced pressure and the crude was purified by FC to yield Reagent 2 (5.38 g, 60%). $^1$H NMR (500 MHz, DMSO-$d_6$) δ 5.44 (d, $J_{2'-OH,2}$=5.1 Hz, 1H, 2'-OH), 5.17 (d, $J_{2-OH,2}$=5.0 Hz, 1H, 2-OH), 4.84 (t, $J_{6'-OH,6}$=5.3 Hz, 1H, 6'-OH), 4.61 (t, $J_{6-OH,6}$=6.0 Hz, 1H, 6-OH), 4.55 (d, $J_{3-OH,3}$=1.7 Hz, 1H, 3-OH), 4.26 (d, $J_{1',2'}$=8.2 Hz, 1H, H-1'), 4.12-4.08 (m, 1H, H-4'), 4.10 (d, $J_{1,2}$=7.7 Hz, 1H, H-1), 3.96 (dd, $J_{2',3'}$=7.1 Hz, $J_{3',4'}$=5.5 Hz, 1H, H-3'), 3.83 (ddd, J=7.3, 5.0, 2.1 Hz, 1H, H-5'), 3.72 (ddd, $J_{6a,6b}$=11.9 Hz, $J_{6-OH,6a}$=5.7 Hz, $J_{5,6a}$=2.3 Hz, 1H, H-6a), 3.62-3.56 (m, 2H, H-6a', H-6b), 3.53 (ddd, $J_{6a',6b'}$=11.0 Hz, $J_{5',6b'}$=7.8 Hz, $J_{6'-OH,6b'}$=5.5 Hz, 1H, H-6b'), 3.39 (s, 3H, $C^1OCH_3$), 3.34-3.30 (m, 2H, H-3, H-4), 3.26 (ddd, J=7.3, 4.6, 2.2 Hz, 1H, H-5), 3.23 (ddd, $J_{1',2'}$=8.2 Hz, $J_{2',3'}$=7.1 Hz, $J_{2'OH,2'}$=5.1 Hz, 1H, H-2'), 3.00 (ddd, $J_{2,3}$=9.0 Hz, $J_{1,2}$=7.8 Hz, $J_{2-OH,2}$=5.0 Hz, 1H, H-2), 1.39 (s, 3H, $CH_3CCH_3$), 1.25 (s, 3H, $CH_3CCH_3$) ppm. $^{13}$C NMR (126 MHz, DMSO-$d_6$) δ 108.66 (1C, $CH_3CCH_3$), 103.59 (1C, C-1), 102.69 (1C, C-1'), 80.48 (1C), 79.24 (1C, C-3'), 74.82 (1C), 74.74 (1C, C-5), 73.33 (1C, C-5'), 73.13 (1C, C-2), 73.08 (1C, C-4'), 72.44 (1C, C-2'), 60.36 (1C, C-6'), 60.26 (1C, C-6), 56.07 (1C, $C^1OCH_3$), 28.09 (1C, $CH_3CCH_3$), 26.30 (1C, $CH_3CCH_3$) ppm.

Synthesis of Methyl-3',4'-O-isopropylidene-6,6'-di-O-tosyl-β-lactoside (Reagent R3)

Reagent R2 (5 g, 12.5 mmol) was dissolved in Pyridine (dry, 50 ml) under $N_2$ and cooled to 0° C. Tosyl chloride (6.25 g, 30.4 mmol) in Pyridine (dry, 15 ml) was added over 30 min, and the mixture was left on ice to slowly warm to room temperature After 24 h TLC (EtOAc-MeOH 9:1) indicated full consumption of Reagent 2 and TEA (12.2 ml) was added to give pH=8.5. Solvents were removed under reduced pressure and the crude was purified by FC (EtOAc-MeOH 95:5) to yield Reagent 3 (5.13 g, 58%) $^1$H NMR (500 MHz, DMSO-$d_6$) δ 7.83 (d, J=8.3 Hz, 2H, Ar), 7.77 (d, J=8.3 Hz, 2H, Ar), 7.52-7.48 (m, 2H, Ar), 7.47-7.44 (m, 2H, Ar), 5.48 (d, $J_{2'-OH,2}$=4.4 Hz, 1H, 2'-OH), 5.34 (d, $J_{2-OH,2}$=5.1 Hz, 1H, 2-OH), 4.50 (d, $J_{3-OH,3}$=2.7 Hz, 1H, 3-OH), 4.37 (dd, $J_{6a,6b}$=10.7 Hz, $J_{5,6}$=2.0 Hz, 1H, H-6a), 4.25 (d, $J_{1',2'}$=8.1 Hz, 1H, H-1'), 4.20 (dd, $J_{6a',6b'}$=10.1 Hz, $J_{5',6a'}$=3.7 Hz, 1H, 6a'), 4.17 (dd, $J_{6a,6b}$=10.7 Hz, $J_{5,6b}$=6.1 Hz, 1H, H-6b), 4.13 (ddd, $J_{5',6b'}$=8.2 Hz, $J_{5',6a'}$=3.8 Hz, $J_{4',5'}$=2.1 Hz, 1H, H-5'), 4.11-4.08 (m, 1H, H-4'), 4.10 (d, $J_{1,2}$=7.7 Hz, 1H, H-1), 3.93 (dd, $J_{6a',6b'}$=10.0 Hz, $J_{5',6b'}$=8.2 Hz, 1H, H-6b'), 3.90 (dd, J=7.0, 5.5 Hz, 1H, H-3'), 3.56 (ddd, $J_{4,5}$=9.4 Hz, $J_{5,6b}$=6.1 Hz, $J_{5,6a}$=2.0 Hz, 1H, H-5), 3.36-3.27 (m, 2H, H-3, H-4), 3.31 (s, 3H, $C^1OCH_3$), 3.15-3.09 (m, 1H, H-2'), 3.04-2.95 (m, 1H, H-2), 2.42 (s, 3H, $C_6H_4CH_3$), 2.41 (s, 3H, $C_6H_4CH_3$), 1.32 (s, 3H, $CH_3CCH_3$), 1.20 (s, 3H, $CH_3CCH_3$) ppm. $^{13}$C NMR (126 MHz, DMSO-$d_6$) δ 145.13 (1C, Ar), 144.76 (1C, Ar), 132.41 (1C, Ar), 131.83 (1C, Ar), 130.23 (2C, 2×Ar), 130.02 (2C, 2×Ar), 127.78 (2C, 2×Ar), 127.62 (2C, 2×Ar), 109.04 (1C, $CH_3CCH_3$), 103.24 (1C, C-1), 101.13 (1C, C-1'), 78.89 (1C, C-3'), 78.41 (1C), 72.89 (1C), 72.39 (1C, C-2), 71.72 (1C, C-4'), 71.62 (1C, C-2'), 71.30 (1C, C-5), 69.75 (1C, C-5'), 69.31 (1C, C-6), 68.72 (1C, C-6'), 55.92 (1C, $C^1OCH_3$), 27.84 (1C, $CH_3CCH_3$), 26.14 (1C, $CH_3CCH_3$), 21.11 (1C, $C_6H_4CH_3$), 21.09 (1C, $C_6H_4CH_3$) ppm.

Synthesis of Methyl-2,3,2',3',4'-penta-O-acetyl-6,6'-di-O-tosyl-β-lactoside (Reagent R4)

Reagent 3 (4.5 g, 6.3 mmol) was dissolved in AcOH (aq. 70% v/v, 50 ml). The mixture was heated to 60° C. After 3.5 h, TLC (100% EtOAc) indicated a full consumption of Reagent 3. Solvents were removed under reduced pressure, and the crude product was re-dissolved in dry pyridine (25 mL, 0.35 mol) and $Ac_2O$ (25 mL, 0.26 mol). After 16 h, solvents were removed under reduced pressure and the crude compound was purified by FC (EtOAc-cyclohexane 1:1) to give Reagent R4 (3.9 g, 73%). $^1$H NMR (400 MHz, $CDCl_3$) δ 7.84-7.75 (m, 4H, Ar), 7.41-7.36 (m, 4H, Ar), 5.32 (dd, $J_{3',4'}$=3.6 Hz, $J_{4',5'}$=1.0 Hz, 1H, H-4'), 5.13 (t, J=9.2 Hz, 1H, H-3), 5.03 (dd, $J_{2',3'}$=10.4 Hz, $J_{1',2'}$=7.9 Hz, 1H, H-2'), 4.88 (dd, $J_{2',3'}$=10.4 Hz, $J_{3',4'}$=3.5 Hz, 1H, H-3'), 4.74 (dd, $J_{2,3}$=9.4 Hz, $J_{1,2}$=7.9 Hz, 1H, H-2), 4.44 (d, $J_{1',2'}$=7.9 Hz, 1H, H-1'), 4.34 (dd, $J_{6a,6b}$=10.9 Hz, $J_{5,6a}$=2.0 Hz, 1H, H-6a), 4.30 (d, $J_{1,2}$=7.8 Hz, 1H, H-1), 4.18 (dd, $J_{6a,6b}$=10.9 Hz, $J_{5,6b}$=4.2

Hz, 1H, H-6b), 4.05 (dd, $J_{6',6'}$=10.2 Hz, $J_{5',6'}$=6.5 Hz, 1H, H-6'), 3.99 (dd, $J_{6',6'}$=10.2 Hz, $J_{5',6'}$=6.5 Hz, 1H, H-6'), 3.84 (td, $J_{5',6'}$=6.6 Hz, $J_{4',5'}$=1.2 Hz, 1H, H-5'), 3.74-3.68 (m, 1H, H-4), 3.56 (ddd, $J_{4,5}$=10.1 Hz, $J_{5,6b}$=4.3 Hz, $J_{5,6a}$=2.1 Hz, 1H, H-5), 3.36 (s, 3H, $C^1OCH_3$), 2.46 (s, 6H, $2 \times C_6H_4CH_3$), 2.06 (s, 3H, $OCOCH_3$), 2.04 (s, 3H, $OCOCH_3$), 2.03 (s, 3H, $OCOCH_3$), 1.97 (s, 3H, $OCOCH_3$), 1.96 (s, 3H, $OCOCH_3$) ppm.

Synthesis of Methyl-2,3,2',3',4'-Penta-O-acetyl-6,6'-dideoxy-6,6'-dithioacetyl-β-lactoside (Reagent R5)

Potassium thioacetate (2.58 g, 22.6 mmol) was added to a solution of Reagent R4 (3.0 g, 3.5 mmol) in DMF (20 mL) and stirred at 110° C. overnight. NMR was used to monitor the reaction. After the competition, the mixture was cooled down to room temperature, diluted with $CH_2Cl_2$ (180 mL) and washed with water (2×80 mL). Organic layers were combined and dried over $MgSO_4$ and concentrated to dryness. Pure compound (1.5 g, 65.0%) was afforded after two FC on silica gel (EtOAc-cyclohexane). $^1H$ NMR (500 MHz, $CDCl_3$) δ 5.38 (dd, $J_{3',4'}$=3.4 Hz, $J_{4',5'}$=1.1 Hz, 1H, H-4'), 5.17 (dd, $J_{2,3}$=9.6 Hz, $J_{3,4}$=9.0 Hz, 1H, H-3), 5.09 (dd, $J_{2',3'}$=10.4 Hz, $J_{1',2'=7.8}$ Hz, 1H, H-2'), 4.96 (dd, $J_{2',3'}$=10.4 Hz, $J_{3',4'}$=3.4 Hz, 1H, H-3'), 4.90 (dd, $J_{2,3}$=9.6 Hz, $J_{1,2}$=7.9 Hz, 1H, H-2), 4.53 (d, $J_{1',2'}$=7.8 Hz, 1H, H-1'), 4.35 (d, $J_{1,2}$=7.9 Hz, 1H, H-1), 3.69-3.62 (m, 2H, H-4, H-5'), 3.59-3.49 (m, 2H, H-5, H-6), 3.47 (s, 3H, $C^1OCH_3$), 3.10-2.92 (m, 3H, H-6, 2×H-6'), 2.36 (s, 3H, $SCOCH_3$), 2.35 (s, 3H, $SCOCH_3$), 2.16 (s, 3H, $OCOCH_3$), 2.09 (s, 3H, $OCOCH_3$), 2.06 (s, 3H, $OCOCH_3$), 2.04 (s, 3H, $OCOCH_3$), 1.96 (s, 3H, $OCOCH_3$) ppm. $^{13}C$ NMR (126 MHz, $CDCl_3$) δ 194.51 (1C, $SCOCH_3$), 194.39 (1C, $SCOCH_3$), 170.37 (1C, $OCOCH_3$), 170.20 (1C, $OCOCH_3$), 170.00 (1C, $OCOCH_3$), 169.85 (1C, $OCOCH_3$), 169.51 (1C, $OCOCH_3$), 101.45 (1C, C-1), 100.80 (1C, C-1'), 78.52 (1C), 73.46 (1C, C-5), 72.67 (1C, C-3), 72.39 (1C), 71.83 (1C, C-2), 71.37 (1C, C-3'), 69.30 (1C, C-2'), 67.71 (1C, C-4'), 57.00 (1C, $C^1OCH_3$), 30.66 (2C, 2×$SCOCH_3$), 30.60 (1C, C-6), 28.43 (1C, C-6'), 21.08 (1C, $OCOCH_3$), 20.93 (1C, $OCOCH_3$), 20.88 (1C, $OCOCH_3$), 20.87 (1C, $OCOCH_3$), 20.69 (1C, $OCOCH_3$) ppm.

Synthesis of Methyl-6,6'-dithio-6,6'-dideoxy-β-lactoside (Compound 6)

A solution of NaOMe (2 M in MeOH) was added to a solution of Reagent 5 (1.0 g, 1.5 mmol) in dry MeOH (13 mL) under $N_2$ until pH=13 was reached and the resulting mixture was stirred for 3 h. After completion of the reaction, the mixture was neutralised with Dowex 50 $H^+$ ion exchange resin, the resin filtered off and the filtrate was concentrated to dryness in vacuo. Obtained solid was dried under high vacuum to yield Cmpd 6 (0.475 g, 81.6%) as a white solid. $^1H$ NMR (500 MHz, $D_2O$) δ 4.51 (d, $J_{1',2'}$=7.9 Hz, 1H, H-1'), 4.45 (d, $J_{1,2}$=8.0 Hz, 1H, H-1), 4.02 (d, J=3.2 Hz, 1H, H-4'), 3.73-3.65 (m, 5H, H-3, H-3', H-4, H-5, H-5'), 3.60 (s, 3H, $C^1OCH_3$), 3.53 (dd, $J_{1',2'}$=10.0 Hz, $J_{2',3'}$=7.8 Hz, 1H, H-2'), 3.38-3.31 (m, 1H, H-2), 3.17-3.11 (m, 1H, H-6a), 2.89-2.84 (m, 1H, H-6b), 2.83 (dd, $J_{6a',6b'}$=14.0 Hz, $J_{5',6b'}$=8.2 Hz, 1H, H-6b'), 2.76 (dd, $J_{6a',6b'}$=13.9 Hz, $J_{5',6a'}$=5.6 Hz, 1H, H-6a') ppm. $^{13}C$ NMR (101 MHz, $D_2O$) δ 103.22 (1C, C-1'), 103.02 (1C, C-1), 81.12 (1C), 76.46 (1C), 74.40 (1C), 74.14 (1C), 72.78 (1C, C-2), 72.42 (1C), 70.70 (1C, C-2'), 68.94 (1C, C-4'), 57.29 (1C, $C^1OCH_3$), 24.67 (1C, C-6), 23.83 (1C, C-6') ppm.

1.6 Synthesis of Compound 7 (Methyl-6,6'-dithio-6,6'-dideoxy-B-cellobioside)

Figure 9:
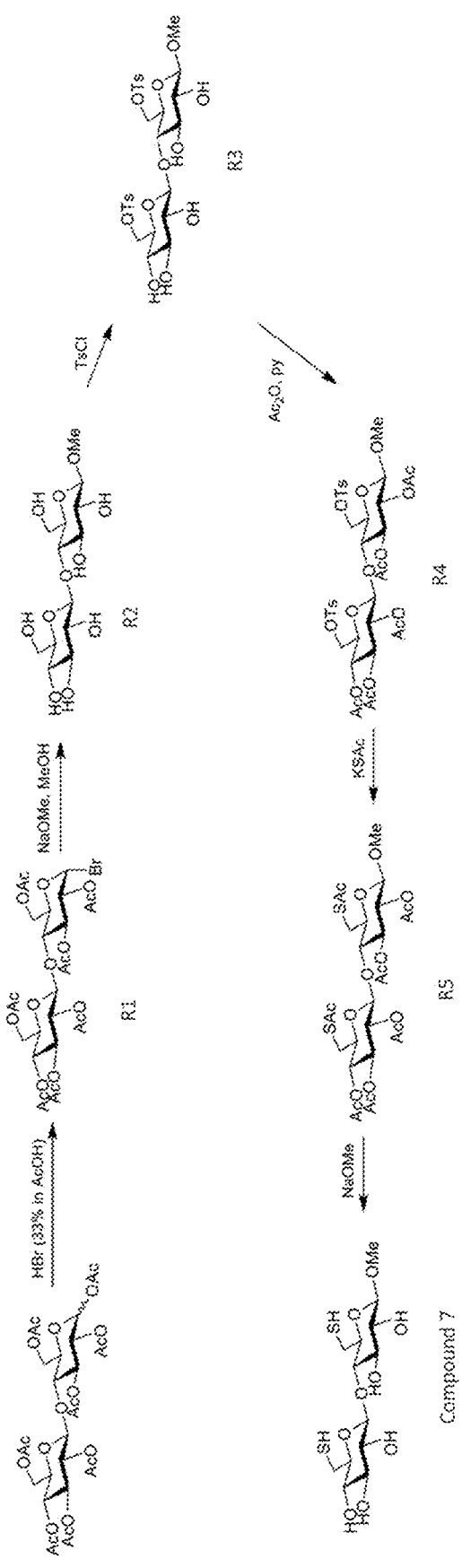
FIG. 9 depicts the synthesis of compound 7 (Methyl-6,6'-dithio-6,6'-dideoxy-β-cellobioside).

FIG. 9 depicts the synthesis of compound 7 (Methyl-6,6'-dithio-6,6'-dideoxy-β-cellobioside).

Synthesis of 1-bromo-2,3,6,2',3',4',6'-Hepta-O-acetyl-β-cellobioside (Reagent R1)

To a solution of β-cellobioside octaacetate (5.06 g, 7.37 mmol) in $CH_2Cl_2$ (25 ml), a solution of HBr (33% in acetic acid; 7.5 mL, 0.144 mol) was added in small portions. The round bottom flask was protected from the light. The solution was left stirring at room temperature overnight. More $CH_2Cl_2$ (80 mL) was then added to the solution and left stirring with a satd. aq. $NaHCO_3$ (120 mL) until no more gas was observed. Afterwards, the organic layer was washed with a satd. aq. $NaHCO_3$ (3×50 mL) and the organic phase was evaporated to dryness and the residue re-dissolved in a minimal amount of acetone. This solution had heptane added to it and was left at 4° C. overnight. The mother liquor was filtered off to yield Reagent R1 (4.35 g, 84%) as a white crystalline solid. $^1H$ NMR (300 MHz, $CDCl_3$) δ 6.52 (d, J=4.1 Hz, 1H, H-1), 5.53 (t, J=9.7 Hz, 1H, H-3), 5.15 (t, J=9.2 Hz, 1H, H-3'), 5.07 (t, J=9.5 Hz, 1H, H-4'), 4.94 (dd, J=9.0, 7.9 Hz, 1H, H-2'), 4.76 (dd, J=10.0, 4.1 Hz, 1H, H-2), 4.55 (d, J=7.9 Hz, 2H, H-1', H-6'), 4.37 (dd, J=12.5, 4.4 Hz, 1H, H-6), 4.25-4.13 (m, 2H, H-5', H-6'), 4.05 (dd, J=12.5, 2.3 Hz, 1H, H-6), 3.84 (t, J=9.8 Hz, 1H, H-4), 3.67 (ddd, J=9.6, 4.4, 2.3 Hz, 1H, H-5), 2.14 (s, 3H, $OCOCH_3$), 2.09 (s, 6H, 2×$OCOCH_3$), 2.06-2.02 (m, 6H, 2×$OCOCH_3$), 2.01 (s, 3H, $OCOCH_3$), 1.99 (s, 3H, $OCOCH_3$) ppm; $^{13}C$ NMR (126 MHz, $CDCl_3$) δ 170.62, 170.39, 170.23, 170.11, 169.42, 169.10, 100.71, 86.55, 75.37, 73.16, 73.09, 72.20, 71.75, 70.92, 69.57, 67.92, 61.75, 61.07, 32.03, 22.84, 20.96, 20.83, 20.74, 20.69, 14.26 ppm.

Synthesis of Methyl-β-cellobioside (Reagent R2)

To a solution of Reagent R1 (37 g, 53.89 mmol) in dry MeOH (500 mL), an aqueous solution of 1.5 M NaOMe (50 mL, 75 mmol) was added dropwise over a period of 15 min. The solution was left stirring at room temperature overnight. The solution was neutralised by the addition of a suspension of ion-exchange resin (Amberlite IR 120 $H^+$ form) in MeOH. The solution was filtered and evaporated in vacuo to give Reagent R2 (17.09 g, 89%) as a white powder. $^1H$ NMR (500 MHz, D2O) δ 4.52 (d, J=7.9 Hz, 1H, H-1'), 4.42 (d, J=8.0 Hz, 1H, H-1), 4.00 (dd, J=12.3, 2.0 Hz, 1H, H-6), 3.92 (dd, J=12.4, 2.2 Hz, 1H, H-6'), 3.83 (dd, J=12.3, 4.8 Hz, 1H, H-6), 3.74 (dd, J=12.4, 5.7 Hz, 1H, H-6'), 3.69-3.63 (m, 3H, H-3, H-5', H-4), 3.58 (s, 3H, $COCH_3$), 3.54-3.48 (m, 2H, H-5, H-3'), 3.44 (d, J=9.2 Hz, 1H, H-4'), 3.32 (m, 2H, H-2, H-2') ppm; 13C NMR (126 MHz, $D_2O$) δ 103.00, 102.50, 78.60, 75.92, 75.43, 74.70, 74.26, 73.10, 72.81, 69.39, 60.51, 59.97, 57.16 ppm.

Synthesis of Methyl-6,6'-di-O-tosyl-β-cellobioside (Reagent R3)

A solution of p-toluenesulphonyl chloride (15 g, 78.68 mmol) in dry pyridine (80 mL) was added to an ice cooled solution of Reagent R2 (12 g, 33.68 mmol) previously dissolved in dry pyridine (100 mL) and the reaction was stirred while allowing to warm to room temperature. Additional p-toluenesulphonyl chloride (3.5 g, 18.36 mmol) dissolved in dry pyridine (20 mL) was added and the mixture was stirred overnight. MeOH (100 mL) was then added, the mixture was concentrated, and two times purified by column chromatography on silica gel via Biotage (MeOH-EtOAc; MeOH—$CH_2Cl_2$) to yield Reagent R3 (2.5, 11%) as an off-white solid. $^1$H NMR (400 MHz, $D_2O$) δ 7.86 (t, J=7.8 Hz, 4H, Ar), 7.53 (t, J=7.6 Hz, 4H, Ar), 4.41 (m, 2H, H-1', H-6/H-6'), 4.35 (d, J=4.0 Hz, 1H, H-1), 4.31 (d, J=8.0 Hz, 1H, H-6/H-6'), 4.25 (dd, J=11.3, 5.5 Hz, 1H, H-5'/H-5), 4.21 (d, J=7.9 Hz, 1H, H-6'/H-6), 3.72 (d, J=9.5 Hz, 1H, H-6'/H-6), 3.63-3.53 (m, 2H, H-5/H-5', H-4'/H-4), 3.50 (m, 4H, $COCH_3$, H-4/H-4'), 3.34-3.28 (m, 2H, H-2, H-2'), 3.23 (t, J=8.6 Hz, 1H, H-3'/H-3), 3.12 (t, J=8.4 Hz, 1H, H-3/H-3'), 2.47 (s, 6H, 2×$C_6O_4CH_3$) ppm.

Synthesis of Methyl-2,3,2',3',4'-penta-O-acetyl-6,6'-di-O-tosyl-β-cellobioside (Reagent R4)

Reagent R3 (2.5 g, 3.76 mmol) was dissolved in pyridine (30.3 mL, 0.38 mol), had acetic anhydride (17.8 mL, 0.19 mol) added to it and the solution was left stirring at room temperature overnight. The mixture was then concentrated and co-evaporated with toluene to dryness. The crude was purified by column chromatography (toluene-acetone) to yield Reagent R4 (2.5 g, 76%) as an off-white solid. $^1$H NMR (400 MHz, $CDCl_3$) δ 7.80 (dd, J=17.7, 8.4 Hz, 4H, Ar), 7.40 (dd, J=8.1, 5.0 Hz, 4H, Ar), 5.08 (t, J=9.4 Hz, 1H, H-3), 5.03 (t, J=9.3 Hz, 1H, H-3'), 4.92 (t, J=9.6 Hz, 1H, H-4'), 4.76 (dd, J=9.4, 7.7 Hz, 2H, H-2, H-2'), 4.38 (d, J=7.9 Hz, 1H, H-1'), 4.33 (dd, J=10.9, 2.0 Hz, 1H, H-6'), 4.29 (d, J=7.9 Hz, 1H, H-1), 4.18 (dd, J=10.9, 3.7 Hz, 1H, H-6), 4.16 (dd, J=11.1, 2.6 Hz, 1H, H-6'), 4.09 (dd, J=11.2, 5.0 Hz, 1H, H-6), 3.68 (t, J=9.6 Hz, 1H, H-4), 3.63 (dq, J=7.7, 5, 2.7 Hz, 1H, H-5'), 3.52 (ddd, J=10.1, 3.7, 1.9 Hz, 1H, H-5), 3.37 (s, 3H, $COCH_3$), 2.47 (s, 3H, $C_6O_4CH_3$), 2.46 (s, 3H, $C_6O_4CH_3$), 2.02 (s, 3H, $OCOCH_3$), 2.00 (s, 3H, $OCOCH_3$), 1.98 (s, 3H, $OCOCH_3$), 1.97 (s, 3H, $OCOCH_3$), 1.90 (s, 3H, $OCOCH_3$) ppm; $^{13}$C NMR (101 MHz, $CDCl_3$) δ 170.25, 170.03, 169.63, 169.41, 168.98, 145.59, 145.51, 132.81, 132.47, 130.21, 129.16, 128.35, 128.19, 128.15, 125.42, 101.43, 100.10, 75.22, 72.93, 72.51, 72.01, 71.65, 71.55, 71.34, 68.19, 67.08, 66.56, 56.92, 21.81, 21.78, 20.82, 20.73, 20.67, 20.62 ppm.

Synthesis of Methyl-2,3,2',3',4'-penta-O-acetyl-6,6'-dideoxy-6,6'-dithioacetyl-β-cellobioside (Reagent R5)

Potassium thioacetate (1.10 g, 9.62 mmol) was added to the solution of Reagent R4 (2 g, 2.29 mmol) in dry DMF (45 mL) and was left stirring at 110° C. over for 72 h. The mixture was cooled down to room temperature and diluted with $CH_2Cl_2$ (150 mL), washed with water (3×100 mL) and satd. aq. $NaHCO_3$ (2×100 mL). The organic layer was dried over $MgSO_4$ and the filtrate was concentrated under reduced pressure to yield Reagent R5 (1.2 g, 77%) as an off-yellow solid. $^1$H NMR (400 MHz, $CDCl_3$) δ 5.16-5.10 (m, 2H, H-3', H-3), 5.01-4.83 (m, 3H, H-4', H-2' H-2), 4.56 (d, J=7.9 Hz, 1H, H-1'), 4.34 (d, J=8.0 Hz, 1H, H-1), 3.64-3.49 (m, 4H, H-6, H-6', H-5', H-4), 3.47 (s, 3H, $COCH_3$), 3.23 (dd, J=14.3, 2.9 Hz, 1H, H-6), 3.04 (dd, J=14.3, 7.0 Hz, 1H, H-6'), 2.97 (dd, J=13.3, 7.8 Hz, 1H, H-4), 2.36 (s, 3H, $SCOCH_3$), 2.35 (s, 3H, $SCOCH_3$), 2.06 (s, 6H, 2×$OCOCH_3$), 2.02 (s, 6H, 2×$OCOCH_3$), 1.98 (s, 3H, $OCOCH_3$) ppm.

Synthesis of Methyl-6,6'-dithio-6,6'-dideoxy-β-D-cellobioside (Cmpd 7)

To an emulsion of Reagent R5 (89 mg, 0.13 mmol) in MeOH (20 mL), a solution of NaOMe (1 M in MeOH; 0.5 mL, 0.5 mmol) was added under $N_2$. Upon the addition of the NaOMe the solution became clear. After the completion of the reaction, the solution was neutralised by the addition of a suspension of ion-exchange resin (Amberlite IR 120 H form) in MeOH and the filtrate was evaporated in vacuo to give Cmpd 7 (45 mg, 89%) as an off-white-yellow powder. $^1$H NMR (400 MHz, $D_2O$) δ 4.60 (d, J=7.9 Hz, 1H, H-1'), 4.45 (d, J=8.0 Hz, 1H, H-1), 3.70-3.65 (m, 3H, H-4', H-4, H-5'/H-5), 3.60 (s, 3H, $COCH_3$), 3.54-3.44 (m, 3H, H-5/H-5', H-3, H-3'), 3.37-3.34 (m, 2H, H-2', H-2), 3.16 (d, J=14.2 Hz, 1H, H-6/H-6'), 3.10-3.02 (m, 1H, H-6/H-6'), 2.92-2.82 (m, 1H, H-6'/H-6), 2.75 (dd, J=14.3, 7.0 Hz, 1H, H-6'/H-6) ppm.

1.8 Synthesis of Compound 8 (3-thiopropyl-6'-thio-6'-deoxy-β-D-lactoside)

Figure 10:
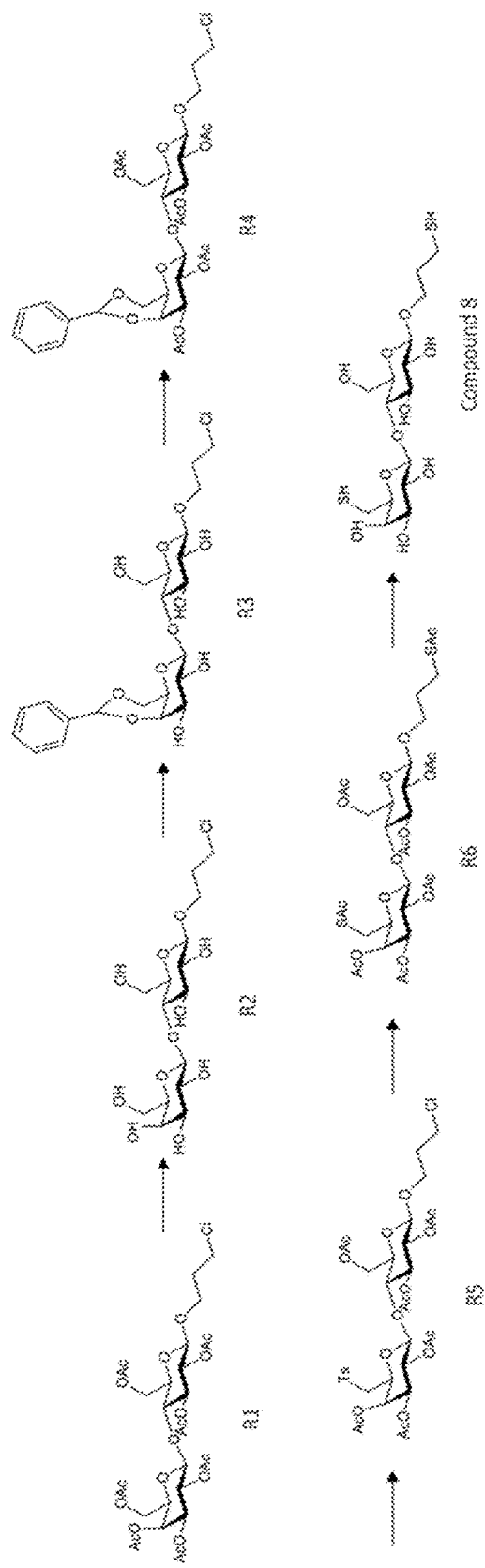
FIG. 10 depicts the synthesis of compound 8 (3-thiopropyl-6'-thio-6'-deoxy-β-D-lactoside).

FIG. 10 depicts the synthesis of compound 8 (3-thiopropyl-6'-thio-6'-deoxy-β-D-lactoside).

Synthesis of 1-Chloropropyl-2,3,6,2',3',4',6'-hepta-O-acetyl-β-lactoside (Reagent R1)

Starting material (2,3,4,6-Tetra-O-acetyl-β-D-galactopyranosyl-(1→4)-1,2,3,6-tetra-O-acetyl-β-D-glucopyranoside) (10.0 g, 14.7 mmol) was placed under $N_2$ and dissolved in dry $CH_2Cl_2$ (73.6 mL). 3-Chloro-1-propanol, which had been dried over $MgSO_4$, (1.5 mL, 18 mmol) was then added. The solution was cooled to 0° C. and $BF_3.Et_2O$ (6.2 mL, 50.0 mmol) was added. The reaction mixture was allowed to warm to room temperature and was stirred for 21 h. The reaction was quenched by the addition of $Et_3N$ at 0° C. and the volatiles were removed by rotary evaporation. The Reagent R1 was obtained after flash chromatography on silica gel (EtOAc/toluene) as a white foam (5.4 g, 52%); $^1$H NMR (400 MHz, $CDCl_3$) δ 5.34 (dd, J=3.5, 1.2 Hz, 1H, H-4'), 5.19 (t, J=9.3 Hz, 1H, H-3), 5.10 (dd, J=10.5, 7.8 Hz, 1H, H-2'), 4.94 (dd, J=10.4, 3.5 Hz, 1H, H-3'), 4.88 (dd, J=9.6, 7.9 Hz, 1H, H-2), 4.52-4.43 (m, 3H, H-1, H-1', H-6$_{(A)}$'), 4.17-4.02 (m, 3H, H-6$_{(A+B)}$', H-6$_{(B)}$), 3.94 (dt, J=9.8, 5.3 Hz, 1H, O$CH_2$$_{(A)}$$CH_2CH_2Cl$), 3.86 (ddd, J=7.6, 6.4, 1.2 Hz, 1H, H-5'), 3.79 (m, 1H, H-4), 3.72-3.53 (m, 4H, H-5, O$CH_2$$_{(B)}$$CH_2CH_2Cl$+O$CH_2CH_2CH_2Cl$), 2.14 (s, 3H, $CH_3C$=O), 2.11 (s, 3H, $CH_3C$=O), 2.09-1.97 (m, 14H, 4×$CH_3C$=O+O$CH_2$$CH_2$$CH_2Cl$), 1.95 (s, 3H, $CH_3C$=O); $^{13}$C NMR (126 MHz, $CDCl_3$) δ 170.49, 170.46, 170.3, 170.2, 169.87, 169.82 and 169.2 (7C, $OCOCH_3$), 101.2 (C-1'), 100.9 (C-1), 76.4 (C-4), 72.83 (C-3), 72.80 (C-5), 71.7 (C-2), 71.1 (C-3'), 70.8 (C-5'), 69.2 (C-2'), 66.7 (C-4'), 66.5 (O$CH_2CH_2CH_2Cl$), 62.1 (C-6), 60.9 (C-6'), 41.4 (O$CH_2$$CH_2$$CH_2Cl$), 32.4 (O$CH_2CH_2$$CH_2Cl$), 20.99, 20.93, 20.81, 20.77, 20.77, 20.76 and 20.64 (7C, $OCOCH_3$); LRMS (ESI) m/z calculated for $C_{29}H_{41}ClO_{18}$ $[M+Na]^+$ 735.19, found 735.22.

Synthesis of 1-Chloropropyl-β-lactoside (Reagent R2)

Freshly made solution of NaOMe (50 mM in MeOH) was added to Reagent R1 (5.4 g, 7.6 mmol) in dry MeOH (25 mL) under $N_2$ and the resulting mixture was stirred for 20 h. After completion of the reaction the mixture was neutralised with Dowex 50 W+ ion exchange resin, the resin was filtered off and the filtrate was concentrated and dried in vacuo to obtain Reagent R2 as a colourless solid (2.6 g 83%). $^1$H NMR (500 MHz, $D_2O$) δ 4.50 (d, J=8.0 Hz, 1H, H-1'), 4.45 (d, J=7.8 Hz, 1H, H-1), 4.06 (dt, J=10.4, 6.0 Hz, 1H, H-2'), 3.99 (dd, J=12.3, 2.1 Hz, 1H, H-3), 3.93 (d, J=3.4 Hz, 1H, H-4'), 3.87-3.84 (m, 1H, H-2), 3.82 (d, J=5.8 Hz, 1H, H-6$_a$), 3.80 (d, J=4.1 Hz, 1H, H-6$_a$'), 3.78-3.76 (m, 1H, H-6$_b$), 3.75-3.71 (m, 4H, OC$\underline{H}_{2(A)}$CH$_2$CH$_2$Cl, H-6$_b$', H-5', H-4), 3.68 (d, J=3.3 Hz, 1H, H-5), 3.67-3.64 (m, 2H, OCH$_2$CH$_2$C$\underline{H}_2$Cl), 3.55 (dd, J=9.9, 7.8 Hz, 1H, OC$\underline{H}_{2(b)}$CH$_2$CH$_2$Cl), 3.32 (td, J=7.7, 2.5 Hz, 1H, H-3'), 2.10 (p, J=6.3 Hz, 2H, OCH$_2$C$\underline{H}_2$CH$_2$Cl) ppm.

Synthesis of 1-Chloropropyl-4',6'-O-benzylidene-β-lactoside (Reagent R3)

Benzaldehyde dimethyl acetal (1.6 mL, 10.6 mmol) and camphorsulfonic acid (0.37 g, 1.5 mmol) were added to a solution of Reagent R2 (2.6 g, 6.2 mmol) in dry DMF (25.0 mL) and the reaction was stirred at 65° C. After 5 h, TLC (EtOAc-MeOH 4:1) did not show any starting materials present. The mixture was dried to dryness under reduced pressure and the Reagent R3 was afforded by precipitation from 100% EtOAc as a white powder (2.5 g 80%). R$_f$ 0.53 (EtOAc-MeOH 4:1) $^1$H NMR (400 MHz, D$_2$O) δ 7.63-7.55 (m, 2H, Ar), 7.50 (ddd, J=3.3, 2.6, 1.5 Hz, 3H, Ar), 5.78 (s, 1H, C$_6$H$_5$CH), 4.58 (d, J=7.8 Hz, 1H, H1'), 4.53 (d, J=8.0 Hz, 1H, H1), 4.40 (dd, J=3.7, 1.0 Hz, 1H, H-4'), 4.29 (t, J=1.5 Hz, 2H, H-3, H-2'), 4.12-3.99 (m, 2H, H-2, H-6$_a$), 3.89-3.79 (m, 4H, H-6$_a$', H-6$_b$, H-6$_b$', OC$\underline{H}_{2(A)}$CH$_2$CH$_2$Cl), 3.77-3.70 (m, 3H, H-5', H-4, H-5), 3.68-3.61 (m, 2H, OCH$_2$CH$_2$C$\underline{H}_2$Cl), 3.38-3.30 (m, 1H, OC$\underline{H}_{2(b)}$CH$_2$CH$_2$Cl), 2.24-1.95 (m, 2H, OCH$_2$C$\underline{H}_2$CH$_2$Cl). $^{13}$C NMR (101 MHz, D$_2$O) δ 136.70, 129.67, 128.55 and 126.15 (6C, Ar), 102.87 (C-1'), 102.12 (C-1), 101.02 (C$_6$H$_5$CH), 78.60 (C-4), 75.62 (C-3), 74.74 (C-5), 74.15 (C-2), 72.70 (C-3'), 71.15 (C-5'), 70.37 (C-2'), 68.90 (C-4'), 67.07 (O$\underline{C}$H$_2$CH$_2$CH$_2$Cl), 66.49 (C-6), 59.85 (C-6'), 41.70 (OC$\underline{H}_2$CH$_2$CH$_2$Cl), 31.70 (OCH$_2$CH$_2$$\underline{C}$H$_2$Cl) ppm.

Synthesis of 1-Chloropropyl-2,3,6,2',3'-penta-O-acetyl-4',6'-O-benzylidene-β-lactoside (Reagent R4)

Acetic anhydride (4.6 mL, 49.2 mmol) and 4-Dimethylaminopyridine (0.05 g, 0.4 mmol) were added to a solution of Reagent R3 (2.5 g, 4.9 mmol) in pyridine (15.0 mL) and the reaction was stirred at room temperature for 3 h. After 3 h, TLC (EtOAc-cyclohexane 1:1) did not show any starting materials present. The mixture was dried to dryness under reduced pressure. 80% Acetic acid aqueous solution (55.0 mL) was added to reaction residue and was left stirring at 90° C. for 4 h. Reaction was monitored by TLC (EtOAc-cyclohexane 4:1). Upon the completion, the volatiles were removed under reduced pressure. The crude was purified by FC on silica gel (EtOAc-cyclohexane) to give Reagent R4 (2.3 g, 76%) as a colourless solid. R$_f$ 0.61 (EtOAc-cyclohexane 4:1) $^1$H NMR (400 MHz, CDCl$_3$) δ 5.25-5.14 (m, 2H, H-4', H-3), 4.94-4.83 (m, 2H, H-2', H-3'), 4.49 (dd, J=9.8, 7.8 Hz, 3H, H-2, H-1, H-1'), 4.14-4.01 (m, 2H, H-6$_a$, OC$\underline{H}_{2(A)}$CH$_2$CH$_2$Cl), 3.92 (ddt, J=16.3, 10.7, 5.3 Hz, 2H, H-6$_a$', H-6$_b$), 3.86-3.78 (m, 2H, H-6$_b$', OC$\underline{H}_{2(b)}$CH$_2$CH$_2$Cl), 3.71-3.62 (m, 2H, H-5', H-4), 3.61-3.55 (m, 3H, H-5, OCH$_2$CH$_2$C$\underline{H}_2$Cl), 2.11 (d, J=1.7 Hz, 3H, CH$_3$C=O), 2.07 (d, J=1.5 Hz, 6H, 2×CH$_3$C=O), 2.04 (d, J=2.4 Hz, 8H, 2×CH$_3$C=O+OCH$_2$C$\underline{H}_2$CH$_2$Cl) ppm.

Synthesis of 1-Chloropropyl-2,3,6,2',3',4'-hexa-O-acetyl-6'-O-tosyl-β-lactoside (Reagent R5)

A solution of tosyl chloride (1.1 g, 5.4 mmol) in dry pyridine (5.0 mL) was added to an ice cooled solution of Reagent R4 (2.3 g, 3.6 mmol) in dry pyridine (10 mL) and the reaction was stirred while allowing to warm to room temperature overnight. Reaction was monitored by TLC (EtOAc-cyclohexane 2:1). After the completion, pH was adjusted to 7 by adding Et$_3$N and volatiles were removed under reduced pressure. The reaction residue was left stirring with pyridine (8 mL), acetic acid (2.0 mL, 21.2 mmol) and 4-Dimethylaminopyridine (0.01 g, 0.08 mmol) at room temperature for 2 h. Afterwards, the volatiles were removed under reduced pressure. The crude was purified by FC on silica gel (EtOAc-cyclohexane) to give Reagent R5 (1.6 g, 55%) as a slightly yellow solid. Rf 0.53 (EtOAc-cyclohexane 1:1) $^1$H NMR (300 MHz, CDCl$_3$) δ 7.78 (d, J=8.3 Hz, 2H, Ar), 7.46-7.32 (m, 2H, Ar), 5.33 (d, J=3.4 Hz, 1H, H-4'), 5.19 (t, J=9.3 Hz, 1H, H-3), 5.07 (dd, J=10.4, 7.8 Hz, H-2'), 4.95-4.84 (m, 2H, H-3', H-2), 4.47 (m, 3H, H-1, H-1', H-6$_a$), 4.10 (d, J=4.7 Hz, OC$\underline{H}_{2(A)}$CH$_2$CH$_2$Cl), 4.09-4.03 (m, 1H, H-6$_a$'), 4.01 (d, J=6.3 Hz, 1H, H-6$_b$), 3.99-3.88 (m, 2H, H-6$_b$', OC$\underline{H}_{2(b)}$CH$_2$CH$_2$Cl), 3.78 (t, J=9.5 Hz, 1H, H-5'), 3.69 (dd, J=8.1, 4.7 Hz, 1H, H-4), 3.59 (dd, J=6.8, 5.6 Hz, 3H, H-5, OCH$_2$CH$_2$C$\underline{H}_2$Cl), 2.46 (s, 3H, —C$_6$H$_4$OCH$_3$)), 2.11 (s, 3H, CH$_3$C=O), 2.06 (m, 6H, 2×CH$_3$C=O), 2.04 (m, 2H, OCH$_2$C$\underline{H}_2$CH$_2$Cl), 2.03 (s, 3H, CH$_3$C=O), 1.98 (s, 3H, CH$_3$C=O), 1.95 (s, 3H, CH$_3$C=O). $^{13}$C NMR (101 MHz, CDCl$_3$) δ 170.38, 169.85, 169.79, 169.67, 169.60 and 168.97 (6C, OCOCH$_3$), 145.45, 132.18, 130.05 and 127.96 (6C, Ar), 100.70 (C-1') 100.67 (C-1), 76.66 (C-4), 72.56 (C-3), 72.49 (C-5), 71.67 (C-2), 70.76 (C-3'), 70.72 (C-5'), 68.89 (C-2'), 66.50 (C-4'), 66.32 (O$\underline{C}$H$_2$CH$_2$CH$_2$Cl), 65.45 (C-6), 61.88 (C-6'), 41.28 (OC$\underline{H}_2$CH$_2$CH$_2$Cl), 32.22 (OCH$_2$CH$_2$$\underline{C}$H$_2$Cl), 21.64 (C$_6$H$_4$OC$\underline{H}_3$), 20.83, 20.72, 20.66, 20.57, 20.47 and 20.43 (6C, OCOCH$_3$) ppm.

Synthesis of 1-deoxy thioacetyl-2,3,6,2',3',4'-hexa-O-acetyl-6-deoxy-6-thioacetyl-β-lactoside (Reagent R6)

Potassium thioacetate (1.80 g, 15.8 mmol) was added to a solution of Reagent R5 (1.6 g, 1.98 mmol) in DMF (20 mL) and left stirring at 110° C. overnight. NMR was used to monitor the reaction progress. Afterwards, the mixture was cooled down to room temperature, diluted with CH$_2$Cl$_2$ (180 mL), washed by water (2×80 mL), organic layer was combined and dried over MgSO$_4$ and concentrated to dryness. Pure compound (1.0 g, 66.7%) was afforded by purification with FC on silica gel (EtOAc-cyclohexane). Rf 0.45 (EtOAc-cyclohexane 1:1) 1H NMR (300 MHz, CDCl$_3$) δ 5.37 (dd, J=3.5, 1.1 Hz, 1H, H-4'), 5.21 (t, J=9.3 Hz, 1H, H-3), 5.07 (dd, J=10.4, 7.8 Hz, 1H, H2'), 4.94-4.86 (m, 2H, H3', H2), 4.52-4.42 (m, 3H, H-1, H-1', H-6$_a$), 4.12-3.99 (m, 1H, OC$\underline{H}_{2(A)}$CH$_2$CH$_2$SCOCH$_3$), 3.90-3.72 (m, 3H, H-6$_{a,b}$', H-6$_b$), 3.62-3.45 (m, 3H, H-5', H-4, H-5), 3.03 (t, J=7.2 Hz, 2H, OCH$_2$CH$_2$C$\underline{H}_2$SCOCH$_3$), 2.90 (td, J=7.2, 2.8 Hz, 1H, OC$\underline{H}_{2(b)}$CH$_2$CH$_2$SCOCH$_3$), 2.35 (s, 3H, SCOCH$_3$), 2.32 (s, 3H, SCOCH$_3$), 2.16 (s, 3H, CH$_3$C=O), 2.12 (s, 3H, CH$_3$C=O), 2.08 (s, 3H, CH$_3$C=O), 2.05 (s, 3H, CH$_3$C=O), 2.04 (m, 2H, OCH$_2$C$\underline{H}_2$CH$_2$SCOCH$_3$), 2.03 (s, 3H, CH$_3$C=O), 1.95 (s, 3H, CH$_3$C=O) ppm.

Synthesis of 3-thiopropyl-6'-thio-6'-deoxy-β-Lactopyranoside (Cmpd 8)

A solution of NaOMe (2 M in MeOH) was added to Reagent R6 (1.0 g, 1.3 mmol) in dry MeOH (10 mL) under N$_2$ until pH=13 was reached and the resulting mixture was stirred for 3 h. After completion of the reaction, the mixture was neutralised with Dowex 50 W+ ion exchange resin and the resin filtered off. The filtrate was concentrated to dryness and the obtained solid was dried under high vacuum to yield Cmpd 8 as a light-yellow solid. (0.49 g, 88.0%) $^1$H NMR (400 MHz, D$_2$O) δ 4.49 (dd, J=12.6, 7.9 Hz, 2H, H-3', H-1'), 4.08-3.95 (m, 3H, H-4', H-2', H-2), 3.81 (dd, J=10.7, 5.9 Hz, 2H, OC$\underline{H}_2$CH$_2$CH$_2$Cl), 3.77-3.59 (m, 5H, H-1, H-6$_a$, H-6$_b$, H-6$_a$', H-5), 3.57-3.52 (m, 1H, H-4), 3.38-3.32 (m, 1H, H-6$_b$'), 2.87-2.76 (m, 2H, H-5', H-3), 2.66 (t, J=7.1 Hz, 2H, OCH$_2$CH$_2$C$\underline{H}_2$Cl), 1.95 (dd, J=13.0, 6.3 Hz, 2H, OCH$_2$C$\underline{H}_2$CH$_2$Cl); $^{13}$C NMR (126 MHz, D$_2$O) δ 103.03 (C$_1$'), 102.01 (C1), 79.04 (C4), 76.41 (C3), 74.80 (C5), 74.33 (C2), 72.86 (C3'), 72.35 (C5'), 70.71 (C2'), 68.83 (C4'), 68.36 (C6), 60.05 (C6'), 32.70 (OC$\underline{H}_2$CH$_2$CH$_2$Cl), 23.78 (OCH$_2$C$\underline{H}_2$CH$_2$Cl), 20.16 (OCH$_2$CH$_2$C$\underline{H}_2$Cl) ppm.

1.9 Synthesis of Compound 9 (Methyl-1,6-dithio-1,6-dideoxy-β-D-fructofuranoside)

Figure 11:
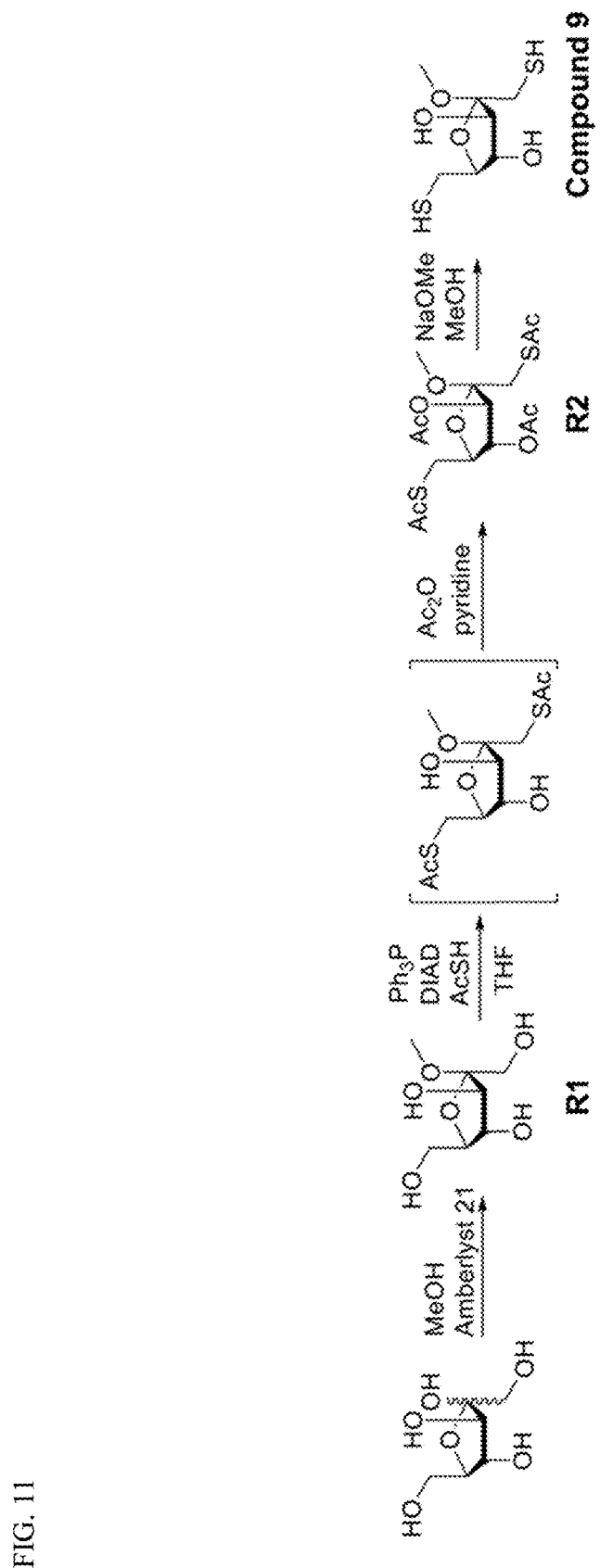
FIG. 11 depicts the synthesis of compound 9 (Methyl-1,6-dithio-1,6-dideoxy-β-D-fructofuranoside).

FIG. 11 depicts the synthesis of compound 9 (Methyl-1,6-dithio-1,6-dideoxy-β-D-fructofuranoside).

Synthesis of methyl β-D-fructofuranoside (Reagent R1)

H$_2$SO$_4$ (2.5 mL, 46.9 mmol) was added to a solution of D-fructose (9.2 g, 51 mmol) in MeOH (600 mL) under N$_2$. After 1 h, Amberlyst A21 free base resin was added, the solution was filtered, and solvents were removed under reduced pressure. Purification by flash chromatography (EtOAc/MeOH) gave Reagent R1 (3.7 g, 37%) as a transparent oil. $^1$H NMR (500 MHz, D$_2$O) δ 4.18 (d, J$_{3,4}$=8.3 Hz, 1H, H-3), 4.07 (t, J=7.9 Hz, 1H, H-4), 3.87 (td, J$_{4,5}$=J$_{5,6a}$=7.3 Hz, J$_{5,6b}$=3.1 Hz, 1H, H-5), 3.81 (dd, J$_{6a,6b}$=12.3 Hz, J$_{5,6b}$=3.2 Hz, 1H, H-6b), 3.74 (d, J$_{1a,1b}$=12.3 Hz, 1H, H-1a), 3.66 (dd, J$_{6a,6b}$=12.3 Hz, J$_{5,6a}$=7.1 Hz, 1H, H-6a), 3.66 (d, J$_{1a,1b}$=12.3 Hz, 1H, H-1b), 3.33 (s, 3H, OCH$_3$) ppm. $^{13}$C NMR (126 MHz, D$_2$O) δ 103.67, 81.15, 76.72, 74.88, 62.55, 59.62, 48.78 ppm.

Synthesis of methyl 3,4-di-O-acetyl-1,6-di-S-acetyl-1,6-dithio-1,6-dideoxy-β-D-fructofuranoside (Reagent R2)

A solution of Reagent R1 (527 mg, 2.74 mmol) and thioacetic acid (0.73 mL, 9.87 mmol) in dry pyridine (6.25 mL) under N$_2$ was added to an ice-cooled solution of diisopropyl azodicarboxylate (2.27 mL, 110 mmol) and triphenylphosphine (2.88 g, 110 mmol) in dry THF (6.25 mL) under N$_2$. The reaction mixture was allowed to warm to room temperature. After 5 days, solvents were removed under reduced pressure. Purification by flash chromatography (cyclohexane/EtOAc/MeOH) gave methyl 1,6-di-S-acetyl-1,6-dithio-1,6-dideoxy-β-D-fructofuranoside, which was dissolved in pyridine (3 mL, 37 mmol) and acetic anhydride (2 mL, 21 mmol) was added. After 17 h solvents were removed under reduced pressure. Purification by flash chromatography (cyclohexane/EtOAc) gave Reagent R2 (391 mg, 37%) as a partly crystallized oil. $^1$H NMR (400 MHz, CDCl$_3$) δ 5.36-5.29 (m, 2H, H-3, H-4), 4.05 (app. dtd, J=7.8, 5.1, 1.0 Hz, 1H, H-5), 3.37 (s, 3H, OCH$_3$), 3.36-3.29 (m, 3H, H-1a, H-1b, H-6$_b$), 3.11 (dd, J$_{6a,6b}$=14.0 Hz, J$_{5,6a}$=7.8 Hz, 1H, H-6a), 2.35 (s, 3H, SCOCH$_3$), 2.35 (s, 3H, SCOCH$_3$), 2.11 (s, 3H, OCOCH$_3$), 2.08 (s, 3H, OCOCH$_3$) ppm. $^{13}$C NMR (126 MHz, CDCl$_3$) δ 194.71, 194.23, 170.38, 170.19, 104.64, 78.68, 78.21, 77.31, 49.68, 32.80, 31.39, 30.66, 30.51, 20.97, 20.90 ppm.

Synthesis of methyl 1,6-dithio-1,6-dideoxy-β-D-fructofuranoside (Compound 9)

Reagent R2 (383 mg, 0.98 mmol) was dissolved in NaOMe (Degassed, 0.1 M, 39 mL, 3.9 mmol) under N$_2$. After 1 h, the reaction mixture was diluted with MeOH (50 mL), and Amberlite IR 120 H$^+$ resin was added. The mixture was stirred until neutral, filtered, and solvents were removed under reduced pressure. The solids were re-dissolved in H$_2$O (30 mL), filtered, and freeze-dried to give Cmpd 9 (226 mg, 96% purity, 95%). H NMR (400 MHz, D$_2$O) δ 4.36 (d, J$_{3,4}$=8.1 Hz, 1H, H-3), 4.14 (dd, J$_{3,4}$=8.1 Hz, J$_{4,5}$=7.1 Hz, 1H, H-4), 3.92 (td, J$_{4,5}$=J$_{5,6a}$=7.1 Hz, J$_{5,6b}$=5.0 Hz, 1H, H-5), 3.34 (s, 3H, OCH$_3$), 3.04 (d, J$_{1a,1b}$=14.5 Hz, 1H, H-1a), 2.89 (dd, J$_{6a,6b}$=14.0 Hz, J$_{5,6b}$=5.0 Hz, 1H, H-6$_b$), 2.84 (d, J$_{1a,1b}$=14.5 Hz, 1H, H-1b), 2.78 (dd, J$_{6a,6b}$=14.0 Hz, J$_{5,6a}$=7.1 Hz, 1H, H-6a) ppm. $^{13}$C NMR (101 MHz, D$_2$O) δ 104.25, 81.82, 77.59, 77.49, 48.36, 27.08, 25.58 ppm.

1.10 Synthesis of Compound 10 (1,6,6'-trithio-1,6,6'-trideoxy-sucrose)

Compound 10: Overall synthetic scheme

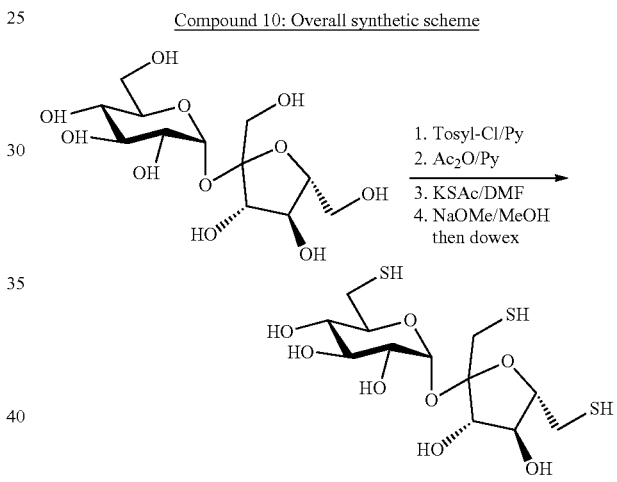

Synthesis of 1,6,6'-tri-O-tosyl-sucrose (Reagent R1)

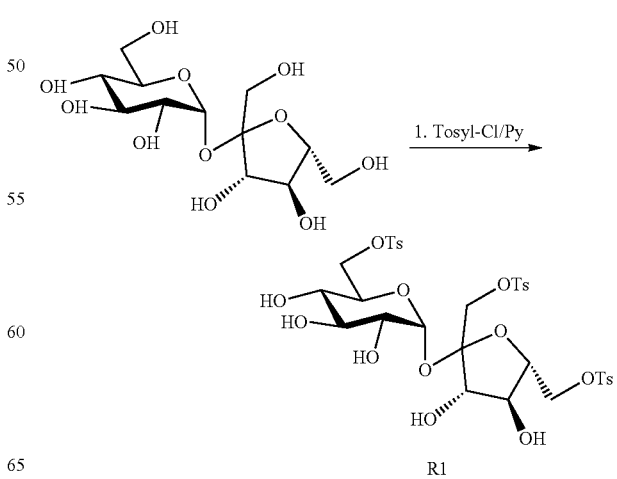

Sucrose (10 g) was dissolved in pyridine (80 ml) and cooled to 0° C. in an ice bath and to this was added Tosyl chloride (17.3 g, dissolved in 100 ml of pyridine) dropwise. The mixture was stirred at ice bath temperature for 4 h. TLC analysis indicated two major products (MeOH 5%/EtOAc 95%, $R_f$=0.6 for a tetra tosylated product and $R_f$=0.36 for the tritosylated product. There is also a minor quantity of monotosylated product at $R_f$=0.1). The mixture was added to ice cold water (1 Litre) and stirred for 15 minutes after which time the mixture was extracted with EtOAc (4×200 ml). The combined organic layers were washed with 1M HCl (3×200 ml) and water (2×200 ml) and then dried (MgSO$_4$). The EtOAc was removed on a rotary evaporator and the resulting oil was purified by chromatography (SiO$_2$/MeOH 5%/EtOAc 95%) which gave the tetra tosylate product as a white solid (3.6 g) and the required tritosylated product as a white solid (4.6 g, 19%).

Synthesis of 1,6,6'-tri-Tosyl-3,4,2',3',4'-penta-O-Acetyl-Sucrose (Reagent R2)

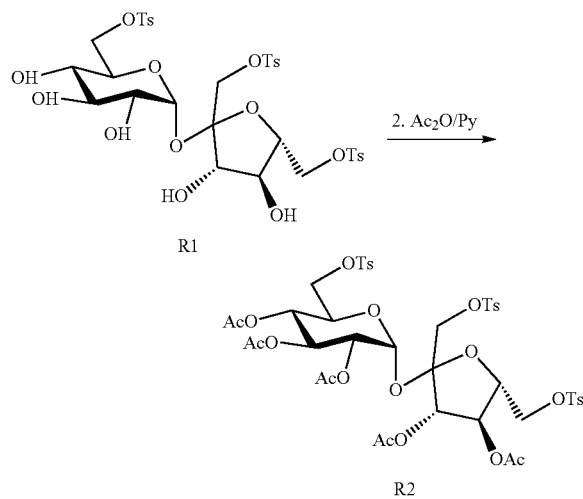

The Tritosylate (R1) was dissolved in pyridine (1 g in 2.5 mL) and cooled in an ice bath and then the Ac$_2$O (1.5 mL) was added dropwise. After the addition the mixture was allowed to come to RT and then stirred for 12 h. The mixture was slowly added into saturated NaHCO$_3$ solution (200 ml) and then stirred for 15 mins. The mixture was then extracted with EtOAc and the organic phase combined and washed with 1M HCl (2×100 ml) and water (1×100 ml). The organic phase was then dried (MgSO$_4$) and concentrated to a white crystalline solid (1.1 g, 87%). $^1$H NMR (500 MHz, CDCl$_3$) δ 7.78 (app. dd, J=8.3, 7.1 Hz, 6H, Ar), 7.40-7.31 (m, 6H, Ar), 5.38 (d, $J_{3,4}$=6.2 Hz, 1H, H-3), 5.27 (dd, $J_{2',3'}$=10.4 Hz, $J_{3',4'}$=9.4 Hz, 1H, H-3'), 5.22 (d, $J_{1',2'}$=3.8 Hz, 1H, H-1'), 5.17 (t, $J_{3,4}$=$J_{4,5}$=6.4 Hz, 1H, H-4), 4.87 (dd, $J_{4',5'}$=10.4 Hz, $J_{3',4'}$=9.4 Hz, 1H, H-4'), 4.66 (dd, $J_{2',3'}$=10.3 Hz, $J_{1',2'}$=3.8 Hz, 1H, H-2'), 4.20 (ddd, $J_{4',5'}$=10.4 Hz, $J_{5',6a}$=4.9 Hz, $J_{5',6b}$=2.4 Hz, 1H, H-5'), 4.18-4.15 (m, 2H, H-6a, H-6$_b$), 4.09-4.05 (m, 2H, H-5, H-6b'), 4.01 (d, $J_{1a,1b}$=10.9 Hz, 1H, H-1a), 3.94 (dd, $J_{6a',6b'}$=11.0 Hz, $J_{5',6a'}$=5.0 Hz, 1H, H-6a'), 3.89 (d, $J_{1a,1b}$=10.9 Hz, 1H, H-1b), 2.46 (s, 3H, C$_6$H$_4$CH$_3$), 2.44 (s, 3H, C$_6$H$_4$CH$_3$), 2.44 (s, 3H, C$_6$H$_4$CH$_3$), 2.07 (s, 3H, OCOCH$_3$), 2.05 (s, 3H, OCOCH$_3$), 1.98 (s, 3H, OCOCH$_3$), 1.97 (s, 3H, OCOCH$_3$), 1.94 (s, 3H, OCOCH$_3$) ppm. $^{13}$C NMR (126 MHz, CDCl$_3$) δ 170.13, 169.90, 169.85, 169.48, 166.52, 145.55, 145.29, 145.23, 132.62, 132.44, 132.36, 130.18, 130.12, 130.03, 128.33, 128.22, 128.20, 103.14, 89.65, 78.90, 75.29, 74.12, 69.63, 69.62, 68.83, 68.24, 68.20, 67.34, 67.31, 22.30, 21.82, 21.78, 20.75, 20.71, 20.60, 20.54, 20.52 ppm.

Synthesis of 1,6,6'-tri-S-Acetyl-3,4,2',3',4'-penta-O-Acetyl-Sucrose (Reagent R3)

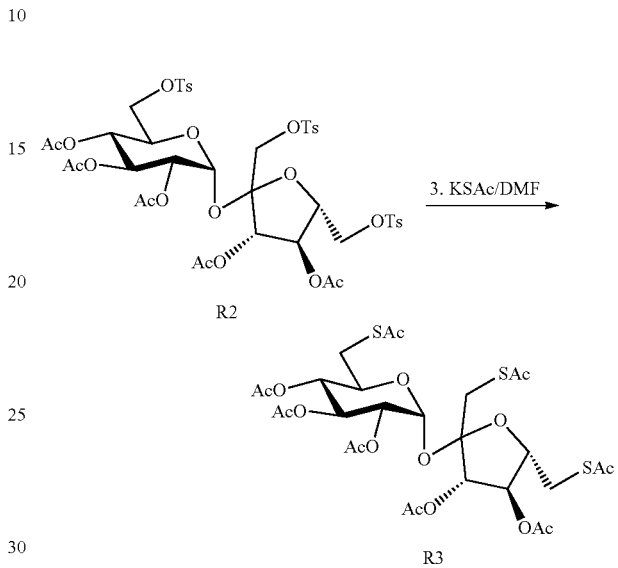

The Sucrose TriTosylate(OAc)$_5$ (R2, 1.3 g) and Potassium thioacetate (1.2 g) were mixed in DMF (10 mL) and heated to 120° C. (internal temp) for 4 h (TLC indicated that the reaction mixture contained two products (EtOAc:Cyclohexane 50:50 $R_f$=0.46 for the required TriThioacetate(OAc)$_5$ and $R_f$=0.32 for Sucrose (1,6')-dithioacetate(OAc)$_5$(6-tosyl). The reaction was cooled to room temperature and diluted with EtOAc (100 ml). The solids were filtered and washed with more EtOAc (2×20 ml) and the combined organic phase was washed (×3) with saturated NaCl solution. The organic phase was dried (MgSO$_4$) and concentrated to approx. 100 ml and to this was added activated charcoal (unknown amount) and the mixture heated to reflux for 20 mins. The charcoal was filtered and the filtrate concentrated and loaded unto silica followed by careful chromatography to give the required product R3 as a light brown solid (0.27 g, 29%).

$^1$H NMR (500 MHz, CDCl$_3$) δ 5.61 (d, $J_{1',2'}$=3.7 Hz, 1H, H-1'), 5.46 (dd, $J_{2',3'}$=10.4 Hz, $J_{3',4'}$=9.4 Hz, 1H, H-3'), 5.34 (d, $J_{3,4}$=6.7 Hz, 1H, H-3), 5.28 (t, $J_{3,4}$=$J_{4,5}$=6.4 Hz, 1H, H-4), 4.98 (app. t, J=9.7 Hz, 1H, H-4'), 4.89 (dd, $J_{2',3'}$=10.4 Hz, $J_{1',2'}$=3.7 Hz, 1H, H-2'), 4.31-4.23 (m, 1H, H-5'), 4.09 (q, $J_{4,5}$=$J_{5,6a}$=$J_{5,6b}$=6.3 Hz, 1H, H-5), 3.43 (d, $J_{1a,1b}$=14.4 Hz, 1H, H-1a), 3.31 (dd, $J_{6a,6b}$=14.1 Hz, $J_{5',6a'}$=5.9 Hz, 1H, H-6$_a$), 3.25-3.21 (m, 2H, H-1b, H-6$_b$), 3.21-3.17 (m, 2H, H-6$_a$', H-6b'), 2.36 (s, 3H, SCOCH$_3$), 2.35 (s, 3H, SCOCH$_3$), 2.34 (s, 3H, SCOCH$_3$), 2.13 (s, 3H, OCOCH$_3$), 2.11 (s, 3H, OCOCH$_3$), 2.09 (s, 3H, OCOCH$_3$), 2.08 (s, 3H, OCOCH$_3$), 2.01 (s, 3H, OCOCH$_3$) ppm. $^{13}$C NMR (126 MHz, CDCl$_3$) δ 194.83, 194.59, 194.01, 170.50, 170.20, 170.18, 169.99, 169.87, 105.66, 90.57, 79.51, 76.85, 76.60, 70.38, 70.35, 69.82, 69.23, 33.59, 32.10, 30.62, 30.60, 30.49, 29.82, 20.94, 20.89 (2×), 20.85, 20.76 ppm.

Synthesis of 1,6,6'-tri-thio-1,6,6'-trideoxy-Sucrose (Compound 10)

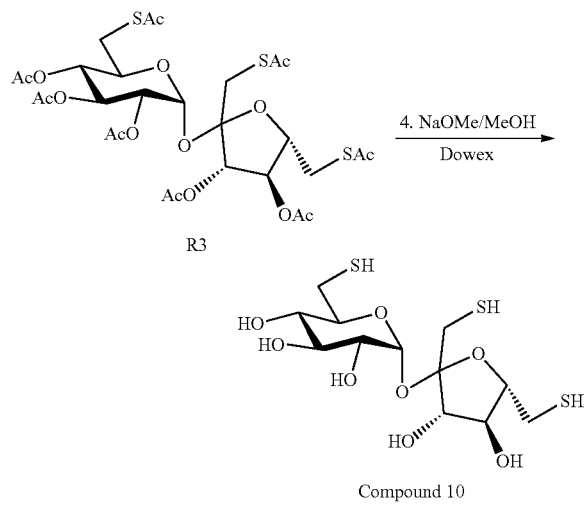

Compound 10

Reagent R3 was suspended in MeOH (0.27 g in 15 ml) and deoxygenated by bubbling a steady stream of Nitrogen through the mixture for 15 mins. To this was added the NaOMe solution (0.5M in methanol, 4.6 mL, also deoxygenated for 15 mins) and the mixture was stirred at RT for 30 mins whilst maintaining the stream of $N_2$ through the mixture. The reaction was brought to approximately pH 6-7 with the addition of the resin. The resin was filtered and the filtrate was concentrated (<25° C.) to approximately 1 ml of solution which was then added dropwise to cold EtOH (30 ml). The product precipitated as a white solid which was collected and dried in vacuo to give Compound 10 as a light brown solid (90 mg, 62%).

$^1$H NMR (300 MHz, $D_2O$) δ 5.42 (d, J=3.8 Hz, 1H, H-1'), 4.49 (d, J=8.7 Hz, 1H, H-3), 4.14 (t, J=8.4 Hz, 1H, H-4), 3.98 (ddd, J=9.4, 5.5, 3.1 Hz, 1H, H-5'), 3.90 (td, J=8.0, 4.7 Hz, 1H, H-5), 3.77 (dd, J=10.0, 9.0 Hz, 1H, H-3'), 3.59 (dd, J=10.0, 3.8 Hz, 1H, H-2'), 3.54-3.47 (m, 1H, H-4'), 3.08 (d, J=14.7 Hz, 1H, H-1a), 3.05-2.86 (m, 3H, H-6$_b$', H-6a, H-6$_b$), 2.84 (d, J=14.5 Hz, 1H, H-1b), 2.85-2.75 (m, H-6a1) ppm.

Example 2: Rheology Studies—General Methods 2.1. Collection of cystic fibrosis (CF) sputum: Spontaneously expectorated sputum samples were collected from subjects diagnosed with cystic fibrosis. Freshly collected sputa were treated with 5× protease inhibitor cocktail (HALT Protease Inhibitor Cocktail, Thermo Fisher Scientific) and 25 mM EDTA to prevent protease degradation. Samples were typically used within 6 hrs of collection.

2.2. Preparation of thiolated hyaluronic acid hydrogel as a model substrate: Thiolated hyaluronic acid hydrogel (Glycosil®, ESI-BIO) was solubilized in 10% DMSO/75 mM NaCl/sodium phosphate pH 7.4 buffer, prepared using degassed water. Aliquots of 250 microliter of gel solution were distributed to 1.5 ml centrifuge tubes, sealed, and incubated overnight (~18 hours) at room temperature to allow for slow oxidation and cross-linking of the hydrogel. Gels formed by this protocol typically yielded elastic moduli of 20-30 Pa, measured by cone-and-plate rheology.

2.3. Rheological measurements: A rheometer was employed to determine the effect of the compounds disclosed herein on the elastic modulus (G') of ex vivo human sputum or model hydrogel substrate. The terms "elastic modulus", G', and the like refer to the elastic modulus as known in the art. Rheological measurements were made with AR2000 or DHR cone-and-plate rheometer (TA instruments), as known in the art. For sputum samples, ~0.8 mL was used per assay, with 40 mm 2° geometry. For thiolated hydrogel samples, 0.25 mL was used per assay, with 40 mm ½° geometry. For timesweep recordings, a solvent trap with water as solvent was employed to minimize drying. Test compounds were dissolved in water and added at 10% v/v, to result in the final concentration of interest in the sample. The effect of test compound was measured by taking measurements every 2 min, for a period of 30 min. Normalized ratio % G' was calculated by dividing the post treatment measurement of G' at particular timepoint by pretreatment measurement of G'. Percent change in elastic modulus (% ΔG') was calculated by comparing the measurement at 30 min to the initial pretreatment baseline.

Figure 1B:
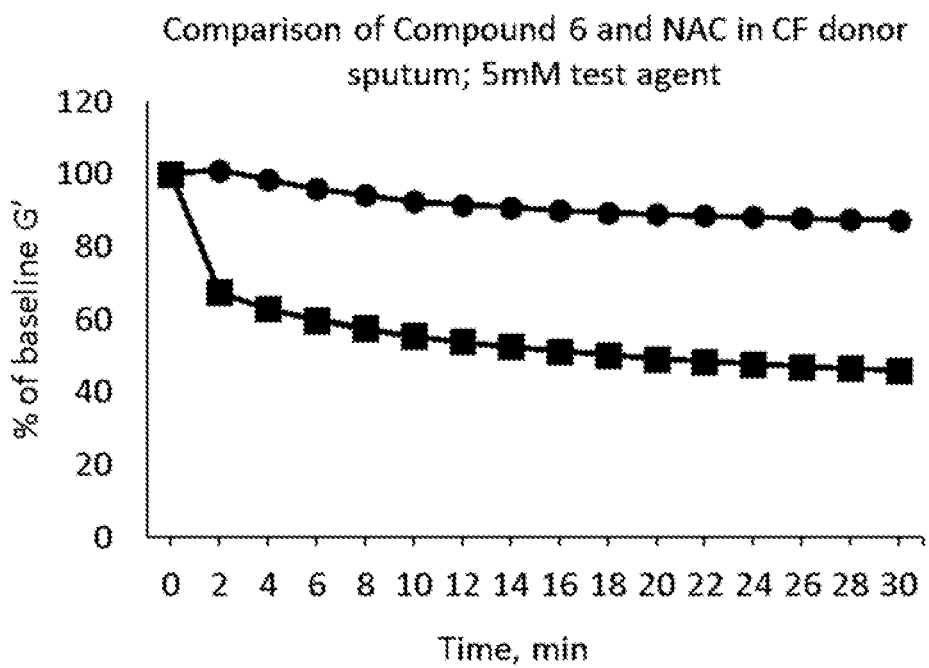
FIG. 1B is a graph showing the performance of Methyl-6,6'-dithio-6,6'-dideoxy-β-lactoside (Compound 6, square) vs. N-acetylcysteine (NAC, circle) on the elastic modulus (G') of spontaneously expectorated sputum collected from a patient with cystic fibrosis (CF). The G' of the sputum is measured using a cone and plate rheometer. The Y-axis is the % of baseline G' of the sputum sample as a function of time, after addition of Compound 6 or NAC to a final concentration of 5 mM in the sputum.
Figure 1C:
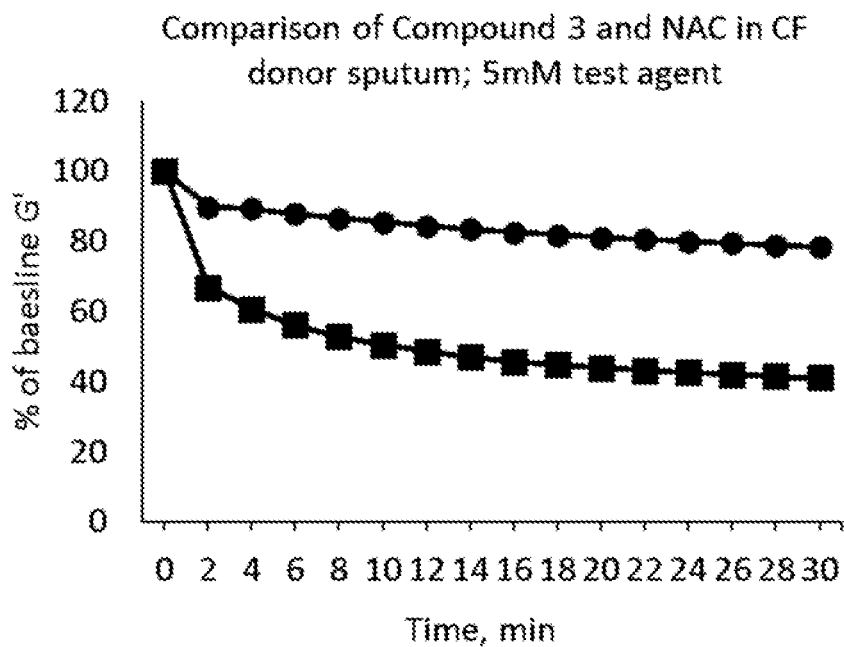
FIG. 1C is a graph showing the performance of 3-thiopropyl-6-thio-6-deoxy-β-D-galactopyranoside (Compound 3, square) vs N-acetylcysteine (NAC, circle) on the elastic modulus (G') of spontaneously expectorated sputum collected from a patient with cystic fibrosis (CF). The G' of the sputum is measured using a cone and plate rheometer. The Y-axis is the % of baseline G' of the sputum sample as a function of time, after addition of Compound 3 or NAC to a final concentration of 5 mM in the sputum.

Example 3: Effect of Dithiolsaccharides on G' of Sputum from Individual CF Patients In order to compare efficacy of a test dithiolsaccharide to efficacy of N-acetylcysteine, both were tested in individual CF patient sputum. The compound or NAC were added to final concentration of 5 mM in sputum, and G' was measured over 30 min, with 2 min measurement intervals. FIG. 1 (A-C) shows performance of three dithiolsaccharides—Cpd 5, Cpd 6, Cpd 3—vs N-Acetylcysteine over time in individual sputa samples.

Figure 2:
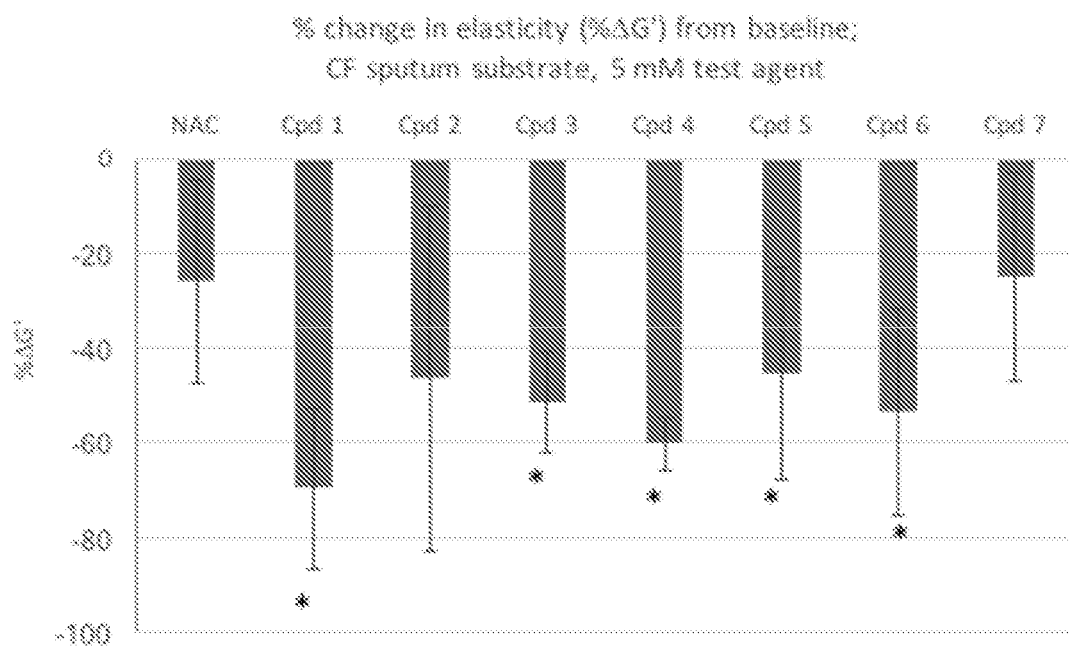
FIG. 2 is a graph showing the relative effects of multiple dithiol saccharides and N-acetylcysteine (NAC) on the elastic modulus (G') of spontaneously expectorated sputum collected from patients with cystic fibrosis (CF). The G' of the sputum samples is measured using a cone and plate rheometer. The Y-axis is the change in G' (ΔG') that occurs after sputum samples are incubated with the mucolytic compound for 30 minutes at a final concentration of 5 mM in the sputum. The histogram bars show the mean and standard deviation for the mucolytic efficacy of each compound tested in sputum samples from multiple subjects. The graph shows that the mucolytic efficacy of the dithiol saccharides is significantly greater than the mucolytic effect of NAC. *Indicates significantly different from NAC, $p<0.05$.

Example 4: Comparison of Mucolytic Effects of Dithiolsaccharides and N-acetylcysteine Using Averaged Data from Multiple Separate Experiments in Sputa of CF Patients Mucolytic efficacy in CF sputa from multiple donors was measured rheologically in order to compare performance of dithiolsaccharides to commercially available mucolytic N-Acetylcysteine, and in order to understand the variability of responses in heterogeneous population. FIG. 2 shows the average change in elastic modulus (% ΔG') post 30 min incubation with 5 mM test agent. While there is variability in response between different donors, many dithiolsacchride mucolytics show robust and statistically significant improvement in mucolytic efficacy over NAC (*indicates p-value<0.05).

Example 5: Mucolytic Dose Response in Thiolated Hydrogel Substrate

Figure 3:
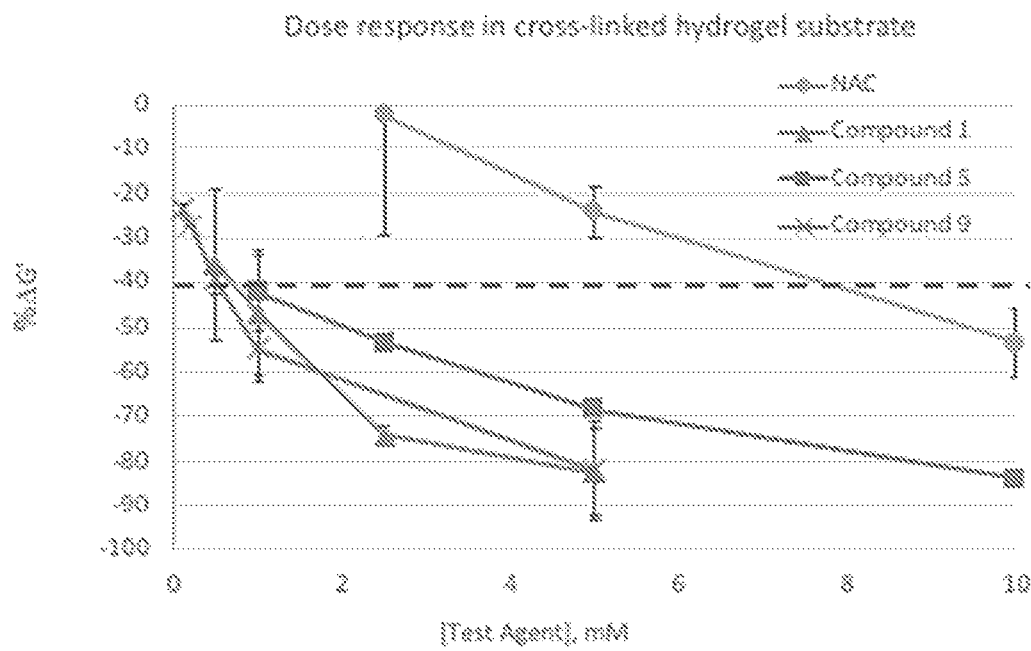
FIG. 3 is a graph showing the mucolytic dose response effects of three dithiols and N-Acetylcysteine (NAC) in a thiolated hydrogel substrate. Compound 1 is 1,6-dithio-6-deoxy-β-D-galactopyranoside; Compound 5 is 6,6'-dithio-6,6'-dideoxy-α,α-trehalose; Compound 9 is methyl-1,6-dithio-1,6-dideoxy-β-D-fructofuranoside. The hydrogel is a thiolated hyaluronic acid hydrogel (Glycosil®) that is stiffened by chemical oxidization to an elastic modulus (G') that mirrors the G' of sputum from patients with cystic fibrosis. The Y-axis is the change in G' (ΔG') that occurs after hydrogel samples are incubated with the mucolytic compound for 30 minutes at a final concentration of 5 mM in the sputum sample. The G' of the hydrogel is measured using a cone and plate rheometer. The graph shows that the concentrations of the test agents needed to cause a 40% decrease in the G' of the hydrogel (ΔG'=−40%) differs markedly. For example, the ΔG'=−40% is achieved by Compound 1 and Compound 9 at 0.7 mM, and by Compound 5 at 1.0 mM. In contrast, the ΔG'=−40% is achieved by NAC at 8 mM.

Rheological measurements with Compound 1, Compound 5, Compound 9 and N-acetylcysteine at concentrations between 0.5-10 mM were conducted in order to understand the dose dependence of mucolytic efficacy on concentration of the dithiol test agents (FIG. 3). Effective concentration that causes 40% change in G' for each test agent was determined. All dithiols tested cause 40% change in G' at concentrations <1 mM, while NAC requires ~8-10× higher dose to achieve the same mucolytic effect.

Figure 4:
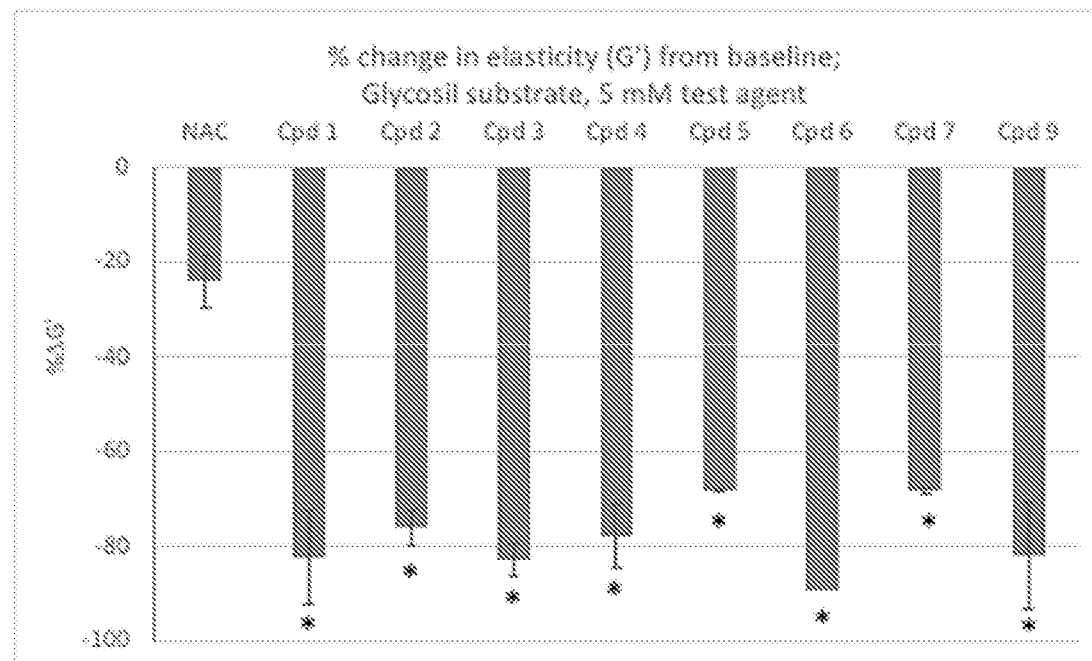
FIG. 4 is a graph showing the relative effects of multiple dithiol saccharides and N-acetylcysteine (NAC) on the elastic modulus (G') of a thiolated hydrogel. The hydrogel is a thiolated hyaluronic acid hydrogel (Glycosil®) that is stiffened by chemical oxidization to an elastic modulus (G') that mirrors the G' of sputum from patients with cystic fibrosis. The Y-axis is the change in G' (ΔG') that occurs after hydrogel samples are incubated with the mucolytic compound for 30 minutes at a final concentration of 5 mM in the sputum sample. The G' of the hydrogel is measured using a cone and plate rheometer. The histogram bars show the mean and standard deviation for the mucolytic efficacy of each compound tested in multiple hydrogel samples. The graph shows that the mucolytic efficacy of the dithiol saccharides is significantly greater than the mucolytic effect of NAC. *Indicates significantly different from NAC, $p<0.05$.

Example 6: Comparison of Mucolytic Effects of Dithiolsaccharides and N-acetylcysteine at a Single Concentration of 5 mM in Thiolated Hydrogel Substrate Mucolytic efficacy data was collected in cross-linked thiolated hydrogel model system for multiple enabled dithiolsaccharide compounds and N-acetylcysteine at 5 mM. In this substrate, all dithiolsaccharides tested demonstrate higher mucolytic efficacy than NAC after 30 min incubation (FIG. 4).

Example 7: Safety Assessment of Compound 1 in Epithelial Cell Culture

Briefly, primary tracheobronchial epithelial cells from ten donors were expanded in culture and differentiated at air-liquid interface for 21 days. Detailed cell culture protocols for airway epithelial cells can be found in Lachowicz-Scroggins et al, Cell Discov, 4, Article 7, 2018 and Widdicombe et al, Biotechniques, 39, 249-255, 2005. Compound 1 (disodium salt) was dissolved in PBS, added to apical surface of the cells at 5, 25 and 50 mM and left for 1 hr at 37° C. PBS was negative control. The apical and basolateral surfaces were washed with PBS, fresh media was added to basolateral side for 6 hr recovery period and collected for G6PD measurements. One control filter was harvested for full lysis with NP-40 lysis buffer to measure total G6PD content in cell lysates.

Figure 5:
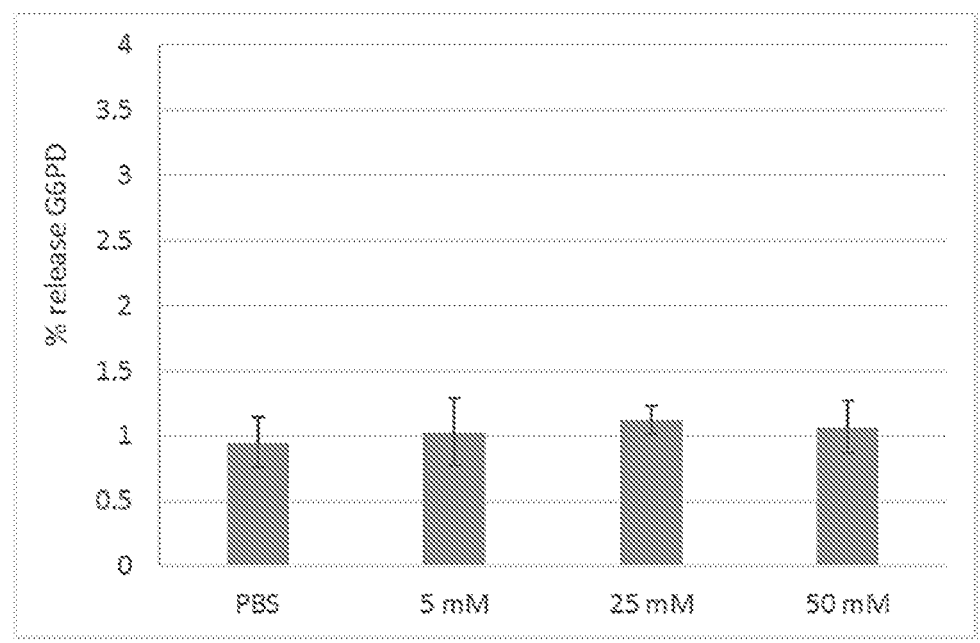
FIG. 5 is a graph showing the effect of Compound 1 (1,6-dithio-6-deoxy-β-D-galactopyranoside, disodium salt) and NAC on a measure of cell toxicity in primary human airway epithelial cells (AECs) cultured at air liquid interface. The measure of cell toxicity was release of glucose 6-phosphase dehydrogenase (G6PD). The Y axis shows the release of G6PD from the AECs into the basolateral media as a percentage of the total G6PD measured in lysates of the AECs. The cells were exposed to Compound 1 on the apical surface for 1 hour at 37° C. at concentrations of 5, 25 and 50 mM. Following an additional 6 hours, the cells and basolateral media were harvested to allow calculation of the % release of G6PD. The graph shows that the % release of G6PD with Compound 1 is minimal and similar to that of the Phosphate Buffered Saline (PBS) control.

G6PD (glucose 6-phosphase dehydrogenase) release is a common method of assessing the extent of cellular damage or death. G6PD was measured using Vybrant® Cytotoxicity Assay Kit (ThermoFisher Scientific) and expressed as percent released relative to the total G6PD content. At all concentrations of Compound 1 tested (5, 25 and 50 mM), G6PD levels were low and similar to the PBS control (FIG. 5).

Example 8: Safety Assessment of Compound 1 In Vivo

Compound 1 (25 mM stock in saline) and saline control were administered intranasally (30 µL volume) to separate groups of mice (N=10 per group, C57BL/6 mice, female, 7 weeks old from Jackson Laboratories) for 10 days (days 1-5 and 8-12 of the study). The total drug load in 30 µL delivery volume was 160 µg and represented 50× margin of effective human lung fluid dose (based on ex vivo sputum studies). Body weights were recorded on days 1, 8 and 15. On day 15, BAL was performed and used for total and differential cell counts. Mice were euthanized on day 15, and whole lung was fixed in 10% formalin, embedded in paraffin, sectioned and H&E stained for subsequent injury scoring by board-certified lung pathologist (Table 1B provides scoring criteria). Scoring was done blindly. Sera were obtained from blood collected by cardiac puncture and tested for renal and metabolic function outcomes. Compared to control saline, intranasal administration of Compound 1 in mice did not cause any discernible systemic or lung toxicity at doses estimated to be significantly higher than human exposure (Table 1A).

Table 1. Effects of 1,6-SH-bGalp on safety outcomes in mouse pulmonary delivery model. Safety outcomes in mouse pulmonary delivery model (A). Mice (N=10 per group) were exposed intranasally to saline control (30 µL) and Compound 1 (30 µL, 25 mM) daily for 10 doses over 2 weeks. Outcome measures of safety included body weight, renal function tests, measures of lung injury in bronchoalveolar lavage (BAL), and histologic appearance of tissue sections from formalin-fixed and paraffin-embedded lungs. Histological scoring was done by a board-certified lung pathologist, blinded to test groups, using scoring system described in B. Compared to control, Compound 1 administration to the mice did not cause any discernible systemic or lung toxicity at doses estimated to be significantly higher than exposure in humans.

TABLE 1A

| Variable (mean ± SEM) | Control (Saline) | 1,6-dithio-β-D-galactopyranoside (160 mg) |
|---|---|---|
| Body weight, g | 18.8 ± 0.25 | 18.6 ± 0.32 |
| BAL data | | |
| Total cell count | (33.6 ± 3.2) × $10^4$ | (37.3 ± 7) × $10^4$ |
| Macrophage % | 100 ± 0.1 | 100 ± 0.1 |
| Neutrophil % | 0 ± 0 | 0 ± 0 |
| Lymphocyte % | 0 ± 0.1 | 0 ± 0.1 |
| Eosinophil % | 0 ± 0 | 0 ± 0 |
| Renal function tests | | |
| Blood urea nitrogen, mg/dL | 27 ± 1 | 25 ± 1.3 |
| Creatinine, mg/dL | 0.22 ± 0.02 | 0.15 ± 0.01 |
| Lung Injury Score | 0.2 ± 0.13 | 0.4 ± 0.16 |

TABLE 1B

| | Lung injury scoring criteria | |
|---|---|---|
| Score | Airway Inflammation: polymorphonuclear leukocytes or lymphocytes | Epithelial necrosis |
| 0 | None | None |
| 1 | Minimal/mild airway inflammation | None |
| 2 | Moderate | None |
| 3 | Moderate | Single cell necrosis |
| 4 | Extensive | Multi-cell with sloughing |

Example 9: Dithiol Saccharide Mucolytic Agents

Increased mucus elasticity ("thickness") is a major cause of morbidity in patients with acute and chronic lower airway diseases (such as asthma, acute and chronic bronchitis, cystic fibrosis, bronchiectasis), patients with acute and chronic upper airway disease (acute and chronic sinusitis), patients with respiratory failure who require positive pressure mechansical ventilation, and patients with mucus associated diseases of the eye. Mucus with pathologically high elasticity does not clear efficiently from airways and leads to recurring cycles of infection and inflammation, and eventual airway damage. We recently showed that airway mucus plugs occurred in 58% of subjects with asthma and in only 4.5% of healthy controls, and that mucus plugs in subjects with asthma persist in the same segment for years (Dunican et al. J Clin Invest 2018). A high mucus plug score (plugs in ≥4 segments) occurred in 67% of subjects with asthma with FEV1 of less than 60% of predicted volume, 19% with FEV1 of 60%-80%, and 6% with FEV1 greater than 80% (P<0.001) and was associated with marked increases in sputum eosinophils and eosinophil peroxidase (EPO). We concluded from these findings that mucus plugs are a plausible mechanism of chronic airflow obstruction in severe asthma, and that EPO-generated oxidants may mediate mucus plug formation. We proposed an approach for quantifying airway mucus plugging using multidetector computed tomography lung scans and suggested that treating mucus plugs with mucolytic drugs (such as the dithiol drugs described here) may improve airflow in chronic severe asthma.

Cysteine rich mucin polymers form the main protein component of mucus gels. We recently showed that oxidation of airway mucus (from inflammation or supplemental oxygen) leads to disulfide cross-linking of thiol containing cysteines in mucin polymers and stiffening of the mucus gel (Yuan et al. Sci Trans Med 2015), and we proposed that breaking disulfide cross-links is a rational strategy to restore the normal rheological properties of mucus and improve its clearance.

There are several mucolytic therapies on the market, none of which can be delivered by hand held inhaler and each with a set of drawbacks that limit their application to a narrow range of patients with mucus-associated lung disease: N-acetylcysteine (NAC) is a currently available therapeutic agent that works by cleaving/reducing disulfide bonds. NAC is limited by its low potency, and thus the need to administer highly concentrated solutions (10% or 20%) via a nebulizer. NAC has a 'rotten egg' smell when nebulized and can be irritating when inhaled. Moreover, the NAC nebulizer formulation is hyperosmolar and it can cause bronchoconstriction in asthmatics, making the drug unacceptable for use in that patient population. rhDNase is a mucolytic agent that reduces mucus elasticity via cleaving long strands of DNA in the mucus. It is only applicable for patients with cystic fibrosis, and in fact has been shown to have detrimental effects in other diseases with lung mucus pathology. Other mucoactive agents include aerosols of hypertonic saline which work by drawing water into the airway to rehydrate mucus and improve its clearance. Like NAC, hypertonic saline is hyperosmolar and it causes bronchoconstriction in asthmatics.

In summary, there is an unmet need for a safe and effective mucolytic agent that can be delivered without side effects to all patients who have mucus-associated lung diseases.

For pulmonary applications, such as asthma, COPD, chronic bronchitis, cystic fibrosis, bronchiectasis, and pneumonia, dithiol-saccharide agents can be developed into small molecule mucolytic therapeutics and delivered to the lung by inhalation, using a variety of delivery devices, including nebulizer, metered dose inhaler, or a dry powder inhaler. Inhaled formulations can contain excipients that are acceptable for pulmonary delivery along with the active dithiol agent.

For other applications, the dithiol-saccharide molecules can be formulated into other dosage forms, appropriate for the disease. For example, for nasal applications, the dithiol-saccharide mucolytic agent can be formulated into nasal sprays and for ocular applications the dithiol-saccharide mucolytic agent can be formulated into eye drops.

This example describes mucolytic agents that have a faster onset of action, and greater mucolytic activity as compared to NAC/Mucomyst (approved mucolytic agent).

The following dithiol-monosaccharide compounds have been synthesized and tested: 1,6-dithio-6-deoxy-β-D-galactopyranose (1,6-SH-bGalp, Compound 1) and respective disodium salt; 1,6-dithio-6-deoxy-β-D-glucopyranose (1,6-SH-bGlcp, Compound 2) and respective disodium salt; 3-thiopropyl-6-thio-6-deoxy-β-D-galactopyranoside (Compound 3); and 5-thiopentyl-6-thio-6-deoxy-β-D-galactopyranoside (Compound 4), methyl-1,6-dithio-1,6-dideoxy-β-D-fructofuranoside (Compound 9).

The following dithiol-disaccharide compounds have been synthesized and tested: 6,6'-dithio-6,6'-dideoxy-α,α-trehalose (Compound 5), Methyl-6,6'-dithio-6,6'-dideoxy-β-lactoside (Compound 6), Methyl-6,6'-dithio-6,6'-dideoxy-β-cellobioside (Compound 7), and 3-thiopropyl-6'-thio-6'-deoxy-β-lactoside (Compound 8).

The following trithiol-disaccharide compound has been synthesized: 1,6,6'-trithio-1,6,6'-trideoxy-sucrose (Compound 10).

Assays in which the compounds have been tested: Mucolytic activity assays in ex vivo sputum from cystic fibrosis patients and in synthetic hydrogel (all); In vitro toxicity in airway primary epithelial cell culture model (1,6-SNa-bGalp, Compound 1 disodium salt); In vivo toxicity in mouse intranasal delivery model (1,6-SH-bGlcp, Compound 1).

TABLE 2

| # | Compound Name | Structure |
|---|---|---|
| 1 | 1,6-dithio-6-deoxy-β-D-galactopyranose (also referred to herein as 1,6-SH-bGalp) | 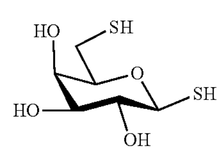 |
| 2 | 1,6-dithio-6-deoxy-β-D-glucopyranose (also referred to herein as 1,6-SH-bGlcp) | 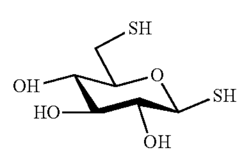 |
| 3 | 3-thiopropyl-6-thio-6'-deoxy-β-D-galactopyranoside (also referred to herein as 1-C3SH-6-SH-bGalp) | 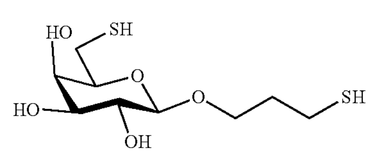 |

TABLE 2-continued

| # | Compound Name | Structure |
|---|---|---|
| 4 | 5-thiopentyl-6-thio-6'-deoxy-β-D-galactopyranoside (also referred to herein as 1-C5SH-6-SH-bGalp) | 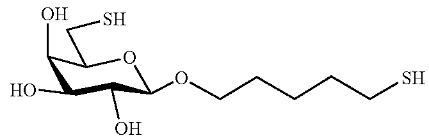 |
| 5 | 6,6'-dithio-6,6'-dideoxy-α,α-trehalose (also referred to herein as 6,6'-SH-Treh) | 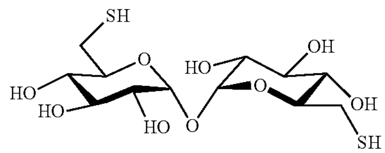 |
| 6 | Methyl-6,6'-dithio-6,6'-dideoxy-β-lactoside (also referred to herein as 1-OMe-6,6'-SH-Lac) | 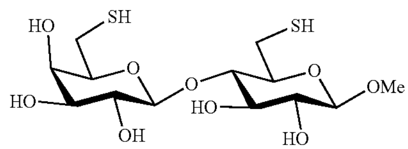 |
| 7 | Methyl-6,6'-dithio-6,6'-dideoxy-β-cellobioside (also referred to herein as 1-OMe-6,6'-SH-Cel) | 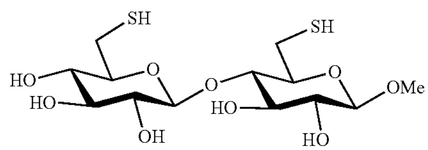 |
| 8 | 3-thiopropyl-6'-thio-6'-deoxy-β-lactoside (also referred to herein as 1-C3SH-6-SH-Lac) | 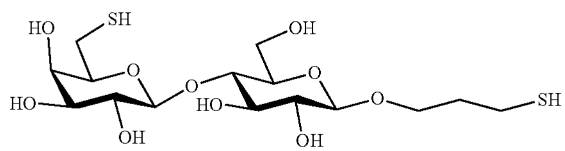 |
| 9 | Methyl-1,6-dithio-1,6-dideoxy-β-D-fructofuranoside (also referred to herein as 2OMe-1,6-SH-bFruc) | 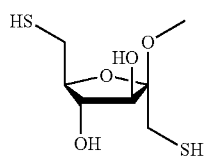 |
| 10 | 1,6,6'-trithio-1,6,6'-trideoxy-sucrose (also referred to herein as 1,6,6'-SH-Sucrose) | 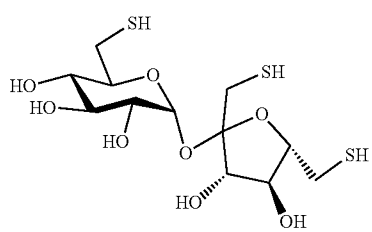 |

An example of a disodium salt of Compound 1 is

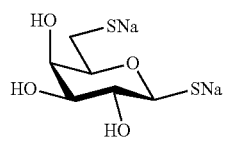

(also referred to herein as 1,6-SNa-bGalp).

Without being bound by any scientific theory, dithiol saccharides do not act as cross-linking agents (through breaking and re-forming disulfide bridges with mucin chains). Rather, the mucolytic effect is additive as the number of thiols on a molecule is increased.

EMBODIMENTS

Embodiment P1 A compound having the formula:

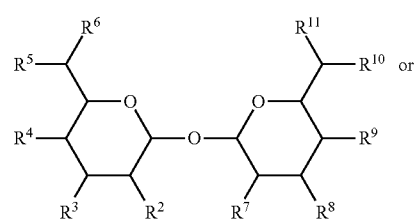

(II)

or

-continued

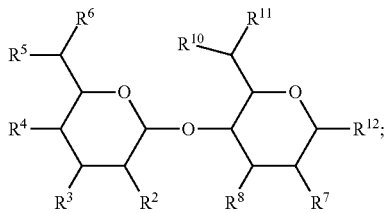

(III)

wherein,

R² is —SR²ᴬ, —OR²ᴬ, —NR²ᴮR²ᶜ, —NR²ᴮC(O)R²ᶜ, —NR²ᴮC(O)OR²ᶜ, substituted or unsubstituted C₁-C₁₀ alkyl, or substituted or unsubstituted 2 to 10 membered heteroalkyl;

R³ is —SR³ᴬ, —OR³ᴬ, —NR³ᴮR³ᶜ, —NR³ᴮC(O)R³ᶜ, —NR³ᴮC(O)OR³ᶜ, substituted or unsubstituted C₁-C₁₀ alkyl, or substituted or unsubstituted 2 to 10 membered heteroalkyl;

R⁴ is —SR⁴ᴬ, —SC(O)R⁴ᴬ, —OR⁴ᴬ, —NR⁴ᴮR⁴ᶜ, —NR⁴ᴮC(O)R⁴ᶜ, —NR⁴ᴮC(O)OR⁴ᶜ, substituted or unsubstituted C₁-C₁₀ alkyl, or substituted or unsubstituted 2 to 10 membered heteroalkyl;

R⁵ is hydrogen, —SR⁵ᴬ, —OR⁵ᴬ, —NR⁵ᴮR⁵ᶜ, —NR⁵ᴮC(O)R⁵ᶜ, —NR⁵ᴮC(O)OR⁵ᶜ, or substituted or unsubstituted C₁-C₁₀ alkyl, substituted or unsubstituted 2 to 10 membered heteroalkyl;

R⁶ is —SR⁶ᴬ, —OR⁶ᴬ, —NR⁶ᴮR⁶ᶜ, —NR⁶ᴮC(O)R⁶ᶜ, —NR⁶ᴮC(O)OR⁶ᶜ, or substituted or unsubstituted C₁-C₁₀ alkyl, substituted or unsubstituted 2 to 10 membered heteroalkyl;

R⁷ is —SR⁷ᴬ, —OR⁷ᴬ, —NR⁷ᴮR⁷ᶜ, —NR⁷ᴮC(O)R⁷ᶜ, —NR⁷ᴮC(O)OR⁷ᶜ, substituted or unsubstituted C₁-C₁₀ alkyl, or substituted or unsubstituted 2 to 10 membered heteroalkyl;

R⁸ is —SR⁸ᴬ, —OR⁸ᴬ, —NR⁸ᴮR⁸ᶜ, —NR⁸ᴮC(O)R⁸ᶜ, —NR⁸ᴮC(O)OR⁸ᶜ, substituted or unsubstituted C₁-C₁₀ alkyl, or substituted or unsubstituted 2 to 10 membered heteroalkyl;

R⁹ is —SR⁹ᴬ, —SC(O)R⁹ᴬ, —OR⁹ᴬ, —NR⁹ᴮR⁹ᶜ, —NR⁹ᴮC(O)R⁹ᶜ, —NR⁹ᴮC(O)OR⁹ᶜ, substituted or unsubstituted C₁-C₁₀ alkyl, or substituted or unsubstituted 2 to 10 membered heteroalkyl;

R¹⁰ is hydrogen, —SR¹⁰ᴬ, —OR¹⁰ᴬ, —NR¹⁰ᴮR¹⁰ᶜ, —NR¹⁰ᴮC(O)R¹⁰ᶜ, —NR¹⁰ᴮC(O)OR¹⁰ᶜ, or substituted or unsubstituted C₁-C₁₀ alkyl, substituted or unsubstituted 2 to 10 membered heteroalkyl;

R¹¹ is —SR¹¹ᴬ, —OR¹¹ᴬ, —NR¹¹ᴮR¹¹ᶜ, —NR¹¹ᴮC(O)R¹¹ᶜ, —NR¹¹ᴮC(O)OR¹¹ᶜ, or substituted or unsubstituted C₁-C₁₀ alkyl, substituted or unsubstituted 2 to 10 membered heteroalkyl;

R¹² is —SR¹²ᴬ, —OR¹²ᴬ, —NR¹²ᴮR¹²ᶜ, —NR¹²ᴮC(O)R¹²ᶜ, —NR¹²ᴮC(O)OR¹²ᶜ, substituted or unsubstituted C₁-C₁₀ alkyl, or substituted or unsubstituted 2 to 10 membered heteroalkyl; and $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, and $R^{12C}$ are each independently hydrogen, substituted or unsubstituted C₁-C₁₀ alkyl, substituted or unsubstituted 2 to 10 membered heteroalkyl;

provided the compound comprises at least two thiol moieties;

wherein the compound is not

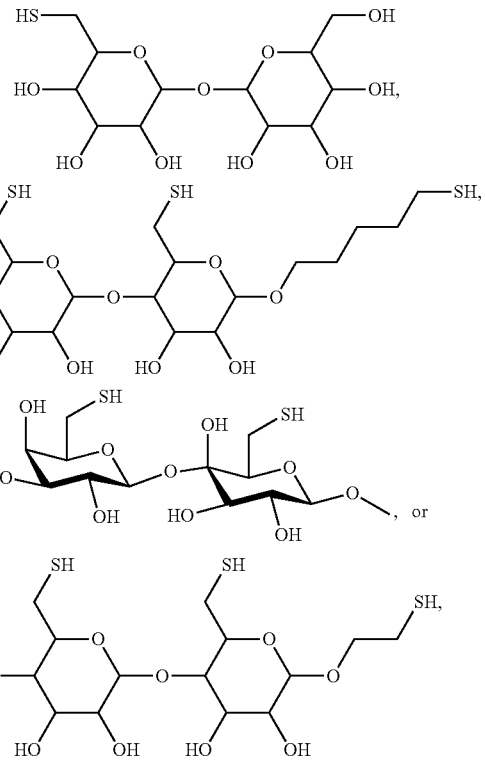

or a pharmaceutically acceptable salt thereof.

Embodiment P2 The compound of embodiment P1, having the formula:

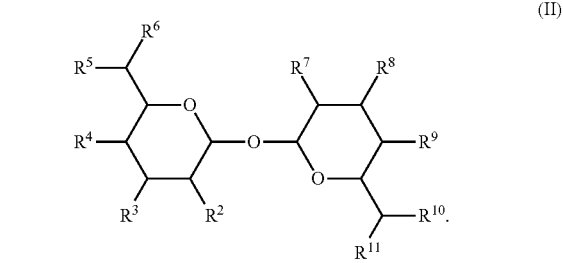

(II)

Embodiment P3 The compound of embodiment P1, having the formula:

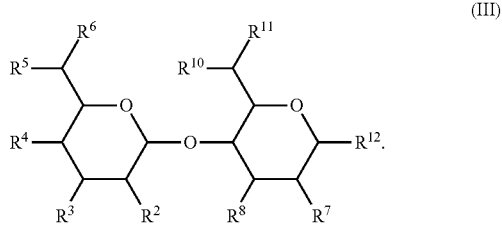

(III)

Embodiment P4 The compound of embodiment P1, having the formula:

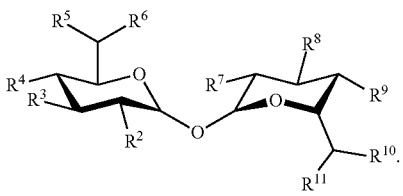

(IIa)

Embodiment P5 The compound of embodiment P1, having the formula:

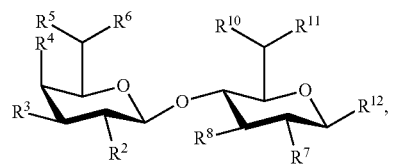

(IIIa)

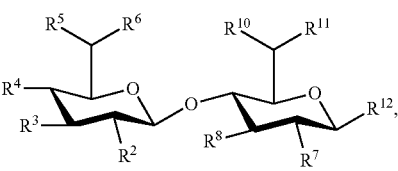

(IIIb)

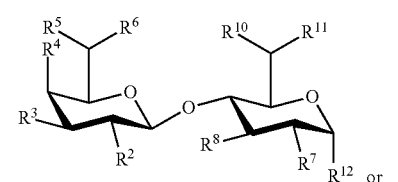

(IIIc) or

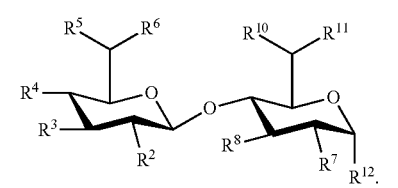

(IIId).

Embodiment P6 The compound of any one of embodiments 1 to 5, wherein
$R^2$ is —$SR^{2A}$, —$OR^{2A}$, substituted or unsubstituted $C_1$-$C_{10}$ alkyl, or substituted or unsubstituted 2 to 10 membered heteroalkyl;
$R^3$ is —$SR^{3A}$, —$OR^{3A}$, substituted or unsubstituted $C_1$-$C_{10}$ alkyl, or substituted or unsubstituted 2 to 10 membered heteroalkyl;
$R^4$ is —$SR^{4A}$, —$OR^{4A}$, substituted or unsubstituted $C_1$-$C_{10}$ alkyl, or substituted or unsubstituted 2 to 10 membered heteroalkyl;
$R^5$ is hydrogen, —$SR^{5A}$, —$OR^{5A}$, or substituted or unsubstituted $C_1$-$C_{10}$ alkyl, substituted or unsubstituted 2 to 10 membered heteroalkyl;
$R^6$ is —$SR^{6A}$, —$OR^{6A}$, or substituted or unsubstituted $C_1$-$C_{10}$ alkyl, substituted or unsubstituted 2 to 10 membered heteroalkyl;
$R^7$ is —$SR^{7A}$, —$OR^{7A}$, substituted or unsubstituted $C_1$-$C_{10}$ alkyl, or substituted or unsubstituted 2 to 10 membered heteroalkyl;
$R^8$ is —$SR^{8A}$, —$OR^{8A}$, substituted or unsubstituted $C_1$-$C_{10}$ alkyl, or substituted or unsubstituted 2 to 10 membered heteroalkyl;
$R^9$ is —$SR^{9A}$, —$OR^{9A}$, substituted or unsubstituted $C_1$-$C_{10}$ alkyl, or substituted or unsubstituted 2 to 10 membered heteroalkyl;
$R^{10}$ is hydrogen, —$SR^{10A}$, —$OR^{10A}$, substituted or unsubstituted $C_1$-$C_{10}$ alkyl, substituted or unsubstituted 2 to 10 membered heteroalkyl;
$R^{11}$ is —$SR^{11A}$, —$OR^{11A}$, or substituted or unsubstituted $C_1$-$C_{10}$ alkyl, substituted or unsubstituted 2 to 10 membered heteroalkyl; and
$R^{12}$ is —$SR^{12A}$, —$OR^{12A}$, substituted or unsubstituted $C_1$-$C_{10}$ alkyl, or substituted or unsubstituted 2 to 10 membered heteroalkyl.

Embodiment P7 The compound of any one of embodiments 1 to 5, wherein
$R^2$ is —$SR^{2A}$, —$OR^{2A}$, thiol-substituted or unsubstituted $C_1$-$C_{10}$ alkyl, or thiol-substituted or unsubstituted 2 to 10 membered heteroalkyl;
$R^3$ is —$SR^{3A}$, —$OR^{3A}$, thiol-substituted or unsubstituted $C_1$-$C_{10}$ alkyl, or thiol-substituted or unsubstituted 2 to 10 membered heteroalkyl;
$R^4$ is —$SR^{4A}$, —$OR^{4A}$, thiol-substituted or unsubstituted $C_1$-$C_{10}$ alkyl, or thiol-substituted or unsubstituted 2 to 10 membered heteroalkyl;
$R^5$ is hydrogen, —$SR^{5A}$, —$OR^{5A}$, or thiol-substituted or unsubstituted $C_1$-$C_{10}$ alkyl, thiol-substituted or unsubstituted 2 to 10 membered heteroalkyl;
$R^6$ is —$SR^{6A}$, —$OR^{6A}$, or thiol-substituted or unsubstituted $C_1$-$C_{10}$ alkyl, thiol-substituted or unsubstituted 2 to 10 membered heteroalkyl;
$R^7$ is —$SR^{7A}$, —$OR^{7A}$, thiol-substituted or unsubstituted $C_1$-$C_{10}$ alkyl, or thiol-substituted or unsubstituted 2 to 10 membered heteroalkyl;
$R^8$ is —$SR^{8A}$, —$OR^{8A}$, thiol-substituted or unsubstituted $C_1$-$C_{10}$ alkyl, or thiol-substituted or unsubstituted 2 to 10 membered heteroalkyl;
$R^9$ is —$SR^{9A}$, —$OR^{9A}$, thiol-substituted or unsubstituted $C_1$-$C_{10}$ alkyl, or thiol-substituted or unsubstituted 2 to 10 membered heteroalkyl;
$R^{10}$ is hydrogen, —$SR^{10A}$, —$OR^{10A}$, thiol-substituted or unsubstituted $C_1$-$C_{10}$ alkyl, thiol-substituted or unsubstituted 2 to 10 membered heteroalkyl;
$R^{11}$ is —$SR^{11A}$, —$OR^{11A}$, or thiol-substituted or unsubstituted $C_1$-$C_{10}$ alkyl, thiol-substituted or unsubstituted 2 to 10 membered heteroalkyl; and
$R^{12}$ is —$SR^{12A}$, —$OR^{12A}$, thiol-substituted or unsubstituted $C_1$-$C_{10}$ alkyl, or thiol-substituted or unsubstituted 2 to 10 membered heteroalkyl.

Embodiment 8 The compound of any one of embodiments 1 to 7, wherein
$R^2$ is —$SR^{2A}$ or —$OR^{2A}$;
$R^3$ is —$SR^{3A}$ or —$OR^{3A}$;
$R^4$ is —$SR^{4A}$ or —$OR^{4A}$;
$R^6$ is —$SR^{6A}$ or —$OR^{6A}$;
$R^7$ is —$SR^{7A}$ or —$OR^{7A}$;
$R^8$ is —$SR^{8A}$ or —$OR^{8A}$;
$R^9$ is —$SR^{9A}$ or —$OR^{9A}$; and
$R^{11}$ is —$SR^{11A}$ or —$OR^{11A}$.

Embodiment 9 The compound of any one of embodiments 1 to 7, wherein
$R^2$ is —SH or —OH;
$R^3$ is —SH or —OH;
$R^4$ is —SH or —OH;
$R^6$ is —SH or —OH;
$R^7$ is —SH or —OH;
$R^8$ is —SH or —OH;
$R^9$ is —SH or —OH; and
$R^{11}$ is —SH or —OH Embodiment 10 The compound of anyone of embodiments 1, 3, 5 to 9, wherein $R^{12}$ is —$OR^{12A}$.

Embodiment 11 The compound of any one of embodiments 1 to 3, wherein $R^5$ is hydrogen.

Embodiment 11.1 The compound of any one of embodiments 1 to 9, wherein $R^5$ is hydrogen.

Embodiment 12 The compound of any one of embodiments 1 to 3, wherein $R^{10}$ is hydrogen.

Embodiment 12.1 The compound of any one of embodiments 1 to 9, wherein $R^{10}$ is hydrogen.

Embodiment 13 The compound of any one of embodiments 1, 3, 5 to 12, wherein $R^{12A}$ is a substituted or unsubstituted 2 to 10 membered heteroalkyl.

Embodiment 14 The compound of any one of embodiments 1, 3, 5 to 12, wherein $R^{12A}$ is an unsubstituted 2 to 10 membered heteroalkyl.

Embodiment 15 The compound of any one of embodiments 1, 3, 5 to 12, wherein $R^{12A}$ is an unsubstituted 2 to 6 membered heteroalkyl.

Embodiment 16 The compound of any one of embodiments 1, 3, 5 to 12, wherein $R^{12A}$ is a substituted or unsubstituted $C_1$-$C_{10}$ alkyl.

Embodiment 17 The compound of any one of embodiments 1, 3, 5 to 12, wherein $R^{12A}$ is an unsubstituted $C_1$-$C_{10}$ alkyl.

Embodiment 18 The compound of any one of embodiments 1, 3, 5 to 12, wherein $R^{12A}$ is an unsubstituted $C_1$-$C_6$ alkyl.

Embodiment 19 The compound of any one of embodiments 1, 3, 5 to 9, wherein $R^{12}$ is —SH.

Embodiment 20 The compound of any one of embodiments 1, 3, 5 to 9, wherein $R^{12}$ is —$OCH_3$, —$OC_2H_5$, —$OC_3H_7$, or —$OC_4H_9$.

Embodiment 21 The compound of embodiment 1, wherein the compound is not:

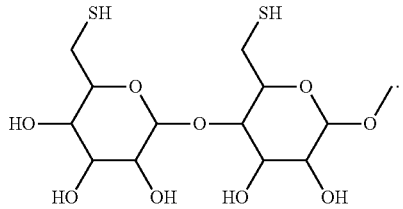 [SMILES: COC1OC(CS)C(OC2OC(CS)C(O)C(O)C2O)C(O)C1O]

Embodiment 22 The compound of embodiment 1, having the formula:

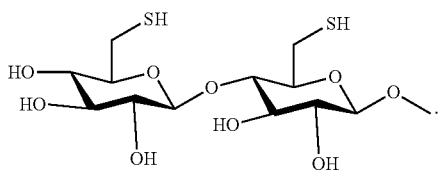

Embodiment 23 The compound of embodiment 1, having the formula:

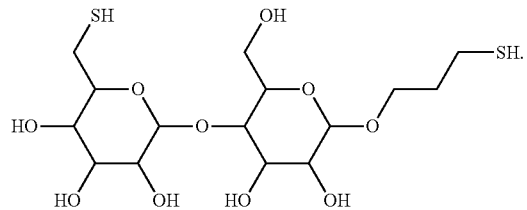 [SMILES: OCC1OC(OCCCS)C(O)C(O)C1OC1OC(CS)C(O)C(O)C1O]

Embodiment 24 The compound of embodiment 1, having the formula:

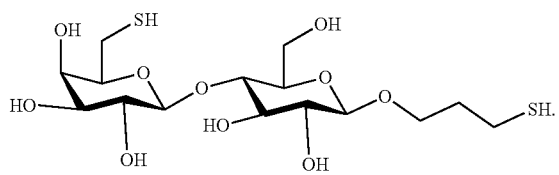

Embodiment 25 A compound having the formula:

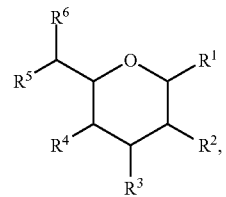

(I)

wherein, $R^1$ is —$SR^{1A}$, —$OR^{1A}$, —$NR^{1B}R^{1C}$, —$NR^{1B}C(O)R^{1C}$, —$NR^{1B}C(O)OR^{1C}$, substituted or unsubstituted $C_1$-$C_{10}$ alkyl, or substituted or unsubstituted 2 to 10 membered heteroalkyl;

$R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted $C_1$-$C_{10}$ alkyl, or substituted or unsubstituted 2 to 10 membered heteroalkyl;

$R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted $C_1$-$C_{10}$ alkyl, or substituted or unsubstituted 2 to 10 membered heteroalkyl;

$R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted $C_1$-$C_{10}$ alkyl, or substituted or unsubstituted 2 to 10 membered heteroalkyl;

$R^5$ is hydrogen, —$SR^{5A}$, —$OR^{5A}$, —$NR^{5B}R^{5C}$, —$NR^{5B}C(O)R^{5C}$, —$NR^{5B}C(O)OR^{5C}$, or substituted or unsubstituted $C_1$-$C_{10}$ alkyl, substituted or unsubstituted 2 to 10 membered heteroalkyl;

$R^6$ is —$SR^{6A}$, —$OR^{6A}$, —$NR^{6B}R^{6C}$, —$NR^{6B}C(O)R^{6C}$, —$NR^{6B}C(O)OR^{6C}$, or substituted or unsubstituted $C_1$-$C_{10}$ alkyl, substituted or unsubstituted 2 to 10 membered heteroalkyl; and $R^{1A}$, $R^{2A}$, $R^{3A}$, $R^{4A}$, $R^{5A}$, $R^{6A}$, $R^{1B}$, $R^{2B}$, $R^{3B}$, $R^{4B}$, $R^{5B}$, $R^{6B}$, $R^{1C}$, $R^{2C}$, $R^{3C}$, $R^{4C}$, $R^{5C}$, and $R^{6C}$ are each independently hydrogen, substituted or unsubstituted $C_1$-$C_{10}$ alkyl, substituted or unsubstituted 2 to 10 membered heteroalkyl;

provided the compound comprises at least two thiol moieties;

wherein the compound is not

[structure showing pyranose with SH, OH substituents and pentyl-SH chain]

or

[structure showing pyranose with SH, OH substituents and ethyl-SH chain]

or a pharmaceutically acceptable salt thereof.

Embodiment 26 The compound of embodiment 25, having the formula:

[structure (Ia) with R¹–R⁶ substituents on pyranose ring]

(Ia)

[structure (Ib)]

(Ib)

[structure (Ic)]

(Ic)

[structure (Id)]

(Id)

Embodiment 27 The compound of embodiments 25 or 26, wherein $R^1$ is —$SR^{1A}$, —$OR^{1A}$, substituted or unsubstituted $C_1$-$C_{10}$ alkyl, or substituted or unsubstituted 2 to 10 membered heteroalkyl;

$R^2$ is —$SR^{2A}$, —$OR^{2A}$, substituted or unsubstituted $C_1$-$C_{10}$ alkyl, or substituted or unsubstituted 2 to 10 membered heteroalkyl;

$R^3$ is —$SR^{3A}$, —$OR^{3A}$, substituted or unsubstituted $C_1$-$C_{10}$ alkyl, or substituted or unsubstituted 2 to 10 membered heteroalkyl;

$R^4$ is —$SR^{4A}$, —$OR^{4A}$, substituted or unsubstituted $C_1$-$C_{10}$ alkyl, or substituted or unsubstituted 2 to 10 membered heteroalkyl;

$R^5$ is hydrogen, —$SR^{5A}$, —$OR^{5A}$, or substituted or unsubstituted $C_1$-$C_{10}$ alkyl, substituted or unsubstituted 2 to 10 membered heteroalkyl;

$R^6$ is —$SR^{6A}$, —$OR^{6A}$, or substituted or unsubstituted $C_1$-$C_{10}$ alkyl, substituted or unsubstituted 2 to 10 membered heteroalkyl.

Embodiment 28 The compound of any one of embodiments 25 to 27, wherein $R^1$ is —$SR^{1A}$, —$OR^{1A}$, thiol-substituted or unsubstituted $C_1$-$C_{10}$ alkyl, or thiol-substituted or unsubstituted 2 to 10 membered heteroalkyl;

$R^2$ is —$SR^{2A}$, —$OR^{2A}$, thiol-substituted or unsubstituted $C_1$-$C_{10}$ alkyl, or thiol-substituted or unsubstituted 2 to 10 membered heteroalkyl;

$R^3$ is —$SR^{3A}$, —$OR^{3A}$, thiol-substituted or unsubstituted $C_1$-$C_{10}$ alkyl, or thiol-substituted or unsubstituted 2 to 10 membered heteroalkyl;

$R^4$ is —$SR^{4A}$, —$OR^{4A}$, thiol-substituted or unsubstituted $C_1$-$C_{10}$ alkyl, or thiol-substituted or unsubstituted 2 to 10 membered heteroalkyl;

$R^5$ is hydrogen, —$SR^{5A}$, —$OR^{5A}$, or thiol-substituted or unsubstituted $C_1$-$C_{10}$ alkyl, thiol-substituted or unsubstituted 2 to 10 membered heteroalkyl;

$R^6$ is —$SR^{6A}$, —$OR^{6A}$, or thiol-substituted or unsubstituted $C_1$-$C_{10}$ alkyl, thiol-substituted or unsubstituted 2 to 10 membered heteroalkyl.

Embodiment 29 The compound of any one of embodiments 25 to 28, wherein $R^1$ is —$SR^{1A}$ or —$OR^{1A}$;
$R^2$ is —$SR^{2A}$ or —$OR^{2A}$;
$R^3$ is —$SR^{3A}$ or —$OR^{3A}$;
$R^4$ is —$SR^{4A}$ or —$OR^{4A}$; and
$R^6$ is —$SR^{6A}$, or —$OR^{6A}$.

Embodiment 30 The compound of any one of embodiments 25 to 28, wherein $R^1$ is —$OR^{1A}$.

Embodiment 31 The compound of any one of embodiments 25 to 28, wherein $R^1$ is —SH.

Embodiment 32 The compound of any one of embodiments 25 to 31, wherein $R^2$ is —SH or —OH;
$R^3$ is —SH or —OH;
$R^4$ is —SH or —OH; and
$R^6$ is —SH, or —OH.

Embodiment 33 The compound of any one of embodiments 25 to 32, wherein $R^5$ is hydrogen.

Embodiment 34 The compound of any one of embodiments 25 to 27, wherein $R^{1A}$ is a substituted or unsubstituted 2 to 10 membered heteroalkyl.

Embodiment 34.1 The compound of any one of embodiments 25 to 32, wherein RA is a substituted or unsubstituted 2 to 10 membered heteroalkyl.

Embodiment 35 The compound of anyone of embodiments 25 to 27, wherein RA is an unsubstituted 2 to 10 membered heteroalkyl.

Embodiment 35.1 The compound of anyone of embodiments 25 to 32, wherein RA is an unsubstituted 2 to 10 membered heteroalkyl.

Embodiment 36 The compound of anyone of embodiments 25 to 27, wherein $R^{1A}$ is an unsubstituted 2 to 6 membered heteroalkyl.

Embodiment 36.1 The compound of any one of embodiments 25 to 32, wherein RA is an unsubstituted 2 to 6 membered heteroalkyl.

Embodiment 37 The compound of any one of embodiments 25 to 27, wherein $R^{1A}$ is

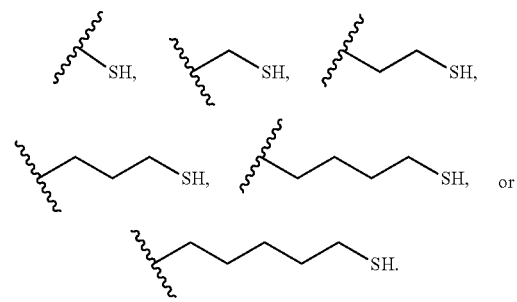

Embodiment 37.1 The compound of any one of embodiments 25 to 32, wherein $R^{1A}$ is

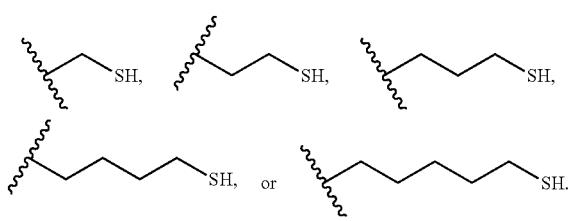

Embodiment 38 The compound of embodiment 25, having the formula:

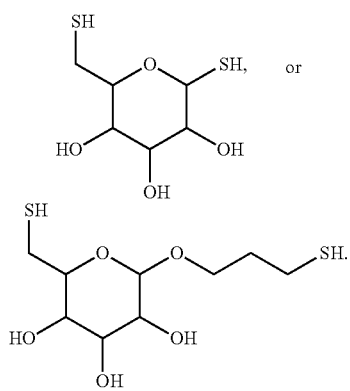

Embodiment 39 The compound of embodiment 25, having the formula:

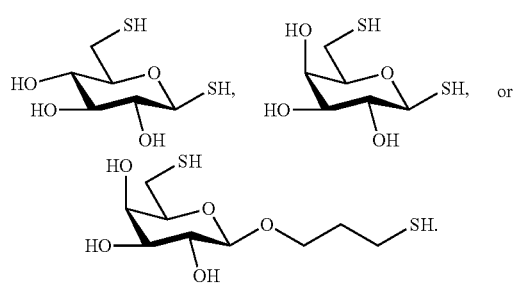

Embodiment 40 The compound of embodiment 25, having the formula:

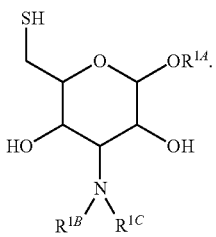

Embodiment 40.1 The compound of embodiment 25, having the formula:

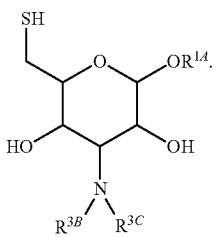

Embodiment 41 The compound of embodiment 25, having the formula:

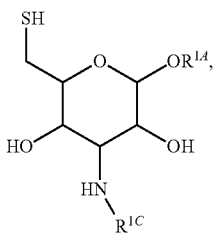

wherein
$R^{1C}$ is a thiol-substituted or unsubstituted $C_1$-$C_{10}$ alkyl.

Embodiment 41.1 The compound of embodiment 25, having the formula:

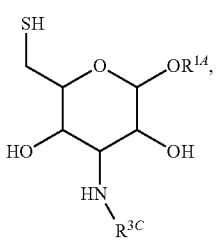

wherein
$R^{3C}$ is a thiol-substituted or unsubstituted $C_1$-$C_{10}$ alkyl.

Embodiment 42 The compound of embodiment 25, having the formula:

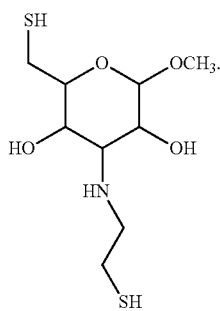

Embodiment 43 A compound having the formula:

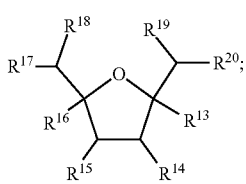

(IV)

wherein,

R$^{13}$ is hydrogen, —SR$^{13A}$, —OR$^{13A}$, —NR$^{13B}$R$^{13C}$, —NR$^{13B}$C(O)R$^{13C}$, —NR$^{13B}$C(O)OR$^{13C}$, substituted or unsubstituted C$_1$-C$_{10}$ alkyl, or substituted or unsubstituted 2 to 10 membered heteroalkyl;

R$^{14}$ is —SR$^{14A}$, —OR$^{14A}$, —NR$^{14B}$R$^{14C}$, —NR$^{14B}$C(O)R$^{14C}$, —NR$^{14B}$C(O)OR$^{14C}$, substituted or unsubstituted C$_1$-C$_{10}$ alkyl, or substituted or unsubstituted 2 to 10 membered heteroalkyl;

R$^{15}$ is —SR$^{15A}$, —OR$^{15A}$, —NR$^{15B}$R$^{15C}$, —NR$^{15B}$C(O)R$^{15C}$, —NR$^{15B}$C(O)OR$^{15C}$, substituted or unsubstituted C$_1$-C$_{10}$ alkyl, or substituted or unsubstituted 2 to 10 membered heteroalkyl;

R$^{16}$ is hydrogen, —SR$^{16A}$, —OR$^{16A}$, —NR$^{16B}$R$^{16C}$, —NR$^{16B}$C(O)R$^{16C}$, —NR$^{16B}$C(O)OR$^{16C}$, substituted or unsubstituted C$_1$-C$_{10}$ alkyl, or substituted or unsubstituted 2 to 10 membered heteroalkyl;

R$^{17}$ is hydrogen, —SR$^{17A}$, —OR$^{17A}$, —NR$^{17B}$R$^{17C}$, —NR$^{17B}$C(O)R$^{17C}$, —NR$^{17B}$C(O)OR$^{17C}$, or substituted or unsubstituted C$_1$-C$_{10}$ alkyl, substituted or unsubstituted 2 to 10 membered heteroalkyl;

R$^{18}$ is —SR$^{18A}$, —OR$^{18A}$, —NR$^{18B}$R$^{18C}$, —NR$^{18B}$C(O)R$^{18C}$, —NR$^{18B}$C(O)OR$^{18C}$, or substituted or unsubstituted C$_1$-C$_{10}$ alkyl, substituted or unsubstituted 2 to 10 membered heteroalkyl;

R$^{19}$ is hydrogen, —SR$^{19A}$, —OR$^{19A}$, —NR$^{19B}$R$^{19C}$, —NR$^{19B}$C(O)R$^{19C}$, —NR$^{19B}$C(O)OR$^{19C}$, or substituted or unsubstituted C$_1$-C$_{10}$ alkyl, substituted or unsubstituted 2 to 10 membered heteroalkyl;

R$^{20}$ is —SR$^{20A}$, —OR$^{20A}$, —NR$^{20B}$R$^{20C}$, —NR$^{20B}$C(O)R$^{20C}$, —NR$^{20B}$C(O)OR$^{20C}$, or substituted or unsubstituted C$_1$-C$_{10}$ alkyl, substituted or unsubstituted 2 to 10 membered heteroalkyl;

R$^{13A}$, R$^{14A}$, R$^{15A}$, R$^{16A}$, R$^{17A}$, R$^{18A}$, R$^{19A}$, R$^{20A}$, R$^{13B}$, R$^{14B}$, R$^{15B}$, R$^{16B}$, R$^{17B}$, R$^{18B}$, R$^{19B}$, R$^{20B}$, R$^{13C}$, R$^{14C}$, R$^{15C}$, R$^{16C}$, R$^{17C}$, R$^{18C}$, R$^{19C}$, and R$^{20C}$ are each independently hydrogen, C$_1$-C$_{10}$ alkyl, substituted or unsubstituted 2 to 10 membered heteroalkyl;

provided the compound comprises at least two thiol moieties or a pharmaceutically acceptable salt thereof.

Embodiment 44 The compound of embodiment 43, having the formula:

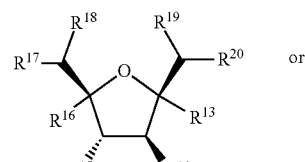

(IVa)

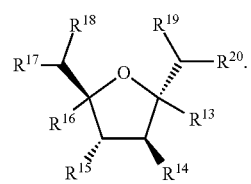

(IVb)

Embodiment 45 The compound of embodiments 43 or 44, wherein,

R$^{13}$ is hydrogen, —SR$^{13A}$, —OR$^{13A}$, thiol-substituted or unsubstituted C$_1$-C$_{10}$ alkyl, or thiol-substituted or unsubstituted 2 to 10 membered heteroalkyl;

R$^{14}$ is —SR$^{14A}$, —OR$^{14A}$, thiol-substituted or unsubstituted C$_1$-C$_{10}$ alkyl, or thiol-substituted or unsubstituted 2 to 10 membered heteroalkyl;

R$^{15}$ is —SR$^{15A}$, —OR$^{15A}$, thiol-substituted or unsubstituted C$_1$-C$_{10}$ alkyl, or thiol-substituted or unsubstituted 2 to 10 membered heteroalkyl;

R$^{16}$ is hydrogen, —SR$^{16A}$, —OR$^{16A}$, thiol-substituted or unsubstituted C$_1$-C$_{10}$ alkyl, or thiol-substituted or unsubstituted 2 to 10 membered heteroalkyl;

R$^{17}$ is hydrogen, —SR$^{17A}$, —OR$^{17A}$, thiol-substituted or unsubstituted C$_1$-C$_{10}$ alkyl, or thiol-substituted or unsubstituted 2 to 10 membered heteroalkyl;

R$^{18}$ is —SR$^{18A}$, —OR$^{18A}$, thiol-substituted or unsubstituted C$_1$-C$_{10}$ alkyl, or thiol-substituted or unsubstituted 2 to 10 membered heteroalkyl R$^{19}$ is hydrogen, —SR$^{19A}$, —OR$^{19A}$, thiol-substituted or unsubstituted C$_1$-C$_{10}$ alkyl, or thiol-substituted or unsubstituted 2 to 10 membered heteroalkyl;

R$^{20}$ is —SR$^{20A}$, —OR$^{20A}$, thiol-substituted or unsubstituted C$_1$-C$_{10}$ alkyl, or thiol-substituted or unsubstituted 2 to 10 membered heteroalkyl.

Embodiment 46 The compound of one of embodiments 43 to 45, wherein,

R$^{13}$ is hydrogen, —SR$^{13A}$ or —OR$^{13A}$;

R$^{14}$ is —SR$^{14A}$ or —OR$^{14A}$;

R$^{15}$ is —SR$^{15A}$ or —OR$^{15A}$;

R$^{16}$ is hydrogen, —SR$^{16A}$ or —OR$^{16A}$;

R$^{18}$ is —SR$^{18A}$ or —OR$^{18A}$; and

R$^{20}$ is —SR$^{20A}$ or —OR$^{20A}$.

Embodiment 47 The compound of any one of embodiments 43 to 46, wherein R$^{16}$ is hydrogen.

Embodiment 48 The compound of embodiment 43, wherein the compound has the structure:

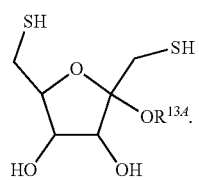

Embodiment 49 The compound of embodiment 43, wherein the compound has the structure:

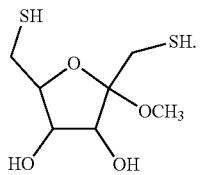 [SMILES: COC1(CS)OC(CS)C(O)C1O]

Embodiment 50 A compound having the formula:

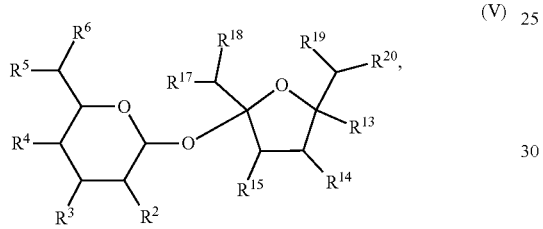

(V)

wherein, $R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted $C_1$-$C_{10}$ alkyl, or substituted or unsubstituted 2 to 10 membered heteroalkyl;

$R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted $C_1$-$C_{10}$ alkyl, or substituted or unsubstituted 2 to 10 membered heteroalkyl;

$R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted $C_1$-$C_{10}$ alkyl, or substituted or unsubstituted 2 to 10 membered heteroalkyl;

$R^5$ is hydrogen, —$SR^{5A}$, —$OR^{5A}$, —$NR^{5B}R^{5C}$, —$NR^{5B}C(O)R^{5C}$, —$NR^{5B}C(O)OR^{5C}$, or substituted or unsubstituted $C_1$-$C_{10}$ alkyl, substituted or unsubstituted 2 to 10 membered heteroalkyl;

$R^6$ is —$SR^{6A}$, —$OR^{6A}$, —$NR^{6B}R^{6C}$, —$NR^{6B}C(O)R^{6C}$, —$NR^{6B}C(O)OR^{6C}$, or substituted or unsubstituted $C_1$-$C_{10}$ alkyl, substituted or unsubstituted 2 to 10 membered heteroalkyl;

$R^{13}$ is hydrogen, —$SR^{13A}$, —$OR^{13A}$, —$NR^{13B}R^{13C}$, —$NR^{13B}C(O)R^{13C}$, —$NR^{13B}C(O)OR^{13C}$, substituted or unsubstituted $C_1$-$C_{10}$ alkyl, or substituted or unsubstituted 2 to 10 membered heteroalkyl;

$R^{14}$ is —$SR^{14A}$, —$OR^{14A}$, —$NR^{14B}R^{14C}$, —$NR^{14B}C(O)R^{14C}$, —$NR^{14B}C(O)OR^{14C}$, substituted or unsubstituted $C_1$-$C_{10}$ alkyl, or substituted or unsubstituted 2 to 10 membered heteroalkyl;

$R^{15}$ is —$SR^{15A}$, —$OR^{15A}$, —$NR^{15B}R^{15C}$, —$NR^{15B}C(O)R^{15C}$, —$NR^{15B}C(O)OR^{15C}$, substituted or unsubstituted $C_1$-$C_{10}$ alkyl, or substituted or unsubstituted 2 to 10 membered heteroalkyl;

$R^{17}$ is hydrogen, —$SR^{17A}$, —$OR^{17A}$, —$NR^{17B}R^{17C}$, —$NR^{17B}C(O)R^{17C}$, —$NR^{17B}C(O)OR^{17C}$, or substituted or unsubstituted $C_1$-$C_{10}$ alkyl, substituted or unsubstituted 2 to 10 membered heteroalkyl;

$R^{18}$ is —$SR^{18A}$, —$OR^{18A}$, —$NR^{18B}R^{18C}$, —$NR^{18B}C(O)R^{18C}$, —$NR^{18B}C(O)OR^{18C}$, or substituted or unsubstituted $C_1$-$C_{10}$ alkyl, substituted or unsubstituted 2 to 10 membered heteroalkyl;

$R^{19}$ is hydrogen, —$SR^{19A}$, —$OR^{19A}$, —$NR^{19B}R^{19C}$, —$NR^{19B}C(O)R^{19C}$, —$NR^{19B}C(O)OR^{19C}$, or substituted or unsubstituted $C_1$-$C_{10}$ alkyl, substituted or unsubstituted 2 to 10 membered heteroalkyl;

$R^{20}$ is —$SR^{20A}$, —$OR^{20A}$, —$NR^{20B}R^{20C}$, —$NR^{20B}C(O)R^{20C}$, —$NR^{20B}C(O)OR^{20C}$, or substituted or unsubstituted $C_1$-$C_{10}$ alkyl, substituted or unsubstituted 2 to 10 membered heteroalkyl; and $R^{2A}$, $R^{3A}$, $R^{4A}$, $R^{5A}$, $R^{6A}$, $R^{2B}$, $R^{3B}$, $R^{4B}$, $R^{5B}$, $R^{6B}$, $R^{2C}$, $R^{3C}$, $R^{4C}$, $R^{5C}$, $R^{6C}$, $R^{13A}$, $R^{14A}$, $R^{15A}$, $R^{17A}$, $R^{18A}$, $R^{19A}$, $R^{20A}$, $R^{13B}$, $R^{14B}$, $R^{15B}$, $R^{17B}$, $R^{18B}$, $R^{19B}$, $R^{20B}$, $R^{13C}$, $R^{14C}$, $R^{15C}$, $R^{17C}$, $R^{18C}$, $R^{19C}$, and $R^{20C}$ are each independently hydrogen, substituted or unsubstituted $C_1$-$C_{10}$ alkyl, substituted or unsubstituted 2 to 10 membered heteroalkyl;

provided the compound comprises at least two thiol moieties, wherein the compound is not

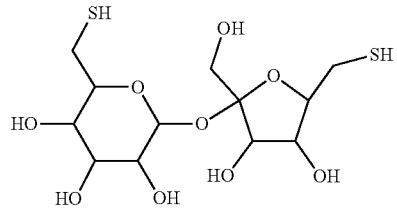

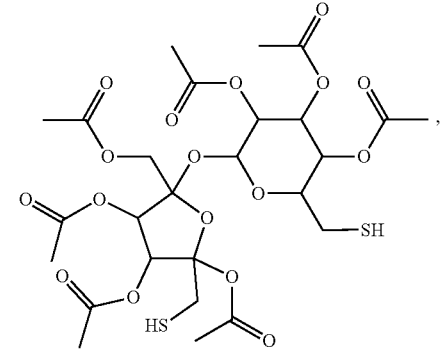

or a pharmaceutically acceptable salt thereof.

Embodiment 51 The compound of any one of embodiments 1 to 50, wherein the compound has two thiol moieties.

Embodiment 51.1 The compound of any one of embodiments 1 to 50, wherein the compound comprises two thiol moieties.

Embodiment 52 A method of decreasing mucus elasticity or decreasing mucus viscosity in a subject in need thereof, the method comprising administering to the subject an effective amount of the compound of any one of embodiments 1 to 51, or a compound having the following structure:

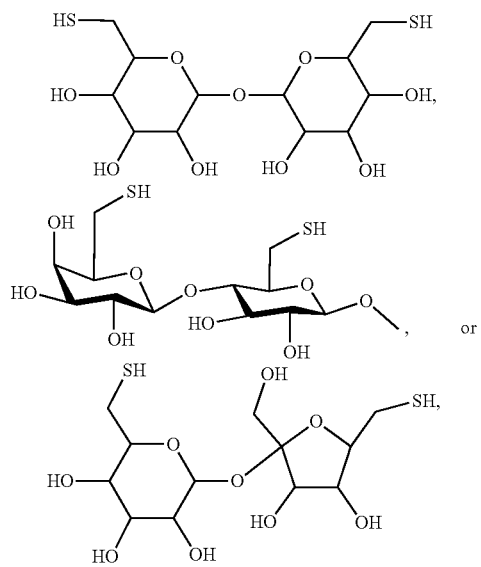
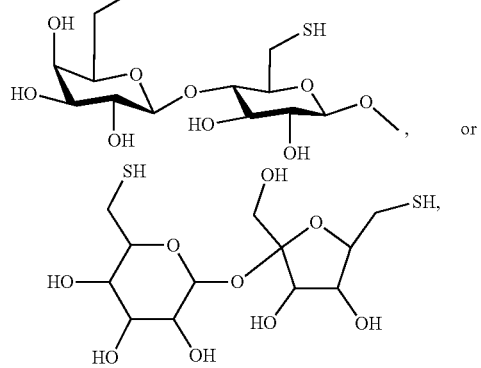
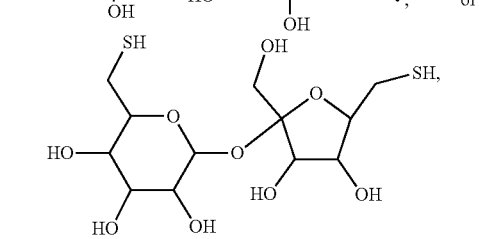

or a pharmaceutically acceptable salt thereof.

Embodiment 53 The method of embodiment 52, wherein the subject has mucus accumulation in an airway.

Embodiment 54 The method of embodiment 53, wherein the airway is in the upper respiratory tract of the subject.

Embodiment 55 The method of embodiment 53, wherein the airway is in a nasal passage, paranasal sinuse, the pharynx, and or larynx of the subject.

Embodiment 56 The method of embodiment 53, wherein the airway is in the lower respiratory tract of the subject.

Embodiment 57 The method of embodiment 53, wherein the airway is in a trachea, main bronchus, lobar bronchus, segmental bronchus, subsegmental bronchus, conducting bronchiole, terminal bronchiole, respiratory bronchiole, alveolar duct, alveolar sac, or alveolus of the subject.

Embodiment 58 The method of anyone of embodiments 52 to 57, wherein the subject has 1, 2, 3, 4, 5, 6, 7, 8, 9, 10, or more complete mucus airway occlusions of one or more airways within one or two lungs in the subject.

Embodiment 59 The method of anyone of embodiments 52 to 58, wherein the subject has chronic obstructive pulmonary disease (COPD), cystic fibrosis (CF), asthma, chronic asthma, acute asthma, bronchitis, chronic bronchitis, bronchiectasis, traction bronchiectasis, bronchiolitis, allergic bronchopulmonary aspergillosis, pneumonia, a mechanical ventilator-associated lung injury, sinusitis, chronic rhinitis, acute sinusitis, chronic sinusitis, chronic rhinosinusitis with nasal polyps, chronic rhinosinusitis without nasal polyps, rhinorrhea, or post-nasal drip.

Embodiment 60 The method of any one of embodiments 52 to 59, wherein the subject has cicatricial pemphigoid, tuberculosis, lung cancer, emphysema, influenza, or primary ciliary dyskinesia.

Embodiment 61 The method of embodiment 52, wherein the subject has mucus accumulation on an eye.

Embodiment 62 The method of embodiment 61, wherein the subject has filamentary keratitis, keratitis sicca, dry eye syndrome, blepharitis, or conjunctivitis.

Embodiment 63 A method of decreasing mucus elasticity or decreasing mucus viscosity in a subject in need thereof, the method comprising administering to the subject an effective amount of the compound of any one of embodiments 1 to 50, or a compound having the following structure:

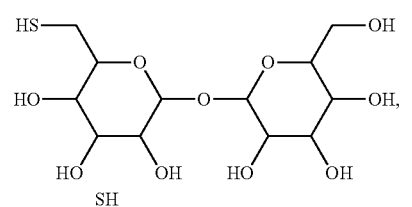
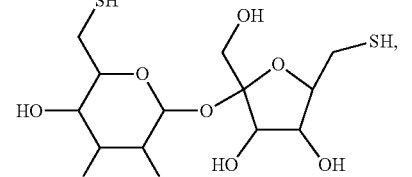
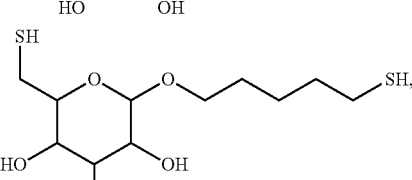
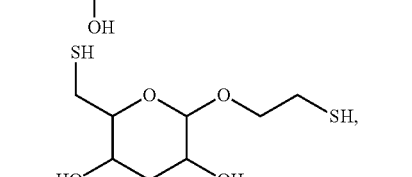
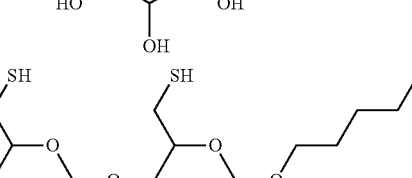
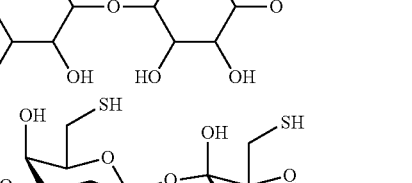
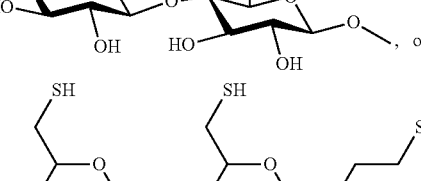
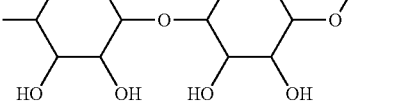

or a pharmaceutically acceptable salt thereof, wherein the subject has 1, 2, 3, 4, 5, 6, 7, 8, 9, 10, or more complete mucus airway occlusions of one or more airways within one or two lungs in the subject, or wherein the subject has cicatricial pemphigoid, tuberculosis, lung cancer, emphysema, influenza, or primary ciliary dyskinesia.

Embodiment 63.1 A method of decreasing mucus elasticity or decreasing mucus viscosity in a subject in need thereof, the method comprising administering to the subject an effective amount of the compound of any one of embodiments 1 to 51, or a compound having the following structure:

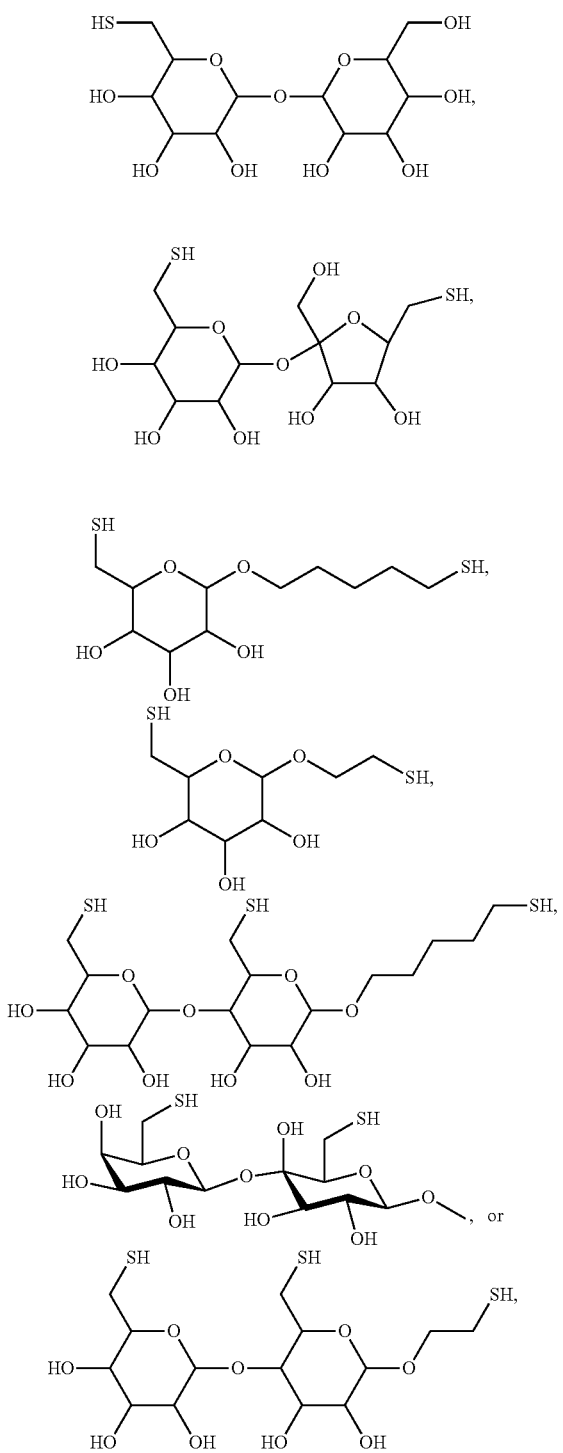

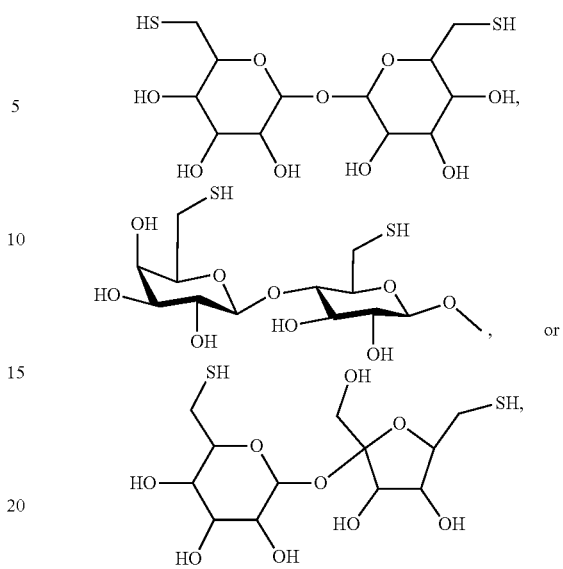

or a pharmaceutically acceptable salt thereof, wherein the subject has 1, 2, 3, 4, 5, 6, 7, 8, 9, 10, or more complete mucus airway occlusions of one or more airways within one or two lungs in the subject, or wherein the subject has cicatricial pemphigoid tuberculosis, lung cancer, emphysema, influenza, or primary ciliary dyskinesia.

Embodiment 64 A pulmonary pharmaceutical composition comprising a pulmonary pharmaceutical carrier and the compound of any one of embodiments 1 to 51, or a compound having the following structure:

or a pharmaceutically acceptable salt thereof.

Embodiment 65 The pulmonary pharmaceutical composition of embodiment 66, wherein the pulmonary pharmaceutical carrier is a pulmonary pharmaceutical liquid or pulmonary pharmaceutical powder.

Embodiment 65.1 The pulmonary pharmaceutical composition of embodiment 64, wherein the pulmonary pharmaceutical carrier is a pulmonary pharmaceutical liquid or pulmonary pharmaceutical powder.

Embodiment 66 The pulmonary pharmaceutical composition of embodiment 67, wherein the pulmonary pharmaceutical liquid comprises a polar liquid, and the compound is dissolved or suspended in the polar liquid.

Embodiment 66.1 The pulmonary pharmaceutical composition of embodiment 65, wherein the pulmonary pharmaceutical liquid comprises a polar liquid, and the compound is dissolved or suspended in the polar liquid.

Embodiment 67 The pulmonary pharmaceutical composition of embodiment 68, wherein the polar liquid is water.

Embodiment 67.1 The pulmonary pharmaceutical composition of embodiment 66, wherein the polar liquid is water.

Embodiment 68 The pulmonary pharmaceutical composition of embodiment 66 or -67, wherein the pulmonary pharmaceutical carrier is lactose, trehalose, mannitol, a phospholipid, or cholesterol.

Embodiment 68.1 The pulmonary pharmaceutical composition of embodiment 64 or 65, wherein the pulmonary pharmaceutical carrier is lactose, trehalose, mannitol, a phospholipid, or cholesterol.

Embodiment 69 The pulmonary pharmaceutical composition of embodiment 66 or 67, wherein the pulmonary pharmaceutical carrier is the parent sugar of the compound, the parent sugar lacking a thiol moiety.

Embodiment 69.1 The pulmonary pharmaceutical composition of embodiment 64 or 65, wherein the pulmonary pharmaceutical carrier is the parent sugar of the compound, the parent sugar lacking a thiol moiety.

Embodiment 70 The pulmonary pharmaceutical composition of any one of embodiments 66 to 71, wherein the pulmonary pharmaceutical composition is within a pulmonary pharmaceutical delivery device.

Embodiment 70.1 The pulmonary pharmaceutical composition of any one of embodiments 64-69, wherein the pulmonary pharmaceutical composition is within a pulmonary pharmaceutical delivery device.

Embodiment 71 The pulmonary pharmaceutical composition of embodiment 72, wherein the pulmonary pharmaceutical delivery device is a pulmonary pharmaceutical nebulizer, a pulmonary pharmaceutical dry powder inhaler, or a pulmonary pharmaceutical pressurized metered dose inhaler.

Embodiment 71.1 The pulmonary pharmaceutical composition of embodiment 70, wherein the pulmonary pharmaceutical delivery device is a pulmonary pharmaceutical nebulizer, a pulmonary pharmaceutical dry powder inhaler, or a pulmonary pharmaceutical pressurized metered dose inhaler.

What is claimed is:

1. A method of decreasing mucus elasticity or decreasing mucus viscosity in a subject in need thereof, the method comprising administering to the subject an effective amount of the compound of Formula II,
   wherein Formula II is represented by:

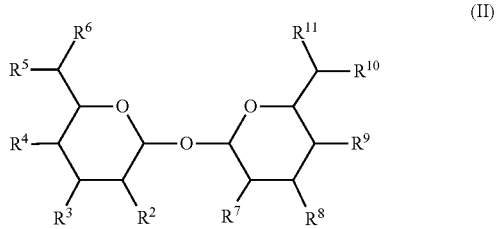

wherein,
$R^2$ is —$OR^{2A}$;
$R^3$ is —$OR^{3A}$;
$R^4$ is $OR^{4A}$;
$R^5$ is hydrogen;
$R^6$ is —SH;
$R^7$ is —$OR^{7A}$;
$R^8$ is —$OR^{8A}$;
$R^9$ is —$OR^{9A}$;
$R^{10}$ is hydrogen;
$R^{11}$ is —SH;
and
$R^{2A}$, $R^{3A}$, $R^{4A}$, $R^{7A}$, $R^{8A}$, and $R^{9A}$ are each independently hydrogen or unsubstituted $C_1$-$C_{10}$ alkyl;
or a pharmaceutically acceptable salt thereof.

2. The method of claim 1, wherein the subject has mucus accumulation in an airway or on an eye.

3. The method of claim 1, wherein the compound is

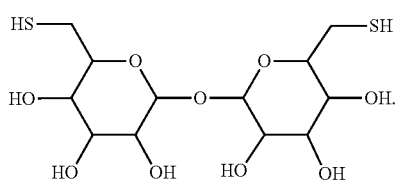 [SMILES: OC1C(CS)OC(OC2OC(CS)C(O)C(O)C2O)C(O)C1O]

4. The method of claim 1, wherein the compound is

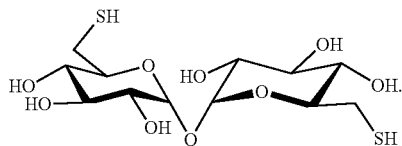

5. The method of claim 4, wherein the subject has mucus accumulation in an airway.

6. The method of claim 5, wherein the airway is in the upper respiratory tract of the subject.

7. The method of claim 5, wherein the airway is in a nasal passage, paranasal sinus, the pharynx, and/or larynx of the subject.

8. The method of claim 5, wherein the airway is in the lower respiratory tract of the subject.

9. The method of claim 5, wherein the airway is in a trachea, main bronchus, lobar bronchus, segmental bronchus, subsegmental bronchus, conducting bronchiole, terminal bronchiole, respiratory bronchiole, alveolar duct, alveolar sac, or alveolus of the subject.

10. The method of claim 5, wherein the subject has 1, 2, 3, 4, 5, 6, 7, 8, 9, 10, or more complete mucus airway occlusions of one or more airways within one or two lungs in the subject.

11. The method of claim 4, wherein the subject has mucus accumulation or mucus occlusion in an airway.

12. The method of claim 4, wherein the subject has chronic obstructive pulmonary disease (COPD), cystic fibrosis (CF), asthma, chronic asthma, acute asthma, bronchitis, chronic bronchitis, acute bronchitis, bronchiectasis, traction bronchiectasis, primary ciliary dyskinesia, bronchiolitis, allergic bronchopulmonary aspergillosis, pneumonia, a mechanical ventilator-associated lung injury, sinusitis, chronic rhinitis, acute sinusitis, chronic sinusitis, chronic rhinosinusitis with nasal polyps, chronic rhinosinusitis without nasal polyps, rhinorrhea, or post-nasal drip.

13. The method of claim 4, wherein the subject has chronic obstructive pulmonary disease (COPD).

14. The method of claim 4, wherein the subject has cystic fibrosis (CF).

15. The method of claim 4, wherein the subject has asthma.

16. The method of claim 4, wherein the subject has cicatricial pemphigoid, tuberculosis, lung cancer, emphysema, influenza, or primary ciliary dyskinesia.

17. The method of claim 4, wherein the method is for decreasing mucus elasticity in the subject.

18. The method of claim 4, wherein the method is for decreasing mucus viscosity in the subject.

19. The method of claim 4, wherein the subject experiences mucociliary clearance to decrease mucus plugging.

20. The method of claim 4, wherein the subject experiences mucociliary clearance to improve measures of lung function.

21. The method of claim 4, wherein the subject experiences an improvement in a chest imaging score that quantifies the number of airway mucus plugs.

22. The method of claim 4, wherein the subject experiences rapid onset of a disorder selected from the group consisting of chronic obstructive pulmonary disease (COPD), cystic fibrosis (CF), asthma, bronchiectasis, traction bronchiectasis, primary ciliary dyskinesia, bronchiolitis, and allergic bronchopulmonary aspergillosis.

23. A method of decreasing mucus elasticity or decreasing mucus viscosity in a subject in need thereof, the method comprising administering to the subject an effective amount of the compound of Formula II:
wherein Formula II is represented by:

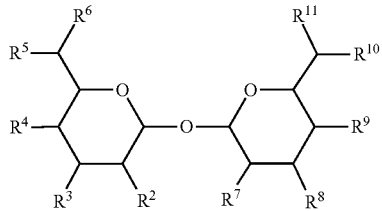
(II)

wherein,
$R^2$ is —$OR^{2A}$;
$R^3$ is —$OR^{3A}$;
$R^4$ is —$OR^{4A}$;
$R^5$ is hydrogen;
$R^6$ is —SH;
$R^7$ is —$OR^{7A}$;
$R^8$ is —$OR^{8A}$;
$R^9$ is —$OR^{9A}$;
$R^{10}$ is hydrogen;
$R^{11}$ is —SH;
and
$R^{2A}$, $R^{3A}$, $R^{4A}$, $R^{7A}$, $R^{8A}$, and $R^{9A}$ are each independently hydrogen or unsubstituted $C_1$-$C_{10}$ alkyl;
or a pharmaceutically acceptable salt thereof;
wherein the subject has 1, 2, 3, 4, 5, 6, 7, 8, 9, 10, or more complete mucus airway occlusions of one or more airways within one or two lungs in the subject, or wherein the subject has cicatricial pemphigoid, tuberculosis, lung cancer, emphysema, influenza, or primary ciliary dyskinesia.

24. The method of claim 23, wherein the compound is

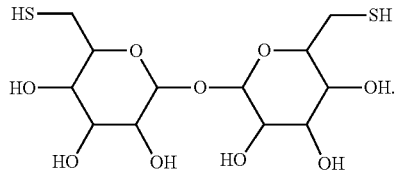 [SMILES: OC1C(CS)OC(OC2OC(CS)C(O)C(O)C2O)C(O)C1O]

25. The method of claim 23, wherein the compound is

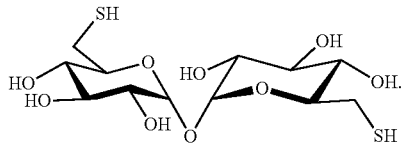

26. The method of claim 25, wherein the subject experiences rapid onset of a disorder selected from the group consisting of chronic obstructive pulmonary disease (COPD), cystic fibrosis (CF), asthma, bronchiectasis, traction bronchiectasis, primary ciliary dyskinesia, bronchiolitis, and allergic bronchopulmonary aspergillosis.

27. A method for treatment of a condition in a subject, comprising administering to a subject in need thereof an effective amount of a compound of Formula II in combination with another therapeutic agent, wherein the therapeutic action of the therapeutic agent is enhanced by decreasing mucus elasticity or decreasing mucus viscosity, wherein the condition is chronic obstructive pulmonary disease (COPD), cystic fibrosis (CF), asthma, chronic asthma, acute asthma, bronchitis, chronic bronchitis, acute bronchitis, bronchiectasis, traction bronchiectasis, primary ciliary dyskinesia, bronchiolitis, allergic bronchopulmonary aspergillosis, pneumonia, a mechanical ventilator-associated lung injury, sinusitis, chronic rhinitis, acute sinusitis, chronic sinusitis, chronic rhinosinusitis with nasal polyps, chronic rhinosinusitis without nasal polyps, rhinorrhea, or post-nasal drip; and wherein Formula II is represented by:

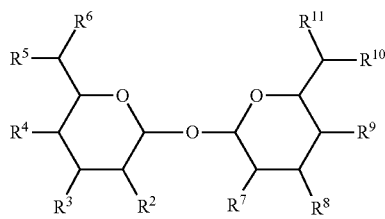
(II)

wherein,
$R^2$ is —$OR^{2A}$;
$R^3$ is —$OR^{3A}$;
$R^4$ is —$OR^{4A}$;
$R^5$ is hydrogen;
$R^6$ is —SH;
$R^7$ is —$OR^{7A}$;
$R^8$ is —$OR^{8A}$;
$R^9$ is —$OR^{9A}$;
$R^{10}$ is hydrogen;
$R^{11}$ is —SH;
and
$R^{2A}$, $R^{3A}$, $R^{4A}$, $R^{7A}$, $R^{8A}$, and $R^{9A}$ are each independently hydrogen or unsubstituted $C_1$-$C_{10}$ alkyl;
or a pharmaceutically acceptable salt thereof.

* * * * *